(12) United States Patent
Janetka et al.

(10) Patent No.: US 9,957,289 B2
(45) Date of Patent: May 1, 2018

(54) COMPOUNDS AND METHODS FOR TREATING BACTERIAL INFECTIONS

(71) Applicant: Washington University, St. Louis, MO (US)

(72) Inventors: James W. Janetka, St. Louis, MO (US); Zhenfu Han, St. Louis, MO (US); Scott Hultgren, St. Louis, MO (US); Jerry Pinkner, St. Louis, MO (US); Corinne Cusumano, St. Louis, MO (US)

(73) Assignee: WASHINGTON UNIVERSITY, St. Louis, MO (US)

( * ) Notice: Subject to any disclaimer, the term of this patent is extended or adjusted under 35 U.S.C. 154(b) by 0 days. days.

(21) Appl. No.: 14/894,927

(22) PCT Filed: May 30, 2014

(86) PCT No.: PCT/US2014/040355
§ 371 (c)(1),
(2) Date: Nov. 30, 2015

(87) PCT Pub. No.: WO2014/194270
PCT Pub. Date: Dec. 4, 2014

(65) Prior Publication Data
US 2016/0145289 A1 May 26, 2016

Related U.S. Application Data

(60) Provisional application No. 61/828,954, filed on May 30, 2013.

(51) Int. Cl.
| C07H 15/203 | (2006.01) |
| C07H 15/26 | (2006.01) |
| A61K 31/7034 | (2006.01) |
| A61K 31/7042 | (2006.01) |
| A61K 31/7056 | (2006.01) |
| A61K 31/706 | (2006.01) |
| A61K 31/7064 | (2006.01) |
| A61K 45/06 | (2006.01) |

(52) U.S. Cl.
CPC ......... *C07H 15/203* (2013.01); *A61K 31/706* (2013.01); *A61K 31/7034* (2013.01); *A61K 31/7042* (2013.01); *A61K 31/7056* (2013.01); *A61K 31/7064* (2013.01); *A61K 45/06* (2013.01); *C07H 15/26* (2013.01)

(58) Field of Classification Search
None
See application file for complete search history.

(56) References Cited

U.S. PATENT DOCUMENTS

| 6,153,396 A | 11/2000 | Hultgren et al. |
| 6,962,791 B2 | 11/2005 | Hultgren et al. |
| 7,790,183 B2 | 9/2010 | Darouiche et al. |
| 8,937,167 B2 | 1/2015 | Janetka et al. |
| 9,567,362 B2 | 2/2017 | Janetka et al. |
| 2007/0167378 A1 | 7/2007 | Saraiva et al. |
| 2008/0171706 A1 | 7/2008 | Berglund et al. |
| 2008/0268006 A1 | 10/2008 | Molin et al. |
| 2010/0015600 A1 | 1/2010 | Barnich et al. |
| 2012/0309701 A1 | 12/2012 | Janetka et al. |
| 2015/0197538 A1 | 7/2015 | Janetka et al. |

FOREIGN PATENT DOCUMENTS

| EP | 0383092 A2 | 8/1990 |
| EP | 0383092 A3 | 3/1992 |
| WO | 9514028 A2 | 5/1995 |
| WO | 0110386 A2 | 2/2001 |
| WO | 2005089733 A2 | 9/2005 |
| WO | 2011050323 A1 | 4/2011 |
| WO | 2011073112 A2 | 6/2011 |
| WO | 2012109263 A1 | 8/2012 |
| WO | 2012164074 A1 | 12/2012 |
| WO | 2014194270 A1 | 12/2014 |

OTHER PUBLICATIONS

Abdel-Megeid et al., "Preparation and Some Reactions of D-Glucosyl Derivatives of 2-Thioxo-1,3,4-Oxadiazoles and 2-Thioxo-1,3,4-Thiadiazoles and Their 2-Oxo Analogues," Carbohydrate Res., 1977, pp. 95-102, vol. 59.

Abgottspon et al., "In vivo Evaluation of FimH Antagonists—A Novel Class of Antimicrobials for the Treatment of Urinary Tract Infection," Chimia, 2012, pp. 166-169, vol. 66, No. 4.

Abgottspon et al., "Development of an aggregation assay to screen FimH antagonists," J. Microb. Methods, 2010, pp. 249-255, vol. 82.

Bouckaert et al., "Receptor binding studies disclose a novel class of high-affinity inhibitors of the *Escherichia coli* FimH adhesin," Mol. Microb., 2005, pp. 441-455, vol. 55, No. 2.

Bognar et al., "N-Glykosyl Derivative: Part III. The subsequent installation of the agiycone. Synthesis of N-glykosyl derivatives of 2-amino-thiazole, 2-amino-1, 3, 4-thiadiazole and 5-amino- 1,2,3,4-thiatriazols," Carbohyd. Res., 1967, pp. 320-328, vol. 5, with English Abstract.

Cusumano et al., "Treatment and Prevention of Urinary Tract Infection with Orally Active FimH Inhibitors," Sci Transl Med., 2011, pp. 1-10, vol. 3, No. 109.

Durka et al., "The functional valency of dodecamannosylated fullerenes with *Escherichia coil* FimH-towards novel bacterial antiadhesives," Chem. Commun., 2011, pp. 1321-1323, vol. 47.

European Search Report from related European Patent Application No. 10825785.8 dated Jan. 7, 2014, 10 pages.

(Continued)

*Primary Examiner* — Layla D Berry
(74) *Attorney, Agent, or Firm* — Polsinelli PC

(57) ABSTRACT

The present invention encompasses compounds and methods for treating and preventing bacterial infections specifically urinary tract infections and those caused by bacteria containing type 1 pili and FimH. The present invention also encompasses compounds and methods for treating inflammatory bowel disease specifically Crohn's Disease.

14 Claims, 66 Drawing Sheets
(43 of 66 Drawing Sheet(s) Filed in Color)

(56) References Cited

OTHER PUBLICATIONS

Firon et al., "Interaction of Mannose-Containing Oligosaccharides with the Fimbrial Lectin of *Escherichia coli*," Biochem. and Biophys. Res. Commun., 1982, pp. 1426-1432, vol. 105, No. 4.

Firon et al., "Aromatic Alpha-Glycosides of Mannose Are Powerful Inhibitors of the Adherence of Type 1 Fimbriated *Escherichia coli* to Yeast and Intestinal Epithelial Cells," Infection and Immunity, 1987, pp. 472-476, vol. 55, No. 2.

Furneaux et al., "New mannotriosides and trimannosides as potential ligands for mannose-specific binding proteins," Can. J. Chem., 2002, pp. 964-972, vol. 80.

Gouin et al., "Synthetic Multimeric Heptyl Mannosides as Potent Antiadhesives of Uropathogenic *Escherichia coli*," ChemMedChem., 2009, pp. 749-755, vol. 4.

Grabosch et al., "Squaric Acid Monoamide Mannosides as Ligands for the Bacterial Lectin FimH: Covalent Inhibition or Not?," Chem. Bio. Chem., 2011, pp. 1066-1074, vol. 12.

Guiton et al., "Combinatorial Small-Molecule Therapy Prevents Uropathogenic *Escherichia coli* Catheter-Associated Urinary Tract Infections in Mice," Antimicrob. Agents Chemother, 2012, pp. 4738-4745, vol. 56, No. 9.

Han et al., "Structure-Based Drug Design and Optimization of Mannoside Bacterial FimH Antagonists," J. Med. Chem., 2010, pp. 4779-4792, vol. 53.

Han et al., "Lead Optimization Studies on FimH Antagonists: Discovery of Potent and Orally Bioavailable Ortho-Substituted Biphenyl Mannosides," J. Med. Chem., 2012, pp. 3945-3959, vol. 55.

Hartmann et al., "The Bacterial Lectin FimH, a Target for Drug Discovery-Carbohydrate Inhibitors of Type 1 Fimbriae-Mediated Bacterial Adhesion," Eur. J. Org. Chem., 2011, pp. 1-28.

Haskins et al., "Relations between Rotatory Power and Structure in the Sugar Group. XXXV. Some 2'-Naphthyl 1-Thioglycopyranosides and their Acetates," J. Am. Chem. Soc., 1947, pp. 1668-1672, vol. 69, No. 7.

Hung et al., "Structural basis of tropism of *Escherichia coli* to the bladder during urinary tract infection," Mol. Microb., 2002, pp. 903-915, vol. 44, No. 4.

Irani et al., "Stannic Chloride Promoted Synthesis of Mannosides," India J. Chem., Sect. B: Org. Chem. Incl. Med. Chem. 30, 1991, vol. 5, pp. 519-521, Natl. Chem. Lab., Pun 411 008, India; EN 1 page (Abstract Only).

International Search Report and Written Opinion dated May 29, 2012 from International Application No. PCT/US12/24169, 8 pages.

International Search Report and Written Opinion dated Dec. 23, 2010 from International Application No. PCT/US10/53848, 9 pages.

International Search Report and Written Opinion, dated Sep. 22, 2014, from International Application No. PCT/US2014/040355,13 pages.

Jiang et al., "Antiadhesion Therapy for Urinary Tract Infections—A Balanced PK/PD Profile Proved to Be Key for Success," J. Med. Chem., 2012, pp. 4700-4713, vol. 55.

Klein et al., "FimH Antagonists for the Oral Treatment of Urinary Tract Infections: From Design and Synthesis to in Vitro and in Vivo Evaluation," J. Med. Chem., 2010, pp. 8627-8641, vol. 53, No. 24.

Kostakioti et al., "Distinguishing the Contribution of Type 1 Pili from That of Other QseB-Misregulated Factors when QseC Is Absent during Urinary Tract Infection," Infect. Immun., 2012, pp. 2826-2834, vol. 80, No. 8.

Lindhorst et al., "Inhibition of the type 1 fimbriae-mediated adhesion of *Escherichia coli* to erythrocytes by multiantennary alpha-mannosyl clusters: The effect of multivalency," Glycoconjugate J., 1998, pp. 605-613, vol. 15.

Nagahori et al., "Inhibition of Adhesion of Type 1 Fimbriated *Escherichia coli* to Highly Mannosylated Ligands," ChemBioChem, 2002, pp. 836-844, vol. 3.

Notice of Allowance and Fee(s) Due related to U.S. Appl. No. 13/453,991, dated Sep. 4, 2014, 11 pages.

Notice of Allowance and Fee(s) Due related to U.S. Appl. No. 13/453,991, dated Jul. 14, 2014, 8 pages.

Notice of Allowance and Fee(s) Due related to U.S. Appl. No. 14/570,322, dated Sep. 9, 2016, 8 pages.

Office Action from U.S. Appl. No. 13/453,991 dated Mar. 6, 2014, 9 pages.

Office Action from U.S. Appl. No. 13/453,991 dated Nov. 20, 2013, 14 pages.

Office Action from U.S. Appl. No. 14/570,322 dated May 20, 2016, 8 pages.

Pang et al., "FimH Antagonists: Structure-Activity and Structure-Property Relationships for Biphenyl alpha-D-Mannopyranosides," ChemMedChem, 2012, pp. 1404-1422, vol. 7.

Qian et al., "Arrays of Self-Assembled Monolayers for Studying Inhibition of Bacterial Adhesion," Anal. Chem., 2002, pp. 1805-1810, vol. 74.

Rabbani et al., "Expression of the carbohydrate recognition domain of FimH and development of a competitive binding assay," Anal. Biochem., 2010, pp. 188-195, vol. 407.

Scharenberg et al., "Target Selectivity of FimH Antagonists," J. Med. Chem., 2012, pp. A-G, vol. 55.

Scharenberg et al., "A Flow Cytometry-Based Assay for Screening FimH Antagonists," Assay and Drug Development Technologies, 2011, pp. 455-464, vol. 9, No. 5.

Schwardt et al., "Design, synthesis and biological evaluation of mannosyl triazoles as FimH antagonists," Bioorg. Med. Chem., 2011, pp. 6454-6473, vol. 19.

Shuman et al., "Synthesis and Biological Activity of Certain 8-Mercaptopurine and 6-Mercaptopyrimidine S-Nucleosides," J. Med. Chem., 1969, pp. 653-657, vol. 12, No. 4.

Sperling et al.,"Evaluation of the carbohydrate recognition domain of the bacterial adhesin FimH: design, synthesis and binding properties of mannoside ligands," Org. Biomol. Chem., 2006, pp. 3913-3922, vol. 4.

Taile et al., "Synthesis and Biological Evaluation of Novel 2-(4-o-B-D-Glucosidoxyphenyl)-4,5-disubstituted Imidazoles," Journal of Heterocyclic Chemistry, 2010, pp. 903-907, vol. 47, No. 4.

Touaibia et al., "Glycodendrimers as Anti-Adhesion Drugs Against Type 1 Fimbriated *E. coli* Uropathogenic Infections," Mini-Rev. in Med. Chem., 2007, pp. 1270-1283, vol. 7.

Touaibia et al., "Mannosylated G(0) Dendrimers with Nanomolar Affinities to *Escherichia coli* FimH," ChemMedChem., 2007, pp. 1190-1201, vol. 2.

Touaibia et al., "Tri- and hexavalent mannoside clusters as potential inhibitors of type 1 fimbriated bacteria using pentaerythritol and triazole linkages," Chem. Commun., 2007, pp. 380-382.

Walter et al., "A Modular System for the Preparation of Diazirine-Labeled Mannose Derivatives Using Thiourea Bridging," Synthesis, 2006, pp. 952-958, No. 6.

Wellens et al., "Intervening with Urinary Tract Infections Using Anti-Adhesives Based on the Crystal Structure of the FimH-Oligomannose-3 Complex," PLoS One, 2008, e2040, pp. 1-13, vol. 3, Issue 4.

Stoll et al., "The furocoumarin and the beta-D-glucosido-furocumarinsaure from the seeds of *Coronilla* species," Helvetica Chimica Acta, 1950, pp. 1637-1647, vol. XXXIII, Fasciculus VI, No. 211-212, with English Abstract.

Supplementary European Search Report related to EP 12744161 dated Aug. 6, 2014, 13 pages.

Office Action dated Jul. 14, 2016 from related European Patent Application No. 10825785.8; 5 pgs.

Extended European Search Report dated Dec. 23, 2016 from related European Patent Application No. 14804252.6; 9 pgs.

Office Action dated Mar. 17, 2017 from related European Patent Application No. 12744161.6; 4 pgs.

Office Action dated Jun. 23, 2017 from related European Patent Application No. 10825785.8; 5 pgs.

Office Action dated Oct. 30, 2017 from related Chinese Patent Application No. 201480043010.1; 21 pgs., including English translation.

Office Action dated Dec. 19, 2017 from related Japanese Patent Application No. 2016-517061; 8 pgs., including partial English translation.

Target hydrophobic or π-π stacking interactions with Tyr48 and Tyr137

4ZFH55 (S-mannoside)

5ZFH049 (C-mannoside)

5ZFH038

5ZFH048

Reagents and conditions:

(a) R'OH, BF$_3$-OEt$_2$, CH$_2$Cl$_2$, reflux;
(b) (i) NaOMe, MeOH; (ii) H$^+$ exchange resin;
(c) R'OH, BF$_3$-OEt$_2$, CH$_2$Cl$_2$, 0 °C to 25 °C;
(d) H$_2$, 10% Pd/C, EtOH, EtOAc.

(a) RPh-B(OR)$_2$, Pd(Ph$_3$P)$_4$, dioxane/water (4:1), Cs$_2$CO$_3$, 80 °C (b) NaOMe, MeOH; (c) Pd(OAc)$_2$, pinacolborane; (d) Pd(0), Het-Br.

COMPOUNDS AND METHODS FOR TREATING BACTERIAL INFECTIONS

CROSS REFERENCE TO RELATED APPLICATIONS

This application claims the benefit of PCT International Patent Application No. PCT/US2014/040355, filed May 30, 2014, which claims the priority of U.S. provisional application No. 61/828,954, filed May 30, 2013, each of the disclosures of which are hereby incorporated by reference in its entirety.

GOVERNMENTAL RIGHTS

This invention was made with government support under RO1AI029549, DK086378, P50DK064540 and RO1BK051406-12 awarded by the National Institutes of Health. The government has certain rights in the invention.

FIELD OF THE INVENTION

The present invention encompasses compounds and methods for inhibiting the adhesin protein FimH and treating and preventing urinary tract infections and inflammatory bowel disease (e.g. Crohn's disease and ulcerative colitis).

BACKGROUND OF THE INVENTION

Urinary tract infection (UTI) caused by uropathogenic *Escherichia coli* (UPEC) is one of the most common infectious diseases in women. The morbidity and economic impact are enormous, with over $2.5 billion spent annually on treatment. Further, recurrent infections are a significant problem despite appropriate antibiotic therapy of the index case. The high rates of recurrence, and the large numbers of women that end up in urology clinics due to their chronic recurrent UTIs highlights the need for a better understanding of the pathogenic mechanisms involved in this disease and the development of new and better therapies.

Gram-negative bacteria are the causative agents of a wide variety of acute and chronic infectious diseases. Many of these infections are initiated by a critical interaction between host ligands (frequently polysaccharide moieties) and bacterial adhesins (frequently expressed at the distal tip of polymeric pilus fibers assembled by the chaperone/usher pathway). The mannose binding FimH adhesin of type 1 pili is critical for the colonization and invasion into the bladder epithelium. After invasion, UPEC are able to rapidly multiply inside superficial umbrella cells of the bladder forming biofilm-like intracellular bacterial communities (IBCs). Upon maturation, bacteria disperse from the IBC, spread to neighboring cells, and form next generation IBCs. This is the mechanism by which UPEC rapidly amplify in numbers in the urinary tract and cause disease.

The X-ray crystal structure of FimH bound to mannose showed that mannose is bound in a negatively charged pocket on FimH. The mannose binding site is highly conserved as it is invariant in 300 fimH genes sequenced from clinical UPEC strains. Thus, FimH is the critical node of the entire UPEC pathogenic cascade.

Recurrence is a serious problem for many women. Women who present with an initial episode of acute UTI have a 25-44% chance of developing a second and a 3% chance of experiencing three episodes within six months of the initial UTI. Recurrence occurs despite appropriate antibiotic treatment and clearance of the initial infection from the urine. A large percentage of recurrent UTI are caused by the same strain of bacteria as the initial infection. One study followed 58 women and found that 68% of recurrences were caused by the same initial index strain of UPEC as determined by restriction fragment length polymorphism (RFLP) analysis. In a separate study, 50% of recurrent strains isolated from female college students appeared genotypically identical to the bacterial strain corresponding to the initial UTI. Another long-term prospective study demonstrated that the same strain of UPEC can cause a recurrent UTI up to 3 years later. The high frequency of same-strain recurrences supports the notion that a UPEC reservoir can exist in the affected individual. The inventors have shown that a quiescent intracellular reservoir (QIR) can form in the bladder tissue itself after acute infection and persist even after antibiotic therapy and urine cultures become sterile. Thus, reactivation of bacteria in QIRs may also be a contributing factor in recurrent UTIs.

Inflammatory bowel disease (IBD) mainly consists of two disorders, ulcerative colitis and Crohn's disease (CD), with a combined prevalence of ~150-200 cases per 100,000 in Western countries. The abnormal inflammatory response observed in IBD requires interplay between host genetic factors and the intestinal microbiota. Adherent-invasive *Escherichia coli* (AIEC) have previously been shown to induce gut inflammation in patients with Crohn's disease (CD). Mannosides have been shown to prevent AIEC attachment to the gut by blocking the FimH bacterial adhesin. Given the key role of AIEC in the chronic intestinal inflammation of CD patients, these results suggest a potential anti-adhesive treatment with the FimH inhibitors developed.

Therefore, there is a need for effective treatments that can cure urinary tract infections and prevent the formation of quiescent intracellular reservoir that are the source of so many recurrent infections. As well as effective treatments that can cure, prevent or reduce symptoms associated with Crohn's disease.

SUMMARY OF THE INVENTION

One aspect of the present invention encompasses a compound comprising formula (I):

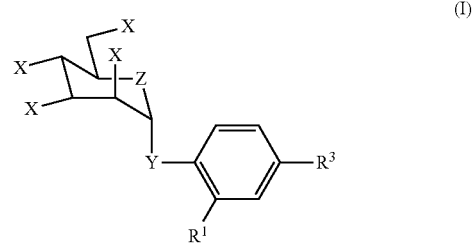

wherein:
X is selected from the group consisting of hydrogen and OR$^2$;
R$^2$ is independently selected from the group consisting of hydrogen, PO(OH)$_2$, acetyl, COR$^5$, CO(OR$^5$), CO(NR$_5$R$_6$), CO(CH$_2$)$_n$NR$^5$R$^6$, hydrocarbyl and substituted hydrocarbyl;
n is an integer from 1 to 10;
Z is O;
Y is selected from the group consisting of O, CH(OH), CH(OR$^5$), CHNR$^5$R$^6$, CH$_2$, S, and NR$^5$;

R[1] is selected from the group consisting of $CH_3$, $CF_3$, halogen, Cl, F, Br, I, OH, $NH_2$, $NR^5R^6$, $OCH_3$, $CO_2CH_3$, $CONHCH_3$, alkyl, cyclopropyl, $OR^5$, $CO_2R^5$, $CONR^5R^6$, hydrocarbyl, and substituted hydrocarbyl;

R[3] is selected from the group consisting of formula (IA) and formula (IB):

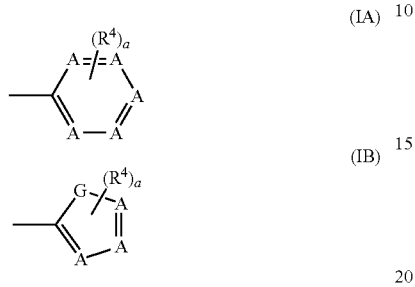

A is independently selected from the group consisting of $CR^5$ and N;

G is independently selected from the group consisting of S, $NR^5$ and O;

a is an integer from 1 to 4;

R[4] is selected from the group consisting of $CONHCH_3$, $COOCH_3$, COOH, CONH(heterocycle), heterocycle, H, alkyl, cyclopropyl, aryl, $OR^5$, $NR^5R^6$, $NR^5COR^6$, $NR^5COOR^6$, $NR^5CONR^6$, $NR^5SO_2R^6$, $COR^5$, $SO_2R^5$, halogen, CN, $NO_2$, $COOR^5$, $CONR^5R^6$, $NCOR^7$, $NCONR^7$, $NCOOR^7$, $SO_2NR^5R^6$, and $NHSO_2R^7$, or when a is greater than or equal to 2, R[4] may optionally form an optionally substituted cycloalkyl, aryl or heterocyclo 5 or 6 membered ring;

R[5] is selected from the group consisting of H and an optionally substituted alkyl, aryl, heterocycle, and cycloalkyl;

R[6] and R[7] are selected from the group consisting of an optionally substituted alkyl, cycolalkyl, aryl, and heterocycle.

Another aspect of the present invention encompasses a compound comprising Formula (II):

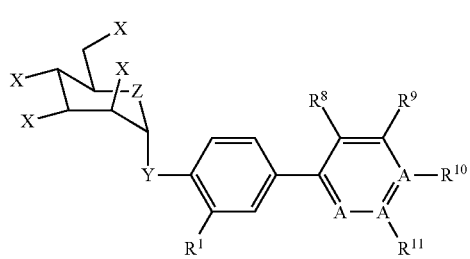

wherein:

X is selected from the group consisting of hydrogen and $OR^2$;

R[2] is independently selected from the group consisting of hydrogen, $PO(OH)_2$, acetyl, $COR^5$, $CO(OR^5)$, $CO(CH_2)_nNR^5R^6$, hydrocarbyl and substituted hydocarbyl;

n is an integer from 1 to 10;

Z is O;

Y is selected from the group consisting of O, CH(OH), $CH(OR^5)$, $CHNR^5R^6$, $CH_2$, S, and $NR^5$;

A is independently selected from the group consisting of $CR^5$ and N;

R[1] is selected from the group consisting of $CH_3$, $CF_3$, halogen, Cl, F, Br, I, OH, $NH_2$, $NR^5R^6$, $OCH_3$, $CO_2CH_3$, $CONHCH_3$, alkyl, cyclopropyl, $OR^5$, $CO_2R^5$, $CONR^5R^6$, hydrocarbyl, and substituted hydrocarbyl;

R[8], R[9], R[10] and R[11] are independently selected from the group consisting of $CONHCH_3$, $COOCH_3$, COOH, CONH(heterocycle), heterocycle, H, alkyl, cyclopropyl, aryl, $OR^5$, $NR^5R^6$, $NR^5COR^6$, $NR^5COOR^6$, $NR^5CONR^6$, $NR^5SO_2R^6$, $COR^5$, $SO_2R^5$, halogen, CN, $NO_2$, $COOR^5$, $CONR^5R^6$, $NCOR^7$, $NCONR^7$, $NCOOR^7$, $SO_2NR^5R^6$, $NHSO_2R^7$, and R[8] and R[9] together can optionally form an optionally substituted cycloalkyl, aryl or heterocyclo 5 or 6 membered ring; and R[9] and R[10] together can optionally form an optionally substituted cycloalkyl, aryl or heterocyclo 5 or 6 membered ring;

R[5] is selected from the group consisting of H and an optionally substituted alkyl, aryl, heterocycle, and cycloalkyl;

R[6] and R[7] is selected from the group consisting of an optionally substituted alkyl, cycolalkyl, aryl and heterocycle.

Still another aspect of the present invention encompasses a compound comprising Formula (III):

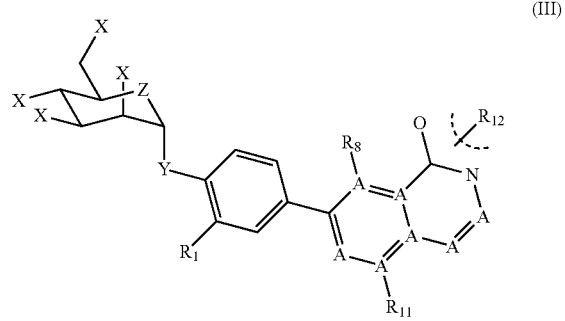

wherein:

X is selected from the group consisting of hydrogen and $OR^2$;

R[2] is independently selected from the group consisting of hydrogen, $PO(OH)_2$, acetyl, $COR^5$, $CO(OR^5)$, $CO(CH_2)_nNR^5R^6$, hydrocarbyl and substituted hydocarbyl;

n is an integer from 1 to 10;

Z is O;

Y is selected from the group consisting of O, CH(OH), $CH(OR^5)$, $CHNR^5R^6$, $CH_2$, S, and $NR^5$;

R[1] is selected from the group consisting of $CH_3$, $CF_3$, halogen, Cl, F, Br, I, OH, $NH_2$, $NR^5R^6$, $OCH_3$, $CO_2CH_3$, $CONHCH_3$, alkyl, cyclopropyl, $OR^5$, $CO_2R^5$, $CONR^5R^6$, hydrocarbyl, and substituted hydrocarbyl;

A is independently selected from the group consisting of $CR^5$ and N;

R[5] is selected from the group consisting of H and an optionally substituted alkyl, aryl, heterocycle, and cycloalkyl;

R⁶ and R⁷ are selected from the group consisting of an optionally substituted alkyl, cycoalkyl, aryl, and heterocycle;

R⁸ and R¹¹ are independently selected from the group consisting of CONHCH₃, COOCH₃, COOH, CONH (heterocycle), heterocycle, H, alkyl, cyclopropyl, aryl, OR⁵, NR⁵R⁶, NR⁵COR⁶, NR⁵COOR⁶, NR⁵CONR⁶, NR⁵SO₂R⁶, COR⁵, SO₂R⁵, halogen, CN, NO₂, COOR⁵, CONR⁵R⁶, NCOR⁷, NCONR⁷, NCOOR⁷, SO₂NR⁵R⁶, and NHSO₂R⁷;

R¹² is substituted at the O or N and is selected from the group consisting of H, alkyl, CH₂R¹³, CH₂COR¹³, CH₂CONHR¹³, CH₂CONHR¹³R¹⁴, CH₂CONH(CH₂)₂R¹⁴, (CH₂)₂NR¹³, (CH₂)ₙNR¹³, CH₂COOH, CH₂CONH(CH₂)₂NH₂, and (CH₂)₂N(CH₃)₂;

R¹³ is selected from the group consisting of —OH and an optionally substituted heterocycle, hydrocarbyl, and substituted hydrocarbyl;

R¹⁴ is selected from the group consisting of alkyl and NH₂.

Yet still another aspect of the present invention encompasses a compound comprising Formula (IV):

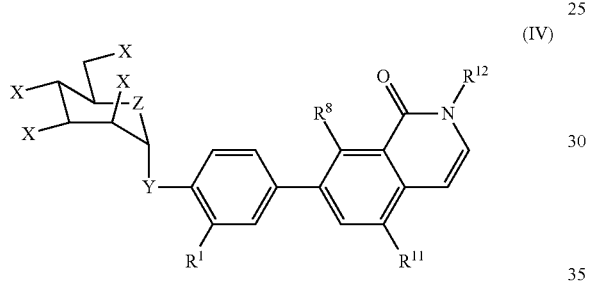

wherein:
X is selected from the group consisting of hydrogen and OR²;

R² is independently selected from the group consisting of hydrogen, PO(OH)₂, acetyl, COR⁵, CO(OR⁵), CO(CH₂)ₙNR⁵R⁶, hydrocarbyl and substituted hydrocarbyl;

n is an integer from 1 to 10;

Z is O;

Y is selected from the group consisting of O, CH(OH), CH(OR⁵), CHNR⁵R⁶, CH₂, S, and NR⁵;

R¹ is selected from the group consisting of CH₃, CF₃, halogen, Cl, F, Br, I, OH, NH₂, NR⁵R⁶, OCH₃, CO₂CH₃, CONHCH₃, alkyl, cyclopropyl, OR⁵, CO₂R⁵, CONR⁵R⁶, hydrocarbyl, and substituted hydrocarbyl;

R⁵ is selected from the group consisting of H and an optionally substituted alkyl, aryl, heterocycle, and cycloalkyl;

R⁶ and R⁷ are selected from the group consisting of an optionally substituted alkyl, cycoalkyl, aryl, and heterocycle;

R⁸ and R¹¹ are independently selected from the group consisting of CONHCH₃, COOCH₃, COOH, CONH (heterocycle), heterocycle, H, alkyl, cyclopropyl, aryl, OR⁵, NR⁵R⁶, NR⁵COR⁶, NR⁵COOR⁶, NR⁵CONR⁶, NR⁵SO₂R⁶, COR⁵, SO₂R⁵, halogen, CN, NO₂, COOR⁵, CONR⁵R⁶, NCOR⁷, NCONR⁷, NCOOR⁷, SO₂NR⁵R⁶, and NHSO₂R⁷;

R¹² is selected from the group consisting of H, alkyl, CH₂R¹³, CH₂COR¹³, CH₂CONHR¹³, CH₂CONHR¹³R¹⁴, CH₂CONH(CH₂)₂R¹⁴, (CH₂)₂NR¹³, (CH₂)ₙNR¹³, CH₂COOH, CH₂CONH(CH₂)₂NH₂, and (CH₂)₂N(CH₃)₂;

R¹³ is selected from the group consisting of —OH and an optionally substituted heterocycle, hydrocarbyl, and substituted hydrocarbyl;

R¹⁴ is selected from the group consisting of alkyl and NH₂.

Yet still another aspect of the present invention encompasses a compound comprising Formula (V):

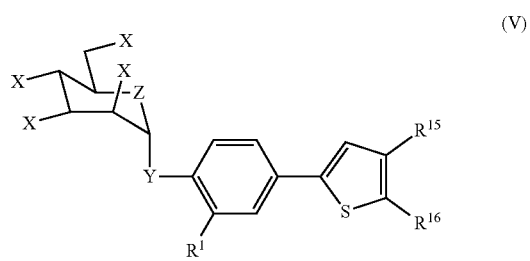

wherein:
X is selected from the group consisting of hydrogen and OR²;

R² is independently selected from the group consisting of hydrogen, PO(OH)₂, acetyl, COR⁵, CO(OR⁵), CO(CH₂)ₙNR⁵R⁶, hydrocarbyl and substituted hydrocarbyl;

n is an integer from 1 to 10;

R⁵ is selected from the group consisting of H and an optionally substituted alkyl, aryl, heterocycle, and cycloalkyl;

R⁶ and R⁷ are selected from the group consisting of an optionally substituted alkyl, cycoalkyl, aryl, and heterocycle;

Z is O;

Y is selected from the group consisting of O, CH(OH), CH(OR⁵), CHNR⁵R⁶, CH₂, S, and NR⁵;

R¹ is selected from the group consisting of CH₃, CF₃, halogen, Cl, F, Br, I, OH, NH₂, NR⁵R⁶, OCH₃, CO₂CH₃, CONHCH₃, alkyl, cyclopropyl, OR⁵, CO₂R⁵, CONR⁵R⁶, hydrocarbyl, and substituted hydrocarbyl;

R¹⁵ and R¹⁶ are independently selected from the group consisting of hydrogen, NHCONH₂, COOCH₃, and CONHCH₃, CONHCH₃, COOCH₃, COOH, CONH (heterocycle), heterocycle, alkyl, cyclopropyl, aryl, OR⁵, NR⁵R⁶, NR⁵COR⁶, NR⁵COOR⁶, NR⁵CONR⁶, NR⁵SO₂R⁶, COR⁵, SO₂R⁵, halogen, CN, NO₂, COOR⁵, CONR⁵R⁶, NCOR⁷, NCONR⁷, NCOOR⁷, SO₂NR⁵R⁶, and NHSO₂R⁷ or R¹⁵ and R¹⁶ can optionally form a cycloalkyl, aryl or heterocyclo ring.

Yet still another aspect of the present invention encompasses a compound comprising Formula (VI):

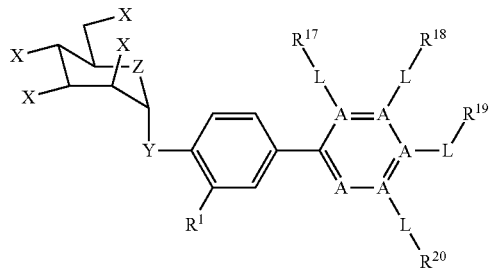

(VI)

wherein:
X is selected from the group consisting of hydrogen and $OR^2$;
$R^2$ is independently selected from the group consisting of hydrogen, $PO(OH)_2$, acetyl, $COR^5$, $CO(OR^5)$, $CO(CH_2)_n NR^5R^6$, hydrocarbyl and substituted hydrocarbyl;
n is an integer from 1 to 10;
$R^5$ is selected from the group consisting of H and an optionally substituted alkyl, aryl, heterocycle, and cycloalkyl;
$R^6$ and $R^7$ are selected from the group consisting of an optionally substituted alkyl, cycolalkyl, aryl, and heterocycle;
Z is O;
Y is selected from the group consisting of O, CH(OH), $CH(OR^5)$, $CHNR^5R^6$, $CH_2$, S, and $NR^5$;
$R^1$ is selected from the group consisting of $CH_3$, $CF_3$, halogen, Cl, F, Br, I, OH, $NH_2$, $NR^5R^6$, $OCH_3$, $CO_2CH_3$, $CONHCH_3$, alkyl, cyclopropyl, $OR^5$, $CO_2R^5$, $CONR^5R^6$, hydrocarbyl, and substituted hydrocarbyl;
A is independently selected from the group consisting of $CR^5$ and N;
L is independently selected from the group consisting of no atom, N, NH, O and S;
$R^{17}$, $R^{18}$, $R^{19}$ and $R^{20}$ are selected from the group consisting of H and an optionally substituted cycloalkyl, aryl or heterocyclo 5 or 6 membered ring, 5-6 fused ring or 6-6 fused ring including but not limited to the following examples, wherein the example is attached via any available CH position:

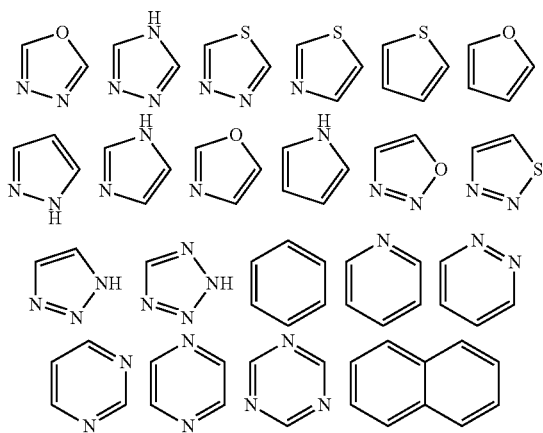

-continued

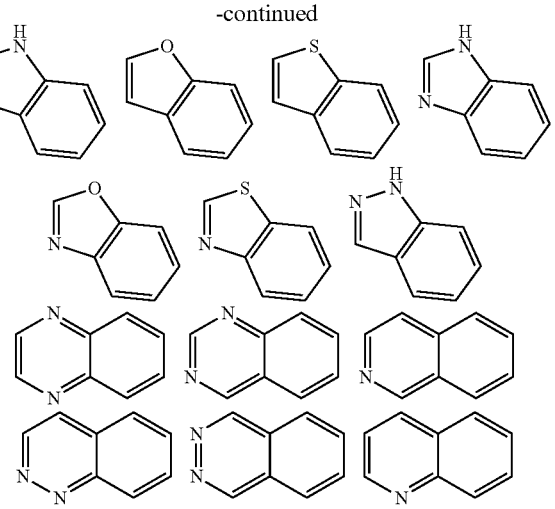

The invention also encompasses a method of treating a urinary tract infection. The method comprises administering a compound of the invention to a subject in need thereof.

Further, the invention encompasses a method of preventing a urinary tract infection. The method comprises administering a compound of the invention to a subject in need thereof.

In another aspect, the invention encompasses a method of reducing the resistance of a bacterium to a bactericidal compound. The method comprises administering a compound of the invention a subject in need thereof.

In yet another aspect, the invention encompasses a method of treating inflammatory bowel disease. The method comprises administering a compound of the invention to a subject in need thereof.

In still yet another aspect, the invention encompasses a method of inhibiting FimH binding to mannose. The method comprises contacting a compound of the invention with FimH, wherein the compound binds FimH and inhibits binding to mannose.

In still yet another aspect, the invention encompasses a method of treating a catheter-associated urinary tract infection. The method comprises administering a compound of the invention to a subject in need thereof.

BRIEF DESCRIPTION OF THE FIGURES

The application file contains at least one drawing executed in color. Copies of this patent application publication with color drawing(s) will be provided by the Office upon request and payment of the necessary fee.

(FIG. 1D) Shows that 50 mg/kg of 269, 254 and 240 reduced bacterial titers in the bladder relative to DMSO and PBS.

(FIG. 2D) Shows that 25 mg/kg of compound ZFH269 most efficiently reduced bacterial titers in the bladder.

(FIG. 6D) Shows the pharmacokinetics of 269, 254, Prodrug and 240.

(FIG. 7A) Shows that 25 mg/kg of ZFH269 and 25 mg/kg of ZFH-4269 prodrug significantly reduced bacterial titers in the bladder in a mouse model of acute infection. (FIG. 7B) showed that all prodrug compounds reduced bacterial titers in the bladder in a mouse model of acute infection.

(FIG. 8A) FIM-1231 (Example 20), (FIG. 8B) FIM-1233 (Example 21) and (FIG. 8C) FIM-6123 (Example 22).

(FIG. 9E) Demonstrates the metabolism of 4ZFH269 in the presence of plasma protease.

(FIG. 10A) depicts the structure of gram positive and gram negative bacteria. (FIG. 10B) depicts carbohydrates expressed by the host and the bacterium that bind via a bacterial lectin. A carbohydrate drug can inhibit binding to the host carbohydrate. (FIG. 10C) depicts the structure of the glycosylation found on host cells.

(FIG. 11A) Uropathogenic *E. coli* (UPEC) infect the bladder epithelium via the FimH adhesin on the Type 1 pilus depicted in (FIG. 11B). (FIG. 11C) FimH of UPEC specifically binds uroplakin on superficial umbrella cells.

(FIG. 12A) Shows the FimH adhesin at the tip of the type 1 pilus. Mannose fits tightly in the FimH mannose binding pocket with numerous interactions with the surrounding amino acid residues. (FIG. 12B) shows that mutations to residues within the binding pocket abolish binding to mannose.

(FIG. 16A) shows the additional of substituents onto the phenyl ring and how this affects the HAI titer. (FIG. 16B) Based on HA titer, the ortho substituent is preferred. (FIG. 16C) A reverse trend is observed with amides.

(FIG. 18A) depicts the structure of SMZ and (FIG. 18B) depicts the structure of TMP antibiotics. (FIG. 18C) depicts the structure of 2ZFH56 mannoside. (FIG. 18D) Total bacterial CFU were quantified 6 hours after infection. UTI89 colonization was reduced in mice treated with 6 (100 mg/kg), TMP-SMZ (54 and 270 μg/ml, respectively), and TMP-SMZ+6. Horizontal lines indicate geometric mean. *P<0.05; P<0.01; *P<0.0001, Mann-Whitney U test. (FIG. 18E) A growth curve was performed with and without ZFH-2056 in the presence of various concentrations of TMP-SMZ on PBC-1 which is a strain of UPEC that is clinically resistant to TMP-SMZ. Antibiotic with or without mannoside did not affect growth of PBC-1.

(FIG. 20C) The ortho methyl substitution binds in the small pocket to Asn138.

(FIG. 21A) Optimized ortho-substituted biphenyl compounds 7 to 10. Cellular HAI titers (EC>90) are shown in parentheses. (FIG. 21B) Compounds 7 to 10 show improved pharmacokinetics. Compounds 8 and 10 at 50 mg/kg yielded concentrations in the urine 6 hours after treatment equivalent to compound 6 at 100 mg/kg. Numbers in the graph show the PAMPA predicted permeability of mannosides correlates with in vivo pharmacokinetics.

(FIG. 22A) depicts the structure of mannoside 8. (FIG. 22B) depicts the structure of mannoside 10. (FIG. 22C) Chronically infected mice were treated with PBS or compound 6, 8, or 10 (orally, 50 mg/kg) or TMP-SMZ. Six hours after treatment, there was a significant drop in bacterial load in mannoside-treated mice relative to PBS-treated mice. The optimized compound 8 showed increased efficacy over 6. (FIG. 22D) Chronically infected mice were treated with PBS or compound 8 at one or three doses every 8 hours. Twenty-four hours after the initial treatment, both compound 8-treated groups showed a significant drop in bacterial counts over the PBS-treated animals. (FIG. 22C and FIG. 22D) Horizontal bars indicate geometric mean. *P<0.05; P<0.01; *P<0.0001, Mann-Whitney U test.

(FIG. 24A) depicts the degradation products of FIM-2056. (FIG. 24B) The degradation product "R" was evaluated after oral dosing.

(FIG. 25A) 2ZFH56, (FIG. 25B) 4ZFH123, (FIG. 25C) 4ZFH89, (FIG. 25D) 4ZFH131, (FIG. 25E) 4ZFH105, (FIG. 25F) 4ZFH44, (FIG. 25G) 4ZFH55, (FIG. 25H) 5ZFH049, (FIG. 25I) 5ZFH038, and (FIG. 25J) 5ZFH048.

(FIG. 26D) depicts a graph of the concentration of mannoside in mouse urine out to 8 h.

(FIG. 27D) ZFH269 and the prodrug of 269 significantly reduce bladder titers in an acute UTI model. (FIG. 27E) Kidney titers were not significantly different.

(FIG. 29A) depicts how glycoproteins are expressed on the mammalian cell surface. (FIG. 29B) depicts the structures of the various glycoproteins.

(FIG. 36A, FIG. 36B) shows two structures with ~2 µM in HA assay but had poor solubility. (FIG. 36C) shows the schematic of the synthesis of the heterocycles.

DETAILED DESCRIPTION OF THE INVENTION

Figure 1A:
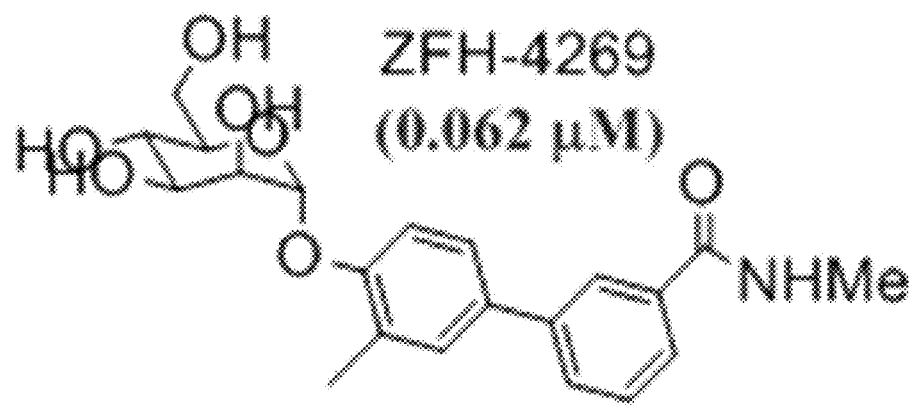
FIG. 1A, FIG. 1B, FIG. 1C and FIG. 1D depict the effect of mannoside compounds on preventing UTI in a mouse model of infection. The structures of compounds (FIG. 1A) ZFH-4269, (FIG. 1B) ZFH-5254 (Example 7) and (FIG. 1C) ZFH-5240 (Example 18A) are depicted.

Compounds that inhibit the function of type 1 pili of bacteria have been developed. The compounds may be useful for the treatment of urinary tract infections and Crohn's Disease. Significantly, the compounds may prevent bacterial colonization and invasion of the bladder tissue to prevent infection and the establishment of reservoirs that can serve as a source of recurrent infections. The invention also encompasses methods of use of a compound of the invention.

I. Compounds

One aspect of the invention is a compound of Formula (I):

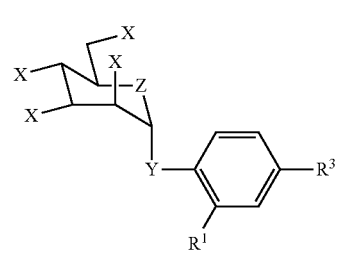

wherein:
- X is selected from the group consisting of hydrogen and $OR^2$;
- $R^2$ is independently selected from the group consisting of hydrogen, $PO(OH)_2$, acetyl, $COR^5$, $CO(OR^5)$, $CO(NR_5R_6)$, $CO(CH_2)_nNR^5R^6$, hydrocarbyl and substituted hydrocarbyl;
- n is an integer from 1 to 10;
- Z is O;
- Y is selected from the group consisting of O, CH(OH), $CH(OR^5)$, $CHNR^5R^6$, $CH_2$, S, and $NR^5$;
- $R^1$ is selected from the group consisting of $CH_3$, $CF_3$, halogen, Cl, F, Br, I, OH, $NH_2$, $NR^5R^6$, $OCH_3$, $CO_2CH_3$, $CONHCH_3$, alkyl, cyclopropyl, $OR^5$, $CO_2R^5$, $CONR^5R^6$, hydrocarbyl, and substituted hydrocarbyl;
- $R^3$ is selected from the group consisting of formula (IA) and formula (IB):

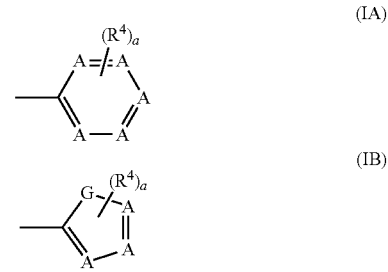

A is independently selected from the group consisting of $CR^5$ and N;
G is independently selected from the group consisting of S, $NR^5$ and O;
a is an integer from 1 to 4;
$R^4$ is selected from the group consisting of $CONHCH_3$, $COOCH_3$, COOH, $CONR_5$, CONH(heterocycle), heterocycle, H, alkyl, cyclopropyl, aryl, $OR^5$, $NR^5R^6$, $NR^5COR^6$, $NR^5COOR^6$, $NR^5CONR^6$, $NR^5SO_2R^6$, $COR^5$, $SO_2R^5$, halogen, CN, $NO_2$, $COOR^5$, $CONR^5R^6$, $NCOR^7$, $NCONR^7$, $NCOOR^7$, $SO_2NR^5R^6$, and $NHSO_2R^7$, or when a is greater than or equal to 2, $R^4$ may optionally form an optionally substituted cycloalkyl, aryl or heterocyclo 5 or 6 membered ring;
$R^5$ is selected from the group consisting of H and an optionally substituted alkyl, aryl, heterocycle, and cycloalkyl;
$R^6$ and $R^7$ are selected from the group consisting of an optionally substituted alkyl, cycoalkyl, aryl, and heterocycle.

In one embodiment, a compound of the invention comprises Formula (I), wherein:

X is selected from the group consisting of hydrogen and $OR^2$;

$R^2$ is independently selected from the group consisting of hydrogen, $PO(OH)_2$, acetyl, $COR^5$, $CO(OR^5)$, $CO(CH_2)_nNR^5R^6$, hydrocarbyl and substituted hydrocarbyl;

n is an integer from 1 to 4;

Z is O;

Y is selected from the group consisting of O, CH(OH), $CH(OR^5)$, $CHNR^5R^6$, $CH_2$, S, and $NR^5$;

$R^1$ is selected from the group consisting of $CH_3$, $CF_3$, halogen, $OCH_3$, $CO_2CH_3$, and $CONHCH_3$;

$R^3$ is selected from the group consisting of formula (IA) and formula (IB):

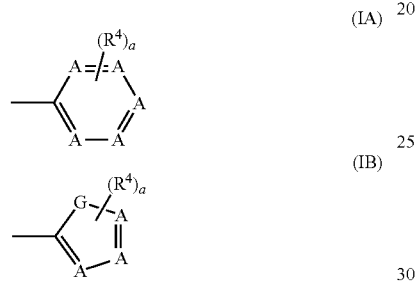

A is independently selected from the group consisting of $CR^5$ and N;

G is independently selected from the group consisting of S, $NR^5$ and O;

a is an integer from 1 to 3;

$R^4$ is selected from the group consisting of $CONHCH_3$, $COOCH_3$, COOH, $CONR_5$, CONH(heterocycle), heterocycle, H, alkyl, cyclopropyl, aryl, $OR^5$, $NR^5R^6$, $NR^5COR^6$, $NR^5COOR^6$, $NR^5CONR^6$, $NR^5SO_2R^6$, $COR^5$, $SO_2R^5$, halogen, CN, $NO_2$, $COOR^5$, $CONR^5R^6$, $NCOR^7$, $NCONR^7$, $NCOOR^7$, $SO_2NR^5R^6$, and $NHSO_2R^7$, or when a is greater than or equal to 2, $R^4$ may optionally form an optionally substituted cycloalkyl, aryl or heterocyclo 5 or 6 membered ring;

$R^5$ is selected from the group consisting of H and an optionally substituted alkyl, aryl, heterocycle, and cycloalkyl;

$R^6$ and $R^7$ are selected from the group consisting of an optionally substituted alkyl, cycolalkyl, aryl, and heterocycle.

In another embodiment, a compound of the invention comprises Formula (I), wherein:

X is selected from the group consisting of hydrogen and $OR^2$;

$R^2$ is independently selected from the group consisting of hydrogen, —$COCH_3$, —$PO(OH)_2$, —$COCH_2N(CH_3)_2$;

Z is O;

Y is selected from the group consisting of O, CH(OH) and $CH_2$;

$R^1$ is $CH_3$;

$R^3$ is selected from the group consisting of formula (IA) and formula (IB):

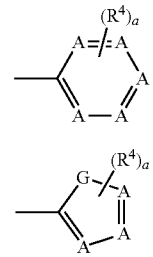

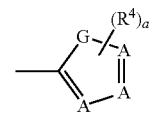

A is independently selected from the group consisting of $CR^5$ and N;

G is S;

a is an integer from 1 to 4;

$R^4$ is selected from the group consisting of hydrogen, $CONHCH_3$, $COOCH_3$, COOH, CONH(heterocycle), $NHCONH_2$, and heterocycle, or when a is greater than or equal to 2, $R^4$ may optionally form an optionally substituted cycloalkyl, aryl or heterocyclo 5 or 6 membered ring;

$R^5$ is selected from the group consisting of H and an optionally substituted alkyl, aryl, heterocycle, and cycloalkyl.

In an exemplary alternative of each of the foregoing embodiments, a compound comprising formula (I) is a compound comprising any of the Formulas in Table 1.

In a further exemplary alternative of each of the foregoing embodiments, a compound of the invention is Examples 1-23 and 25 from Table 1.

Another aspect of the invention is a compound of Formula (II):

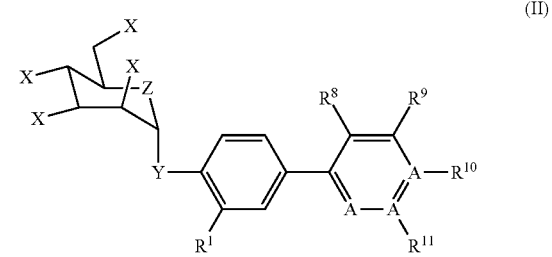

wherein:

X is selected from the group consisting of hydrogen and $OR^2$;

$R^2$ is independently selected from the group consisting of hydrogen, $PO(OH)_2$, acetyl, $COR^5$, $CO(OR^5)$, $CO(CH_2)_nNR^5R^6$, hydrocarbyl and substituted hydrocarbyl;

n is an integer from 1 to 10;

Z is O;

Y is selected from the group consisting of O, CH(OH), $CH(OR^5)$, $CHNR^5R^6$, $CH_2$, S, and $NR^5$;

A is independently selected from the group consisting of $CR^5$ and N;

$R^1$ is selected from the group consisting of $CH_3$, $CF_3$, halogen, Cl, F, Br, I, OH, $NH_2$, $NR^5R^6$, $OCH_3$, $CO_2CH_3$, $CONHCH_3$, alkyl, cyclopropyl, $OR^5$, $CO_2R^5$, $CONR^5R^6$, hydrocarbyl, and substituted hydrocarbyl;

$R^8$, $R^9$, $R^{10}$ and $R^{11}$ are independently selected from the group consisting of $CONHCH_3$, $COOCH_3$, $COOH$, $CONH(heterocycle)$, heterocycle, H, alkyl, cyclopropyl, aryl, $OR^5$, $NR^5R^6$, $NR^5COR^6$, $NR^5COOR^6$, $NR^5CONR^6$, $NR^5SO_2R^6$, $COR^5$, $SO_2R^5$, halogen, CN, $NO_2$, $COOR^5$, $CONR^5R^6$, $NCOR^7$, $NCONR^7$, $NCOOR^7$, $SO_2NR^5R^6$, $NHSO_2R^7$, and $R^8$ and $R^9$ together can optionally form an optionally substituted cycloalkyl, aryl or heterocyclo 5 or 6 membered ring; and $R^9$ and $R^{10}$ together can optionally form an optionally substituted cycloalkyl, aryl or heterocyclo 5 or 6 membered ring;

$R^5$ is selected from the group consisting of H and an optionally substituted alkyl, aryl, heterocycle, and cycloalkyl;

$R^6$ and $R^7$ is selected from the group consisting of an optionally substituted alkyl, cycolalkyl, aryl and heterocycle.

In one embodiment, a compound of the invention comprises Formula (II), wherein:

X is selected from the group consisting of hydrogen and $OR^2$;

$R^2$ is independently selected from the group consisting of hydrogen, $PO(OH)_2$, acetyl, $COR^5$, $CO(OR^5)$, $CO(CH_2)_nNR^5R^6$, hydrocarbyl and substituted hydrocarbyl;

n is an integer from 1 to 10;

Z is O;

Y is selected from the group consisting of O, CH(OH), $CH(OR^5)$, $CHNR^5R^6$, $CH_2$, S, and $NR^5$;

A is independently selected from the group consisting of $CR^5$ and N;

$R^1$ is selected from the group consisting of $CH_3$, $CF_3$, halogen, Cl, F, Br, I, OH, $NH_2$, $NR^5R^6$, $OCH_3$, $CO_2CH_3$, $CONHCH_3$, alkyl, cyclopropyl, $OR^5$, $CO_2R^5$, $CONR^5R^6$, hydrocarbyl, and substituted hydrocarbyl;

$R^8$, $R^9$, $R^{10}$ and $R^{11}$ are independently selected from the group consisting of hydrogen, $CONHCH_3$, $COOCH_3$, $COOH$, $CONH(heterocycle)$, and heterocycle, or $R^8$ and $R^9$ together may optionally form an optionally substituted cycloalkyl, aryl or heterocyclo 5 or 6 membered ring, and $R^9$ and $R^{10}$ together may optionally form an optionally substituted cycloalkyl, aryl or heterocyclo 5 or 6 membered ring;

$R^5$ is selected from the group consisting of H and an optionally substituted alkyl, aryl, heterocycle, and cycloalkyl;

$R^6$ and $R^7$ are selected from the group consisting of an optionally substituted alkyl, cycolalkyl, aryl and heterocycle.

In another embodiment, a compound of the invention comprises Formula (II), wherein:

X is selected from the group consisting of hydrogen and $OR^2$;

$R^2$ is independently selected from the group consisting of hydrogen, $PO(OH)_2$, acetyl, $COR^5$, $CO(OR^5)$, $CO(CH_2)_nNR^5R^6$, hydrocarbyl and substituted hydrocarbyl;

n is an integer from 1 to 10;

Z is O;

Y is selected from the group consisting of O, CH(OH), $CH(OR^5)$, $CHNR^5R^6$, $CH_2$, S, and $NR^5$;

A is independently selected from the group consisting of $CR^5$ and N;

$R^1$ is selected from the group consisting of $CH_3$, $CF_3$, halogen, $OCH_3$, $CO_2CH_3$, and $CONHCH_3$;

$R^8$, $R^{10}$ and $R^{11}$ are hydrogen;

$R^9$ is selected from the group consisting of $CONHCH_3$, $COOCH_3$, $COOH$, $CONH(heterocycle)$, heterocycle, H, alkyl, cyclopropyl, aryl, $OR^5$, $NR^5R^6$, $NR^5COR^6$, $NR^5COOR^6$, $NR^5CONR^6$, $NR^5SO_2R^6$, $COR^5$, $SO_2R^5$, halogen, CN, $NO_2$, $COOR^5$, $CONR^5R^6$, $NCOR^7$, $NCONR^7$, $NCOOR^7$, $SO_2NR^5R^6$, $NHSO_2R^7$, and $R^8$ and $R^9$ together can optionally form an optionally substituted cycloalkyl, aryl or heterocyclo 5 or 6 membered ring; and $R^9$ and $R^{10}$ together can optionally form an optionally substituted cycloalkyl, aryl or heterocyclo 5 or 6 membered ring;

$R^5$ is selected from the group consisting of H and an optionally substituted alkyl, aryl, heterocycle, and cycloalkyl;

$R^6$ and $R^7$ are selected from the group consisting of an optionally substituted alkyl, cycolalkyl, aryl, and heterocycle.

In another embodiment, a compound of the invention comprises Formula (II), wherein:

X is selected from the group consisting of hydrogen and $OR^2$;

$R^2$ is independently selected from the group consisting of hydrogen, $PO(OH)_2$, acetyl, $COR^5$, $CO(OR^5)$, $CO(CH_2)_nNR^5R^6$, hydrocarbyl and substituted hydrocarbyl;

n is an integer from 1 to 10;

Z is O;

Y is selected from the group consisting of O, CH(OH) and $CH_2$;

$R^1$ is selected from the group consisting of $CH_3$, $CF_3$, halogen, Cl, F, Br, I, OH, $NH_2$, $NR^5R^6$, $OCH_3$, $CO_2CH_3$, $CONHCH_3$, alkyl, cyclopropyl, $OR^5$, $CO_2R^5$, $CONR^5R^6$, hydrocarbyl, and substituted hydrocarbyl;

$R^8$, $R^9$, $R^{10}$ and $R^{11}$ are independently selected from the group consisting of $CONHCH_3$, $COOCH_3$, $COOH$, $CONH(heterocycle)$, heterocycle, H, alkyl, aryl, cyclopropyl, $OR^5$, $NR^5R^6$, $NR^5COR^6$, $NR^5COOR^6$, $NR^5CONR^6$, $NR^5SO_2R^6$, $COR^5$, $SO_2R^5$, halogen, CN, NO$_2$, COOR$^5$, CONR$^5$R$^6$, NCOR$^7$, NCONR$^7$, NCOOR$^7$, SO$_2$NR$^5$R$^6$, NHSO$_2$R$^7$, and R$^8$ and R$^9$ together can optionally form an optionally substituted cycloalkyl, aryl or heterocyclo 5 or 6 membered ring; and R$^9$ and R$^{10}$ together can optionally form an optionally substituted cycloalkyl, aryl or heterocyclo 5 or 6 membered ring;

R$^5$ is selected from the group consisting of H and an optionally substituted alkyl, aryl, heterocycle, and cycloalkyl;

R$^6$ and R$^7$ are selected from the group consisting of an optionally substituted alkyl, cycolalkyl, aryl, and heterocycle.

In still another embodiment, a compound of the invention comprises Formula (II), wherein:

X is selected from the group consisting of hydrogen and OR$^2$;

R$^2$ is independently selected from the group consisting of hydrogen, —COCH$_3$, —PO(OH)$_2$, and —COCH$_2$N(CH$_3$)$_2$;

Z is O;

Y is selected from the group consisting of O, CH(OH) and CH$_2$;

A is independently selected from the group consisting of CR$^5$ and N;

R$^1$ is selected from the group consisting of CH$_3$, CF$_3$, halogen, Cl, F, Br, I, OH, NH$_2$, NR$^5$R$^6$, OCH$_3$, CO$_2$CH$_3$, CONHCH$_3$, alkyl, cyclopropyl, OR$^5$, CO$_2$R$^5$, CONR$^5$R$^6$, hydrocarbyl, and substituted hydrocarbyl;

R$^8$, R$^9$, R$^{10}$ and R$^{11}$ are independently selected from the group consisting of CONHCH$_3$, COOCH$_3$, COOH, CONH(heterocycle), heterocycle, H, alkyl, cyclopropyl, aryl, OR$^5$, NR$^5$R$^6$, NR$^5$COR$^6$, NR$^5$COOR$^6$, NR$^5$CONR$^6$, NR$^5$SO$_2$R$^6$, COR$^5$, SO$_2$R$^5$, halogen, CN, NO$_2$, COOR$^5$, CONR$^5$R$^6$, NCOR$^7$, NCONR$^7$, NCOOR$^7$, SO$_2$NR$^5$R$^6$, NHSO$_2$R$^7$, and R$^8$ and R$^9$ together can optionally form an optionally substituted cycloalkyl, aryl or heterocyclo 5 or 6 membered ring; and R$^9$ and R$^{10}$ together can optionally form an optionally substituted cycloalkyl, aryl or heterocyclo 5 or 6 membered ring;

R$^5$ is selected from the group consisting of H and an optionally substituted alkyl, aryl, heterocycle, and cycloalkyl;

R$^6$ and R$^7$ are selected from the group consisting of an optionally substituted alkyl, cycolalkyl, aryl, and heterocycle.

In still another embodiment, a compound of the invention comprises Formula (II), wherein:

X is selected from the group consisting of hydrogen and OR$^2$;

R$^2$ is independently selected from the group consisting of hydrogen, —COCH$_3$, —PO(OH)$_2$, and —COCH$_2$N(CH$_3$)$_2$;

Z is O;

Y is selected from the group consisting of O, CH(OH) and CH$_2$;

A is independently selected from the group consisting of CR$^5$ and N;

R$^1$ is CH$_3$;

R$^8$, R$^9$, R$^{10}$ and R$^{11}$ are independently selected from the group consisting of CONHCH$_3$, COOCH$_3$, COOH, CONH(heterocycle), heterocycle, H, alkyl, cyclopropyl, aryl, OR$^5$, NR$^5$R$^6$, NR$^5$COR$^6$, NR$^5$COOR$^6$, NR$^5$CONR$^6$, NR$^5$SO$_2$R$^6$, COR$^5$, SO$_2$R$^5$, halogen, CN, NO$_2$, COOR$^5$, CONR$^5$R$^6$, NCOR$^7$, NCONR$^7$, NCOOR$^7$, SO$_2$NR$^5$R$^6$, and NHSO$_2$R$^7$, and R$^8$ and R$^9$ together can optionally form an optionally substituted cycloalkyl, aryl or heterocyclo 5 or 6 membered ring; and R$^9$ and R$^{10}$ together can optionally form an optionally substituted cycloalkyl, aryl or heterocyclo 5 or 6 membered ring;

R$^5$ is selected from the group consisting of H and an optionally substituted alkyl, aryl, heterocycle, and cycloalkyl;

R$^6$ and R$^7$ are selected from the group consisting of an optionally substituted alkyl, cycolalkyl, aryl and heterocycle.

In still another embodiment, a compound of the invention comprises Formula (II), wherein:

X is selected from the group consisting of hydrogen and OR$^2$;

R$^2$ is independently selected from the group consisting of hydrogen, —COCH$_3$, —PO(OH)$_2$, and —COCH$_2$N(CH$_3$)$_2$;

Z is O;

Y is selected from the group consisting of O, CH(OH) and CH$_2$;

A is independently selected from the group consisting of CR$^5$ and N;

R$^1$ is CH$_3$;

R$^8$, R$^9$, R$^{10}$ and R$^{11}$ are independently selected from the group consisting of hydrogen, CONHCH$_3$, COOCH$_3$, COOH, CONH(heterocycle), and heterocycle, or R$^8$ and R$^9$ together may optionally form an optionally substituted cycloalkyl, aryl or heterocyclo 5 or 6 membered ring, and R$^9$ and R$^{10}$ together may optionally form an optionally substituted cycloalkyl, aryl or heterocyclo 5 or 6 membered ring;

R$^5$ is selected from the group consisting of H and an optionally substituted alkyl, aryl, heterocycle, and cycloalkyl.

In still yet another embodiment, a compound of the invention comprises Formula (II), wherein:

X is selected from the group consisting of hydrogen and OR$^2$;

R$^2$ is independently selected from the group consisting of hydrogen, —COCH$_3$, —PO(OH)$_2$, and —COCH$_2$N(CH$_3$)$_2$;

Z is O;

Y is selected from the group consisting of O, CH(OH) and CH$_2$;

A is independently selected from the group consisting of CR$^5$ and N;

R$^1$ is CH$_3$;

R$^8$, R$^{10}$ and R$^{11}$ are hydrogen;

R$^9$ is selected from the group consisting of CONHCH$_3$, COOCH$_3$, COOH, CONH(heterocycle), heterocycle, H, alkyl, cyclopropyl, aryl, OR$^5$, NR$^5$R$^6$, NR$^5$COR$^6$, NR$^5$COOR$^6$, NR$^5$CONR$^6$, NR$^5$SO$_2$R$^6$, COR$^5$, SO$_2$R$^5$, halogen, CN, NO$_2$, COOR$^5$, CONR$^5$R$^6$, NCOR$^7$, NCONR$^7$, NCOOR$^7$, SO$_2$NR$^5$R$^6$, and NHSO$_2$R$^7$, or R$^8$ and R$^9$ together can optionally form an optionally substituted cycloalkyl, aryl or heterocyclo 5 or 6 membered ring; and R$^9$ and R$^{10}$ together can optionally form an optionally substituted cycloalkyl, aryl or heterocyclo 5 or 6 membered ring;

R$^5$ is selected from the group consisting of H and an optionally substituted alkyl, aryl, heterocycle, and cycloalkyl;

R$^6$ and R$^7$ are selected from the group consisting of an optionally substituted alkyl, cycolalkyl, aryl and heterocycle.

In still yet another embodiment, a compound of the invention comprises Formula (II), wherein:

X is selected from the group consisting of hydrogen and $OR^2$;

$R^2$ is independently selected from the group consisting of hydrogen, —$COCH_3$, —$PO(OH)_2$, and —$COCH_2N(CH_3)_2$;

Z is O;

Y is selected from the group consisting of O, CH(OH) and $CH_2$;

A is independently selected from the group consisting of $CR^5$ and N;

$R^1$ is $CH_3$;

$R^8$, $R^{19}$ and $R^{11}$ are hydrogen;

$R^9$ is selected from the group consisting of hydrogen, $CONHCH_3$, $COOCH_3$, COOH, CONH(heterocycle), and heterocycle;

$R^5$ is selected from the group consisting of H and an optionally substituted alkyl, aryl, heterocycle, and cycloalkyl.

In an exemplary alternative of each of the foregoing embodiments, a compound comprising formula (II) is a compound comprising any of the Formulas in Table 1.

In a further exemplary alternative of each of the foregoing embodiments, a compound of the invention is Example 1-16, 18-23 and 25 from Table 1.

Another aspect of the invention is a compound of Formula (III):

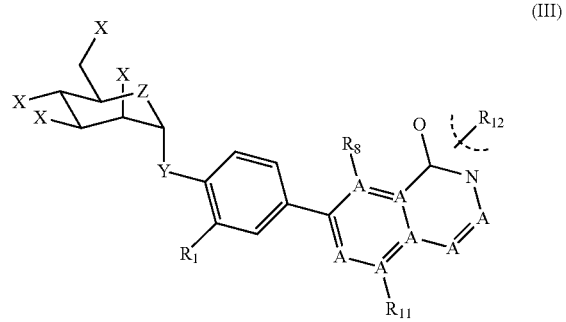

(III)

wherein:

X is selected from the group consisting of hydrogen and $OR^2$;

$R^2$ is independently selected from the group consisting of hydrogen, $PO(OH)_2$, acetyl, $COR^5$, $CO(OR^5)$, $CO(CH_2)_nNR^5R^6$, hydrocarbyl and substituted hydrocarbyl;

n is an integer from 1 to 10;

Z is O;

Y is selected from the group consisting of O, CH(OH), $CH(OR^5)$, $CHNR^5R^6$, $CH_2$, S, and $NR^5$;

$R^1$ is selected from the group consisting of $CH_3$, $CF_3$, halogen, Cl, F, Br, I, OH, $NH_2$, $NR^5R^6$, $OCH_3$, $CO_2CH_3$, $CONHCH_3$, alkyl, cyclopropyl, $OR^5$, $CO_2R^5$, $CONR^5R^6$, hydrocarbyl, and substituted hydrocarbyl;

A is independently selected from the group consisting of $CR^5$ and N;

$R^5$ is selected from the group consisting of H and an optionally substituted alkyl, aryl, heterocycle, and cycloalkyl;

$R^6$ and $R^7$ are selected from the group consisting of an optionally substituted alkyl, cycolalkyl, aryl, and heterocycle;

$R^8$ and $R^{11}$ are independently selected from the group consisting of $CONHCH_3$, $COOCH_3$, COOH, CONH(heterocycle), heterocycle, H, alkyl, cyclopropyl, aryl, $OR^5$, $NR^5R^6$, $NR^5COR^6$, $NR^5COOR^6$, $NR^5CONR^6$, $NR^5SO_2R^6$, $COR^5$, $SO_2R^5$, halogen, CN, $NO_2$, $COOR^5$, $CONR^5R^6$, $NCOR^7$, $NCONR^7$, $NCOOR^7$, $SO_2NR^5R^6$, and $NHSO_2R^7$;

$R^{12}$ is substituted at the O or N and is selected from the group consisting of H, alkyl, $CH_2R^{13}$, $CH_2COR^{13}$, $CH_2CONHR^{13}$, $CH_2CONHR^{13}R^{14}$, $CH_2CONH(CH_2)_2R^{14}$, $(CH_2)_2NR^{13}$, $(CH_2)_nNR^{13}$, $CH_2COOH$, $CH_2CONH(CH_2)_2NH_2$, and $(CH_2)_2N(CH_3)_2$;

$R^{13}$ is selected from the group consisting of —OH and an optionally substituted heterocycle, hydrocarbyl, and substituted hydrocarbyl;

$R^{14}$ is selected from the group consisting of alkyl and $NH_2$.

In one embodiment, a compound of the invention comprises Formula (IV), wherein:

X is selected from the group consisting of hydrogen and $OR^2$;

$R^2$ is independently selected from the group consisting of hydrogen, $PO(OH)_2$, acetyl, $COR^5$, $CO(OR^5)$, $CO(CH_2)_nNR^5R^6$, hydrocarbyl and substituted hydrocarbyl;

n is an integer from 1 to 10;

Z is O;

Y is selected from the group consisting of O, CH(OH), $CH(OR^5)$, $CHNR^5R^6$, $CH_2$, S, and $NR^5$;

$R^1$ is selected from the group consisting of $CH_3$, $CF_3$, halogen, Cl, F, Br, I, OH, $NH_2$, $NR^5R^6$, $OCH_3$, $CO_2CH_3$, $CONHCH_3$, alkyl, cyclopropyl, $OR^5$, $CO_2R^5$, $CONR^5R^6$, hydrocarbyl, and substituted hydrocarbyl;

A is independently selected from the group consisting of $CR^5$ and N;

$R^5$ is selected from the group consisting of H and an optionally substituted alkyl, aryl, heterocycle, and cycloalkyl;

$R^6$ and $R^7$ are selected from the group consisting of an optionally substituted alkyl, cycolalkyl, aryl and heterocycle;

$R^8$ and $R^{11}$ are independently selected from the group consisting of $CONHCH_3$, $COOCH_3$, COOH, CONH(heterocycle), heterocycle, H, alkyl, cyclopropyl, aryl, $OR^5$, $NR^5R^6$, $NR^5COR^6$, $NR^5COOR^6$, $NR^5CONR^6$, $NR^5SO_2R^6$, $COR^5$, $SO_2R^5$, halogen, CN, $NO_2$, $COOR^5$, $CONR^5R^6$, $NCOR^7$, $NCONR^7$, $NCOOR^7$, $SO_2NR^5R^6$, and $NHSO_2R^7$;

$R^{12}$ is substituted at the O or N and is selected from the group consisting of H, alkyl, $CH_2$(heterocycle), $(CH_2)_2N(CH_3)_2$, $CH_2COOH$, $CH_2CONH$(heterocycle), $CH_2CONH(CH_2)_2NH_2$ and $CH_2CO$(heterocycle).

In another embodiment, a compound of the invention comprises Formula (IV), wherein:

X is selected from the group consisting of hydrogen and $OR^2$;

$R^2$ is independently selected from the group consisting of hydrogen, $PO(OH)_2$, acetyl, $COR^5$, $CO(OR^5)$, $CO(CH_2)_nNR^5R^6$, hydrocarbyl and substituted hydrocarbyl;

n is an integer from 1 to 10;

Z is O;

Y is selected from the group consisting of O, CH(OH), CH(OR$^5$), CHNR$^5$R$^6$, CH$_2$, S, and NR$^5$;

R$^1$ is selected from the group consisting of CH$_3$, CF$_3$, halogen, OCH$_3$, CO$_2$CH$_3$, and CONHCH$_3$;

A is independently selected from the group consisting of CR$^5$ and N;

R$^8$ and R$^{11}$ are independently selected from the group consisting of CONHCH$_3$, COOCH$_3$, COOH, CONH(heterocycle), heterocycle, H, alkyl, cyclopropyl, aryl, OR$^5$, NR$^5$R$^6$, NR$^5$COR$^6$, NR$^5$COOR$^6$, NR$^5$CONR$^6$, NR$^5$SO$_2$R$^6$, COR$^5$, SO$_2$R$^5$, halogen, CN, NO$_2$, COOR$^5$, CONR$^5$R$^6$, NCOR$^7$, NCONR$^7$, NCOOR$^7$, SO$_2$NR$^5$R$^6$, and NHSO$_2$R$^7$;

R$^{12}$ is substituted at the O or N and is selected from the group consisting of H, alkyl, CH$_2$(heterocycle), (CH$_2$)$_2$N(CH$_3$)$_2$, CH$_2$COOH, CH$_2$CONH(heterocycle), CH$_2$CONH(CH$_2$)$_2$NH$_2$ and CH$_2$CO(heterocycle);

R$^5$ is selected from the group consisting of H and an optionally substituted alkyl, aryl, heterocycle, and cycloalkyl;

R$^6$ and R$^7$ are selected from the group consisting of an optionally substituted alkyl, cycolalkyl, aryl, and heterocycle.

In still another embodiment, a compound of the invention comprises Formula (IV), wherein:

X is selected from the group consisting of hydrogen and OR$^2$;

R$^2$ is independently selected from the group consisting of hydrogen, PO(OH)$_2$, acetyl, COR$^5$, CO(OR$^5$), CO(CH$_2$)$_n$NR$^5$R$^6$, hydrocarbyl and substituted hydrocarbyl;

n is an integer from 1 to 10;

Z is O;

Y is selected from the group consisting of O, CH(OH), CH(OR$^5$), CHNR$^5$R$^6$, CH$_2$, S, and NR$^5$;

R$^1$ is selected from the group consisting of CH$_3$, CF$_3$, halogen, OCH$_3$, CO$_2$CH$_3$, and CONHCH$_3$;

A is independently selected from the group consisting of CR$^5$ and N;

R$^5$ is selected from the group consisting of H and an optionally substituted alkyl, aryl, heterocycle, and cycloalkyl;

R$^6$ and R$^7$ are selected from the group consisting of an optionally substituted alkyl, cycolalkyl, aryl, and heterocycle;

R$^8$ and R$^{11}$ are hydrogen;

R$^{12}$ is substituted at the O or N and is selected from the group consisting of H, alkyl, CH$_2$R$^{13}$, CH$_2$COR$^{13}$, CH$_2$CONHR$^{13}$, CH$_2$CONHR$^{13}$R$^{14}$, CH$_2$CONH(CH$_2$)$_2$R$^{14}$, (CH$_2$)$_2$NR$^{13}$, (CH$_2$)$_n$NR$^{13}$, CH$_2$COOH, CH$_2$CONH(CH$_2$)$_2$NH$_2$, and (CH$_2$)$_2$N(CH$_3$)$_2$;

R$^{13}$ is selected from the group consisting of —OH and an optionally substituted heterocycle, hydrocarbyl, and substituted hydrocarbyl;

R$^{14}$ is selected from the group consisting of alkyl and NH$_2$.

In still another embodiment, a compound of the invention comprises Formula (IV), wherein:

X is selected from the group consisting of hydrogen and OR$^2$;

R$^2$ is independently selected from the group consisting of hydrogen, PO(OH)$_2$, acetyl, COR$^5$, CO(OR$^5$), CO(CH$_2$)$_n$NR$^5$R$^6$, hydrocarbyl and substituted hydrocarbyl;

n is an integer from 1 to 10;

Z is O;

Y is selected from the group consisting of O, CH(OH) and CH$_2$;

R$^1$ is selected from the group consisting of CH$_3$, CF$_3$, halogen, Cl, F, Br, I, OH, NH$_2$, NR$^5$R$^6$, OCH$_3$, CO$_2$CH$_3$, CONHCH$_3$, alkyl, cyclopropyl, OR$^5$, CO$_2$R$^5$, CONR$^5$R$^6$, hydrocarbyl, and substituted hydrocarbyl;

A is independently selected from the group consisting of CR$^5$ and N;

R$^5$ is selected from the group consisting of H and an optionally substituted alkyl, aryl, heterocycle, and cycloalkyl;

R$^6$ and R$^7$ are selected from the group consisting of an optionally substituted alkyl, cycolalkyl, aryl, and heterocycle;

R$^8$ and R$^{11}$ are independently selected from the group consisting of CONHCH$_3$, COOCH$_3$, COOH, CONH(heterocycle), heterocycle, H, alkyl, cyclopropyl, aryl, OR$^5$, NR$^5$R$^6$, NR$^5$COR$^6$, NR$^5$COOR$^6$, NR$^5$CONR$^6$, NR$^5$SO$_2$R$^6$, COR$^5$, SO$_2$R$^5$, halogen, CN, NO$_2$, COOR$^5$, CONR$^5$R$^6$, NCOR$^7$, NCONR$^7$, NCOOR$^7$, SO$_2$NR$^5$R$^6$, and NHSO$_2$R$^7$;

R$^{12}$ is substituted at the O or N and is selected from the group consisting of H, CH$_2$R$^{13}$, CH$_2$COR$^{13}$, CH$_2$CONHR$^{13}$, CH$_2$CONHR$^{13}$R$^{14}$, CH$_2$CONH(CH$_2$)$_2$R$^{14}$, (CH$_2$)$_2$NR$^{13}$, (CH$_2$)$_n$NR$^{13}$, CH$_2$COOH, CH$_2$CONH(CH$_2$)$_2$NH$_2$, and (CH$_2$)$_2$N(CH$_3$)$_2$;

R$^{13}$ is selected from the group consisting of —OH and an optionally substituted heterocycle, hydrocarbyl and substituted hydrocarbyl;

R$^{14}$ is selected from the group consisting of alkyl and NH$_2$.

In still yet another embodiment, a compound of the invention comprises Formula (IV), wherein:

X is selected from the group consisting of hydrogen and OR$^2$;

R$^2$ is independently selected from the group consisting of hydrogen, —COCH$_3$, —PO(OH)$_2$, and —COCH$_2$N(CH$_3$)$_2$;

Z is O;

Y is selected from the group consisting of O, CH(OH) and CH$_2$;

R$^1$ is selected from the group consisting of CH$_3$, CF$_3$, halogen, Cl, F, Br, I, OH, NH$_2$, NR$^5$R$^6$, OCH$_3$, CO$_2$CH$_3$, CONHCH$_3$, alkyl, cyclopropyl, OR$^5$, CO$_2$R$^5$, CONR$^5$R$^6$, hydrocarbyl, and substituted hydrocarbyl;

A is independently selected from the group consisting of CR$^5$ and N;

R$^5$ is selected from the group consisting of H and an optionally substituted alkyl, aryl, heterocycle, and cycloalkyl;

R$^6$ and R$^7$ are selected from the group consisting of an optionally substituted alkyl, cycolalkyl, aryl, and heterocycle;

R$^8$ and R$^{11}$ are independently selected from the group consisting of CONHCH$_3$, COOCH$_3$, COOH, CONH(heterocycle), heterocycle, H, alkyl, cyclopropyl, aryl, OR$^5$, NR$^5$R$^6$, NR$^5$COR$^6$, NR$^5$COOR$^6$, NR$^5$CONR$^6$, NR$^5$SO$_2$R$^6$, COR$^5$, SO$_2$R$^5$, halogen, CN, NO$_2$, COOR$^5$, CONR$^5$R$^6$, NCOR$^7$, NCONR$^7$, NCOOR$^7$, SO$_2$NR$^5$R$^6$, and NHSO$_2$R$^7$;

R$^{12}$ is substituted at the O or N and is independently selected from the group consisting of H, alkyl, CH$_2$R$^{13}$, CH$_2$COR$^{13}$, CH$_2$CONHR$^{13}$, CH$_2$CONHR$^{13}$R$^{14}$, CH$_2$CONH(CH$_2$)$_2$R$^{14}$, (CH$_2$)$_2$NR$^{13}$, (CH$_2$)$_n$NR$^{13}$, CH$_2$COOH, CH$_2$CONH(CH$_2$)$_2$NH$_2$, and (CH$_2$)$_2$N(CH$_3$)$_2$;

R$^{13}$ is selected from the group consisting of —OH and an optionally substituted heterocycle, hydrocarbyl and substituted hydrocarbyl;

R$^{14}$ is selected from the group consisting of alkyl and NH$_2$.

In still yet another embodiment, a compound of the invention comprises Formula (IV), wherein:

X is selected from the group consisting of hydrogen and OR$^2$;

R$^2$ is independently selected from the group consisting of hydrogen, —COCH$_3$, —PO(OH)$_2$, and —COCH$_2$N(CH$_3$)$_2$;

Z is O;

Y is selected from the group consisting of O, CH(OH) and CH$_2$;

R$^1$ is CH$_3$;

A is independently selected from the group consisting of CR$^5$ and N;

R$^8$ and R$^{11}$ are independently selected from the group consisting of CONHCH$_3$, COOCH$_3$, COOH, CONH(heterocycle), heterocycle, H, alkyl, cyclopropyl, aryl, OR$^5$, NR$^5$R$^6$, NR$^5$COR$^6$, NR$^5$COOR$^6$, NR$^5$CONR$^6$, NR$^5$SO$_2$R$^6$, COR$^5$, SO$_2$R$^5$, halogen, CN, NO$_2$, COOR$^5$, CONR$^5$R$^6$, NCOR$^7$, NCONR$^7$, NCOOR$^7$, SO$_2$NR$^5$R$^6$, and NHSO$_2$R$^7$;

R$^5$ is selected from the group consisting of H and an optionally substituted alkyl, aryl, heterocycle, and cycloalkyl;

R$^6$ and R$^7$ are selected from the group consisting of an optionally substituted alkyl, cycolalkyl, aryl, and heterocycle;

R$^{12}$ is substituted at the O or N and is selected from the group consisting of H, alkyl, CH$_2$R$^{13}$, CH$_2$COR$^{13}$, CH$_2$CONHR$^{13}$, CH$_2$CONHR$^{13}$R$^{14}$, CH$_2$CONH(CH$_2$)$_2$R$^{14}$, (CH$_2$)$_2$NR$^{13}$, (CH$_2$)$_n$NR$^{13}$, CH$_2$COOH, CH$_2$CONH(CH$_2$)$_2$NH$_2$, and (CH$_2$)$_2$N(CH$_3$)$_2$;

R$^{13}$ is selected from the group consisting of —OH and an optionally substituted heterocycle, hydrocarbyl and substituted hydrocarbyl;

R$^{14}$ is selected from the group consisting of alkyl and NH$_2$.

In still yet another embodiment, a compound of the invention comprises Formula (IV), wherein:

X is selected from the group consisting of hydrogen and OR$^2$;

R$^2$ is independently selected from the group consisting of hydrogen, —COCH$_3$, —PO(OH)$_2$, and —COCH$_2$N(CH$_3$)$_2$;

Z is O;

Y is selected from the group consisting of O, CH(OH) and CH$_2$;

R$^1$ is CH$_3$;

A is independently selected from the group consisting of CR$^5$ and N;

R$^8$ and R$^{11}$ are independently selected from the group consisting of CONHCH$_3$, COOCH$_3$, COOH, CONH(heterocycle), heterocycle, H, alkyl, cyclopropyl, aryl, OR$^5$, NR$^5$R$^6$, NR$^5$COR$^6$, NR$^5$COOR$^6$, NR$^5$CONR$^6$, NR$^5$SO$_2$R$^6$, COR$^5$, SO$_2$R$^5$, halogen, CN, NO$_2$, COOR$^5$, CONR$^5$R$^6$, NCOR$^7$, NCONR$^7$, NCOOR$^7$, SO$_2$NR$^5$R$^6$, and NHSO$_2$R$^7$;

R$^5$ is selected from the group consisting of H and an optionally substituted alkyl, aryl, heterocycle, and cycloalkyl;

R$^6$ and R$^7$ are selected from the group consisting of an optionally substituted alkyl, cycolalkyl, aryl, and heterocycle;

R$^{12}$ is substituted at the O or N and is selected from the group consisting of H, CH$_2$(heterocycle), (CH$_2$)$_2$N(CH$_3$)$_2$, CH$_2$COOH, CH$_2$CONH(heterocycle), CH$_2$CONH(CH$_2$)$_2$NH$_2$ and CH$_2$CO(heterocycle).

In still yet another embodiment, a compound of the invention comprises Formula (IV), wherein:

X is selected from the group consisting of hydrogen and OR$^2$;

R$^2$ is independently selected from the group consisting of hydrogen, —COCH$_3$, —PO(OH)$_2$, and —COCH$_2$N(CH$_3$)$_2$;

Z is O;

Y is selected from the group consisting of O, CH(OH) and CH$_2$;

R$^1$ is CH$_3$;

A is independently selected from the group consisting of CR$^5$ and N;

R$^5$ is selected from the group consisting of H and an optionally substituted alkyl, aryl, heterocycle, and cycloalkyl;

R$^6$ and R$^7$ are selected from the group consisting of an optionally substituted alkyl, cycolalkyl, aryl, and heterocycle;

R$^8$ and R$^{11}$ are hydrogen;

R$^{12}$ is substituted at the O or N and is selected from the group consisting of H, alkyl, CH$_2$R$^{13}$, CH$_2$COR$^{13}$, CH$_2$CONHR$^{13}$, CH$_2$CONHR$^{13}$R$^{14}$, CH$_2$CONH(CH$_2$)$_2$R$^{14}$, (CH$_2$)$_2$NR$^{13}$, (CH$_2$)$_n$NR$^{13}$, CH$_2$COOH, CH$_2$CONH(CH$_2$)$_2$NH$_2$, and (CH$_2$)$_2$N(CH$_3$)$_2$;

R$^{13}$ is selected from the group consisting of —OH and an optionally substituted heterocycle, hydrocarbyl and substituted hydrocarbyl;

R$^{14}$ is selected from the group consisting of alkyl and NH$_2$.

In still yet another embodiment, a compound of the invention comprises Formula (IV), wherein:

X is selected from the group consisting of hydrogen and OR$^2$;

R$^2$ is independently selected from the group consisting of hydrogen, —COCH$_3$, —PO(OH)$_2$, and —COCH$_2$N(CH$_3$)$_2$;

Z is O;

Y is selected from the group consisting of O, CH(OH) and CH$_2$;

R$^1$ is CH$_3$;

A is independently selected from the group consisting of CR$^5$ and N;

R$^5$ is selected from the group consisting of H and an optionally substituted alkyl, aryl, heterocycle, and cycloalkyl;

R$^6$ and R$^7$ are selected from the group consisting of an optionally substituted alkyl, cycolalkyl, aryl, and heterocycle;

R$^8$ and R$^{11}$ are hydrogen;

R$^{12}$ is substituted at the O or N and is selected from the group consisting of H, CH$_2$(heterocycle), (CH$_2$)$_2$N(CH$_3$)$_2$, CH$_2$COOH, CH$_2$CONH(heterocycle), CH$_2$CONH(CH$_2$)$_2$NH$_2$ and CH$_2$CO(heterocycle).

In an exemplary alternative of each of the foregoing embodiments, a compound comprising formula (IV) is a compound comprising any of the Formulas in Table 1.

In a further exemplary alternative of each of the foregoing embodiments, a compound of the invention is Example 7-16 from Table 1.

Another aspect of the invention is a compound of Formula (IV):

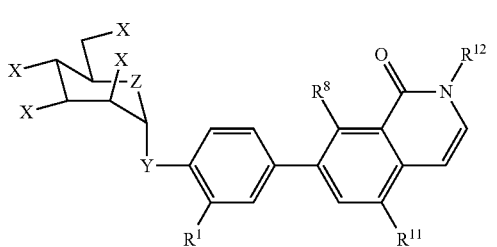

wherein:
- X is selected from the group consisting of hydrogen and $OR^2$;
- $R^2$ is independently selected from the group consisting of hydrogen, $PO(OH)_2$, acetyl, $COR^5$, $CO(OR^5)$, $CO(CH_2)_nNR^5R^6$, hydrocarbyl and substituted hydrocarbyl;
- n is an integer from 1 to 10;
- Z is O;
- Y is selected from the group consisting of O, CH(OH), $CH(OR^5)$, $CHNR^5R^6$, $CH_2$, S, and $NR^5$;
- $R^1$ is selected from the group consisting of $CH_3$, $CF_3$, halogen, Cl, F, Br, I, OH, $NH_2$, $NR^5R^6$, $OCH_3$, $CO_2CH_3$, $CONHCH_3$, alkyl, cyclopropyl, $OR^5$, $CO_2R^5$, $CONR^5R^6$, hydrocarbyl, and substituted hydrocarbyl;
- $R^5$ is selected from the group consisting of H and an optionally substituted alkyl, aryl, heterocycle, and cycloalkyl;
- $R^6$ and $R^7$ are selected from the group consisting of an optionally substituted alkyl, cycolalkyl, aryl, and heterocycle;
- $R^8$ and $R^{11}$ are independently selected from the group consisting of $CONHCH_3$, $COOCH_3$, COOH, CONH(heterocycle), heterocycle, H, alkyl, cyclopropyl, aryl, $OR^5$, $NR^5R^6$, $NR^5COR^6$, $NR^5COOR^6$, $NR^5CONR^6$, $NR^5SO_2R^6$, $COR^5$, $SO_2R^5$, halogen, CN, $NO_2$, $COOR^5$, $CONR^5R^6$, $NCOR^7$, $NCONR^7$, $NCOOR^7$, $SO_2NR^5R^6$, and $NHSO_2R^7$;
- $R^{12}$ is selected from the group consisting of H, alkyl, $CH_2R^{13}$, $CH_2COR^{13}$, $CH_2CONHR^{13}$, $CH_2CONHR^{13}R^{14}$, $CH_2CONH(CH_2)_2R^{14}$, $(CH_2)_2NR^{13}$, $(CH_2)_nNR^{13}$, $CH_2COOH$, $CH_2CONH(CH_2)_2NH_2$, and $(CH_2)_2N(CH_3)_2$;
- $R^{13}$ is selected from the group consisting of —OH and an optionally substituted heterocycle, hydrocarbyl, and substituted hydrocarbyl;
- $R^{14}$ is selected from the group consisting of alkyl and $NH_2$.

In one embodiment, a compound of the invention comprises Formula (IV), wherein:
- X is selected from the group consisting of hydrogen and $OR^2$;
- $R^2$ is independently selected from the group consisting of hydrogen, $PO(OH)_2$, acetyl, $COR^5$, $CO(OR^5)$, $CO(CH_2)_nNR^5R^6$, hydrocarbyl and substituted hydrocarbyl;
- n is an integer from 1 to 10;
- Z is O;
- Y is selected from the group consisting of O, CH(OH), $CH(OR^5)$, $CHNR^5R^6$, $CH_2$, S, and $NR^5$;
- $R^1$ is selected from the group consisting of $CH_3$, $CF_3$, halogen, Cl, F, Br, I, OH, $NH_2$, $NR^5R^6$, $OCH_3$, $CO_2CH_3$, $CONHCH_3$, alkyl, cyclopropyl, $OR^5$, $CO_2R^5$, $CONR^5R^6$, hydrocarbyl, and substituted hydrocarbyl;
- $R^5$ is selected from the group consisting of H and an optionally substituted alkyl, aryl, heterocycle, and cycloalkyl;
- $R^6$ and $R^7$ are selected from the group consisting of an optionally substituted alkyl, cycolalkyl, aryl and heterocycle;
- $R^8$ and $R^{11}$ are independently selected from the group consisting of $CONHCH_3$, $COOCH_3$, COOH, CONH(heterocycle), heterocycle, H, alkyl, cyclopropyl, aryl, $OR^5$, $NR^5R^6$, $NR^5COR^6$, $NR^5COOR^6$, $NR^5CONR^6$, $NR^5SO_2R^6$, $COR^5$, $SO_2R^5$, halogen, CN, $NO_2$, $COOR^5$, $CONR^5R^6$, $NCOR^7$, $NCONR^7$, $NCOOR^7$, $SO_2NR^5R^6$, and $NHSO_2R^7$;
- $R^{12}$ is selected from the group consisting of H, alkyl, $CH_2$(heterocycle), $(CH_2)_2N(CH_3)_2$, $CH_2COOH$, $CH_2CONH$(heterocycle), $CH_2CONH(CH_2)_2NH_2$ and $CH_2CO$(heterocycle).

In another embodiment, a compound of the invention comprises Formula (IV), wherein:
- X is selected from the group consisting of hydrogen and $OR^2$;
- $R^2$ is independently selected from the group consisting of hydrogen, $PO(OH)_2$, acetyl, $COR^5$, $CO(OR^5)$, $CO(CH_2)_nNR^5R^6$, hydrocarbyl and substituted hydrocarbyl;
- n is an integer from 1 to 10;
- Z is O;
- Y is selected from the group consisting of O, CH(OH), $CH(OR^5)$, $CHNR^5R^6$, $CH_2$, S, and $NR^5$;
- $R^1$ is selected from the group consisting of $CH_3$, $CF_3$, halogen, $OCH_3$, $CO_2CH_3$, and $CONHCH_3$;
- $R^8$ and $R^{11}$ are independently selected from the group consisting of $CONHCH_3$, $COOCH_3$, COOH, CONH(heterocycle), heterocycle, H, alkyl, cyclopropyl, aryl, $OR^5$, $NR^5R^6$, $NR^5COR^6$, $NR^5COOR^6$, $NR^5CONR^6$, $NR^5SO_2R^6$, $COR^5$, $SO_2R^5$, halogen, CN, $NO_2$, $COOR^5$, $CONR^5R^6$, $NCOR^7$, $NCONR^7$, $NCOOR^7$, $SO_2NR^5R^6$, and $NHSO_2R^7$;
- $R^{12}$ is selected from the group consisting of H, alkyl, $CH_2$(heterocycle), $(CH_2)_2N(CH_3)_2$, $CH_2COOH$, $CH_2CONH$(heterocycle), $CH_2CONH(CH_2)_2NH_2$ and $CH_2CO$(heterocycle);
- $R^5$ is selected from the group consisting of H and an optionally substituted alkyl, aryl, heterocycle, and cycloalkyl;
- $R^6$ and $R^7$ are selected from the group consisting of an optionally substituted alkyl, cycolalkyl, aryl, and heterocycle.

In still another embodiment, a compound of the invention comprises Formula (IV), wherein:
- X is selected from the group consisting of hydrogen and $OR^2$;
- $R^2$ is independently selected from the group consisting of hydrogen, $PO(OH)_2$, acetyl, $COR^5$, $CO(OR^5)$, $CO(CH_2)_nNR^5R^6$, hydrocarbyl and substituted hydrocarbyl;
- n is an integer from 1 to 10;
- Z is O;
- Y is selected from the group consisting of O, CH(OH), $CH(OR^5)$, $CHNR^5R^6$, $CH_2$, S, and $NR^5$;

$R^5$ is selected from the group consisting of H and an optionally substituted alkyl, aryl, heterocycle, and cycloalkyl;

$R^6$ and $R^7$ are selected from the group consisting of an optionally substituted alkyl, cycolalkyl, aryl, and heterocycle;

$R^1$ is selected from the group consisting of $CH_3$, $CF_3$, halogen, $OCH_3$, $CO_2CH_3$, and $CONHCH_3$;

$R^8$ and $R^{11}$ are hydrogen;

$R^{12}$ is selected from the group consisting of H, alkyl, $CH_2R^{13}$, $CH_2COR^{13}$, $CH_2CONHR^{13}$, $CH_2CONHR^{13}R^{14}$, $CH_2CONH(CH_2)_2R^{14}$, $(CH_2)_2NR^{13}$, $(CH_2)_nNR^{13}$, $CH_2COOH$, $CH_2CONH(CH_2)_2NH_2$, and $(CH_2)_2N(CH_3)_2$;

$R^{13}$ is selected from the group consisting of —OH and an optionally substituted heterocycle, hydrocarbyl, and substituted hydrocarbyl;

$R^{14}$ is selected from the group consisting of alkyl and $NH_2$.

In still another embodiment, a compound of the invention comprises Formula (IV), wherein:

X is selected from the group consisting of hydrogen and $OR^2$;

$R^2$ is independently selected from the group consisting hydrogen, $PO(OH)_2$, acetyl, $COR^5$, $CO(OR^5)$, $CO(CH_2)_nNR^5R^6$, hydrocarbyl and substituted hydrocarbyl;

n is an integer from 1 to 10;

Z is O;

Y is selected from the group consisting of O, CH(OH) and $CH_2$;

$R^1$ is selected from the group consisting of $CH_3$, $CF_3$, halogen, Cl, F, Br, I, OH, $NH_2$, $NR^5R^6$, $OCH_3$, $CO_2CH_3$, $CONHCH_3$, alkyl, cyclopropyl, $OR^5$, $CO_2R^5$, $CONR^5R^6$, hydrocarbyl, and substituted hydrocarbyl;

$R^5$ is selected from the group consisting of H and an optionally substituted alkyl, aryl, heterocycle, and cycloalkyl;

$R^6$ and $R^7$ are selected from the group consisting of an optionally substituted alkyl, cycolalkyl, aryl, and heterocycle;

$R^8$ and $R^{11}$ are independently selected from the group consisting of $CONHCH_3$, $COOCH_3$, COOH, CONH (heterocycle), heterocycle, H, alkyl, cyclopropyl, aryl, $OR^5$, $NR^5R^6$, $NR^5COR^6$, $NR^5COOR^6$, $NR^5CONR^6$, $NR^5SO_2R^6$, $COR^5$, $SO_2R^5$, halogen, CN, $NO_2$, $COOR^5$, $CONR^5R^6$, $NCOR^7$, $NCONR^7$, $NCOOR^7$, $SO_2NR^5R^6$, and $NHSO_2R^7$;

$R^{12}$ is selected from the group consisting of H, $CH_2R^{13}$, $CH_2COR^{13}$, $CH_2CONHR^{13}$, $CH_2CONHR^{13}R^{14}$, $CH_2CONH(CH_2)_2R^{14}$, $(CH_2)_2NR^{13}$, $(CH_2)_nNR^{13}$, $CH_2COOH$, $CH_2CONH(CH_2)_2NH_2$, and $(CH_2)_2N(CH_3)_2$;

$R^{13}$ is selected from the group consisting of —OH and an optionally substituted heterocycle, hydrocarbyl and substituted hydrocarbyl;

$R^{14}$ is selected from the group consisting of alkyl and $NH_2$.

In still yet another embodiment, a compound of the invention comprises Formula (IV), wherein:

X is selected from the group consisting of hydrogen and $OR^2$;

$R^2$ is independently selected from the group consisting of hydrogen, —$COCH_3$, —$PO(OH)_2$, and —$COCH_2N(CH_3)_2$;

Z is O;

Y is selected from the group consisting of O, CH(OH) and $CH_2$;

$R^1$ is selected from the group consisting of $CH_3$, $CF_3$, halogen, Cl, F, Br, I, OH, $NH_2$, $NR^5R^6$, $OCH_3$, $CO_2CH_3$, $CONHCH_3$, alkyl, cyclopropyl, $OR^5$, $CO_2R^5$, $CONR^5R^6$, hydrocarbyl, and substituted hydrocarbyl;

$R^5$ is selected from the group consisting of H and an optionally substituted alkyl, aryl, heterocycle, and cycloalkyl;

$R^6$ and $R^7$ are selected from the group consisting of an optionally substituted alkyl, cycolalkyl, aryl, and heterocycle;

$R^8$ and $R^{11}$ are independently selected from the group consisting of $CONHCH_3$, $COOCH_3$, COOH, CONH (heterocycle), heterocycle, H, alkyl, cyclopropyl, aryl, $OR^5$, $NR^5R^6$, $NR^5COR^6$, $NR^5COOR^6$, $NR^5CONR^6$, $NR^5SO_2R^6$, $COR^5$, $SO_2R^5$, halogen, CN, $NO_2$, $COOR^5$, $CONR^5R^6$, $NCOR^7$, $NCONR^7$, $NCOOR^7$, $SO_2NR^5R^6$, and $NHSO_2R^7$;

$R^{12}$ are independently selected from the group consisting of H, alkyl, $CH_2R^{13}$, $CH_2COR^{13}$, $CH_2CONHR^{13}$, $CH_2CONHR^{13}R^{14}$, $CH_2CONH(CH_2)_2R^{14}$, $(CH_2)_2NR^{13}$, $(CH_2)_nNR^{13}$, $CH_2COOH$, $CH_2CONH(CH_2)_2NH_2$, and $(CH_2)_2N(CH_3)_2$;

$R^{13}$ is selected from the group consisting of —OH and an optionally substituted heterocycle, hydrocarbyl and substituted hydrocarbyl;

$R^{14}$ is selected from the group consisting of alkyl and $NH_2$.

In still yet another embodiment, a compound of the invention comprises Formula (IV), wherein:

X is selected from the group consisting of hydrogen and $OR^2$;

$R^2$ is independently selected from the group consisting of hydrogen, —$COCH_3$, —$PO(OH)_2$, and —$COCH_2N(CH_3)_2$;

Z is O;

Y is selected from the group consisting of O, CH(OH) and $CH_2$;

$R^1$ is $CH_3$;

$R^8$ and $R^{11}$ are independently selected from the group consisting of $CONHCH_3$, $COOCH_3$, COOH, CONH (heterocycle), heterocycle, H, alkyl, cyclopropyl, aryl, $OR^5$, $NR^5R^6$, $NR^5COR^6$, $NR^5COOR^6$, $NR^5CONR^6$, $NR^5SO_2R^6$, $COR^5$, $SO_2R^5$, halogen, CN, $NO_2$, $COOR^5$, $CONR^5R^6$, $NCOR^7$, $NCONR^7$, $NCOOR^7$, $SO_2NR^5R^6$, and $NHSO_2R^7$;

$R^5$ is selected from the group consisting of H and an optionally substituted alkyl, aryl, heterocycle, and cycloalkyl;

$R^6$ and $R^7$ are selected from the group consisting of an optionally substituted alkyl, cycolalkyl, aryl, and heterocycle;

$R^{12}$ is selected from the group consisting of H, alkyl, $CH_2R^{13}$, $CH_2COR^{13}$, $CH_2CONHR^{13}$, $CH_2CONHR^{13}R^{14}$, $CH_2CONH(CH_2)_2R^{14}$, $(CH_2)_2NR^{13}$, $(CH_2)_nNR^{13}$, $CH_2COOH$, $CH_2CONH(CH_2)_2NH_2$, and $(CH_2)_2N(CH_3)_2$;

$R^{13}$ is selected from the group consisting of —OH and an optionally substituted heterocycle, hydrocarbyl and substituted hydrocarbyl;

$R^{14}$ is selected from the group consisting of alkyl and $NH_2$.

In still yet another embodiment, a compound of the invention comprises Formula (IV), wherein:

X is selected from the group consisting of hydrogen and OR$^2$;

R$^2$ is independently selected from the group consisting of hydrogen, —COCH$_3$, —PO(OH)$_2$, and —COCH$_2$N(CH$_3$)$_2$;

Z is O;

Y is selected from the group consisting of O, CH(OH) and CH$_2$;

R$^1$ is CH$_3$;

R$^8$ and R$^{11}$ are independently selected from the group consisting of CONHCH$_3$, COOCH$_3$, COOH, CONH(heterocycle), heterocycle, H, alkyl, cyclopropyl, aryl, OR$^5$, NR$^5$R$^6$, NR$^5$COR$^6$, NR$^5$COOR$^6$, NR$^5$CONR$^6$, NR$^5$SO$_2$R$^6$, COR$^5$, SO$_2$R$^5$, halogen, CN, NO$_2$, COOR$^5$, CONR$^5$R$^6$, NCOR$^7$, NCONR$^7$, NCOOR$^7$, SO$_2$NR$^5$R$^6$, and NHSO$_2$R$^7$;

R$^5$ is selected from the group consisting of H and an optionally substituted alkyl, aryl, heterocycle, and cycloalkyl;

R$^6$ and R$^7$ are selected from the group consisting of an optionally substituted alkyl, cycolalkyl, aryl, and heterocycle;

R$^{12}$ is selected from the group consisting of H, CH$_2$(heterocycle), (CH$_2$)$_2$N(CH$_3$)$_2$, CH$_2$COOH, CH$_2$CONH(heterocycle), CH$_2$CONH(CH$_2$)$_2$NH$_2$ and CH$_2$CO(heterocycle).

In still yet another embodiment, a compound of the invention comprises Formula (IV), wherein:

X is selected from the group consisting of hydrogen and OR$^2$;

R$^2$ is independently selected from the group consisting of hydrogen, —COCH$_3$, —PO(OH)$_2$, and —COCH$_2$N(CH$_3$)$_2$;

Z is O;

Y is selected from the group consisting of O, CH(OH) and CH$_2$;

R$^1$ is CH$_3$;

R$^8$ and R$^{11}$ are hydrogen;

R$^{12}$ is selected from the group consisting of H, alkyl, CH$_2$R$^{13}$, CH$_2$COR$^{13}$, CH$_2$CONHR$^{13}$, CH$_2$CONHR$^{13}$R$^{14}$, CH$_2$CONH(CH$_2$)$_2$R$^{14}$, (CH$_2$)$_2$NR$^{13}$, (CH$_2$)$_n$NR$^{13}$, CH$_2$COOH, CH$_2$CONH(CH$_2$)$_2$NH$_2$, and (CH$_2$)$_2$N(CH$_3$)$_2$;

R$^{13}$ is selected from the group consisting of —OH and an optionally substituted heterocycle, hydrocarbyl and substituted hydrocarbyl;

R$^{14}$ is selected from the group consisting of alkyl and NH$_2$.

In still yet another embodiment, a compound of the invention comprises Formula (IV), wherein:

X is selected from the group consisting of hydrogen and OR$^2$;

R$^2$ is independently selected from the group consisting of hydrogen, —COCH$_3$, —PO(OH)$_2$, and —COCH$_2$N(CH$_3$)$_2$;

Z is O;

Y is selected from the group consisting of O, CH(OH) and CH$_2$;

R$^1$ is CH$_3$;

R$^8$ and R$^{11}$ are hydrogen;

R$^{12}$ is selected from the group consisting of H, CH$_2$(heterocycle), (CH$_2$)$_2$N(CH$_3$)$_2$, CH$_2$COOH, CH$_2$CONH(heterocycle), CH$_2$CONH(CH$_2$)$_2$NH$_2$ and CH$_2$CO(heterocycle).

In an exemplary alternative of each of the foregoing embodiments, a compound comprising formula (IV) is a compound comprising any of the Formulas in Table 1.

In a further exemplary alternative of each of the foregoing embodiments, a compound of the invention is Example 7-16 from Table 1.

Yet another aspect of the invention is a compound of Formula (V):

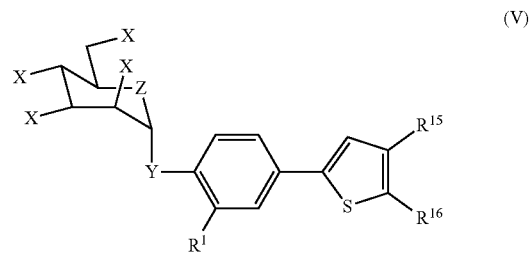

(V)

wherein:

X is selected from the group consisting of hydrogen and OR$^2$;

R$^2$ is independently selected from the group consisting of hydrogen, PO(OH)$_2$, acetyl, COR$^5$, CO(OR$^5$), CO(CH$_2$)$_n$NR$^5$R$^6$, hydrocarbyl and substituted hydrocarbyl;

n is an integer from 1 to 10;

R$^5$ is selected from the group consisting of H and an optionally substituted alkyl, aryl, heterocycle, and cycloalkyl;

R$^6$ and R$^7$ are selected from the group consisting of an optionally substituted alkyl, cycolalkyl, aryl, and heterocycle;

Z is O;

Y is selected from the group consisting of O, CH(OH), CH(OR$^5$), CHNR$^5$R$^6$, CH$_2$, S, and NR$^5$;

R$^1$ is selected from the group consisting of CH$_3$, CF$_3$, halogen, Cl, F, Br, I, OH, NH$_2$, NR$^5$R$^6$, OCH$_3$, CO$_2$CH$_3$, CONHCH$_3$, alkyl, cyclopropyl, OR$^5$, CO$_2$R$^5$, CONR$^5$R$^6$, hydrocarbyl, and substituted hydrocarbyl;

R$^{15}$ and R$^{16}$ are independently selected from the group consisting of hydrogen, NHCONH$_2$, COOCH$_3$, and CONHCH$_3$, CONHCH$_3$, COOCH$_3$, COOH, CONH(heterocycle), heterocycle, alkyl, cyclopropyl, aryl, OR$^5$, NR$^5$R$^6$, NR$^5$COR$^6$, NR$^5$COOR$^6$, NR$^5$CONR$^6$, NR$^5$SO$_2$R$^6$, COR$^5$, SO$_2$R$^5$, halogen, CN, NO$_2$, COOR$^5$, CONR$^5$R$^6$, NCOR$^7$, NCONR$^7$, NCOOR$^7$, SO$_2$NR$^5$R$^6$, and NHSO$_2$R$^7$ or R$^{15}$ and R$^{16}$ can optionally form a cycloalkyl, aryl or heterocyclo ring.

In one embodiment, a compound of the invention comprises Formula (V), wherein:

X is selected from the group consisting of hydrogen and OR$^2$;

R$^2$ is independently selected from the group consisting of hydrogen, PO(OH)$_2$, acetyl, COR$^5$, CO(OR$^5$), CO(CH$_2$)$_n$NR$^5$R$^6$, hydrocarbyl and substituted hydrocarbyl;

n is an integer from 1 to 10;

R$^5$ is selected from the group consisting of H and an optionally substituted alkyl, aryl, heterocycle, and cycloalkyl;

R$^6$ and R$^7$ are selected from the group consisting of an optionally substituted alkyl, cycolalkyl, aryl, and heterocycle;

Z is O;

Y is selected from the group consisting of O, CH(OH), CH(OR$^5$), CHNR$^5$R$^6$, CH$_2$, S, and NR$^5$;

$R^1$ is selected from the group consisting of $CH_3$, $CF_3$, halogen, $OCH_3$, $CO_2CH_3$, and $CONHCH_3$;

$R^{15}$ and $R^{16}$ are independently selected from the group consisting of hydrogen, $NHCONH_2$, $COOCH_3$, and $CONHCH_3$, $CONHCH_3$, $COOCH_3$, $COOH$, $CONH$ (heterocycle), heterocycle, alkyl, cyclopropyl, aryl, $OR^5$, $NR^5R^6$, $NR^5COR^6$, $NR^5COOR^6$, $NR^5CONR^6$, $NR^5SO_2R^6$, $COR^5$, $SO_2R^5$, halogen, CN, $NO_2$, $COOR^5$, $CONR^5R^6$, $NCOR^7$, $NCONR^7$, $NCOOR^7$, $SO_2NR^5R^6$, and $NHSO_2R^7$ or $R^{15}$ and $R^{16}$ can optionally form a cycloalkyl, aryl or heterocyclo ring.

In another embodiment, a compound of the invention comprises Formula (V), wherein:

X is selected from the group consisting of hydrogen and $OR^2$;

$R^2$ is independently selected from the group consisting of hydrogen, $PO(OH)_2$, acetyl, $COR^5$, $CO(OR^5)$, $CO(CH_2)_nNR^5R^6$, hydrocarbyl and substituted hydrocarbyl;

n is an integer from 1 to 10;

Z is O;

Y is selected from the group consisting of O, CH(OH), $CH(OR^5)$, $CHNR^5R^6$, $CH_2$, S, and $NR^5$;

$R^1$ is selected from the group consisting of $CH_3$, $CF_3$, halogen, Cl, F, Br, I, OH, $NH_2$, $NR^5R^6$, $OCH_3$, $CO_2CH_3$, $CONHCH_3$, alkyl, cyclopropyl, $OR^5$, $CO_2R^5$, $CONR^5R^6$, hydrocarbyl, and substituted hydrocarbyl;

$R^5$ is selected from the group consisting of H and an optionally substituted alkyl, aryl, heterocycle, and cycloalkyl;

$R^6$ and $R^7$ are selected from the group consisting of an optionally substituted alkyl, cycoalkyl, aryl, and heterocycle;

$R^{15}$ and $R^{16}$ are independently selected from the group consisting of hydrogen, $NHCONH_2$, $COOCH_3$, and $CONHCH_3$, and $R^{15}$ and $R^{16}$ can optionally form an optionally substituted cycloalkyl or heterocyclo 5 or 6 membered ring.

In yet another embodiment, a compound of the invention comprises Formula (V), wherein:

X is selected from the group consisting of hydrogen and $OR^2$;

$R^2$ is independently selected from the group consisting of hydrogen, $PO(OH)_2$, acetyl, $COR^5$, $CO(OR^5)$, $CO(CH_2)_nNR^5R^6$, hydrocarbyl and substituted hydrocarbyl;

n is an integer from 1 to 10;

Z is O;

Y is selected from the group consisting of O, CH(OH), $CH(OR^5)$, $CHNR^5R^6$, $CH_2$, S, and $NR^5$;

$R^5$ is selected from the group consisting of H and an optionally substituted alkyl, aryl, heterocycle, and cycloalkyl;

$R^6$ and $R^7$ are selected from the group consisting of an optionally substituted alkyl, cycoalkyl, aryl, and heterocycle;

$R^1$ is selected from the group consisting of $CH_3$, $CF_3$, halogen, $OCH_3$, $CO_2CH_3$, and $CONHCH_3$;

$R^{15}$ and $R^{16}$ are independently selected from the group consisting of hydrogen, $NHCONH_2$, $COOCH_3$, and $CONHCH_3$, and $R^{15}$ and $R^{16}$ can optionally form an optionally substituted cycloalkyl or heterocyclo 5 or 6 membered ring.

In another embodiment, a compound of the invention comprises Formula (V), wherein:

X is selected from the group consisting of hydrogen and $OR^2$;

$R^2$ is independently selected from the group consisting of hydrogen, $PO(OH)_2$, acetyl, $COR^5$, $CO(OR^5)$, $CO(CH_2)_nNR^5R^6$, hydrocarbyl and substituted hydrocarbyl;

n is an integer from 1 to 10;

Z is O;

Y is selected from the group consisting of O, CH(OH) and $CH_2$;

$R^1$ is selected from the group consisting of $CH_3$, $CF_3$, halogen, Cl, F, Br, I, OH, $NH_2$, $NR^5R^6$, $OCH_3$, $CO_2CH_3$, $CONHCH_3$, alkyl, cyclopropyl, $OR^5$, $CO_2R^5$, $CONR^5R^6$, hydrocarbyl, and substituted hydrocarbyl;

$R^5$ is selected from the group consisting of H, or an optionally substituted alkyl, aryl, heterocycle, and cycloalkyl;

$R^6$ and $R^7$ are selected from the group consisting of an optionally substituted alkyl, cycoalkyl, aryl, and heterocycle;

$R^{15}$ and $R^{16}$ are independently selected from the group consisting of hydrogen, $NHCONH_2$, $COOCH_3$, and $CONHCH_3$, $CONHCH_3$, $COOCH_3$, $COOH$, $CONH$ (heterocycle), heterocycle, alkyl, cyclopropyl, aryl, $OR^5$, $NR^5R^6$, $NR^5COR^6$, $NR^5COOR^6$, $NR^5CONR^6$, $NR^5SO_2R^6$, $COR^5$, $SO_2R^5$, halogen, CN, $NO_2$, $COOR^5$, $CONR^5R^6$, $NCOR^7$, $NCONR^7$, $NCOOR^7$, $SO_2NR^5R^6$, and $NHSO_2R^7$ or $R^{15}$ and $R^{16}$ can optionally form a cycloalkyl, aryl or heterocyclo ring.

In still another embodiment, a compound of the invention comprises Formula (V), wherein:

X is selected from the group consisting of hydrogen and $OR^2$;

$R^2$ is independently selected from the group consisting of hydrogen, $PO(OH)_2$, acetyl, $COR^5$, $CO(OR^5)$, $CO(CH_2)_nNR^5R^6$, hydrocarbyl and substituted hydrocarbyl;

n is an integer from 1 to 10;

Z is O;

Y is selected from the group consisting of O, CH(OH) and $CH_2$;

$R^1$ is selected from the group consisting of $CH_3$, $CF_3$, halogen, $OCH_3$, $CO_2CH_3$, and $CONHCH_3$;

$R^{15}$ and $R^{16}$ are independently selected from the group consisting of hydrogen, $NHCONH_2$, $COOCH_3$, and $CONHCH_3$, and $R^{15}$ and $R^{16}$ can optionally form an optionally substituted cycloalkyl or heterocyclo 5 or 6 membered ring.

In still yet another embodiment, a compound of the invention comprises Formula (V), wherein:

X is selected from the group consisting of hydrogen and $OR^2$;

$R^2$ is independently selected from the group consisting of hydrogen, —$COCH_3$, —$PO(OH)_2$, —$COCH_2N(CH_3)_2$;

Z is O;

Y is selected from the group consisting of O, CH(OH) and $CH_2$;

$R^1$ is selected from the group consisting of $CH_3$, $CF_3$, halogen, $OCH_3$, $CO_2CH_3$, and $CONHCH_3$;

$R^{15}$ and $R^{16}$ are independently selected from the group consisting of hydrogen, $NHCONH_2$, $COOCH_3$, and $CONHCH_3$, $CONHCH_3$, $COOCH_3$, $COOH$, $CONH$ (heterocycle), heterocycle, alkyl, cyclopropyl, aryl, $OR^5$, $NR^5R^6$, $NR^5COR^6$, $NR^5COOR^6$, $NR^5CONR^6$, $NR^5SO_2R^6$, $COR^5$, $SO_2R^5$, halogen, CN, $NO_2$, COOR$^5$, CONR$^5$R$^6$, NCOR$^7$, NCONR$^7$, NCOOR$^7$, SO$_2$NR$^5$R$^6$, and NHSO$_2$R$^7$ or R$^{15}$ and R$^{16}$ can optionally form a cycloalkyl, aryl or heterocyclo ring;

R$^5$ is selected from the group consisting of H and an optionally substituted alkyl, aryl, heterocycle, and cycloalkyl;

R$^6$ and R$^7$ are selected from the group consisting of an optionally substituted alkyl, cycolalkyl, aryl, and heterocycle.

In still yet another embodiment, a compound of the invention comprises Formula (V), wherein:

X is selected from the group consisting of hydrogen and OR$^2$;

R$^2$ is independently selected from the group consisting of hydrogen, —COCH$_3$, —PO(OH)$_2$, —COCH$_2$N(CH$_3$)$_2$;

Z is O;

Y is selected from the group consisting of O, CH(OH) and CH$_2$;

R$^1$ is CH$_3$;

R$^{15}$ and R$^{16}$ are independently selected from the group consisting of hydrogen, NHCONH$_2$, COOCH$_3$, and CONHCH$_3$, and R$^{15}$ and R$^{16}$ can optionally form an optionally substituted cycloalkyl or heterocyclo 5 or 6 membered ring.

In an exemplary alternative of each of the foregoing embodiments, a compound comprising formula (V) is a compound comprising any of the Formulas in Table 1.

In a further exemplary alternative of each of the foregoing embodiments, a compound of the invention is Example 17 from Table 1.

Yet still another aspect of the invention is a compound of Formula (VI):

(VI)

wherein:

X is selected from the group consisting of hydrogen and OR$^2$;

R$^2$ is independently selected from the group consisting of hydrogen, PO(OH)$_2$, acetyl, COR$^5$, CO(OR$^5$), CO(CH$_2$)$_n$NR$^5$R$^6$, hydrocarbyl and substituted hydrocarbyl;

n is an integer from 1 to 10;

R$^5$ is selected from the group consisting of H and an optionally substituted alkyl, aryl, heterocycle, and cycloalkyl;

R$^6$ and R$^7$ are selected from the group consisting of an optionally substituted alkyl, cycolalkyl, aryl, and heterocycle;

Z is O;

Y is selected from the group consisting of O, CH(OH), CH(OR$^5$), CHNR$^5$R$^6$, CH$_2$, S, and NR$^5$;

R$^1$ is selected from the group consisting of CH$_3$, CF$_3$, halogen, Cl, F, Br, I, OH, NH$_2$, NR$^5$R$^6$, OCH$_3$, CO$_2$CH$_3$, CONHCH$_3$, alkyl, cyclopropyl, OR$^5$, CO$_2$R$^5$, CONR$^5$R$^6$, hydrocarbyl, and substituted hydrocarbyl;

A is independently selected from the group consisting of CR$^5$ and N;

L is independently selected from the group consisting of no atom, N, O and S;

R$^{17}$, R$^{18}$, R$^{19}$ and R$^{20}$ are selected from the group consisting of H and an optionally substituted cycloalkyl, aryl or heterocyclo 5 or 6 membered ring including but not limited to the following examples, wherein the example is attached via any available CH position:

In one embodiment, a compound of the invention comprises Formula (VI), wherein:

X is selected from the group consisting of hydrogen and OR$^2$;

R$^2$ is independently selected from the group consisting of hydrogen, PO(OH)$_2$, acetyl, COR$^5$, CO(OR$^5$), CO(CH$_2$)$_n$NR$^5$R$^6$, hydrocarbyl and substituted hydrocarbyl;

n is an integer from 1 to 10;

R$^5$ is selected from the group consisting of H and an optionally substituted alkyl, aryl, heterocycle, and cycloalkyl;

R$^6$ and R$^7$ are selected from the group consisting of an optionally substituted alkyl, cycolalkyl, aryl, and heterocycle;

Z is O;
Y is selected from the group consisting of O, CH(OH), CH(OR$^5$), CHNR$^5$R$^6$, CH$_2$, S, and NR$^5$;
R$^1$ is selected from the group consisting of CH$_3$, CF$_3$, halogen, OCH$_3$, CO$_2$CH$_3$, and CONHCH$_3$;
A is independently selected from the group consisting of CR$^5$ and N;
L is independently selected from the group consisting of no atom, N, O and S;
R$^{17}$, R$^{18}$, R$^{19}$ and R$^{20}$ are selected from the group consisting of H and an optionally substituted cycloalkyl, aryl or heterocyclo 5 or 6 membered ring including but not limited to the following examples, wherein the example is attached via any CH position:

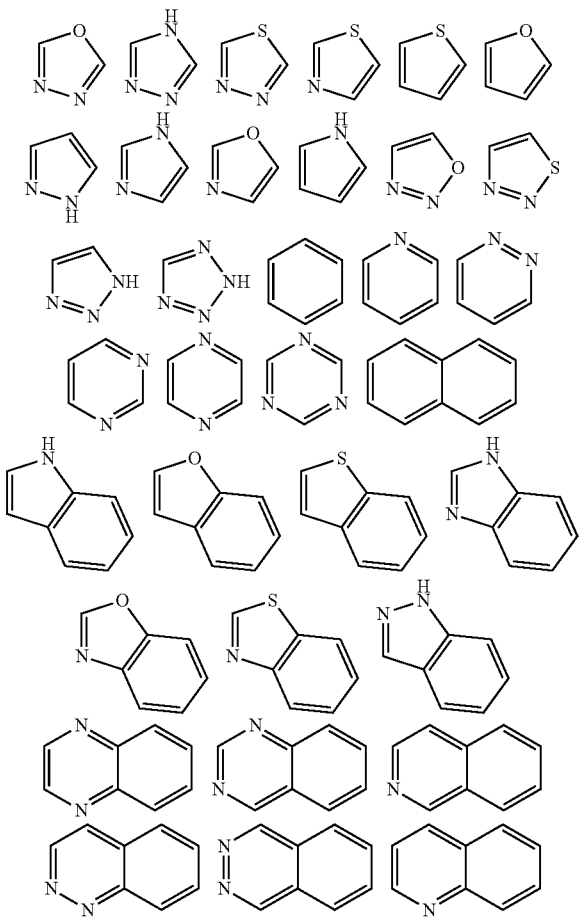

In another embodiment, a compound of the invention comprises Formula (VI), wherein:
X is selected from the group consisting of hydrogen and OR$^2$;
R$^2$ is independently selected from the group consisting of hydrogen, —COCH$_3$, —PO(OH)$_2$, and —COCH$_2$N(CH$_3$)$_2$;
Z is O;
Y is selected from the group consisting of O, CH$_2$O and CH$_2$;
R$^1$ is CH$_3$;
A is independently selected from the group consisting of CR$^5$ and N;
L is independently selected from the group consisting of no atom, N, O and S;

R$^{17}$ and R$^{20}$ are H;
R$^{15}$ and R$^{19}$ are selected from the group consisting of H and an optionally substituted cycloalkyl, aryl or heterocyclo 5 or 6 membered ring including but not limited to the following examples, wherein the example is attached via any CH position:

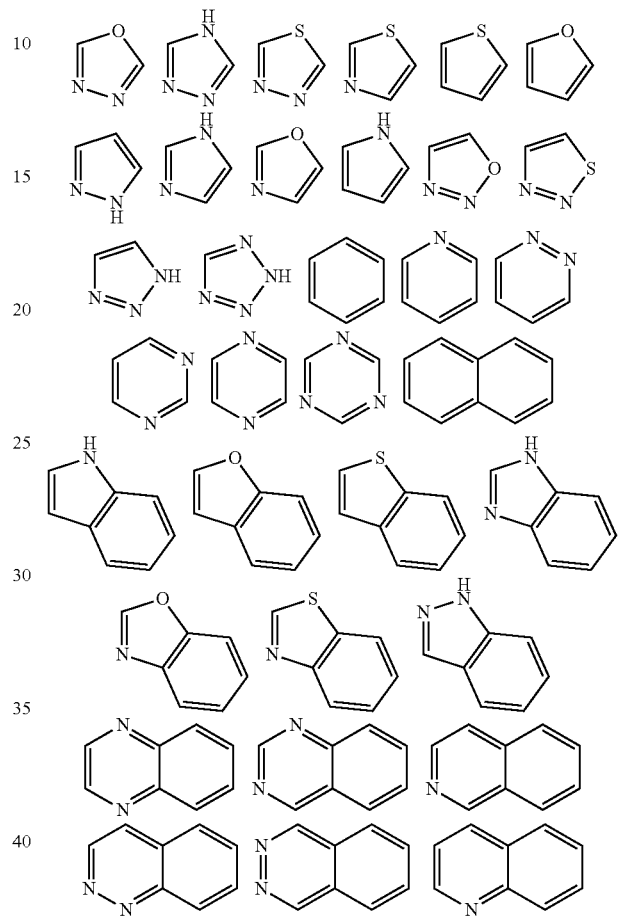

In an exemplary alternative of each of the foregoing embodiments, a compound comprising formula (VI) is a compound comprising any of the Formulas in Table 1.

In a further exemplary alternative of each of the foregoing embodiments, a compound of the invention is Examples 5-6 from Table 1.

In certain embodiments, the sugar residue of the above compounds may encompass a stereoisomer of mannose. In other embodiments, the sugar residue of the above compounds may encompass any stereoisomer of mannose other than glucose. In an exemplary embodiment, the sugar residue of the above compounds is alpha D mannose.

Exemplary methods of synthesizing a compound of the invention are detailed in the Examples.

A compound of the invention may also be an intermediate in the synthesis of a compound of formula (I)-(IV). For instance, in one embodiment, a compound of the invention may be an ester intermediate in the synthesis of a compound of formula (I)-(IV). In another embodiment, a compound of the invention may be a boronate ester of a mannoside or a boronic acid ester of a mannoside. In still another embodiment, a compound of the invention may be a compound illustrated in Schemes I-XII in the Examples below.

A compound of the invention may also comprise an imaging agent, such as a fluorescent moiety. In an embodiment, the imaging agent is bound to the sugar portion of a compound of the invention, either directly, or via a linker.

Compounds of the invention may block the function of FimH of the type 1 pili of pathogenic bacteria and prevent bacterial adherence and invasion and thus prevent bacterial amplification in the IBC and subsequent spreading and repeated rounds of amplification via new generation IBCs.

FimH functional assays used to measure activity of the compounds are known to individuals skilled in the art. Non-limiting examples of functional assays include hemmagglutination titer using guinea pig red blood cells, affinity of binding to FimH, and the ability of the compounds to prevent biofilm formation.

In some embodiments, activity of the compound is measured using hemmagglutination titer of guinea pig red blood cells. Hemagglutination of guinea pig red blood cells by type1 piliated UPEC is dependent upon FimH mannose binding ability and serial dilutions allow a quantitative analysis. Hemagglutination titer may generally be defined as the amount of compound required for decreasing hemagglutination by 75%. In some embodiments, the hemmagglutination titer of the compound of the invention may be less than about 5, 4, 3, 2, or 1 µM. In a preferred alternative of the embodiments, the hemmagglutination titer of the compound of the invention may be less than about 1, 0.5, 0.4, 0.3, 0.2, or 0.1 µM. In another preferred alternative of the embodiments, the hemmagglutiantion titer of the compound of the invention may be less than about 0.1, 0.05, 0.04, 0.03, 0.02, 0.01 µM. In yet another preferred alternative of the embodiments, the hemmagglutination titer of the compound of the invention may less than about 0.01 µM.

In yet other embodiments, activity of the compound may be measured using the ability of the compound to prevent or disrupt biofilm formation. In general, titration curves measuring the ability of a compound inhibit biofilm formation may be performed to determine the $IC_{50}$. In some embodiments, the $IC_{50}$ of the compound may be less than about 700, 600, 500, 400, 300, 200 or 100 µM. In other embodiments, the $IC_{50}$ of the compound may be less than about 500, 400, 300, 200, 100, 50, 40, 30, 20 10, 9, 8, 7, 6, or 5 µM. In preferred embodiments, the $IC_{50}$ of the compound may be less than about 20 µM. In other preferred embodiments, the $IC_{50}$ of the compound may be less than about 9 µM.

II. Combinations

Another aspect of the present invention encompasses a combination of a compound of the invention (described in Section I above) with one or more bactericidal compounds. In some embodiments, a compound of the invention may comprise a combination with 1, 2, 3, 4, or 5 bactericidal compounds. In one embodiment, the bactericidal compound is an antibiotic. Suitable antibiotics are known in the art, and may include Amikacin, Gentamicin, Kanamycin, Neomycin, Netilmicin, Tobramycin, Paromomycin, Geldanamycin, Herbimycin, Carbacephem, Loracarbef, Ertapenem, Doripenem, Imipenem/Cilastatin, Meropenem, Cefadroxil, Cefazolin, Cefalotin, Cefalexin, Cephalosporins, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftobiprole, Teicoplanin, Vancomycin, Telavancin, Clindamycin, Lincomycin, Azithromycin, Clarithromycin, Dirithromycin, Erythromycin, Roxithromycin, Troleandomycin, Telithromycin, Spectinomycin, Aztreonam, Furazolidone, Nitrofurantoin, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Temocillin, Ticarcillin, Bacitracin, Colistin, Polymyxin B, Ciprofloxacin, Enoxacin, Gatifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin, Mafenide, Sulfonamidochrysoidine, Sulfacetamide, Sulfadiazine, Silver sulfadiazine, Sulfamethizole, Sulfamethoxazole (SMZ), Sulfanilimide, Sulfasalazine, Sulfisoxazole, Trimethoprim (TMP), Trimethoprim-Sulfamethoxazole (such as Bactrim, Septra), Demeclocycline, Doxycycline, Minocycline, Oxytetracycline, Tetracycline, Clofazimine, Dapsone, Capreomycin, Cycloserine, Ethambutol, Ethionamide, Isoniazid, Pyrazinamide, Rifampicin, Rifabutin, Rifapentine, Streptomycin, Arsphenamine, Chloramphenicol, Fosfomycin, Fusidic acid, Linezolid, Metronidazole, Mupirocin, Platensimycin, Quinupristin/Dalfopristin, Rifaximin, Thiamphenicol, or Tinidazole. In an exemplary embodiment, the antibiotic is TMP, SMZ, or a combination thereof.

III. Pharmaceutical Compositions

Yet another aspect of the invention encompasses a pharmaceutical composition. A compound of the invention described in Section I above may exist in tautomeric, geometric or stereoisomeric forms. The present invention contemplates all such compounds, including cis- and trans-geometric isomers, E- and Z-geometric isomers, R- and S-enantiomers, diastereomers, d-isomers, I-isomers, the racemic mixtures thereof and other mixtures thereof. Pharmaceutically acceptable salts of such tautomeric, geometric or stereoisomeric forms are also included within the invention. The terms "cis" and "trans", as used herein, denote a form of geometric isomerism in which two carbon atoms connected by a double bond will each have a hydrogen atom on the same side of the double bond ("cis") or on opposite sides of the double bond ("trans"). Some of the compounds described contain alkenyl groups, and are meant to include both cis and trans or "E" and "Z" geometric forms. Furthermore, some of the compounds described contain one or more stereocenters and are meant to include R, S, and mixtures of R and S forms for each stereocenter present.

In a further embodiment, the inhibitors of the present invention may be in the form of free bases or pharmaceutically acceptable acid addition salts thereof. The term "pharmaceutically-acceptable salts" are salts commonly used to form alkali metal salts and to form addition salts of free acids or free bases. The nature of the salt may vary, provided that it is pharmaceutically acceptable. Suitable pharmaceutically acceptable acid addition salts of compounds for use in the present methods may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, stearic, algenic, algenic, hydroxybutyric, salicylic, galactaric and galacturonic acid. Suitable pharmaceutically-acceptable base addition salts of compounds of use in the present methods include metallic salts made from aluminum, calcium, lithium, magnesium, potassium, sodium and zinc or organic salts made from N, N'-dibenzylethylenediamine, chloroprocaine, choline, diethanolamine, ethylenediamine, meglumine-(N-methylglucamine) and procaine. All of these salts may be prepared by conventional means from the corresponding compound by reacting, for example, the appropriate acid or base with any of the compounds of the invention.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

Solid dosage forms for oral administration may include capsules, tablets, pills, powders, and granules. In such solid dosage forms, the compound is ordinarily combined with one or more adjuvants appropriate to the indicated route of administration. If administered per os, the compound can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, or magnesium or calcium carbonate or bicarbonate. Tablets and pills can additionally be prepared with enteric coatings.

For therapeutic purposes, formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art. For instance, a compound of the invention may be administered with a carrier. Non-limiting examples of such a carrier include protein carriers and lipid carriers.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The amount of the compound of the invention that may be combined with the carrier materials to produce a single dosage of the composition will vary depending upon the subject and the particular mode of administration. Those skilled in the art will appreciate that dosages may also be determined with guidance from Goodman & Goldman's The Pharmacological Basis of Therapeutics, Ninth Edition (1996), Appendix II, pp. 1707-1711 and from Goodman & Goldman's The Pharmacological Basis of Therapeutics, Tenth Edition (2001), Appendix II, pp. 475-493.

A compound of the invention may also be formulated as a prodrug. Such a prodrug formulation may increase the bioavailability of a compound of the invention. In one embodiment, the sugar portion of a compound of the invention may encompass a prodrug. In another embodiment $R_3$ may comprise a prodrug. Non-limiting examples of a compound of the invention formulated as a prodrug include the compounds below:

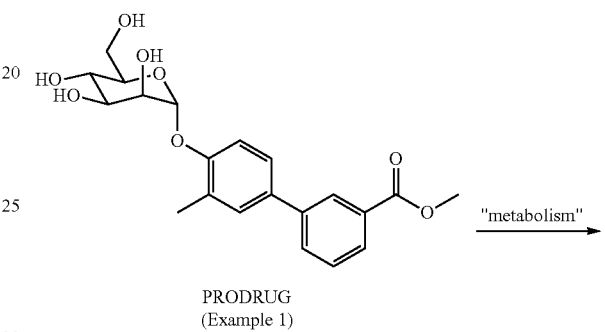

PRODRUG
(Example 1)

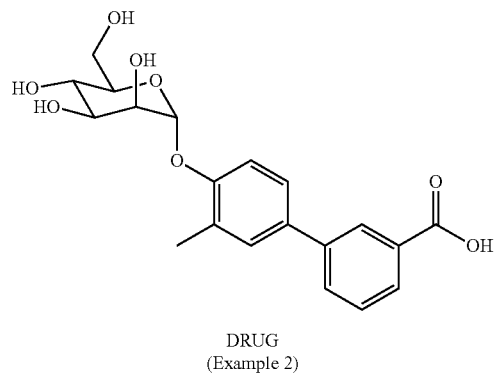

DRUG
(Example 2)

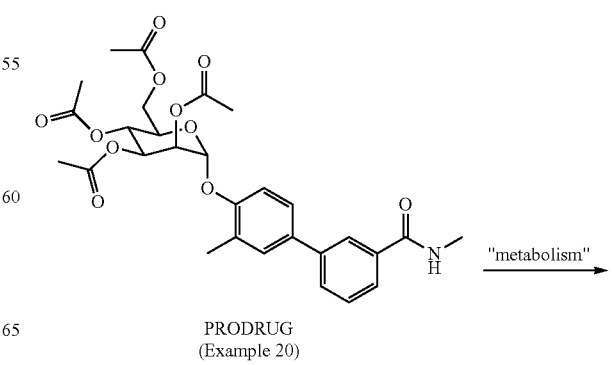

PRODRUG
(Example 20)

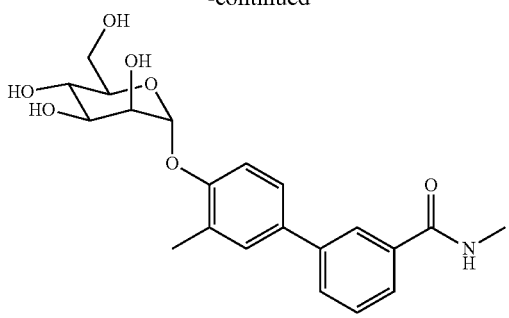

DRUG
(Example 23)

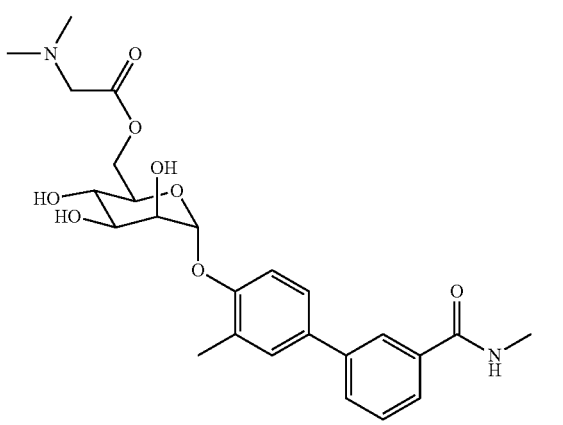

Example 22

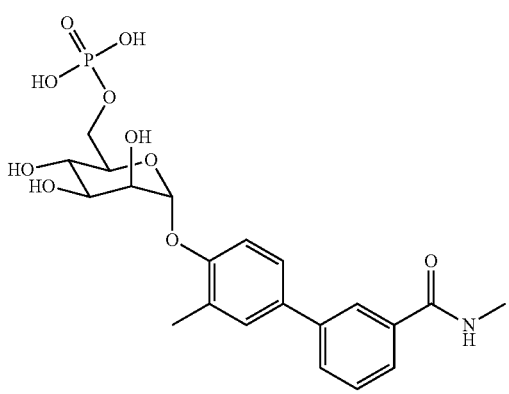

Example 21

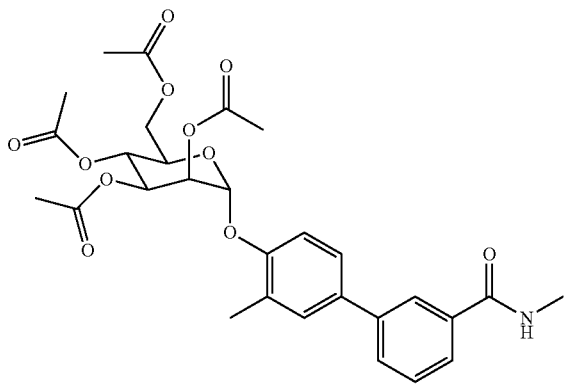

Example 20

IV. Methods of the Invention

Compounds of the invention may be used in methods of treating a bacterial infection and methods of reducing resistance to a bactericidal compound in a bacterium.

(a) Methods of Treating a Bacterial Infection

One embodiment of the invention encompasses a method for treating bacterial infections. Or, more specifically, the invention encompasses a method for treating a urinary tract infection. As used herein, "treating" refers to preventing infection in a subject not currently infected, and reducing or eliminating infection in a subject that is currently infected. As such, the invention also encompasses a method for preventing UTI. Generally, such a method comprises administering a pharmaceutical composition comprising a compound of the invention to a subject. As used herein, "subject" includes any mammal prone to urinary tract infections by $E.$ $coli$. In one embodiment, a subject is prone to recurring UTIs. In some embodiments, a subject may not have clinical symptoms of a UTI. In such embodiments, the subject may have a latent infection. In other embodiments, a subject may have clinical symptoms of a UTI.

In some embodiments, a compound of the invention may be administered to a subject in combination with a bactericidal compound as described in Section II above. When administered in a combination, a compound of the invention may be administered before, simultaneously, or after administration of a bactericidal compound. When administered before or after a bactericidal compound, the time between administration of a compound of the invention and a bactericidal compound may be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 min. In another embodiment, the time between administration of a compound of the invention and a bactericidal compound may be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72 hours.

A compound or pharmaceutical composition of the invention may be administered by several different means that will deliver a therapeutically effective dose. Such compositions may be administered orally, parenterally, by inhalation spray, rectally, intradermally, intracisternally, intraperitoneally, transdermally, bucally, as an oral or nasal spray, topically (i.e. powders, ointments or drops), or via a urinary cathetar in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. In an exemplary embodiment, the pharmaceutical composition will be administered in an oral dosage form. Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

The amount of a compound of the invention that constitutes an "effective amount" can and will vary. The amount will depend upon a variety of factors, including whether the administration is in single or multiple doses, and individual subject parameters including age, physical condition, size, and weight. Those skilled in the art will appreciate that dosages may also be determined with guidance from Goodman & Goldman's The Pharmacological Basis of Therapeutics, Ninth Edition (1996), Appendix II, pp. 1707-1711 and from Goodman & Goldman's The Pharmacological Basis of Therapeutics, Tenth Edition (2001), Appendix II, pp. 475-493.

In order to selectively control the release of an inhibitor to a particular region of the gastrointestinal tract for release, the pharmaceutical compositions of the invention may be manufactured into one or several dosage forms for the controlled, sustained or timed release of one or more of the ingredients. In this context, typically one or more of the ingredients forming the pharmaceutical composition is microencapsulated or dry coated prior to being formulated into one of the above forms. By varying the amount and type of coating and its thickness, the timing and location of release of a given ingredient or several ingredients (in either the same dosage form, such as a multi-layered capsule, or different dosage forms) may be varied.

In an exemplary embodiment, the coating may be an enteric coating. The enteric coating generally will provide for controlled release of the ingredient, such that drug release can be accomplished at some generally predictable location in the lower intestinal tract below the point at which drug release would occur without the enteric coating. In certain embodiments, multiple enteric coatings may be utilized. Multiple enteric coatings, in certain embodiments, may be selected to release the ingredient or combination of ingredients at various regions in the lower gastrointestinal tract and at various times.

As will be appreciated by a skilled artisan, the encapsulation or coating method can and will vary depending upon the ingredients used to form the pharmaceutical composition and coating, and the desired physical characteristics of the microcapsules themselves. Additionally, more than one encapsulation method may be employed so as to create a multi-layered microcapsule, or the same encapsulation method may be employed sequentially so as to create a multi-layered microcapsule. Suitable methods of microencapsulation may include spray drying, spinning disk encapsulation (also known as rotational suspension separation encapsulation), supercritical fluid encapsulation, air suspension microencapsulation, fluidized bed encapsulation, spray cooling/chilling (including matrix encapsulation), extrusion encapsulation, centrifugal extrusion, coacervation, alginate beads, liposome encapsulation, inclusion encapsulation, colloidosome encapsulation, sol-gel microencapsulation, and other methods of microencapsulation known in the art. Detailed information concerning materials, equipment and processes for preparing coated dosage forms may be found in Pharmaceutical Dosage Forms: Tablets, eds. Lieberman et al. (New York: Marcel Dekker, Inc., 1989), and in Ansel et al., Pharmaceutical Dosage Forms and Drug Delivery Systems, 6th Ed. (Media, Pa.: Williams & Wilkins, 1995).

A bacterium may be contacted with a compound of the invention in vivo, in vitro, in situ, or ex vivo. In some embodiments, a bacterium may be directly contacted with the compound of the invention. In other embodiments, an intracellular bacterium may be contacted with a compound of the invention. Suitable cells comprising one or more bacteria may be grown, sub-cultured, stored and manipulated using standard techniques known to individuals skilled in the art. Cell culture and microbiological techniques for growing, culturing, storing, and manipulating cells comprising one or more bacteria are commonly known in the art.

(b) Methods of Reducing Bactericidal Resistance

Another method of the invention comprises reducing the resistance of a bacterium to a bactericidal compound. Such a method comprises contacting a bacterium resistant to a bactericidal compound with a compound of the invention. For instance, a subject infected with a bacterium resistant to a bactericidal compound may be administered a compound of the invention, as described in Section IV(a) above. In an exemplary embodiment, a method comprises contacting a bacterium resistant to an antibiotic with a compound of the invention. In a further exemplary embodiment, a method comprises contacting a bacterium resistant to TMP or SMZ with a compound of the invention.

Methods of measuring resistance of a bacterium to an antibiotic are known in the art. For more details, see the examples.

(c) Methods of Treating Catheter-Associated Urinary Tract Infections

In a further embodiment, a method of the invention encompasses a method for treating catheter-associated urinary tract infections. As used herein, "treating" refers to preventing infection in a subject not currently infected, and reducing or eliminating infection in a subject that is currently infected. Generally, such a method comprises administering a pharmaceutical composition comprising a compound of the invention to a subject. For this embodiment, "subject" refers to any mammal with an indwelling urinary catheter. In one embodiment, a subject with a urinary catheter is prone to recurring UTIs. In some embodiments, a subject with a urinary catheter may not have clinical symptoms of a UTI. In such embodiments, the subject may have a latent infection. In other embodiments, a subject with a urinary catheter may have clinical symptoms of a UTI.

In some embodiments, a compound of the invention may be administered to a subject in combination with a bactericidal compound as described in Section II and Section IV(a) above.

(d) Methods of Treating Inflammatory Bowel Disease

In a further embodiment, a method of the invention encompasses a method for treating inflammatory bowel disease. Inflammatory bowel disease (IBD) involves chronic inflammation of all or part of the digestive tract. IBD may include ulcerative colitits, Crohn's disease, collagenous colitis, lymphocytic colitis, ischaemic colitis, diversion colitis, Behcet's disease and indeterminate colitis. As used herein, "treating" refers to reducing symptoms associated with inflammatory bowel disease. Alternatively, a method of the invention encompasses a method for reducing symptoms associated with inflammatory bowel disease. Symptoms may include ulcers, reduced appetite, rectal bleeding, rectal pain, a feeling of urgency or frequent, small bowel movements, bloody diarrhea, abdominal cramps and pain, inability to move the bowels in spite of the urge to do so (tenesmus), pain on the left side, unintended weight loss, fatigue, significant weight loss, profuse diarrhea, dehydration, shock, fever, fatigue, arthritis, eye inflammation, skin disorders, and inflammation of the liver or bile ducts.

Generally, such a method comprises administering a pharmaceutical composition comprising a compound of the invention to a subject. For this embodiment, "subject" refers to any mammal with inflammatory bowel disease.

V. Coatings

An additional aspect of the present invention encompasses coatings comprising a compound of the invention. Such a coating may be used on a medical device to prevent bacterial adherence or infection of the host. Suitable means of coating medical devices are known in the art. In one embodiment, a catheter may be coated with a compound of the invention. In another embodiment, a urinary catheter may be coated with a compound of the invention.

VI. Nutritional Supplement

An alternative aspect of the present invention encompasses a nutritional supplement that comprises a compound of the invention. Such a supplement may be used to treat a bacterial infection as described in section IV above.

Definitions

The term "acyl," as used herein alone or as part of another group, denotes the moiety formed by removal of the hydroxyl group from the group —COOH of an organic carboxylic acid, e.g., RC(O)—, wherein R is R', R1O—, R'R2 N—, or R1S—, R1 is hydrocarbyl, heterosubstituted hydrocarbyl, or heterocyclo and R2 is hydrogen, hydrocarbyl or substituted hydrocarbyl.

The term "acyloxy," as used herein alone or as part of another group, denotes an acyl group as described above bonded through an oxygen linkage (—O—), e.g., RC(O) O— wherein R is as defined in connection with the term "acyl."

Unless otherwise indicated, the alkyl groups described herein are preferably lower alkyl containing from one to eight carbon atoms in the principal chain and up to 20 carbon atoms. They may be straight or branched chain or cyclic, also known as a cycloalkyl, and include methyl, ethyl, propyl, isopropyl, butyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

As used herein, the term "functional group" includes a group of atoms within a molecule that is responsible for certain properties of the molecule and/or reactions in which it takes part. Non-limiting examples of functional groups include, alkyl, carboxyl, hydroxyl, amino, sulfonate, phosphate, phosphonate, thiol, alkyne, azide, halogen, and the like.

The terms "halogen" or "halo" as used herein alone or as part of another group refer to chlorine, bromine, fluorine, and iodine.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted (i.e. replaced) with a hetero atom such as nitrogen, oxygen, silicon, phosphorous, boron, sulfur, or a halogen atom. These moieties may include halogen, carbocycle, aryl, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

EXAMPLES

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

Introduction to Examples: General Synthesis, Purification, and Analytical Chemistry Procedures.

Certain compounds may exist as mixtures of isomers in equilibrium as described for isoquinolone isomer A in the scheme below which is in equilibrium with the hydroxyquinoline isomer B:

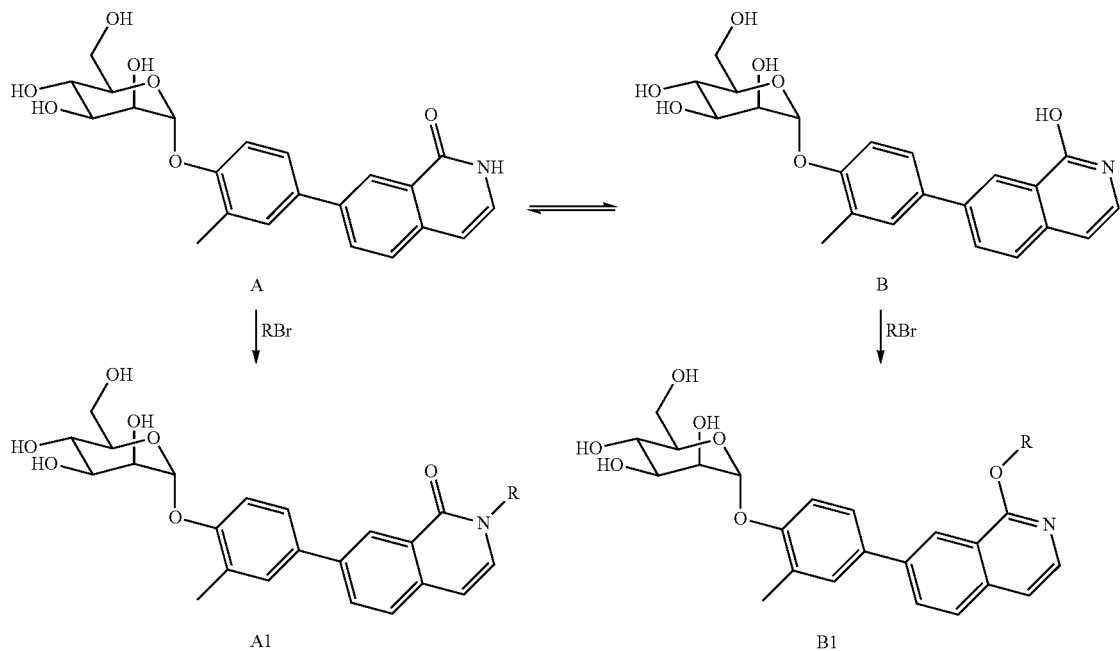

Therefore, it is understood that compounds containing isoquinolones may exist in the hydroxyisoquinoline form and the synthesis of analogs thereof may lead to the production of either one isomer A1 or B1 exclusively or a mixture. It is not always possible to confirm the identity of each individual isomer (e.g. A1 or B1). Thus, all possible isomers are claimed as the final product in examples which contain the isoquinolone ring.

Starting materials, reagents, and solvents were purchased from commercial vendors unless otherwise noted. In general anhydrous solvents are used for carrying out all reactions. $^1$H NMR spectra were measured on a Varian 400 MHz NMR instrument equipped with an auto sampler. The chemical shifts were reported as δ ppm relative to TMS using residual solvent peak as the reference unless otherwise noted. The following abbreviations were used to express the peak multiplicities: s=singlet; d=doublet; t=triplet; q=quartet; m=multiplet; br=broad. High-performance liquid chromatography (HPLC) was carried out on GILSON GX-281 using Waters C18 5 μM, 4.6*50 mm and Waters Prep C18 5 μM, 19*150 mm reverse phase columns, eluted with a gradient system of 5:95 to 95:5 acetonitrile:water with a buffer consisting of 0.05-0.1% TFA. Mass spectroscopy (MS) was performed on HPLC/MSD using a gradient system of 5:95 to 95:5 acetonitrile:water with a buffer consisting of 0.05-0.1% TFA on a C18 or C8 reversed phased column and electrospray ionization (ESI) for detection. All reactions were monitored by thin layer chromatography (TLC) carried out on Merck silica gel plates (0.25 mm thick, 60F254), visualized by using UV (254 nm) or dyes such as KMnO$_4$, p-Anisaldehyde and CAM (Hannesian's Stain). Silica gel chromatography was carried out on a Teledyne ISCO CombiFlash purification system using pre-packed silica gel columns (12 g~330 g sizes). All compounds used for biological assays are greater than 95% purity based on NMR and HPLC by absorbance at 220 nm and 254 nm wavelengths.

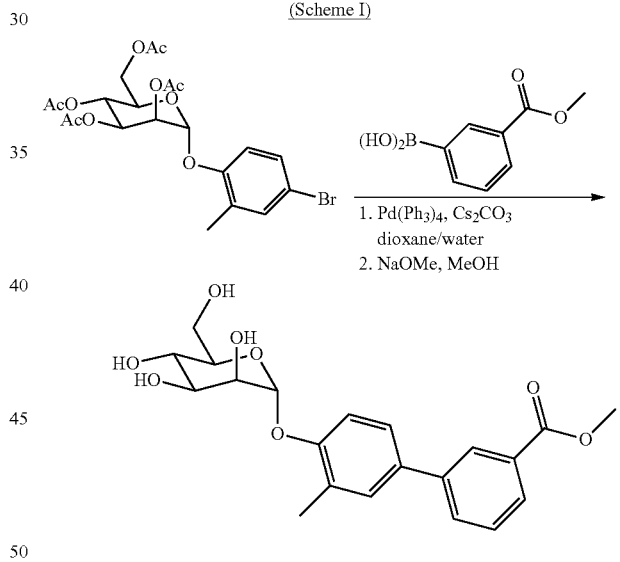

(Scheme I)

Example 1. methyl 3-[3-methyl-4-[(2R,3R,4S,5S,6S)-3,4,5-trihydroxy-6-(hydroxymethyl)tetrahydropyran-2-yl]oxy-phenyl]benzoate (Han et. al., *J. Med. Chem.* 2012, 55, 3945-3959)

To a round-bottomed flask equipped with a reflux condenser and N$_2$ line was added [(2R,3R,4S,5R,6S)-4,5-diacetoxy-6-(acetoxymethyl)-2-(4-bromo-2-methyl-phenoxy) tetrahydropyran-3-yl]acetate (0.52 g, 1.0 mmol), (3-methoxycarbonylphenyl)boronic acid (0.22 g, 1.2 mmol), Cs$_2$CO$_3$ (0.98 g, 3 mmol) and Pd(Ph$_3$)$_4$ (0.12 g, 0.1 mmol) followed by 5:1 mixture of 1,4-dioxane/water (30 mL). The reaction flask was placed under high vacuum and then repressurized with N$_2$ repeated 3 times. The reaction was heated to 80° C. under a N$_2$ atmosphere for 1 h. The solvent was removed in vacuo and the residue was dissolved in CHCl₃ and filtered. The filtrate was purified by silica gel chromatography (ISCO MPLC, MeOH/CH₂Cl₂, 0-10% gradient). Pure fractions as determined by TLC and LCMS were combined and then concentrated in vacuo. The residue was dissolved in MeOH (10 mL) and then charged with 0.002 M NaOMe/MeOH (5 mL). After the reaction was complete determined by LCMS, DOWEX 50WX4-100 ion exchange resin was added. After 15 minutes, the resin was filtered, washed with MeOH and then the filtrate was concentrated in vacuo. The residue was purified by silica gel chromatography (0-25% MeOH/CH₂Cl₂) to yield the title compound (0.222 q, 55%) as a white solid. LCMS (ESI, M+Na⁺=427.3), (Scheme II)

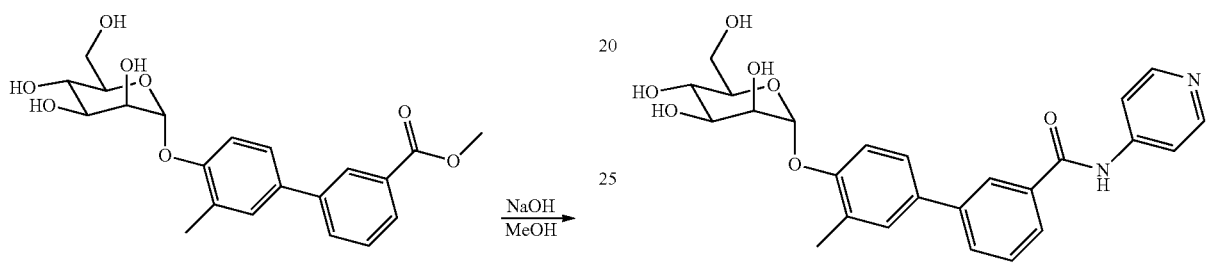

(Scheme III)

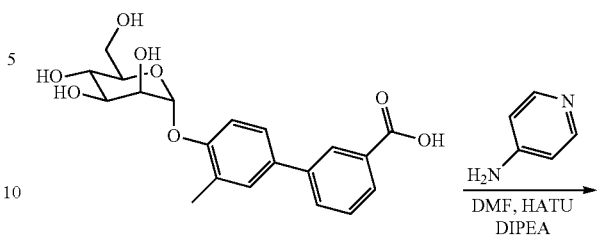

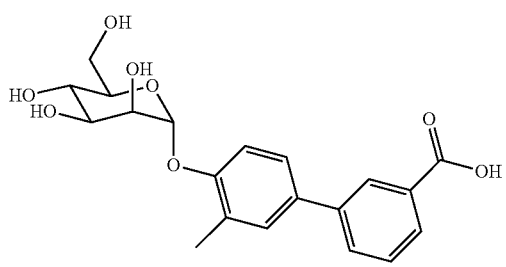

Example 2. 3-[3-methyl-4-[(2R,3R,4S,5S,6S)-3,4,5-trihydroxy-6-(hydroxymethyl)tetrahydropyran-2-yl]oxy-phenyl]benzoic acid To a solution of methyl 3-[3-methyl-4-[(2R,3R,4S,5S,6S)-3,4,5-trihydroxy-6-(hydroxymethyl)tetrahydropyran-2-yl]oxy-phenyl]benzoate (0.222 g, 0.55 mmol) in MeOH (70 mL) was added 0.2 M NaOH (30 mL). The reaction was stirred overnight at RT. DOWEX 50WX4-100 ion exchange resin was added. After 15 minutes, the resin was filtered, washed with MeOH and then the filtrate was concentrated in vacuo to yield the title compound (0.2025 g, 94%) as a white solid. LCMS (ESI, M+Na⁺=413.3); ¹H NMR δ ppm (d₃-MeOD; 2.31 (s, 3H) 3.61 (ddd, J=9.78, 5.09, 2.74 Hz, 1H) 3.69-3.84 (m, 3H) 3.97 (dd, J=9.39, 3.52 Hz, 1H) 4.08 (dd, J=3.33, 1.76 Hz, 1H) 5.56 (d, J=1.96 Hz, 1H) 7.31 (d, J=8.22 Hz, 1H) 7.39-7.48 (m, 2H) 7.51 (t, J=7.83 Hz, 1H) 7.76-7.84 (m, 1H) 7.95 (dt, J=7.83, 1.37 Hz, 1H) 8.21 (t, J=1.76 Hz, 1H)).

Example 3. 3-[3-methyl-4-[(2R,3R,4S,5S,6S)-3,4,5-trihydroxy-6-(hydroxymethyl)tetrahydropyran-2-yl]oxy-phenyl]-N-(4-pyridyl)benzamide To a stirred solution of 3-[3-methyl-4-[(2R,3R,4S,5S,6S)-3,4,5-trihydroxy-6-(hydroxymethyl)tetrahydropyran-2-yl]oxy-phenyl]benzoic acid (0.039 g, 0.1 mmol) and HATU (0.046 g, 0.12 mmol) in DMF (5 mL) under a N₂ atmosphere and cooled to 0° C. was added 4-aminopyridine (0.011 g, 0.12 mmol), and DIPEA (0.054 mL, 0.3 mmol). The reaction was allowed to warm to RT and then stirred overnight. The solvent was removed in vacuo and the residue purified by reversed phase HPLC (5-85% acetonitrile/water/0.05% TFA). Pure fractions were combined and lyophilized to give the title compound as a white powder (0.047 g, 100%). LCMS (ESI, M+H⁺=467.3); ¹H NMR δ ppm (d₃-MeOD; 2.34 (s, 3H) 3.60 (ddd, J=9.78, 5.28, 2.54 Hz, 1H) 3.68-3.85 (m, 3H) 3.98 (dd, J=9.59, 3.33 Hz, 1H) 4.09 (dd, J=3.33, 1.76 Hz, 1H) 5.58 (d, J=1.57 Hz, 1H) 7.34 (d, J=8.61 Hz, 1H) 7.44-7.58 (m, 2H) 7.63 (t, J=7.63 Hz, 1H) 7.84-8.00 (m, 2H) 8.19-8.27 (m, 1H) 8.37-8.45 (m, 2H) 8.62-8.72 (m, 2H)).

Example 4. 3-[3-methyl-4-[(2R,3R,4S,5S,6S)-3,4,5-trihydroxy-6-(hydroxymethyl)tetrahydropyran-2-yl]oxy-phenyl]-N-(3-pyridyl)benzamide Synthesized in a similar manner to Example 3 using 3-aminopyridine to give (0.043 g, 94%). LCMS (ESI, M+H⁺= 467.3); ¹H NMR δ ppm (d₃-MeOD; 2.33 (s, 3H) 3.61 (m, 1H) 3.76 (m, 3H) 3.97 (d, J=9.39 Hz, 1H) 4.08 (m, 1H) 5.57 (d, 1H) 7.33 (d, J=6.26 Hz, 1H) 7.43-7.56 (m, 2H) 7.61 (m, 1H) 7.85 (m, 1H) 7.94 (m, 2H) 8.22 (m, 1H) 8.55 (m, 1H) 8.66 (d, J=6.26 Hz, 1H) 9.47 (m, 1H)).

(Scheme IV)

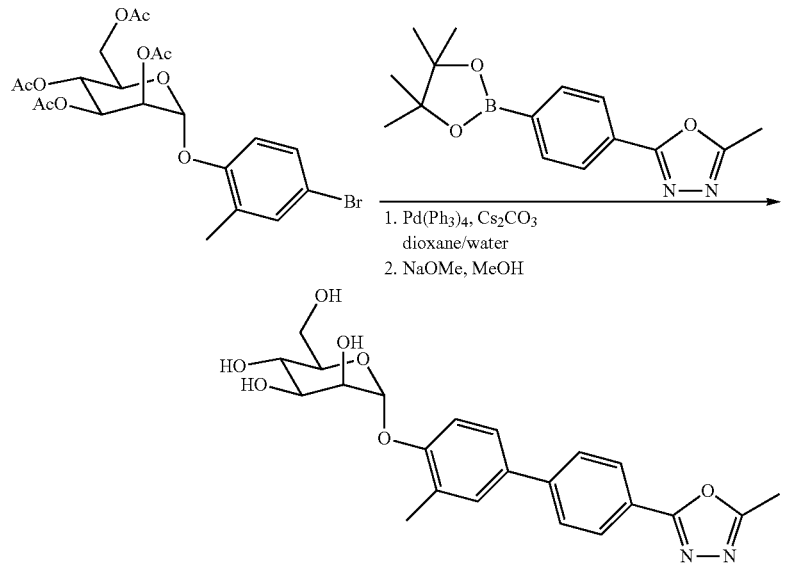

Example 5. (2S,3S,4S,5R,6R)-2-(hydroxymethyl)-6-[2-methyl-4-[4-(5-methyl-1,3,4-oxadiazol-2-yl)phenyl]phenoxy]tetrahydropyran-3,4,5-triol Synthesized in a similar manner to Example 1 using 2-methyl-5-[4-(4,4,5,5-tetramethyl-1,3,2-dioxaborolan-2-yl)phenyl]-1,3,4-oxadiazole (purchased from Boron Molecular). LCMS (ESI, M+H$^+$=429.3); $^1$H NMR δ ppm (d$_3$-MeOD; 2.28 (s, 3H) 2.63 (s, 3H) 3.53-3.65 (m, 1H) 3.70-3.88 (m, 3H) 3.98 (dd, J=9.59, 3.33 Hz, 1H) 4.09 (dd, J=3.13, 1.96 Hz, 1H) 5.57 (d, J=1.17 Hz, 1H) 7.24 (d, J=8.22 Hz, 1H) 7.38-7.45 (m, 2H) 7.48 (s, 1H) 7.69 (m, J=8.61 Hz, 1.5H) 8.02 (m, J=8.22 Hz, 1.5H)).

Example 6. (2S,3S,4S,5R,6R)-2-(hydroxymethyl)-6-[2-methyl-4-[3-(5-methyl-1,3,4-oxadiazol-2-yl)phenyl]phenoxy]tetrahydropyran-3,4,5-triol Synthesized in a similar manner to Example 1 using [3-(5-methyl-1,3,4-oxadiazol-2-yl)phenyl]boronic acid (purchased from Apollo Scientific). LCMS (ESI, M+H$^+$=429.3); $^1$H NMR δ ppm (d$_3$-MeOD; 2.08 (s, 1.5H) 2.32 (s, 1.5H) 2.33 (s, 1.5H) 2.65 (s, 1.5H) 3.55-3.65 (m, 1H) 3.69-3.83 (m, 3H) 3.98 (dt, J=9.49, 2.69 Hz, 1H) 4.06-4.12 (m, 1H) 5.54-5.60 (m, 1H) 7.27-7.38 (m, 1H) 7.44-7.65 (m, 3H) 7.75-7.98 (m, 2H) 8.07-8.25 (m, 1H)).

Example 7. 7-[3-methyl-4-[(2R,3R,4S,5S,6S)-3,4,5-trihydroxy-6-(hydroxymethyl)tetrahydropyran-2-yl]oxy-phenyl]-2H-isoquinolin-1-one Synthesized in a similar manner to Example 1 using [4,5-diacetoxy-6-(acetoxymethyl)-2-[2-methyl-4-(4,4,5,5-tetramethyl-1,3,2-dioxaborolan-2-yl)phenoxy]tetrahydropyran-3-yl]acetate (Han et. al., *J. Med. Chem.* 2012, 55, 3945-3959) and 7-bromo-2H-isoquinolin-1-one (purchased from AstaTech). LCMS (ESI, M+H$^+$=414.3); $^1$H NMR δ ppm (d$_3$-MeOD; 2.32 (s, 3H) 3.57-3.67 (m, 1H) 3.70-3.85 (m, 3H) 3.94-4.02 (m, 1H) 4.05-4.13 (m, 1H) 5.57 (d, J=1.57 Hz, 1H) 6.70 (d, J=7.00 Hz, 1H) 7.17 (d, J=7.04 Hz, 1H) 7.33 (d, J=8.22 Hz, 1H) 7.54 (s, 2H) 7.70 (d, J=8.61 Hz, 1H) 7.89-8.04 (m, 1H) 8.49 (d, J=1.96 Hz, 1H)).

(Scheme V)

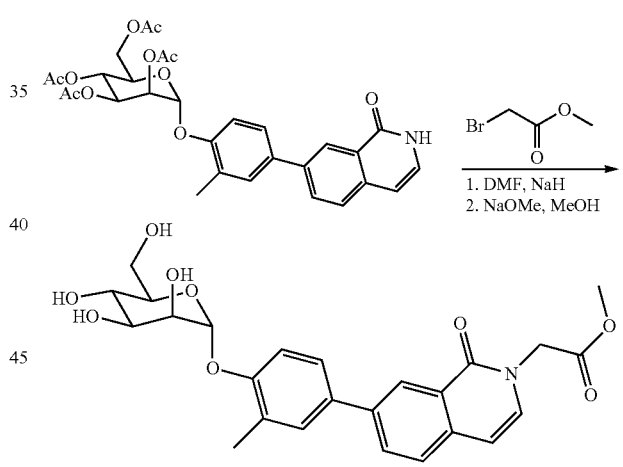

Example 8. methyl 2-[7-[3-methyl-4-[(2R,3R,4S,5S,6S)-3,4,5-trihydroxy-6(hydroxymethyl)tetrahydropyran-2-yl]oxy-phenyl]-1-oxo-2-isoquinolyl]acetate To a solution of [4,5-diacetoxy-6-(acetoxymethyl)-2-[2-methyl-4-(1-oxo-2H-isoquinolin-7-yl)phenoxy]tetrahydropyran-3-yl]acetate (0.116 g, 0.2 mmol) in DMF (5 mL) cooled to 0° C. under a N$_2$ atmosphere was slowly added NaH (0.024 g, 0.6 mmol, 60% dispersion in mineral oil). After 10 min, methyl 2-bromoacetate (0.018 mL, 0.19 mmol) was added and the reaction was stirred for 1 h at 0° C. under a N$_2$ atmosphere. The solvent was removed under high vacuum and the residue was dissolved in MeOH (5 mL) followed by the addition of 0.02 M NaOMe/MeOH (3 mL) and the reaction was stirred overnight at RT. DOWEX 50WX4-100 ion exchange resin was added. After 15 minutes, the resin was filtered, washed with MeOH and then the filtrate was concentrated in vacuo. The residue was purified by slica gel chromatography (0-20% MeOH/CH$_2$Cl$_2$) to give the title product (0.0558 g, 57%) as a white solid. LCMS (ESI, M+H$^+$=486.3); $^1$H NMR δ ppm (d$_3$-MeOD; 2.32 (s, 3H) 3.61 (ddd, J=9.68, 4.99, 2.54 Hz, 1H) 3.68-3.85 (m, 3H) 3.78 (s, 3H) 3.98 (dd, J=9.59, 3.33 Hz, 1H) 4.04-4.14 (m, 1H) 4.82 (s, 2H) 5.53-5.62 (m, 1H) 6.72 (d, J=7.04 Hz, 1H) 7.32 (dd, J=7.83, 3.91 Hz, 2H) 7.44-7.58 (m, 2H) 7.70 (d, J=8.22 Hz, 1H) 7.97 (dd, J=8.22, 1.96 Hz, 1H) 8.43-8.49 (m, 1H)).

2-isoquinolyl]acetate (0.050 g, 0.1 mmol) the title product was obtained as a white solid (0.045 g, 96%). LCMS (ESI, M+H$^+$=472.3); $^1$H NMR δ ppm (d$_3$-MeOD; 2.32 (s, 3H) 3.61 (ddd, J=9.59, 5.28, 2.35 Hz, 1H) 3.67-3.86 (m, 3H) 3.98 (dd, J=9.59, 3.33 Hz, 1H) 4.08 (dd, J=3.33, 1.76 Hz, 1H) 4.79 (s, 2H) 5.50-5.62 (m, 1H) 6.72 (d, J=7.43 Hz, 1H) 7.32 (dd, J=8.02, 2.93 Hz, 2H) 7.44-7.59 (m, 2H) 7.70 (d, J=8.22 Hz, 1H) 7.97 (dd, J=8.22, 1.96 Hz, 1H) 8.44-8.55 (m, 1H)).

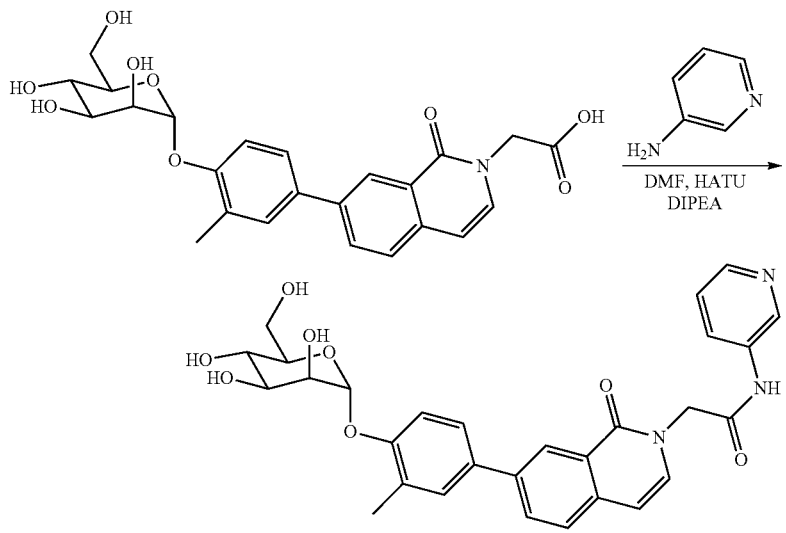

(Scheme VI)

Example 9. 2-[7-[3-methyl-4-[(2R,3R,4S,5S,6S)-3,4,5-trihydroxy-6-(hydroxymethyl)tetrahydropyran-2-yl]oxy-phenyl]-1-oxo-2-isoquinolyl]acetic acid Following a similar procedure to Example 2 using methyl 2-[7-[3-methyl-4-[(2R,3R,4S,5S,6S)-3,4,5-trihydroxy-6-(hydroxymethyl)tetrahydropyran-2-yl]oxy-phenyl]-1-oxo- Example 10. 2-[7-[3-methyl-4-[(2R,3R,4S,5S,6S)-3,4,5-trihydroxy-6-(hydroxymethyl)tetrahydropyran-2-yl]oxy-phenyl]-1-oxo-2-isoquinolyl]-N-(3-pyridyl)acetamide Following a similar procedure to Example 3 using 2-[7-[3-methyl-4-[(2R,3R,4S,5S,6S)-3,4,5-trihydroxy-6-(hydroxymethyl)tetrahydropyran-2-yl]oxy-phenyl]-1-oxo-2-isoquinolyl]acetic acid (0.024 g, 0.05 mmol) and 3-aminopyridine the title compound was obtained (22 mg, 81%) as a white solid. LCMS (ESI, M+H$^+$=548.4); $^1$H NMR δ ppm (d$_3$-MeOD; 2.32 (s, 3H) 3.55-3.66 (m, 1H) 3.66-3.85 (m, 3H) 3.97 (dd, J=9.59, 3.33 Hz, 1H) 4.08 (dd, J=3.13, 1.96 Hz, 1H) 4.96 (s, 2H) 5.46-5.63 (m, 1H) 6.77 (d, J=7.04 Hz, 1H) 7.27-7.44 (m, 2H) 7.46-7.58 (m, 2H) 7.73 (d, J=8.22 Hz, 1H) 7.88 (dd, J=8.61, 5.48 Hz, 1H) 8.00 (dd, J=8.22, 1.96 Hz, 1H) 8.42 (dd, J=8.61, 1.17 Hz, 1H) 8.49 (s, 2H) 9.18-9.29 (m, 1H)).

Example 11. 2-[7-[3-methyl-4-[(2R,3R,4S,5S,6S)-3,4,5-trihydroxy-6-(hydroxymethyl)tetrahydropyran-2-yl]oxy-phenyl]-1-oxo-2-isoquinolyl]-N-(4-pyridyl)acetamide Following a similar procedure to Example 10 using 4-aminopyridine the title compound was obtained (13.3 mg, 52%). LCMS (ESI, M+H$^+$=548.4); $^1$H NMR δ ppm (d$_3$-MeOD; 2.32 (s, 3H) 3.60 (ddd, J=9.78, 5.09, 2.74 Hz, 1H) 3.67-3.84 (m, 3H) 3.97 (dd, J=9.59, 3.33 Hz, 1H) 4.08 (dd, J=3.33, 1.76 Hz, 1H) 5.00 (s, 2H) 5.57 (d, J=1.57 Hz, 1H) 6.78 (d, J=7.43 Hz, 1H) 7.38 (d, J=8.61 Hz, 2H) 7.33 (d, J=8.61 Hz, 1H) 7.49-7.58 (m, 2H) 7.75 (d, J=8.22 Hz, 1H)

8.01 (dd, J=8.41, 2.15 Hz, 1H) 8.18 (m, J=7.04 Hz, 2H) 8.49 (d, J=1.96 Hz, 1H) 8.64 (m, J=7.43 Hz, 2H)).

Example 12. 2-[2-(4-methylpiperazin-1-yl)-2-oxo-ethyl]-7-[3-methyl-4-[(2R,3R,4S,5S,6S)-3,4,5-trihydroxy-6-(hydroxymethyl)tetrahydropyran-2-yl]oxy-phenyl]isoquinolin-1-one Following a similar procedure to Example 10 using 1-methylpiperazine the title compound was obtained (25.9 mg, 88%). LCMS (ESI, M+H$^+$=554.4); $^1$H NMR δ ppm (d$_3$-MeOD; 2.33 (s, 3H) 2.99 (s, 3H) 3.26 (dt, J=3.23, 1.71 Hz, 1H) 3.34-3.42 (m, 1H) 3.49 (dd, J=3.52, 1.57 Hz, 1H) 3.61 (ddd, J=9.78, 5.28, 2.54 Hz, 3H) 3.70-3.86 (m, 4H) 3.97 (dd, J=9.59, 3.33 Hz, 2H) 4.08 (dd, J=3.52, 1.96 Hz, 2H) 4.81 (s, 1H) 5.57 (d, J=1.96 Hz, 1H) 6.75 (d, J=7.43 Hz, 1H) 7.20-7.40 (m, 3H) 7.45-7.59 (m, 2H) 7.72 (d, J=8.22 Hz, 1H) 7.99 (dd, J=8.22, 1.96 Hz, 1H) 8.49 (d, J=1.96 Hz, 1H)).

Example 13. N-(2-aminoethyl)-2-[7-[3-methyl-4-[(2R,3R,4S,5S,6S)-3,4,5-trihydroy-6-(hydroxymethyl)tetrahydropyran-2-yl]oxy-phenyl]-1-oxo-2-isoquinolyl]acetamide Following a similar procedure to Example 10 using 1,2-diaminoethane the title compound was obtained (11.2 mg, 55%). LCMS (ESI, M+H$^+$=514.4); $^1$H NMR δ ppm (d$_3$-MeOD; 2.33 (s, 3H) 3.11 (t, J=5.67 Hz, 2H) 3.54 (t, J=5.67 Hz, 2H) 3.56-3.67 (m, 1H) 3.68-3.84 (m, 3H) 3.97 (dd, J=9.59, 3.33 Hz, 2H) 4.08 (dd, J=3.33, 1.76 Hz, 1H) 4.73 (s, 2H) 5.48-5.64 (m, 1H) 6.78 (d, J=7.43 Hz, 1H) 7.34 (d, J=7.83 Hz, 2H) 7.46-7.59 (m, 2H) 7.74 (d, J=8.22 Hz, 1H) 8.00 (dd, J=8.22, 1.96 Hz, 1H) 8.50 (s, 1H))

(Scheme VIII)

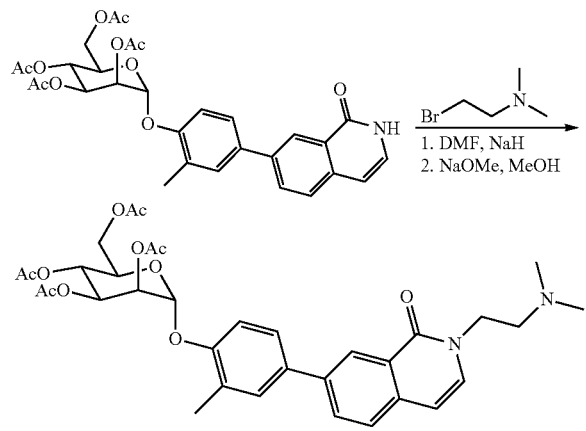

Example 14. 2-(2-dimethylaminoethyl)-7-[3-methyl-4-[(2R,3R,4S,5S,6S)-3,4,5-trihydroxy-6-(hydroxymethyl)tetrahydropyran-2-yl]oxy-phenyl]isoquinolin-1-one Following a similar procedure to Example 8 using [4,5-diacetoxy-6-(acetoxymethyl)-2-[2-methyl-4-(1-oxo-2H-isoquinolin-7-yl)phenoxy]tetrahydropyran-3-yl]acetate (0.1 mmol) and 2-bromo-N,N-dimethyl-ethanamine (0.1 mmol), the title compound was obtained (0.0426 g, 88%). LCMS (ESI, M+H+=485.4); $^1$H NMR δ ppm (d$_3$-MeOD; 2.33 (s, 3H) 3.05 (s, 6H) 3.52-3.67 (m, 3H) 3.68-3.84 (m, 3H) 3.97 (dd, J=9.39, 3.52 Hz, 1H) 4.08 (dd, J=3.33, 1.76 Hz, 1H) 4.46 (t, J=5.87 Hz, 2H) 5.47-5.64 (m, 1H) 6.80 (d, J=7.43 Hz, 1H) 7.38 (d, J=7.43 Hz, 1H) 7.34 (d, J=8.61 Hz, 1H) 7.47-7.59 (m, 2H) 7.73 (d, J=8.61 Hz, 1H) 8.01 (dd, J=8.41, 1.76 Hz, 1H) 8.49-8.60 (m, 1H)).

Example 15. 7-[3-methyl-4-[(2R,3R,4S,5S,6S)-3,4,5-trihydroxy-6-(hydroxymethyl)tetrahydropyran-2-yl]oxy-phenyl]-2-(4-pyridylmethyl)isoquinolin-1-one Following a similar procedure to Example 14 using 4-(bromomethyl)pyridine, the title compound was obtained (0.046 g, 92%). LCMS (ESI, M+H$^+$=505.4); $^1$H NMR δ ppm (d$_3$-MeOD; 2.32 (s, 3H) 3.53-3.66 (m, 1H) 3.67-3.83 (m, 3H) 3.96 (dd, J=9.59, 3.33 Hz, 1H) 4.07 (dd, J=3.13, 1.96 Hz, 1H) 5.52 (s, 2H) 5.56 (s, 1H) 6.84 (d, J=7.43 Hz, 1H) 7.33 (d, J=8.61 Hz, 1H) 7.44-7.57 (m, 3H) 7.70-7.86 (m, 3H) 8.02 (dd, J=8.22, 1.96 Hz, 1H) 8.49 (s, 1H) 8.73 (d, J=6.65 Hz, 2H)).

Example 16. 7-[3-methyl-4-[(2R,3R,4S,5S,6S)-3,4,5-trihydroxy-6-(hydroxymethyl)tetrahydropyran-2-yl]oxy-phenyl]-2-(3-pyridylmethyl)isoquinolin-1-one Following a similar procedure to Example 14 using 3-(bromomethyl)pyridine, the title compound was obtained (0.046 g, 92%). LCMS (ESI, M+H$^+$=505.4); $^1$H NMR δ ppm (d$_3$-MeOD; 2.32 (s, 3H) 3.51-3.66 (m, 1H) 3.66-3.85 (m, 3H) 3.97 (dd, J=9.59, 3.33 Hz, 1H) 4.08 (dd, J=3.13, 1.57 Hz, 1H) 5.42 (s, 2H) 5.56 (s, 1H) 6.80 (d, J=7.43 Hz, 1H) 7.33 (d, J=8.22 Hz, 1H) 7.43-7.61 (m, 3H) 7.72 (d, J=8.22 Hz, 1H) 7.89 (dd, J=8.02, 5.67 Hz, 1H) 7.99 (dd, J=8.41, 1.76 Hz, 1H) 8.42 (d, J=8.22 Hz, 1H) 8.46-8.54 (m, 1H) 8.71 (d, J=5.48 Hz, 1H) 8.86 (s, 1H)).

(Scheme IX)

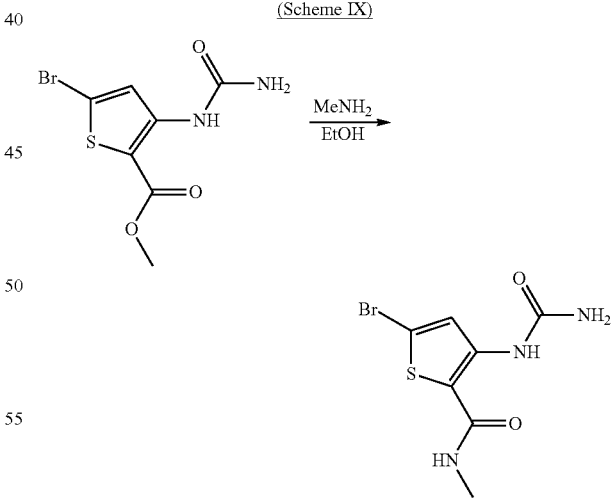

Example 17-SM. 5-bromo-N-methyl-3-ureido-thiophene-2-carboxamide

Methyl 5-bromo-3-ureido-thiophene-2-carboxylate (Han et. al., *J. Med. Chem.* 2012, 55, 3945-3959) (0.5 g) was stirred with 40 mL of 33% methylamine in EtOH overnight at RT. The solvent was removed in vacuo and the residue was triturated in CH$_2$Cl$_2$. The precipitate was filtered and dried to yield the title product as a white solid (0.26 g). LCMS (ESI, M+Na$^+$=300.1).

Example 17. N-methyl-5-[3-methyl-4-[(2R,3R,4S, 5S,6S)-3,4,5-trihydroxy-6-(hydroxymethyl)tetrahydropyran-2-yl]oxy-phenyl]-3-ureido-thiophene-2-carboxamide Synthesized in a similar manner to Example 7 using 5-bromo-N-methyl-3-ureido-thiophene-2-carboxamide to give the title compound as a white powder (19 mg). LCMS (ESI, M+H$^+$=468.3); $^1$H NMR δ ppm (d$_3$-MeOD; 2.27 (s, 3H) 2.87 (s, 3H) 3.52-3.61 (m, 1H) 3.76 (d, J=1.17 Hz, 3H) 3.91-3.99 (m, 1H) 4.03-4.09 (m, 1H) 5.56 (d, J=1.17 Hz, 1H) 7.27 (m, 1H) 7.47 (m, 2H) 8.06 (s, 1H)).

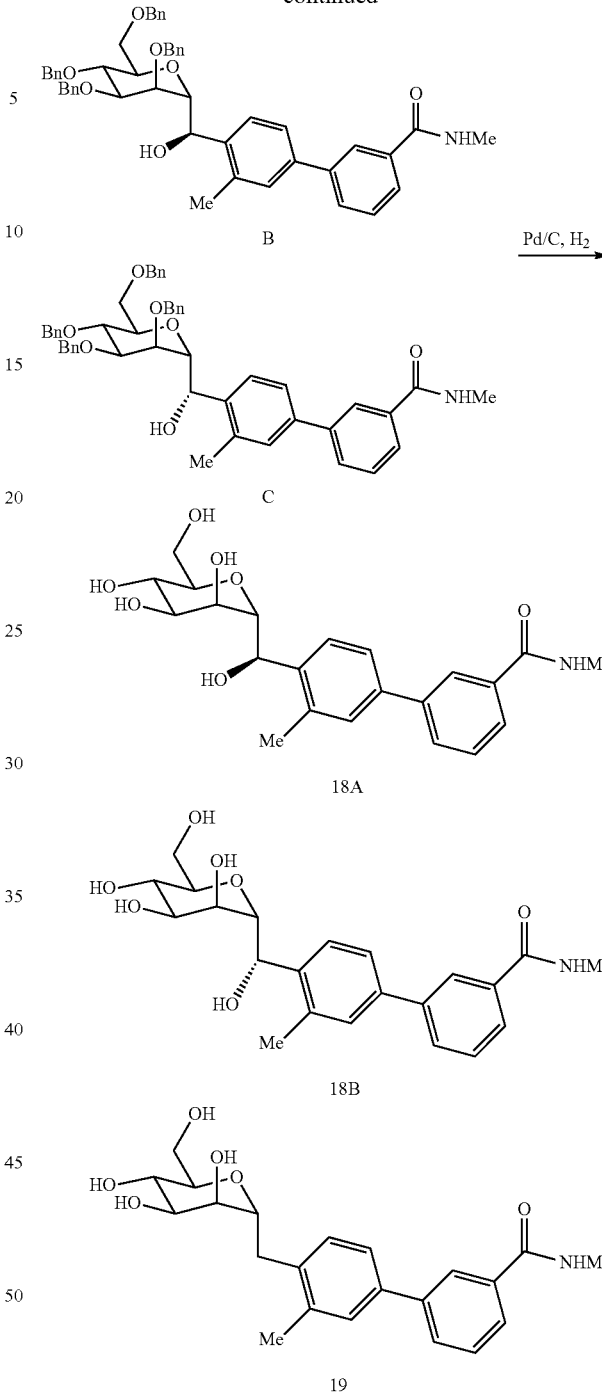

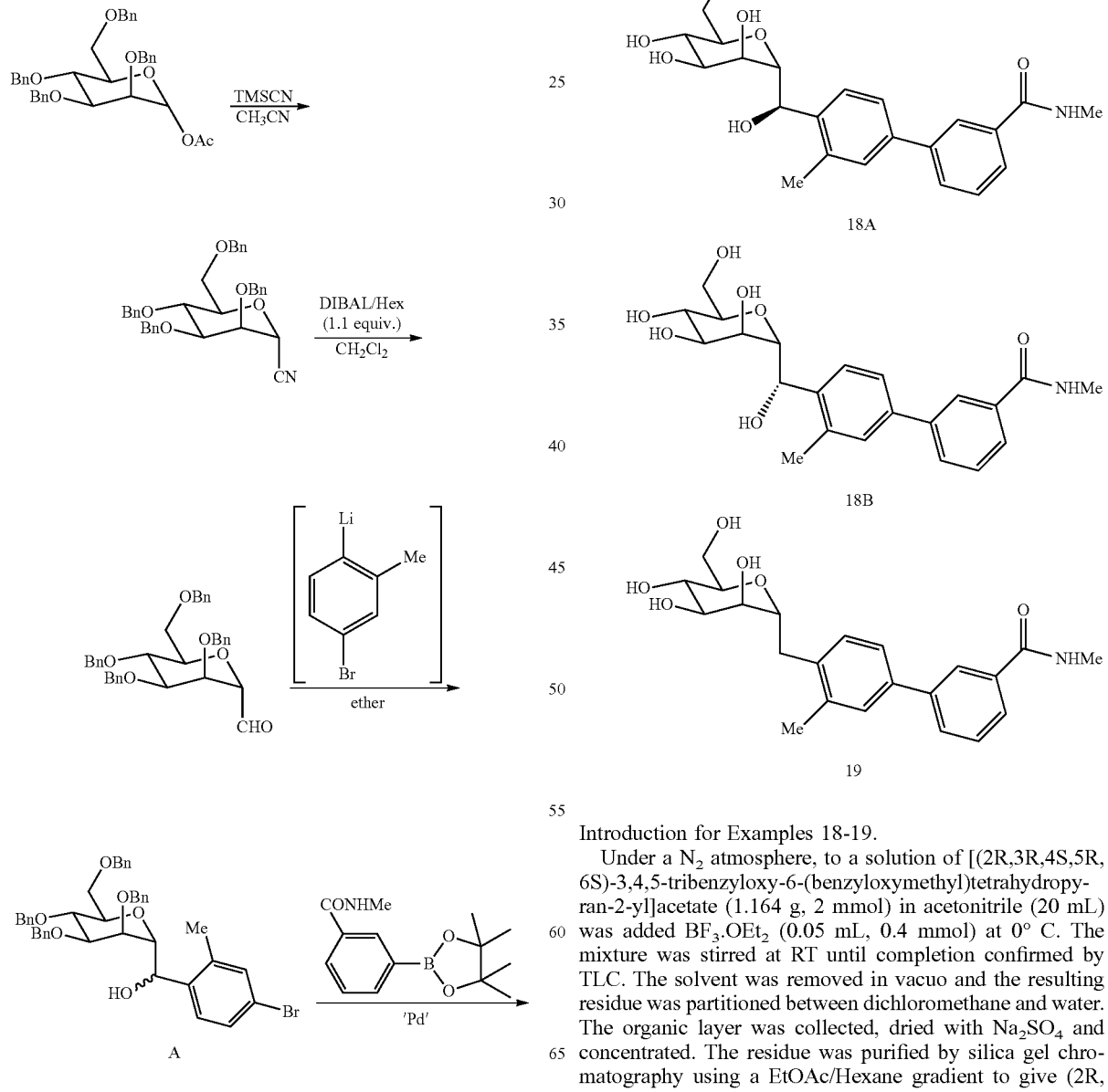

Introduction for Examples 18-19.

Under a N$_2$ atmosphere, to a solution of [(2R,3R,4S,5R,6S)-3,4,5-tribenzyloxy-6-(benzyloxymethyl)tetrahydropyran-2-yl]acetate (1.164 g, 2 mmol) in acetonitrile (20 mL) was added BF$_3$.OEt$_2$ (0.05 mL, 0.4 mmol) at 0° C. The mixture was stirred at RT until completion confirmed by TLC. The solvent was removed in vacuo and the resulting residue was partitioned between dichloromethane and water. The organic layer was collected, dried with Na$_2$SO$_4$ and concentrated. The residue was purified by silica gel chromatography using a EtOAc/Hexane gradient to give (2R, 3S,4R,5R,6S)-3,4,5-tribenzyloxy-6-(benzyloxymethyl)tetrahydropyran-2-carbonitrile (0.560 g) in 51% yield. MS (ESI): found [M+Na+], 572.2.

At −78° C., DIBAL/Hexanes (1.0 M, 0.52 mL) was added dropwise into the solution of (2R,3S,4R,5R,6S)-3,4,5-tribenzyloxy-6-(benzyloxymethyl)tetrahydropyran-2-carbonitrile (0.258 g, 0.47 mmol) in CH$_2$Cl$_2$ (5 mL). Then the mixture was warmed slowly to −40° C. over 1 h. 0.5 N HCl aqueous was used to quench the reaction and EtOAc was used for extraction. The organic layer was collected, dried with Na$_2$SO$_4$ and concentrated to give (2S,3R,4S,5R,6S)-3,4,5-tribenzyloxy-6-(benzyloxymethyl)tetrahydropyran-2-carbaldehyde (0.235 g) as crude product for the next step without further purification. Into another flask containing 5-bromo-2-iodotoluene (0.42 mL, 3.0 mmol) in ether (5 mL) was added BuLi/Hexanes (2.5 M, 1.0 mL) at −78° C. One hour later, (2S,3R,4S,5R,6S)-3,4,5-tribenzyloxy-6-(benzyloxymethyl)tetrahydropyran-2-carbaldehyde (0.235 g) was added. The mixture was warmed slowly to −20° C. over 1 h 40 min. 0.5 N HCl aqueous was used to quench the reaction and EtOAc was use for extraction. The organic layer was collected, dried with Na$_2$SO$_4$ and concentrated. The resulting residue was purified by silica gel chromatography with a EtOAct/Hexane gradient as eluent to give (4-bromo-2-methyl-phenyl)-[(2R,3R,4S,5R,6S)-3,4,5-tribenzyloxy-6-(benzyloxymethyl)tetrahydropyran-2-yl]methanol (A), (0.130 g) in 38% yield. MS (ESI): found [M+Na+], 745.4.

Under nitrogen atmosphere, the mixture of A (0.130 g, 0.18 mmol), N-methyl-3-(4,4,5,5-tetramethyl-[1,3,2]dioxaborolan-2-yl)-benzamide (0.071 g, 0.27 mmol), cesium carbonate (0.176 g, 0.54 mmol) and tetrakis(triphenylphosphine)palladium (0.021 g, 0.018 mmol) in dioxane/water (5 mL/1 mL) was heated at 80° C. with stirring for 1 h. The solvent was removed and the resulting residue was purified by silica gel chromatography to give 3-[4-[(R)-hydroxy-[(2R,3R,4S,5R,6S)-3,4,5-tribenzyloxy-6-(benzyloxymethyl)tetrahydropyran-2-yl]methyl]-3-methyl-phenyl]-N-methyl-benzamide (B), (0.046 g) and 3-[4-[(S)-hydroxy-[(2R,3R,4S,5R,6S)-3,4,5-tribenzyloxy-6-(benzyloxymethyl)tetrahydropyran-2-yl]methyl]-3-methyl-phenyl]-N-methyl-benzamide (C), (0.055 g). MS (ESI): found [M+Na+], 800.6.

A mixture of intermediate B (0.046 g, 0.059 mmol) and Pd/C (10 wt %) (0.050 g, 0.024 mmol) in MeOH (5 mL) was stirred under H2 atmosphere overnight. Pd/C was filtered off and the filtrate was concentrated in vacuo. The resulting residue was purified by purified by HPLC (C18, 15*150 mm column; eluent: acetonitrile/water (0.05% TFA) to give Example 18A (0.020 g) in 81% yield. Example 19 was also isolated as a product (0.0030 g). Following the same procedure for Intermediate B, Intermediate C was converted to Example 18B and 19 in the same fashion.

Example 18A*. 3-[4-[(R)-hydroxy-[(2R,3R,4S5S,6S)-3,4,5-trihydroxy-6-(hydroxymethyl)tetrahydropyran-2-yl]methyl]-3-methyl-phenyl]-N-methyl-benzamide LCMS (ESI, M+Na$^+$=440.3); $^1$H NMR δ ppm (d$_3$-MeOD; 2.51 (s, 3H) 2.95 (s, 3H) 3.57-3.78 (m, 4H) 4.00-4.07 (m, 1H) 4.10 (dd, J=6.85, 2.54 Hz, 1H) 4.25 (t, J=2.93 Hz, 1H) 5.24 (d, J=6.65 Hz, 1H) 7.45-7.57 (m, 3H) 7.62 (d, J=8.22 Hz, 1H) 7.71-7.83 (m, 2H) 8.07 (t, J=1.56 Hz, 1H)).

Example 18B*. 3-[4-[(S)-hydroxy-[2R,3R,4S,5S,6S)-3,4,5-trihydroxy-6-(hydroxymethyl)tetrahydropyran-2-yl]methyl]-3-methyl-phenyl]-N-methyl-benzamide LCMS (ESI, M+Na$^+$=440.3); $^1$H NMR δ ppm (d$_3$-MeOD; 2.51 (s, 3H) 2.95 (s, 3H) 3.56 (dd, J=1.00 Hz, 1H) 3.67 (m, 1H) 3.70-3.82 (m, 3H) 3.91 (m, 1H) 4.10 (dd, J=9.00, 1.96 Hz, 1H) 5.28 (d, J=8.61 Hz, 1H) 7.34-7.63 (m, 4H) 7.69-7.90 (m, 2H) 8.07 (s, 1H)).

*Note: the assignment of the R stereochemistry for 18A and S stereochemistry for 18B is only arbitrary and tentatively assigned by but not confirmed.

Example 19. N-methyl-3-[3-methyl-4-[[(2R,3R,4R,5S,6S)-3,4,5-trihydroxy-6-(hydroxymethyl)tetrahydropyran-2-yl]methyl]phenyl]benzamide LCMS (ESI, M+H$^+$=402.3); $^1$H NMR δ ppm (d$_3$-MeOD; 2.44 (s, 3H) 2.95 (s, 3H) 3.04 (d, J=7.43 Hz, 2H) 3.69 (m, 3H) 3.83 (m, 2H) 3.86-3.92 (m, 1H) 4.04-4.21 (m, 1H) 7.31 (d, J=7.83 Hz, 1H) 7.42-7.47 (m, 1H) 7.50 (m, 2H) 7.75 (m, 2H) 8.05 (s, 1H)).

Example 20. [(2S,3R,4S,5R,6R)-3,4,5-triacetoxy-6-[2-methyl-4-[3-(methylcarbamoyl)phenyl]phenoxy]tetrahydropyran-2-yl]methyl acetate N-methyl-3-[3-methyl-4-[(2R,3R,4S,5S,6S)-3,4,5-trihydroxy-6-(hydroxymethyl)tetrahydropyran-2-yl]oxy-phenyl]benzamide (Han et. al., J. Med. Chem. 2012, 55, 3945-3959), (0.072 g, 0.178 mmol) was dissolved in anhydrous pyridine (1 mL) and acetic anhydride (1 mL). The solvent was removed in vacuo and the residue purified by reversed phase HPLC (5-95% acetonitrile/water/0.05% TFA). Pure fractions were combined and lyophilized to give the title compound as a white powder (0.063 g). LCMS (ESI, M+Na$^+$=594.3); $^1$H NMR δ ppm (d$_6$-DMSO; 1.94 (s, 3H) 2.00 (s, 3H) 2.05 (s, 3H) 2.16 (s, 3H) 2.32 (s, 3H) 2.81 (d, J=4.30 Hz, 3H) 3.93-4.11 (m, 2H) 4.19 (dd, J=12.13, 5.09 Hz, 1H) 5.22 (t, J=9.98 Hz, 1H) 5.33-5.45 (m, 2H) 5.80 (s, 1H) 7.23 (d, J=8.61 Hz, 1H) 7.46-7.65 (m, 3H) 7.77 (d, J=7.83 Hz, 2H) 8.07 (s, 1H) 8.54 (d, J=4.30 Hz, 1H)).

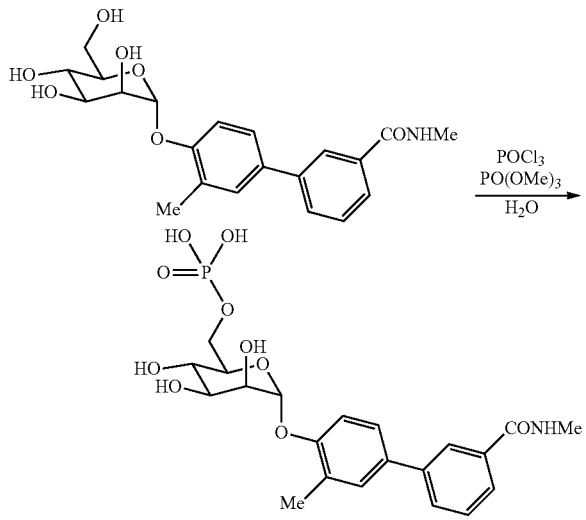

(Scheme XI)

Example 21. [(2S,3S,4S,5R,6R)-3,4,5-trihydroxy-6-[2-methyl-4-[3-(methylcarbamoyl)phenyl]phenoxy]tetrahydropyan-2-yl]methyl dihydrogen phosphate N-methyl-3-[3-methyl-4-[(2R,3R,4S,5S,6S)-3,4,5-trihydroxy-6-(hydroxymethyl)tetrahydropyran-2-yl]oxy-phenyl]benzamide (Han et. al., *J. Med. Chem.* 2012, 55, 3945-

3959), (0.20 g, 0.5 mmol) was dissolved in trimethyl phosphate (5 mL) and water (9 uL, 0.5 mmol). The reaction was cooled to 0° C. and then phosphoryl trichloride (142 uL, 1.5 mmol) was slowly added and then stirred for 3 h at 0° C. The reaction was neutralized by adding crushed ice and then conc. ammonia. The solvent was removed in vacuo and the residue purified by reversed phase HPLC (5-95% acetonitrile/water/0.05% TFA). Pure fractions were combined and lyophilized to give the title compound as a white powder (0.070 g). LCMS (ESI, M+H$^+$=484.3); $^1$H NMR δ ppm (d$_6$-DMSO; 2.26 (s, 3H) 2.81 (d, J=4.70 Hz, 3H) 3.42-3.68 (m, 3H) 3.75 (dd, J=9.00, 3.13 Hz, 1H) 3.86-3.97 (m, 2H) 4.03 (dd, J=9.78, 5.87 Hz, 1H) 5.45 (d, J=1.96 Hz, 1H) 7.24 (d, J=8.61 Hz, 1H) 7.43-7.60 (m, 3H) 7.76 (dd, J=7.43, 1.57 Hz, 2H) 8.06 (s, 1H) 8.56 (d, J=4.30 Hz, 1H)).

trated. To the resulting residue, acetone (1 mL) and MeOH (1.5 mL) was added. Then the mixture was cooled at 0° C. while AcOH (0.055 mL, 0.96 mmol) was added. The mixture was stirred at RT for 9 h, then NaHCO$_3$ (0.16 g, 1.9 mmol) was added. The solvents were removed. The resulting residue was purified by silica gel chromatography with a EtOAc/Hexanes gradient as eluent to give 3-[4-[(2R,3R,4S,5R,6S)-6-(hydroxymethyl)-3,4,5-tris(trimethylsilyloxy)tetrahydropyran-2-yl]oxy-3-methyl-phenyl]-N-methyl-benzamide (D), (0.190 g) in 61% yield. Into the mixture of N,N'-dimethylglycine hydrochloride (0.0154, 0.11 mmol), DMAP (0.0024 g, 0.02 mmol), $^i$Pr$_2$NEt (0.035 mL, 0.2 mmol) and intermediate D (0.062 g, 0.1 mmol) in dichloromethane (2 mL) was added N,N'-diisopropylcarbodiimide (0.02 mL, 0.13 mmol). The mixture was stirred overnight at

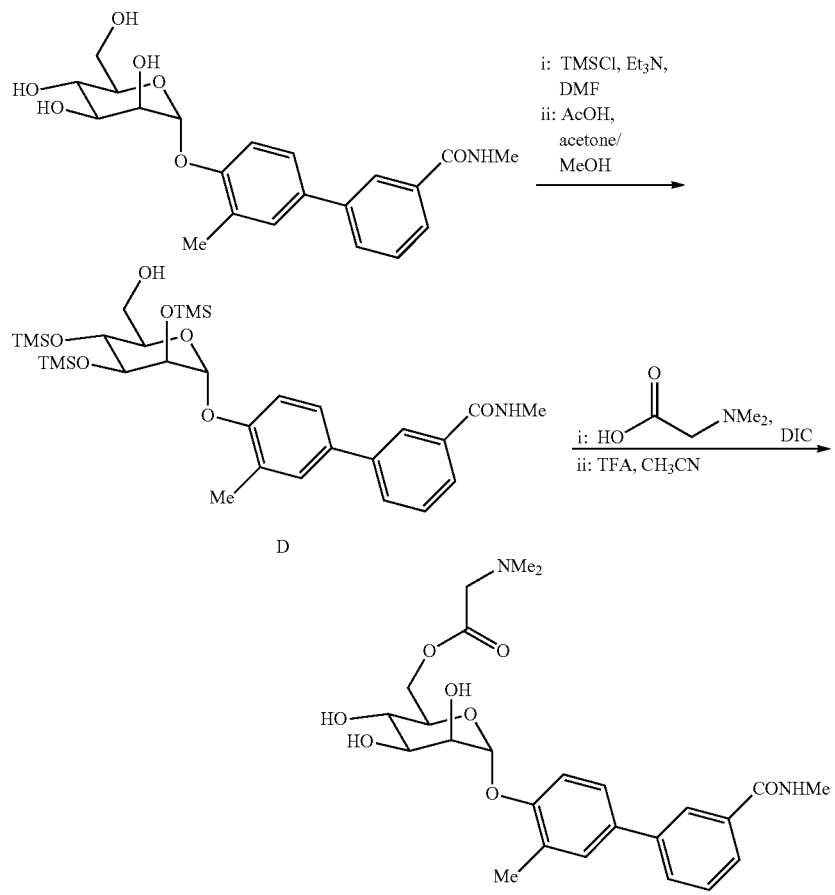

(Scheme XII)

D

Example 22. [(2S,3S,4S,5R,6R)-3,4,5-trihydroxy-6-[2-methyl-4-[3-(methylcarbamoyl)phenyl]phenoxy]tetrahydropyran-2-yl]methyl 2-dimethylaminoacetate At 0° C. TMSCl (0.35 mL, 2.75 mmol) was added slowly into the solution of N-methyl-3-[3-methyl-4-[(2R,3R,4S,5S,6S)-3,4,5-trihydroxy-6-(hydroxymethyl)tetrahydropyran-2-yl]oxy-phenyl]benzamide (Han et. al., *J. Med. Chem.* 2012, 55, 3945-3959), (0.202 g, 0.5 mmol) and Et$_3$N (0.38 mL, 2.75 mmol) in DMF (2 mL). The mixture was stirred at RT for 3.5 h, then partitioned between EtOAc and water. The organic layer was collected, dried with Na$_2$SO$_4$ and concen- RT. The solvent was removed and the resulting residue was dissolved in acetonitrile (3 mL).

Then trifluoroacetic acid (0.08 mL) was added at 0° C. The mixture was stirred for 2 h at 0° C. The solvent was removed and the resulting residue was purified by HPLC (C18, 15*50 mm column; eluent: acetonitrile/water (0.05% TFA) to give the title compound (0.015 g) in 31% yield. LCMS (ESI, M+H$^+$=489.4); $^1$H NMR δ ppm (d$_3$-MeOD; 2.32 (s, 3H) 2.89 (s, 6H) 2.95 (s, 3H) 3.71-3.85 (m, 2H) 3.94-4.00 (m, 1H) 4.06 (d, J=5.48 Hz, 2H) 4.11 (t, J=2.54 Hz, 1H) 4.42 (m, 1H) 4.61 (dd, J=11.74, 1.56 Hz, 1H) 5.57 (d, J=1.57 Hz, 1H) 7.23 (d, J=8.61 Hz, 1H) 7.34-7.61 (m, 3H) 7.66-7.88 (m, 2H) 7.99-8.17 (m, 1H)).

TABLE 1

*Structural, analytical and biological data for Examples 1-22.*

| Ex. | Cmpnd Name | Structure | IUPAC Name | HAI Titer EC$_{>90}$ (μM) | Molecular Formula | MS (ESI, M + H$^+$) | $^1$H NMR δ ppm (d$_3$-MeOD unless otherwise noted) |
|---|---|---|---|---|---|---|---|
| 1 | 1CJ84 | 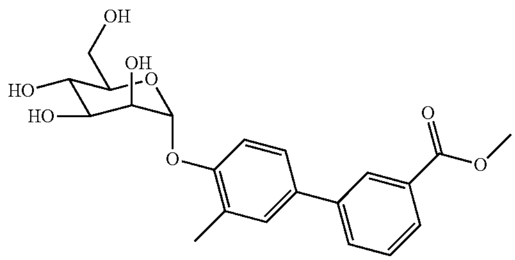 [SMILES: COC(=O)c1cccc(-c2ccc(OC3OC(CO)C(O)C(O)C3O)c(C)c2)c1] | methyl 3-[3-methyl-4-[(2R,3R,4S,5S,6S)-3,4,5-trihydroxy-6-(hydroxymethyl)tetrahydropyran-2-yl]oxyphenyl]benzoate | 0.12 | C21H24O8 | 427.3 (M + Na$^+$) | 8.20 (t, J = 1.51 Hz, 1H), 7.94 (td, J = 1.41, 7.90 Hz, 1H), 7.77-7.87 (m, 1H), 7.52 (t, J = 7.55 Hz, 1H), 7.39-7.48 (m, 2H), 7.27-7.38 (m, 1H), 5.56 (d, J = 1.65 Hz, 1H), 4.08 (dd, J = 1.92, 3.30 Hz, 1H), 3.94-4.01 (m, 1H), 3.90-3.94 (m, 3H), 3.68-3.83 (m, 3H), 3.55-3.65 (m, 1H), 2.31 (s, 3H). |
| 2 | 1CJ85 | 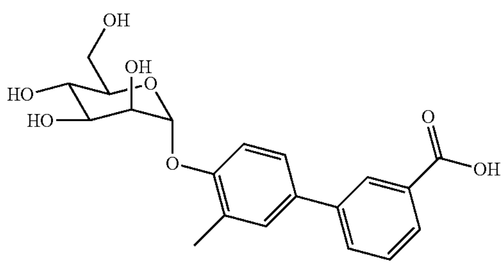 [SMILES: Cc1cc(-c2cccc(C(=O)O)c2)ccc1OC1OC(CO)C(O)C(O)C1O] | 3-[3-methyl-4-[(2R,3R,4S,5S,6S)-3,4,5-trihydroxy-6-(hydroxymethyl)tetrahydropyran-2-yl]oxyphenyl]benzoic acid | | C20H22O8 | 413.3 (M + Na$^+$) | 2.31 (s, 3 H) 3.61 (ddd, J = 9.78, 5.09, 2.74 Hz, 1 H) 3.69-3.84 (m, 3 H) 3.97 (dd, J = 9.39, 3.52 Hz, 1 H) 4.08 (dd, J = 3.33, 1.76 Hz, 1 H) 5.56 (d, J = 1.96 Hz, 1 H) 7.31 (d, J = 8.22 Hz, 1 H) 7.39-7.48 (m, 2 H) 7.51 (t, J = 7.83 Hz, 1 H) 7.76-7.84 (m, 1 H) 7.95 (dt, J = 7.83, 1.37 Hz, 1 H) 8.21 (t, J = 1.76 Hz, 1 H) |
| 3 | 1CJ86 | 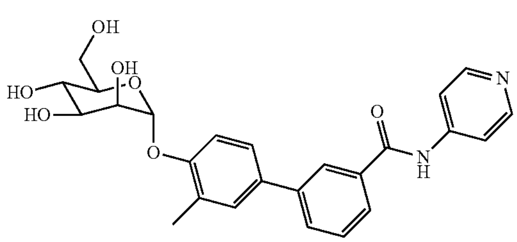 [SMILES: Cc1cc(-c2cccc(C(=O)Nc3ccncc3)c2)ccc1OC1OC(CO)C(O)C(O)C1O] | 3-[3-methyl-4-[(2R,3R,4S,5S,6S)-3,4,5-trihydroxy-6-(hydroxymethyl)tetrahydropyran-2-yl]oxyphenyl]-N-(4- | 0.064 | C25H26N2O7 | 467.3 | 2.34 (s, 3 H) 3.60 (ddd, J = 9.78, 5.28, 2.54 Hz, 1 H) 3.68-3.85 (m, 3 H) 3.98 (dd, J = 9.59, 3.33 Hz, 1 H) 4.09 (dd, J = 3.33, 1.76 Hz, 1 H) 5.58 |

TABLE 1-continued

Structural, analytical and biological data for Examples 1-22.

| Ex. | Cmpnd Name | Structure | IUPAC Name | HAI Titer EC$_{>90}$ (μM) | Molecular Formula | MS (ESI, M + H$^+$) | $^1$H NMR δ ppm (d$_3$-MeOD unless otherwise noted) |
|---|---|---|---|---|---|---|---|
| | | | pyridyl) benzamide | | | | (d, J = 1.57 Hz, 1 H) 7.34 (d, J = 8.61 Hz, 1 H) 7.44-7.58 (m, 2 H) 7.63 (t, J = 7.63 Hz, 1 H) 7.84-8.00 (m, 2 H) 8.19-8.27 (m, 1 H) 8.37-8.45 (m, 2 H) 8.62-8.72 (m, 2 H) |
| 4 | 1CJ87 | 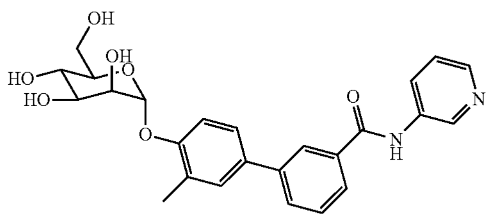 [SMILES: Cc1cc(-c2cccc(C(=O)Nc3cccnc3)c2)ccc1OC1OC(CO)C(O)C(O)C1O] | 3-[3-methyl-4-[(2R,3R,4S,5S,6S)-3,4,5-trihydroxy-6-(hydroxymethyl) tetrahydropyran-2-yl]oxy-phenyl]-N-(3-pyridyl) benzamide | 0.032 | C25H26N2O7 | 467.3 | 2.33 (s, 3 H) 3.61 (m, 1 H) 3.76 (m, 3 H) 3.97 (d, J = 9.39 Hz, 1 H) 4.08 (m, 1 H) 5.57 (d, 1 H) 7.33 (d, J = 6.26 Hz, 1 H) 7.43-7.56 (m, 2 H) 7.61 (m, 1 H) 7.85 (m, 1 H) 7.94 (m, 2 H) 8.22 (m, 1 H) 8.55 (m, 1 H) 8.66 (d, J = 6.26 Hz, 1 H) 9.47 (m, 1 H) |
| 5 | 1JWJ245 | 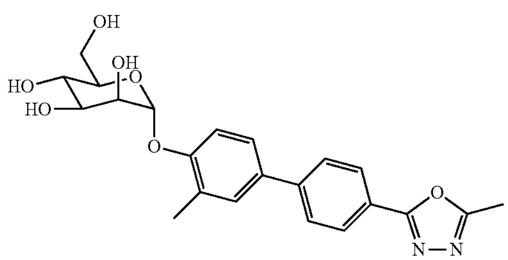 [SMILES: Cc1nnc(-c2ccc(-c3ccc(OC4OC(CO)C(O)C(O)C4O)c(C)c3)cc2)o1] | (2S,3S,4S,5R,6R)-2-(hydroxymethyl)-6-[2-methyl-4-[4-(5-methyl-1,3,4-oxadiazol-2-yl)phenyl] phenoxy] tetrahydropyran-3,4,5-triol | 0.062 | C22H24N2O7 | 429.3 | 2.28 (s, 3 H) 2.63 (s, 3 H) 3.53-3.65 (m, 1 H) 3.70-3.88 (m, 3 H) 3.98 (dd, J = 9.59, 3.33 Hz, 1 H) 4.09 (dd, J = 3.13, 1.96 Hz, 1 H) 5.57 (d, J = 1.17 Hz, 1 H) 7.24 (d, J = 8.22 Hz, 1 H) 7.38-7.45 (m, 2 H) 7.48 (s, 1 H) 7.69 (m, J = 8.61 Hz, 1.5 H) 8.02 (m, J = 8.22 Hz, 1.5 H) |

TABLE 1-continued

Structural, analytical and biological data for Examples 1-22.

| Ex. | Cmpnd Name | Structure | IUPAC Name | HAI Titer EC$_{>90}$ (μM) | Molecular Formula | MS (ESI, M + H$^+$) | $^1$H NMR δ ppm (d$_3$-MeOD unless otherwise noted) |
|---|---|---|---|---|---|---|---|
| 6 | 1JWJ244 | 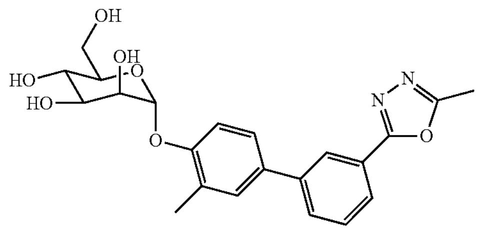 [SMILES: Cc1nnc(-c2cccc(-c3ccc(OC4OC(CO)C(O)C(O)C4O)c(C)c3)c2)o1] | (2S,3S,4S,5R,6R)-2-(hydroxymethyl)-6-[2-methyl-4-[3-(5-methyl-1,3,4-oxadiazol-2-yl)phenyl]phenoxy]tetrahydropyran-3,4,5-triol | 0.062 | C22H24N2O7 | 429.3 | 2.08 (s, 1.5 H) 2.32 (s, 1.5 H) 2.33 (s, 1.5 H) 2.65 (s, 1.5 H) 3.55-3.65 (m, 1 H) 3.69-3.83 (m, 3 H) 3.98 (dt, J = 9.49, 2.69 Hz, 1 H) 4.06-4.12 (m, 1 H) 5.54-5.60 (m, 1 H) 7.27-7.38 (m, 1 H) 7.44-7.65 (m, 3 H) 7.75-7.98 (m, 2 H) 8.07-8.25 (m, 1 H) |
| 7 | 5ZFH254 | 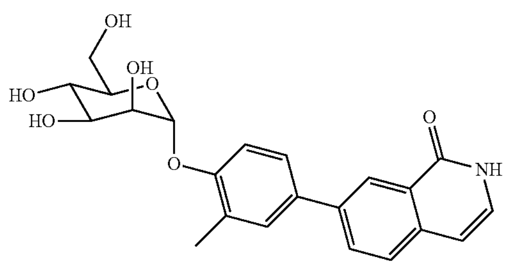 [SMILES: Cc1cc(-c2ccc3cc[nH]c(=O)c3c2)ccc1OC1OC(CO)C(O)C(O)C1O] | 7-[3-methyl-4-[(2R,3R,4S,5S,6S)-3,4,5-trihydroxy-6-(hydroxymethyl)tetrahydropyran-2-yl]oxy-phenyl]-2H-isoquinolin-1-one | 0.030 | C22H23NO7 | 414.3 | 2.32 (s, 3 H) 3.57-3.67 (m, 1 H) 3.70-3.85 (m, 3 H) 3.94-4.02 (m, 1 H) 4.05-4.13 (m, 1 H) 5.57 (d, J = 1.57 Hz, 1 H) 6.70 (d, J = 7.00 Hz, 1 H) 7.17 (d, J = 7.04 Hz, 1 H) 7.33 (d, J = 8.22 Hz, 1 H) 7.54 (s, 2 H) 7.70 (d, J = 8.61 Hz, 1 H) 7.89-8.04 (m, 1 H) 8.49 (d, J = 1.96 Hz, 1 H) |
| 8 | 1CJ74 | 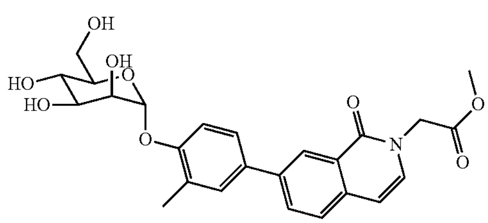 [SMILES: COC(=O)Cn1ccc2ccc(-c3ccc(OC4OC(CO)C(O)C(O)C4O)c(C)c3)cc2c1=O] | methyl 2-[7-[3-methyl-4-[(2R,3R,4S,5S,6S)-3,4,5-trihydroxy-6-(hydroxymethyl)tetrahydropyran-2-yl]oxy-phenyl]-1-oxo-2-isoquinolyl]acetate | 0.006 | C25H27NO9 | 486.3 | 2.32 (s, 3 H) 3.61 (ddd, J = 9.68, 4.99, 2.54 Hz, 1 H) 3.68-3.85 (m, 3 H) 3.78 (s, 3H) 3.98 (dd, J = 9.59, 3.33 Hz, 1 H) 4.04-4.14 (m, 1 H) 4.82 (s, 2 H) 5.53-5.62 (m, 1 H) 6.72 (d, J = 7.04 Hz, 1 H) 7.32 (dd, J = 7.83, 3.91 Hz, 2 H) 7.44-7.58 (m, 2 H) 7.70 (d, J = 8.22 Hz, 1 H) 7.97 (dd, J = 8.22, 1.96 Hz, 1 H) 8.43-8.49 (m, 1 H) |

TABLE 1-continued

Structural, analytical and biological data for Examples 1-22.

| Ex. | Cmpnd Name | Structure | IUPAC Name | HAI Titer EC$_{>90}$ (μM) | Molecular Formula | MS (ESI, M + H$^+$) | $^1$H NMR δ ppm (d$_3$-MeOD unless otherwise noted) |
|---|---|---|---|---|---|---|---|
| 9 | 1CJ72B | 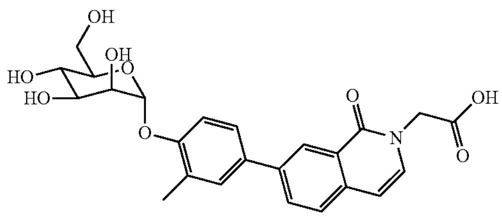 [SMILES: Cc1cc(-c2ccc3ccn(CC(=O)O)c(=O)c3c2)ccc1OC1OC(CO)C(O)C(O)C1O] | 2-[7-[3-methyl-4-[(2R,3R,4S,5S,6S)-3,4,5-trihydroxy-6-(hydroxymethyl)tetrahydropyran-2-yl]oxyphenyl]-1-oxo-2-isoquinolyl]acetic acid | 0.016 | C24H25NO9 | 472.3 | 2.32 (s, 3 H) 3.61 (ddd, J = 9.59, 5.28, 2.35 Hz, 1 H) 3.67-3.86 (m, 3 H) 3.98 (dd, J = 9.59, 3.33 Hz, 1 H) 4.08 (dd, J = 3.33, 1.76 Hz, 1 H) 4.79 (s, 2 H) 5.50-5.62 (m, 1 H) 6.72 (d, J = 7.43 Hz, 1 H) 7.32 (dd, J = 8.02, 2.93 Hz, 2 H) 7.44-7.59 (m, 2 H) 7.70 (d, J = 8.22 Hz, 1 H) 7.97 (dd, J = 8.22, 1.96 Hz, 1 H) 8.44-8.55 (m, 1 H) |
| 10 | 1CJ75 | 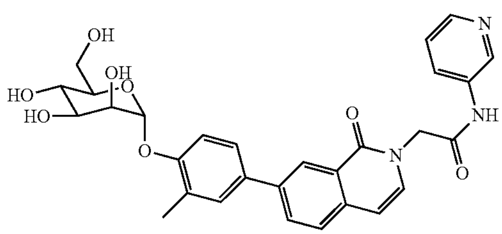 [SMILES: Cc1cc(-c2ccc3ccn(CC(=O)Nc4cccnc4)c(=O)c3c2)ccc1OC1OC(CO)C(O)C(O)C1O] | 2-[7-[3-methyl-4-[(2R,3R,4S,5S,6S)-3,4,5-trihydroxy-6-(hydroxymethyl)tetrahydropyran-2-yl]oxyphenyl]-1-oxo-2-isoquinolyl]-N-(3-pyridyl)acetamide | 0.001 | C29H29N3O8 | 548.4 | 2.32 (s, 3 H) 3.55-3.66 (m, 1 H) 3.66-3.85 (m, 3 H) 3.97 (dd, J = 9.59, 3.33 Hz, 1 H) 4.08 (dd, J = 3.13, 1.96 Hz, 1 H) 4.96 (s, 2 H) 5.46-5.63 (m, 1 H) 6.77 (d, J = 7.04 Hz, 1 H) 7.27-7.44 (m, 2 H) 7.46-7.58 (m, 2 H) 7.73 (d, J = 8.22 Hz, 1 H) 7.88 (dd, J = 8.61, 5.48 Hz, 1 H) 8.00 (dd, J = 8.22, 1.96 Hz, 1 H) 8.42 (dd, J = 8.61, 1.17 Hz, 1 H) 8.49 (s, 2 H) 9.18-9.29 (m, 1 H) |

TABLE 1-continued

Structural, analytical and biological data for Examples 1-22.

| Ex. | Cmpnd Name | Structure | IUPAC Name | HAI Titer EC$_{>90}$ (μM) | Molecular Formula | MS (ESI, M + H$^+$) | $^1$H NMR δ ppm (d$_3$-MeOD unless otherwise noted) |
|---|---|---|---|---|---|---|---|
| 11 | 1CJ81 | 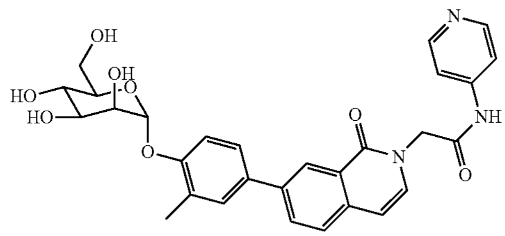 [SMILES: Cc1cc(-c2ccc3ccn(CC(=O)Nc4ccncc4)c(=O)c3c2)ccc1OC1OC(CO)C(O)C(O)C1O] | 2-[7-[3-methyl-4-[(2R,3R,4S,5S,6S)-3,4,5-trihydroxy-6-(hydroxymethyl)tetrahydropyran-2-yl]oxyphenyl]-1-oxo-2-isoquinolyl]-N-(4-pyridyl)acetamide | 0.001 | C29H29N3O8 | 548.4 | 2.32 (s, 3 H) 3.60 (ddd, J = 9.78, 5.09, 2.74 Hz, 1 H) 3.67-3.84 (m, 3 H) 3.97 (dd, J = 9.59, 3.33 Hz, 1 H) 4.08 (dd, J = 3.33, 1.76 Hz, 1 H) 5.00 (s, 2 H) 5.57 (d, J = 1.57 Hz, 1 H) 6.78 (d, J = 7.43 Hz, 1 H) 7.38 (d, J = 7.43 Hz, 2 H) 7.33 (d, J = 8.61 Hz, 1 H) 7.49-7.58 (m, 2 H) 7.75 (d, J = 8.22 Hz, 1 H) 8.01 (dd, J = 8.41, 2.15 Hz, 1 H) 8.18 (m, J = 7.04 Hz, 2 H) 8.49 (d, J = 1.96 Hz, 1 H) 8.64 (m, J = 7.43 Hz, 2 H) |
| 12 | 1CJ82 | 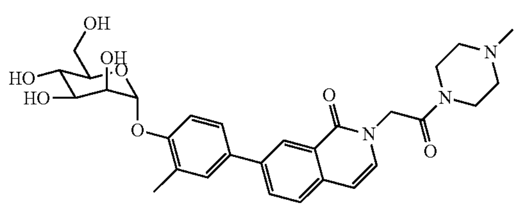 [SMILES: Cc1cc(-c2ccc3ccn(CC(=O)N4CCN(C)CC4)c(=O)c3c2)ccc1OC1OC(CO)C(O)C(O)C1O] | 2-[2-(4-methyl-piperazin-1-yl)-2-oxo-ethyl]-7-[3-methyl-4-[(2R,3R,4S,5S,6S)-3,4,5-trihydroxy-6-(hydroxymethyl)tetrahydropyran-2-yl]oxyphenyl]isoquinolin-1-one | 0.008 | C29H35N3O8 | 554.4 | 2.33 (s, 3 H) 2.99 (s, 3 H) 3.26 (dt, J = 3.23, 1.71 Hz, 1 H) 3.34-3.42 (m, 1 H) 3.49 (dd, J = 3.52, 1.57 Hz, 1 H) 3.61 (ddd, J = 9.78, 5.28, 2.54 Hz, 3 H) 3.70-3.86 (m, 4 H) 3.97 (dd, J = 9.59, 3.33 Hz, 2 H) 4.08 (dd, J = 3.52, 1.96 Hz, 2 H) 4.81 (s, 1 H) 5.57 (d, J = 1.96 Hz, 1 H) 6.75 (d, J = 7.43 Hz, 1 H) 7.20-7.40 (m, 3 H) 7.45-7.59 (m, 2 H) 7.72 (d, J = 8.22 Hz, 1 H) 7.99 (dd, J = 8.22, 1.96 Hz, 1 H) 8.49 (d, J = 1.96 Hz, 1 H) |

TABLE 1-continued

Structural, analytical and biological data for Examples 1-22.

| Ex. | Cmpnd Name | Structure | IUPAC Name | HAI Titer EC$_{>90}$ (μM) | Molecular Formula | MS (ESI, M + H$^+$) | $^1$H NMR δ ppm (d$_3$-MeOD unless otherwise noted) |
|---|---|---|---|---|---|---|---|
| 13 | 1CJ76 | 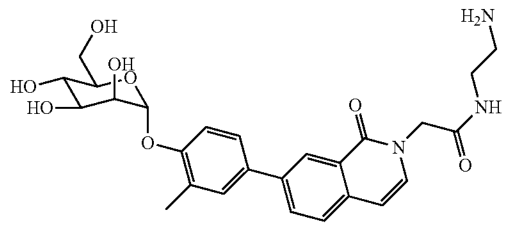 [SMILES: Cc1cc(-c2ccc3ccn(CC(=O)NCCN)c(=O)c3c2)ccc1OC1OC(CO)C(O)C(O)C1O] | N-(2-aminoethyl)-2-[7-[3-methyl-4-[(2R,3R,4S,5S,6S)-3,4,5-trihydroxy-6-(hydroxymethyl)tetrahydropyran-2-yl]oxyphenyl]-1-oxo-2-isoquinolyl]acetamide | 0.016 | C26H31N3O8 | 514.4 | 2.33 (s, 3 H) 3.11 (t, J = 5.67 Hz, 2 H) 3.54 (t, J = 5.67 Hz, 2 H) 3.56-3.67 (m, 1 H) 3.68-3.84 (m, 3 H) 3.97 (dd, J = 9.59, 3.33 Hz, 1 H) 4.08 (dd, J = 3.33, 1.76 Hz, 1 H) 4.73 (s, 2 H) 5.48-5.64 (m, 1 H) 6.78 (d, J = 7.43 Hz, 1 H) 7.34 (d, J = 7.83 Hz, 2 H) 7.46-7.59 (m, 2 H) 7.74 (d, J = 8.22 Hz, 1 H) 8.00 (dd, J = 8.22, 1.96 Hz, 1 H) 8.50 (s, 1 H) |
| 14 | 1CJ70 | 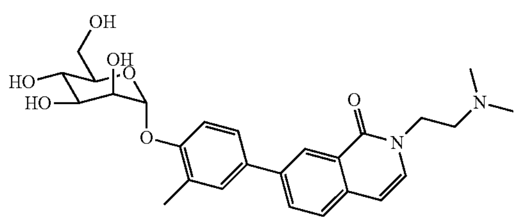 [SMILES: Cc1cc(-c2ccc3ccn(CCN(C)C)c(=O)c3c2)ccc1OC1OC(CO)C(O)C(O)C1O] | 2-(2-dimethylaminoethyl)-7-[3-methyl-4-[(2R,3R,4S,5S,6S)-3,4,5-trihydroxy-6-(hydroxymethyl)tetrahydropyran-2-yl]oxyphenyl]isoquinolin-1-one | 0.012 | C26H32N2O7 | 485.4 | 2.33 (s, 3 H) 3.05 (s, 6 H) 3.52-3.67 (m, 3 H) 3.68-3.84 (m, 3 H) 3.97 (dd, J = 9.39, 3.52 Hz, 1 H) 4.08 (dd, J = 3.33, 1.76 Hz, 1 H) 4.46 (t, J = 5.87 Hz, 2 H) 5.47-5.64 (m, 1 H) 6.80 (d, J = 7.43 Hz, 1 H) 7.38 (d, J = 7.43 Hz, 1 H) 7.34 (d, J = 8.61 Hz, 1 H) 7.47-7.59 (m, 2 H) 7.73 (d, J = 8.61 Hz, 1 H) 8.01 (dd, J = 8.41, 1.76 Hz, 1 H) 8.49-8.60 (m, 1 H) |
| 15 | 1CJ66 | 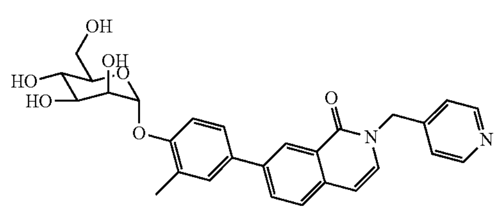 [SMILES: Cc1cc(-c2ccc3ccn(Cc4ccncc4)c(=O)c3c2)ccc1OC1OC(CO)C(O)C(O)C1O] | 7-[3-methyl-4-[(2R,3R,4S,5S,6S)-3,4,5-trihydroxy-6-(hydroxymethyl)tetrahydropyran-2- | 0.004 | C28H28N2O7 | 505.4 | 2.32 (s, 3 H) 3.53-3.66 (m, 1 H) 3.67-3.83 (m, 3 H) 3.96 (dd, J = 9.59, 3.33 Hz, 1 H) 4.07 (dd, J = 3.13, 1.96 Hz, 1 H) 5.52 (s, 2 H) 5.56 |

//

TABLE 1-continued

Structural, analytical and biological data for Examples 1-22.

| Ex. | Cmpnd Name | Structure | IUPAC Name | HAI Titer EC$_{>90}$ (μM) | Molecular Formula | MS (ESI, M + H$^+$) | $^1$H NMR δ ppm (d$_3$-MeOD unless otherwise noted) |
|---|---|---|---|---|---|---|---|
| | | | yl]oxy-phenyl]-2-(4-pyridyl-methyl)isoquinolin-1-one | | | | (s, 1 H) 6.84 (d, J = 7.43 Hz, 1 H) 7.33 (d, J = 8.61 Hz, 1 H) 7.44-7.57 (m, 3 H) 7.70-7.86 (m, 3 H) 8.02 (dd, J = 8.22, 1.96 Hz, 1 H) 8.49 (s, 1 H) 8.73 (d, J = 6.65 Hz, 2 H) |
| 16 | 1CJ68 | 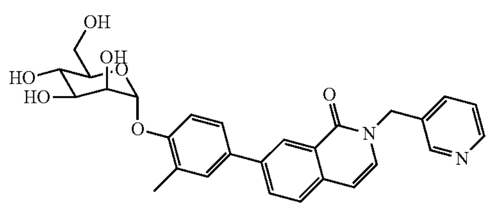 [SMILES: Cc1cc(-c2ccc3ccn(Cc4cccnc4)c(=O)c3c2)ccc1OC1OC(CO)C(O)C(O)C1O] | 7-[3-methyl-4-[(2R,3R,4S,5S,6S)-3,4,5-trihydroxy-6-(hydroxymethyl)tetrahydropyran-2-yl]oxy-phenyl]-2-(3-pyridyl-methyl)isoquinolin-1-one | 0.008 | C28H28N2O7 | 505.4 | 2.32 (s, 3 H) 3.51-3.66 (m, 1 H) 3.66-3.85 (m, 3 H) 3.97 (dd, J = 9.59, 3.33 Hz, 1 H) 4.08 (dd, J = 3.13, 1.57 Hz, 1 H) 5.42 (s, 2 H) 5.56 (s, 1 H) 6.80 (d, J = 7.43 Hz, 1 H) 7.33 (d, J = 8.22 Hz, 1 H) 7.43-7.61 (m, 3 H) 7.72 (d, J = 8.22 Hz, 1 H) 7.89 (dd, J = 8.02, 5.67 Hz, 1 H) 7.99 (dd, J = 8.41, 1.76 Hz, 1 H) 8.42 (d, J = 8.22 Hz, 1 H) 8.46-8.54 (m, 1 H) 8.71 (d, J = 5.48 Hz, 1 H) 8.86 (s, 1 H) |
| 17 | 5ZFH302 | 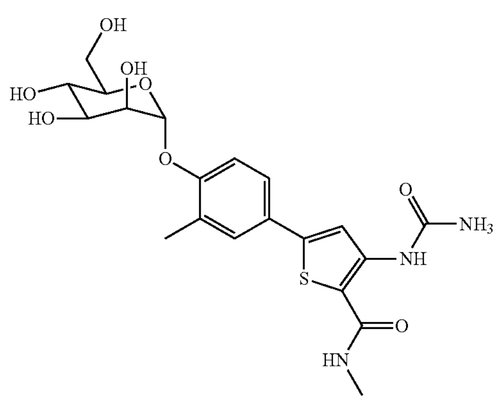 [SMILES: CNC(=O)c1sc(-c2ccc(OC3OC(CO)C(O)C(O)C3O)c(C)c2)cc1NC(N)=O] | N-methyl-5-[3-methyl-4-[(2R,3R,4S,5S,6S)-3,4,5-trihydroxy-6-(hydroxymethyl)tetrahydropyran-2-yl]oxy-phenyl]-3-ureido-thiophene-2-carboxamide | 0.024 | C20H25N3O8S | 468.3 | 2.27 (s, 3 H) 2.87 (s, 3 H) 3.52-3.61 (m, 1 H) 3.76 (d, J = 1.17 Hz, 3 H) 3.91-3.99 (m, 1 H) 4.03-4.09 (m, 1 H) 5.56 (d, J = 1.17 Hz, 1 H) 7.27 (m, 1 H) 7.47 (m, 2 H) 8.06 (s, 1 H) |

TABLE 1-continued

Structural, analytical and biological data for Examples 1-22.

| Ex. | Cmpnd Name | Structure | IUPAC Name | HAI Titer EC$_{>90}$ (μM) | Molecular Formula | MS (ESI, M + H$^+$) | $^1$H NMR δ ppm (d$_3$-MeOD unless otherwise noted) |
|---|---|---|---|---|---|---|---|
| 18A | 5ZFH240 | 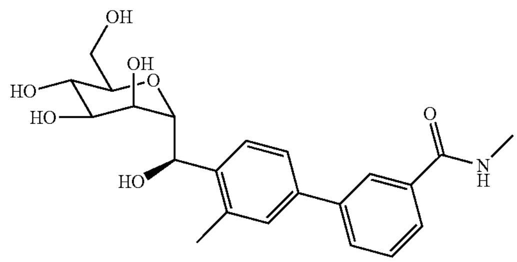 [SMILES: CNC(=O)c1cccc(-c2ccc([C@@H](O)C3OC(CO)C(O)C(O)C3O)c(C)c2)c1] | 3-[4-[(R)-hydroxy-[(2R,3R,4S,5S,6S)-3,4,5-trihydroxy-6-(hydroxy-methyl) tetrahydro-pyran-2-yl]methyl]-3-methyl-phenyl]-N-methyl-benzamide | 0.031 | C21H26NO7 | 440.3 (M + Na$^+$) | 2.51 (s, 3 H) 2.95 (s, 3 H) 3.57-3.78 (m, 4 H) 4.00-4.07 (m, 1 H) 4.10 (dd, J = 6.85, 2.54 Hz, 1 H) 4.25 (t, J = 2.93 Hz, 1 H) 5.24 (d, J = 6.65 Hz, 1 H) 7.45-7.57 (m, 3 H) 7.62 (d, J = 8.22 Hz, 1 H) 7.71-7.83 (m, 2 H) 8.07 (t, J = 1.56 Hz, 1 H) |
| 18B | 5ZFH244 | 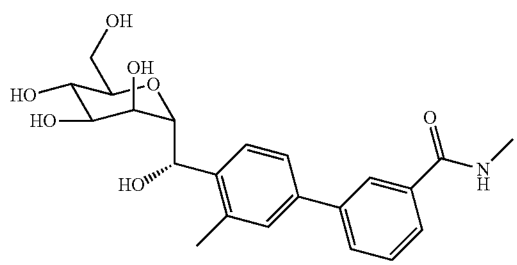 [SMILES: CNC(=O)c1cccc(-c2ccc([C@H](O)C3OC(CO)C(O)C(O)C3O)c(C)c2)c1] | 3-[4-[(S)-hydroxy-[(2R,3R,4S,5S,6S)-3,4,5-trihydroxy-6-(hydroxy-methyl) tetrahydro-pyran-2-yl]methyl]-3-methyl-phenyl]-N-methyl-benzamide | 6.000 | C21H26NO7 | 440.3 (M + Na$^+$) | 2.51 (s, 3 H) 2.95 (s, 3 H) 3.56 (dd, J = 1.00 Hz, 1 H) 3.67 (m, 1 H) 3.70-3.82 (m, 3 H) 3.91 (m, 1 H) 4.10 (dd, J = 9.00, 1.96 Hz, 1 H) 5.28 (d, J = 8.61 Hz, 1 H) 7.34-7.63 (m, 4 H) 7.69-7.90 (m, 2 H) 8.07 (s, 1 H) |
| 19 | 5ZFH247 | 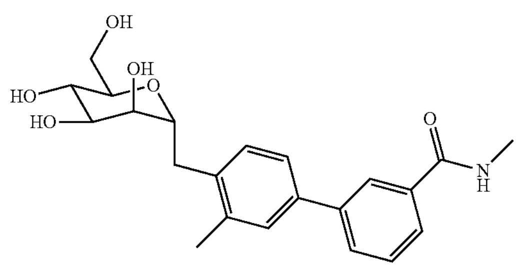 [SMILES: CNC(=O)c1cccc(-c2ccc(CC3OC(CO)C(O)C(O)C3O)c(C)c2)c1] | N-methyl-3-[3-methyl-4-[[(2R,3R,4R,5S,6S)-3,4,5-trihydroxy-6-(hydroxy-methyl) tetrahydro-pyran-2-yl]methyl] phenyl] benzamide | 2.000 | C22H27NO6 | 402.3 | 2.44 (s, 3 H) 2.95 (s, 3 H) 3.04 (d, J = 7.43 Hz, 2 H) 3.69 (m, 3 H) 3.83 (m, 2 H) 3.86-3.92 (m, 1 H) 4.04-4.21 (m, 1 H) 7.31 (d, J = 7.83 Hz, 1 H) 7.42-7.47 (m, 1 H) 7.50 (m, 2 H) 7.75 (m, 2 H) 8.05 (s, 1 H) |
| 20 | 1JWJ231 | 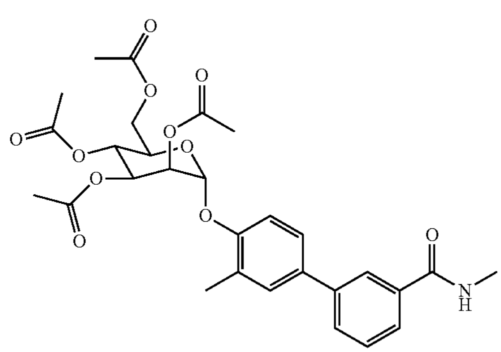 [SMILES: CNC(=O)c1cccc(-c2ccc(OC3OC(COC(C)=O)C(OC(C)=O)C(OC(C)=O)C3OC(C)=O)c(C)c2)c1] | [(2S,3R,4S,5R,6R)-3,4,5-triacetoxy-6-[2-methyl-4-[3-(methyl-carbamoyl) phenyl] phenoxy] tetrahydro-pyran-2-yl]methyl acetate | | C29H33NO11 | 594.3 (M + Na$^+$) | [d$_6$-DMSO] 1.94 (s, 3 H) 2.00 (s, 3 H) 2.05 (s, 3 H) 2.16 (s, 3 H) 2.32 (s, 3 H) 2.81 (d, J = 4.30 Hz, 3 H) 3.93-4.11 (m, 2 H) 4.19 (dd, J = 12.13, 5.09 Hz, 1 H) 5.22 (t, J = 9.98 Hz, 1 H) 5.33-5.45 (m, 2 H) 5.80 (s, |

TABLE 1-continued

Structural, analytical and biological data for Examples 1-22.

| Ex. | Cmpnd Name | Structure | IUPAC Name | HAI Titer EC$_{>90}$ (μM) | Molecular Formula | MS (ESI, M + H$^+$) | $^1$H NMR δ ppm (d$_3$-MeOD unless otherwise noted) |
|---|---|---|---|---|---|---|---|
| | | | | | | | 1 H) 7.23 (d, J = 8.61 Hz, 1 H) 7.46-7.65 (m, 3 H) 7.77 (d, J = 7.83 Hz, 2 H) 8.07 (s, 1 H) 8.54 (d, J = 4.30 Hz, 1 H) |
| 21 | 1JWJ232 | 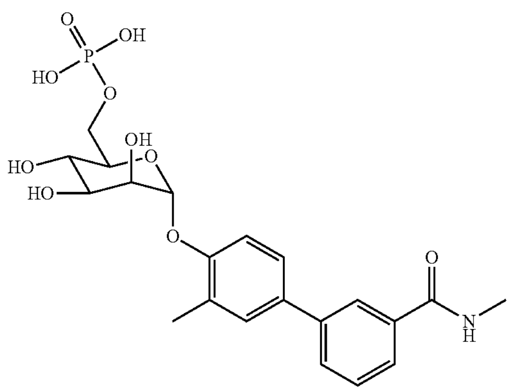 [SMILES: CNC(=O)c1cccc(-c2ccc(OC3OC(COP(=O)(O)O)C(O)C(O)C3O)c(C)c2)c1] | [(2S,3S,4S,5R,6R)-3,4,5-trihydroxy-6-[2-methyl-4-[3-(methyl-carbamoyl)phenyl]phenoxy]tetrahydro-pyran-2-yl]methyl dihydrogen phosphate | | C21H26NO10P | 484.3 | [d$_6$-DMSO] 2.26 (s, 3 H) 2.81 (d, J = 4.70 Hz, 3 H) 3.42-3.68 (m, 3 H) 3.75 (dd, J = 9.00, 3.13 Hz, 1 H) 3.86-3.97 (m, 2 H) 4.03 (dd, J = 9.78, 5.87 Hz, 1 H) 5.45 (d, J = 1.96 Hz, 1 H) 7.24 (d, J = 8.61 Hz, 1 H) 7.43-7.60 (m, 3 H) 7.76 (dd, J = 7.43, 1.57 Hz, 2 H) 8.06 (s, 1 H) 8.56 (d, J = 4.30 Hz, 1 H) |
| 22 | 6ZFH123 | 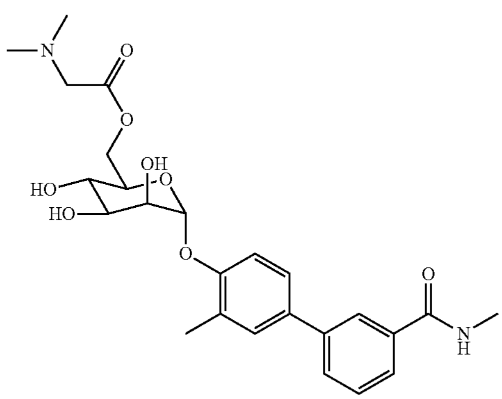 | [(2S,3S,4S,5R,6R)-3,4,5-trihydroxy-6-[2-methyl-4-[3-(methyl-carbamoyl)phenyl]phenoxy]tetrahydro-pyran-2-yl]methyl 2-dimethyl-aminoacetate | | C25H32N2O8 | 489.4 | 2.32 (s, 3 H) 2.89 (s, 6 H) 2.95 (s, 3 H) 3.71-3.85 (m, 2 H) 3.94-4.00 (m, 1 H) 4.06 (d, J = 5.48 Hz, 2 H) 4.11 (t, J = 2.54 Hz, 1 H) 4.42 (m, 1 H) 4.61 (dd, J = 11.74, 1.56 Hz, 1 H) 5.57 (d, J = 1.57 Hz, 1 H) 7.23 (d, J = 8.61 Hz, 1 H) 7.34-7.61 (m, 3 H) 7.66-7.88 (m, 2 H) 7.99-8.17 (m, 1 H) |
| 23 | | 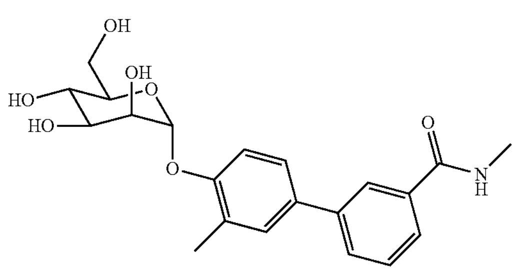 [SMILES: CNC(=O)c1cccc(-c2ccc(OC3OC(CO)C(O)C(O)C3O)c(C)c2)c1] | | | | | |

TABLE 1-continued

Structural, analytical and biological data for Examples 1-22.

| Ex. | Cmpnd Name | Structure | IUPAC Name | HAI Titer EC$_{>90}$ (μM) | Molecular Formula | MS (ESI, M + H$^+$) | $^1$H NMR δ ppm (d$_3$-MeOD unless otherwise noted) |
|---|---|---|---|---|---|---|---|
| 24 | | 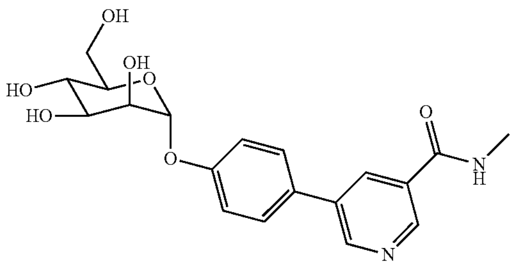 [SMILES: CNC(=O)c1cncc(-c2ccc(OC3OC(CO)C(O)C(O)C3O)cc2)c1] | | | | | |
| 25 | | 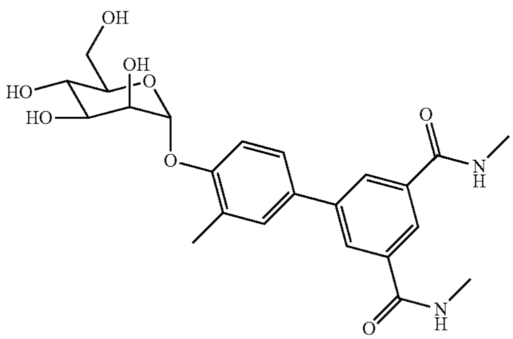 [SMILES: CNC(=O)c1cc(C(=O)NC)cc(-c2ccc(OC3OC(CO)C(O)C(O)C3O)c(C)c2)c1] | | | | | |
| 26 | | 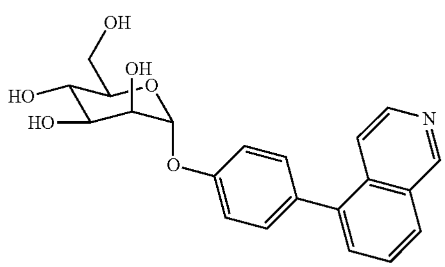 [SMILES: OCC1OC(Oc2ccc(-c3cccc4cnccc34)cc2)C(O)C(O)C1O] | | | | | |
| 27 | | 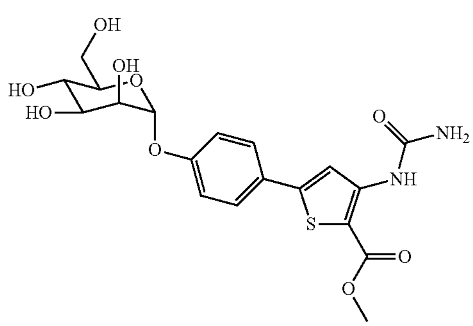 [SMILES: COC(=O)c1sc(-c2ccc(OC3OC(CO)C(O)C(O)C3O)cc2)cc1NC(N)=O] | | | | | |
| 28 | | 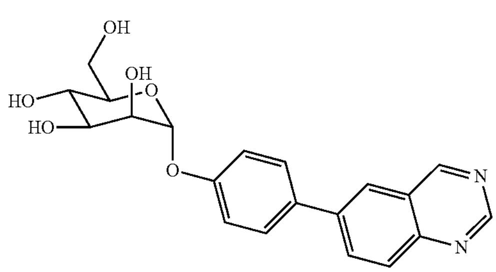 [SMILES: OCC1OC(Oc2ccc(-c3ccc4ncncc4c3)cc2)C(O)C(O)C1O] | | | | | |

Example 23. Biological and In Vivo Activity of Compounds of Examples 1-22

The inventors set out to develop and optimize orally active mannoside small-molecule antagonists of FimH bacterial adhesion for treatment and prevention of recurring urinary tract infection (UTI). The endpoint desired to determine orally active compounds was drug unchanged in the urine and/or bladder. First, the inventors rationally designed biaryl mannosides with potency and desirable properties. To do this, structure activity relationships (SAR) of substituents was determined. Ortho substitution on the biaryl ring was evaluated for FimH activity. Solubility, Log D and pKa was improved with heterocycles. It was further discovered that replacements to the glycosidic bond could improve metabolic stability and bioavailability. Alternate linkers of mannose to the biaryl ring were identified. N-, S- and C-mannosides were synthesized. Murine animal models of both acute and chronic UTI were used to further evaluate compound efficacy.

The inventors have developed compounds with a 2000-fold increase in cellular potency by X-ray structure-based design. Mannosides show good oral compound exposure for 6 h at 100 mg/kg dose and prophylactically prevent IBC formation of UTI89 bacteria in vivo. Some metabolism/hydrolysis products (phenol) detected in the urine. Importantly, mannosides reverse antibiotic TMP-SMZ resistant strains of UTI in vivo. Ongoing optimization for decreased Cl, increase $t_{1/2}$, $V_{dss}$ (tissue exposure), and improved bioavailability by compound PK screeining in plasma and urine. Also, ongoing efficacy model development for demonstrating antibacterial effects post-infection as monotherapy and in combination with antibiotics. Further, the inventors are optimizing prodrugs and non-sugar mannoside mimetics.

Figure 1B:
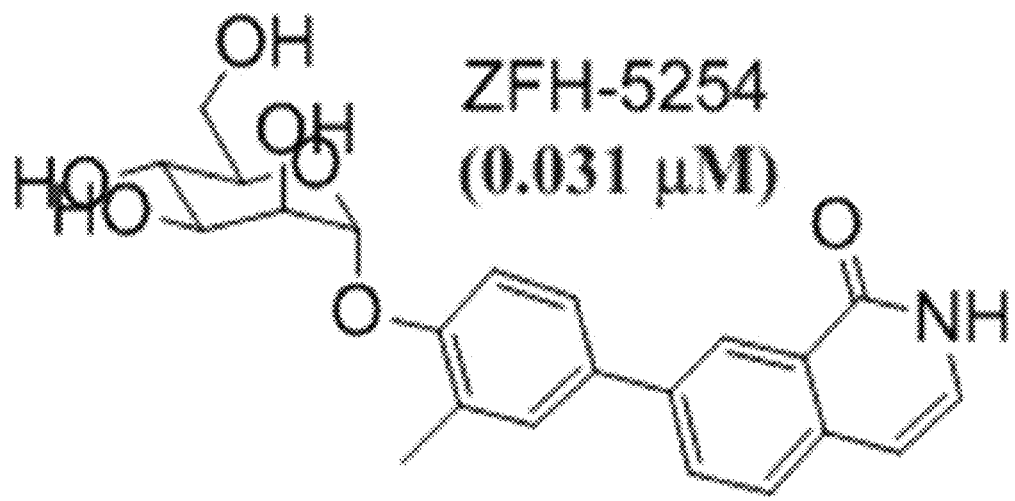
Figure 1C:
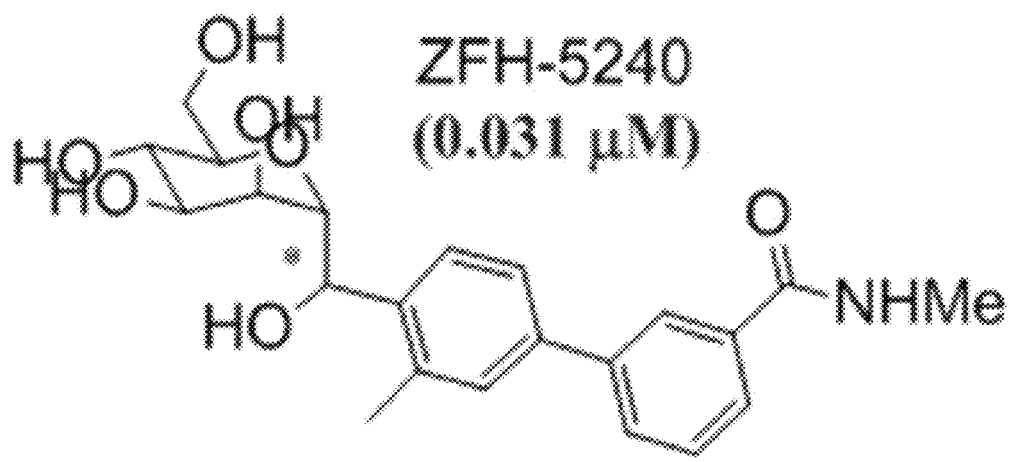
Figure 1D:
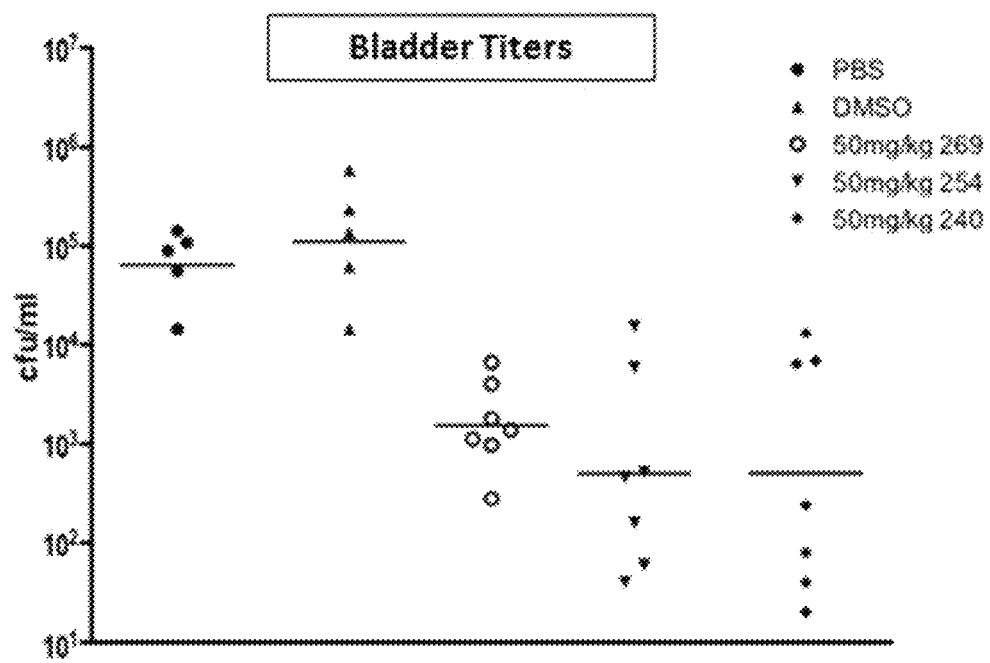
Figure 2A:
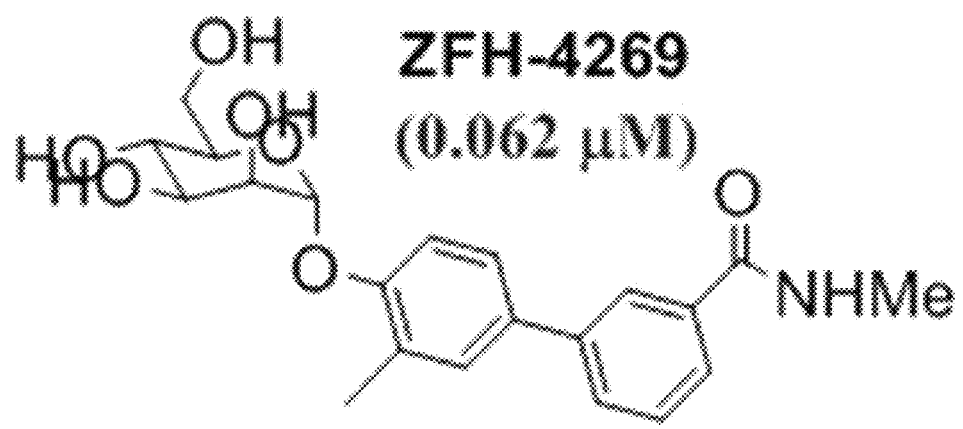
FIG. 2A, FIG. 2B, FIG. 2C and FIG. 2D depict the effects of mannoside compounds that are analogs of ZFH-5254 on preventing UTI in a mouse model of infection. The structures of compounds (FIG. 2A) ZFH-4269, (FIG. 2B) 1CJ68 (Example 16) and (FIG. 2C) 1CJ70 (Example 14) are depicted.
Figure 2B:
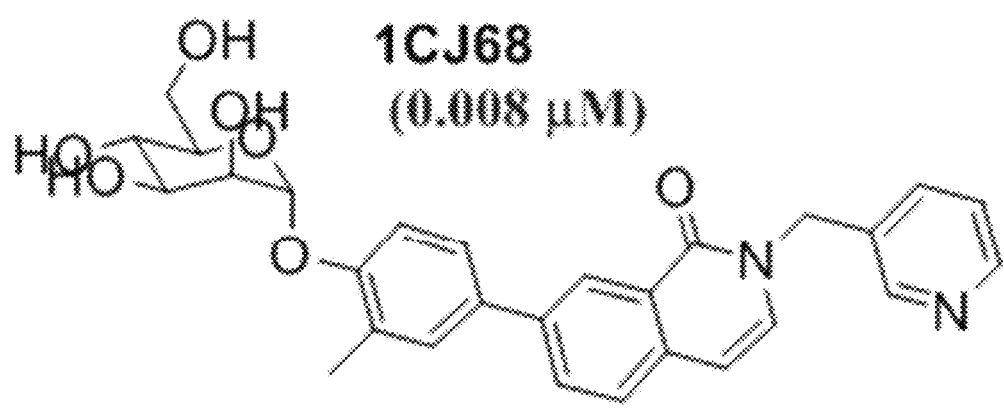
Figure 2C:
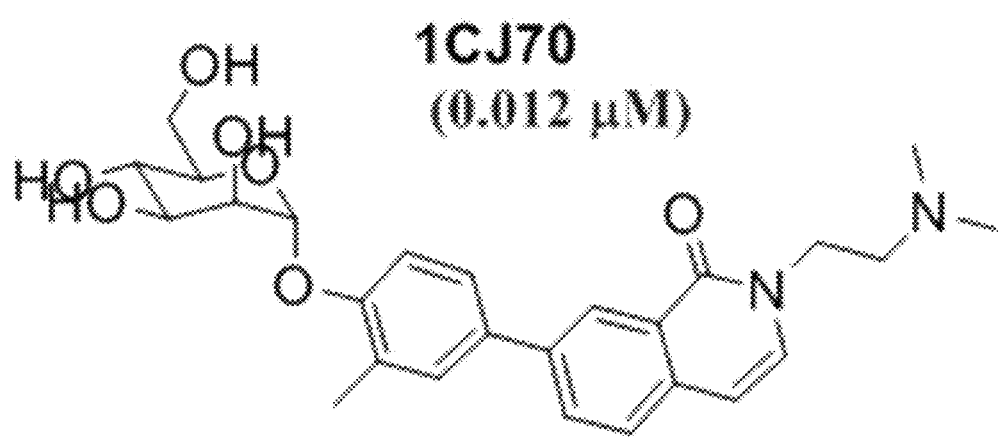
Figure 2D:
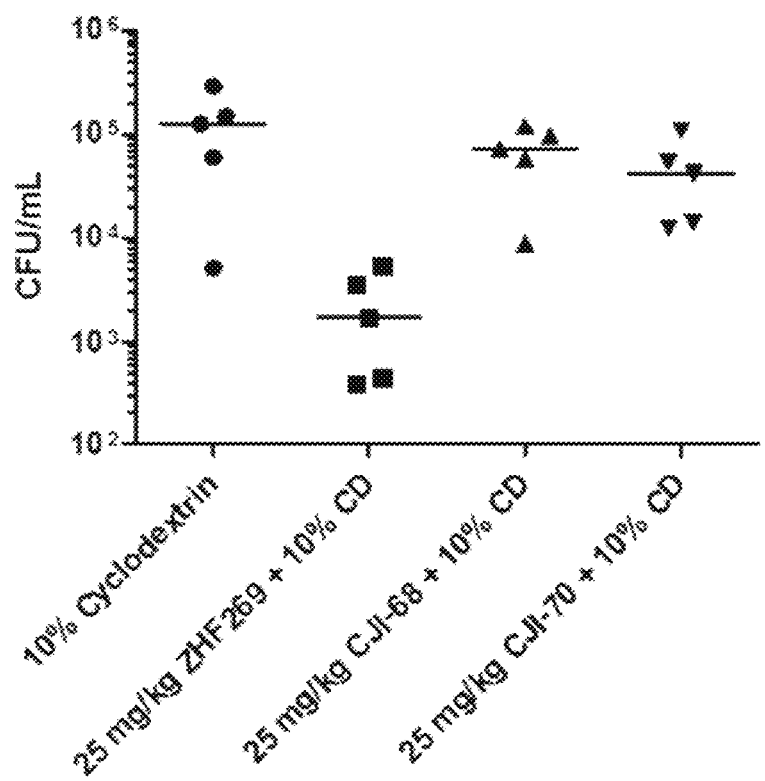
Figure 10A:
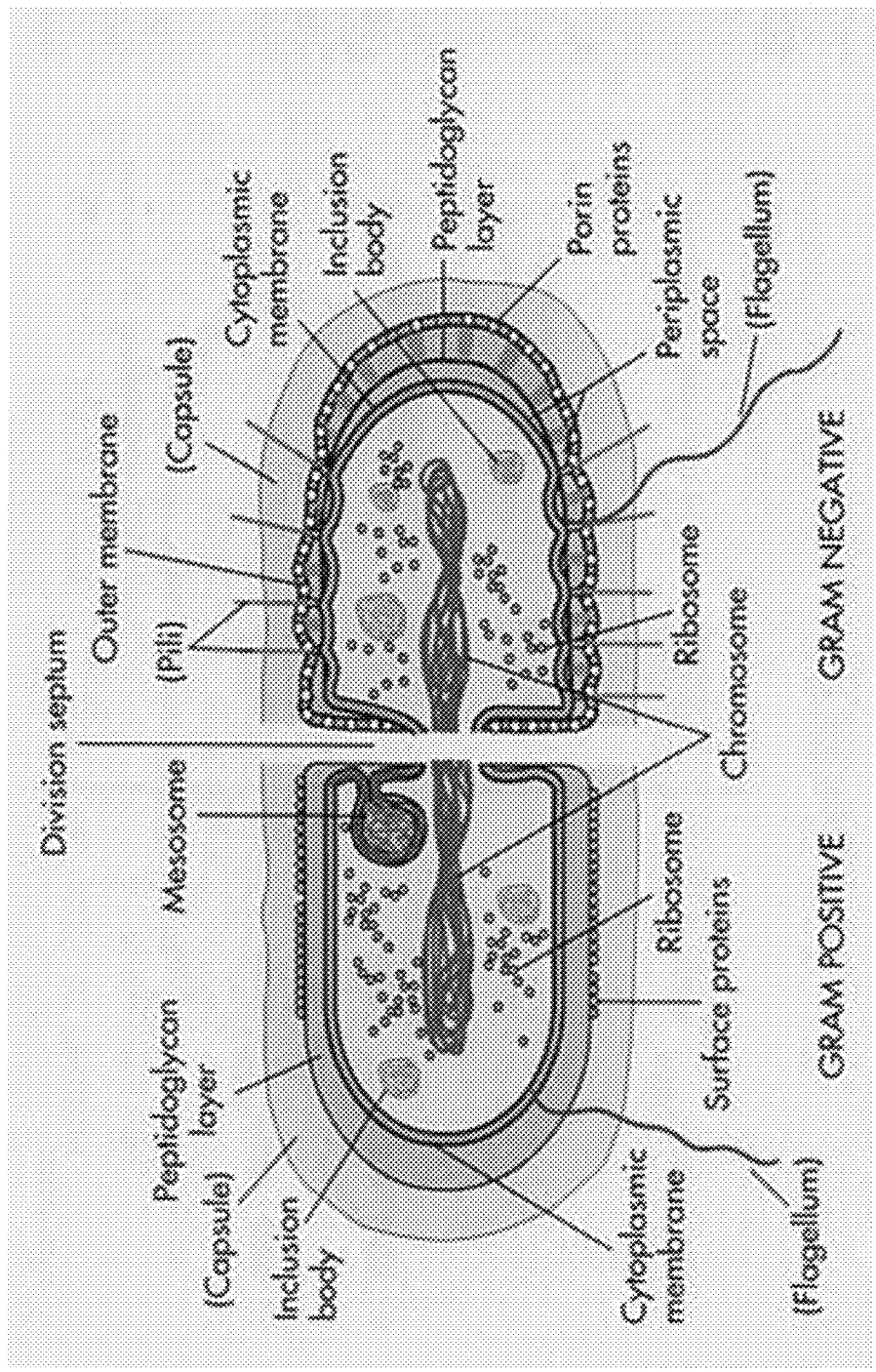
FIG. 10A, FIG. 10B and FIG. 10C depict illustrations of bacterial surface lectins and pili.
Figure 10B:
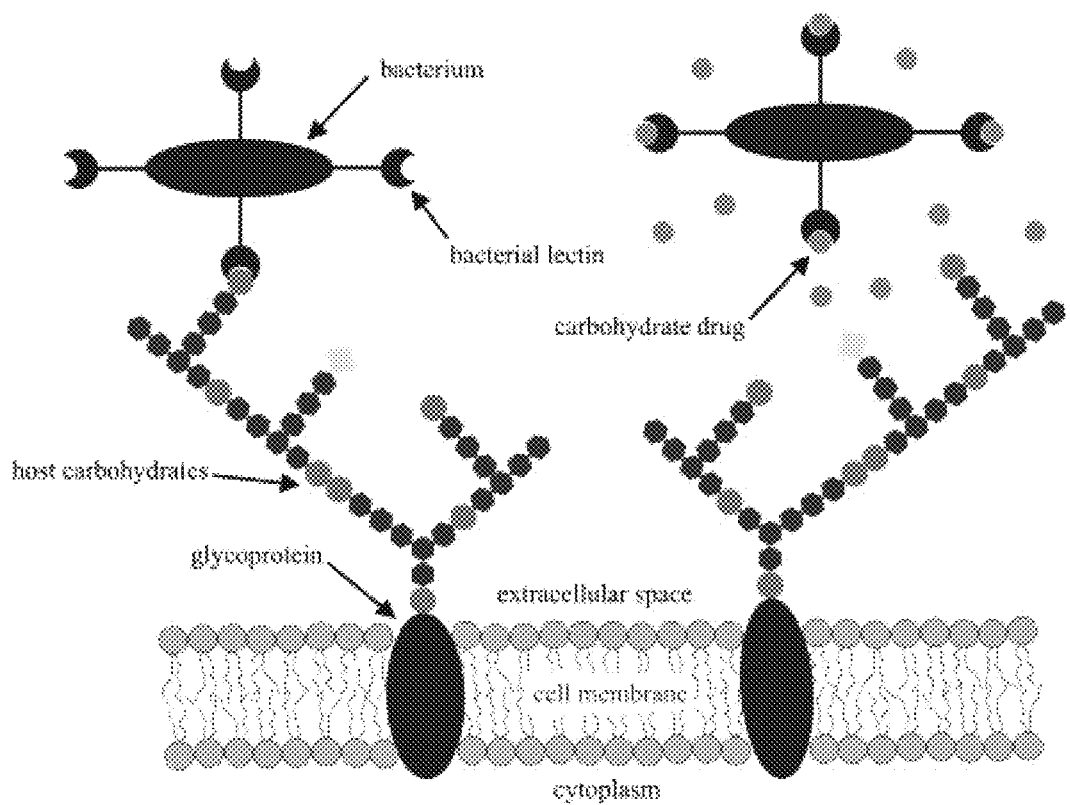
Figure 10C:
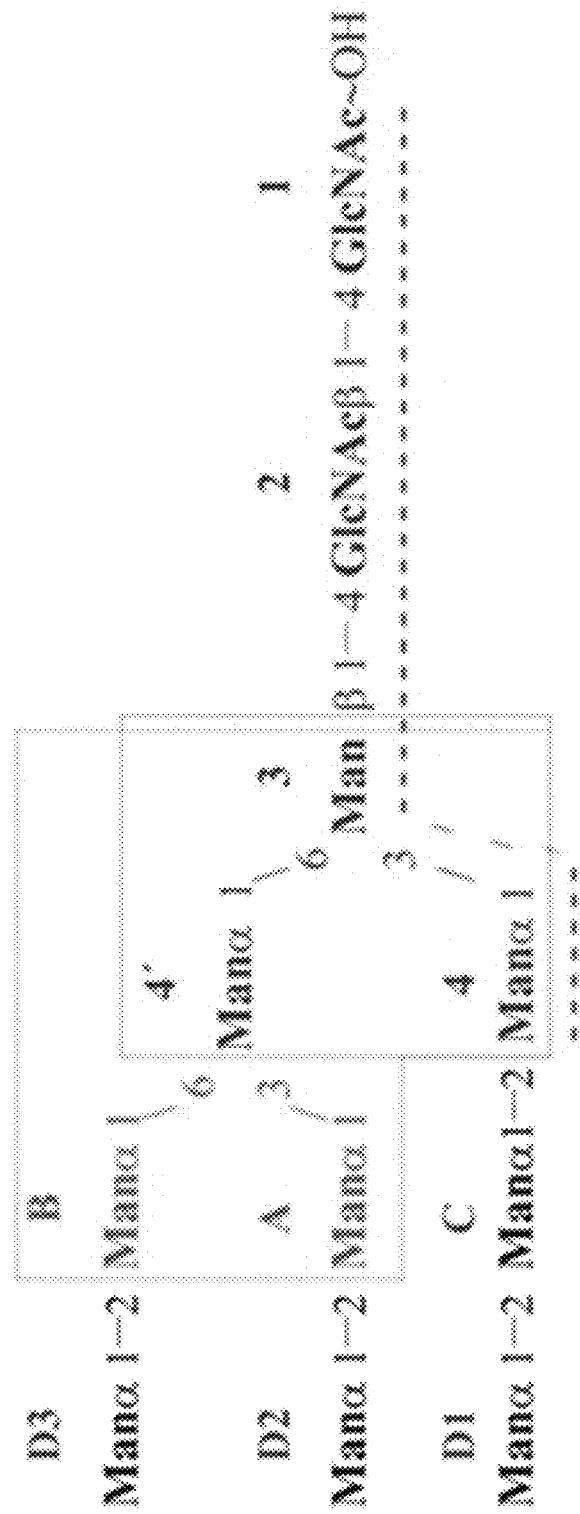

The efficacy of in vivo mannoside treatment was evaluated after orally dosing animals with 50 mg/kg of mannosides ZFH-4269 (FIG. 1A), ZFH-5254 (FIG. 1B) and ZFH-5240 (FIG. 1C) or DMSO or PBS 30 min prior to infecting with UTI89. At 6 hours post-infection (hpi) the bladders were removed and total bacterial CFUs were quantitated. In all three of the mannoside-treated cohorts, there was a drop in bacterial counts demonstrating the efficacy of these mannosides in reducing overall colonization of the bladder (FIG. 10). Next, analogs of 254 were evaluated in the same mouse model of urinary tract infection. Animals were orally dosed with 25 mg/kg of mannosides ZFH-4269 (FIG. 2A), 1CJ68 (FIG. 2B) and 1CJ70 (FIG. 2C) in 10% cyclodextrin or 10% cyclodextrin 30 min prior to infecting with UT189. In the ZFH269-treated cohort, there was a drop in bacterial counts demonstrating the efficacy of this mannoside in reducing overall colonization of the bladder (FIG. 2D).

Figure 3:
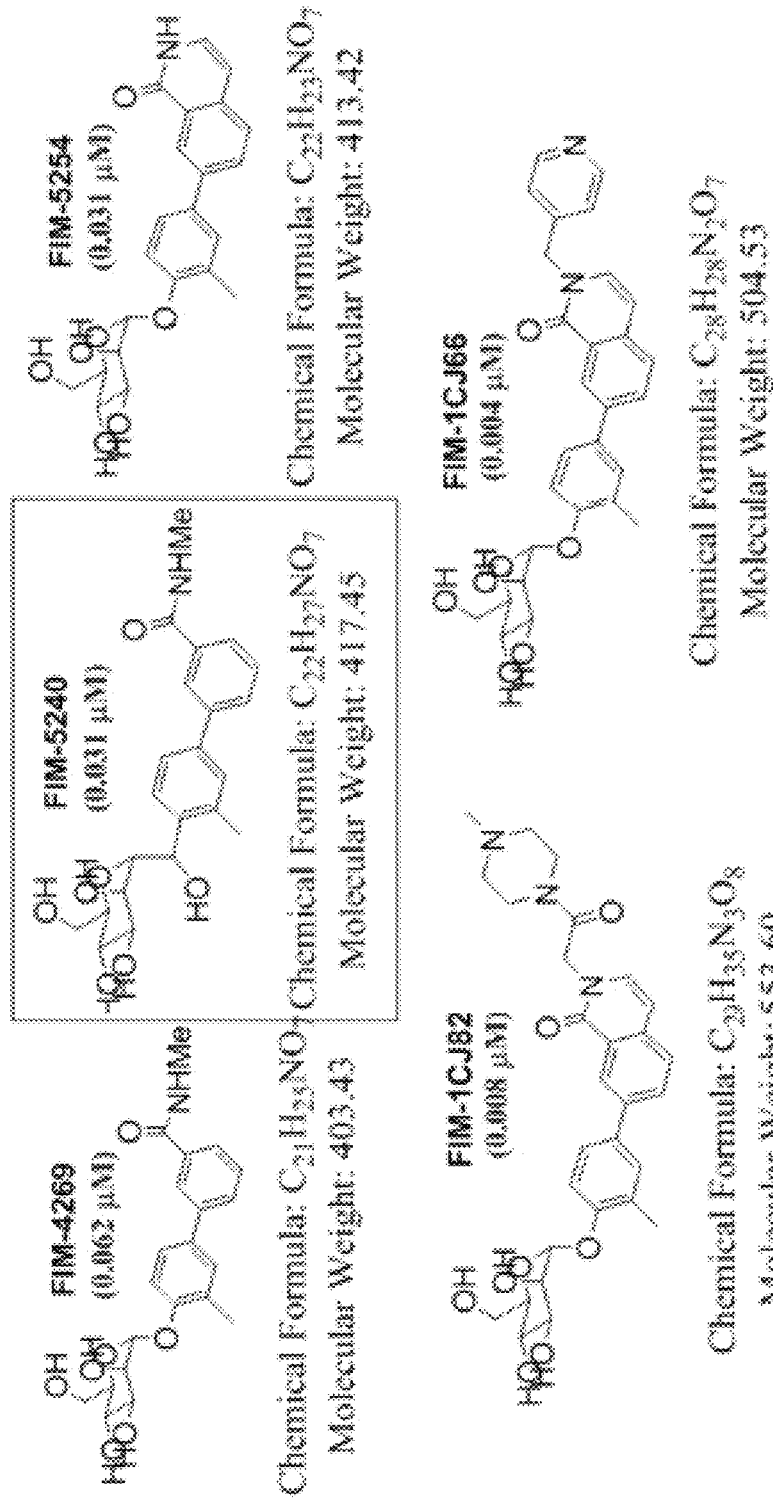
FIG. 3 depicts the structures of the mannoside compounds evaluated for rat PK.
Figure 4:
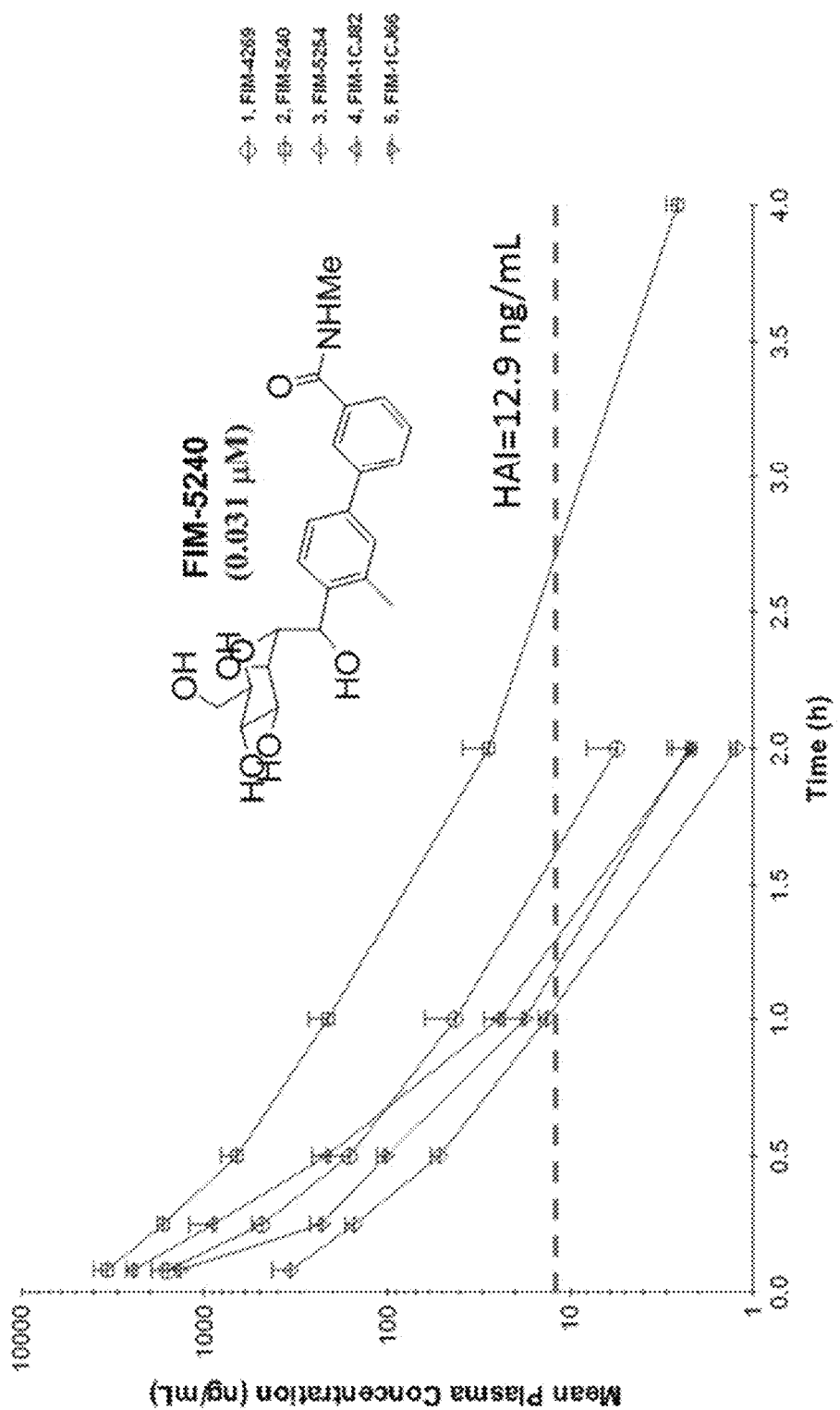
FIG. 4 depicts a graph of the pharamacokinetics of the IV dose of the mannoside compounds in rats. FIM-5240 (Example 18A) showed the best PK.
Figure 5:
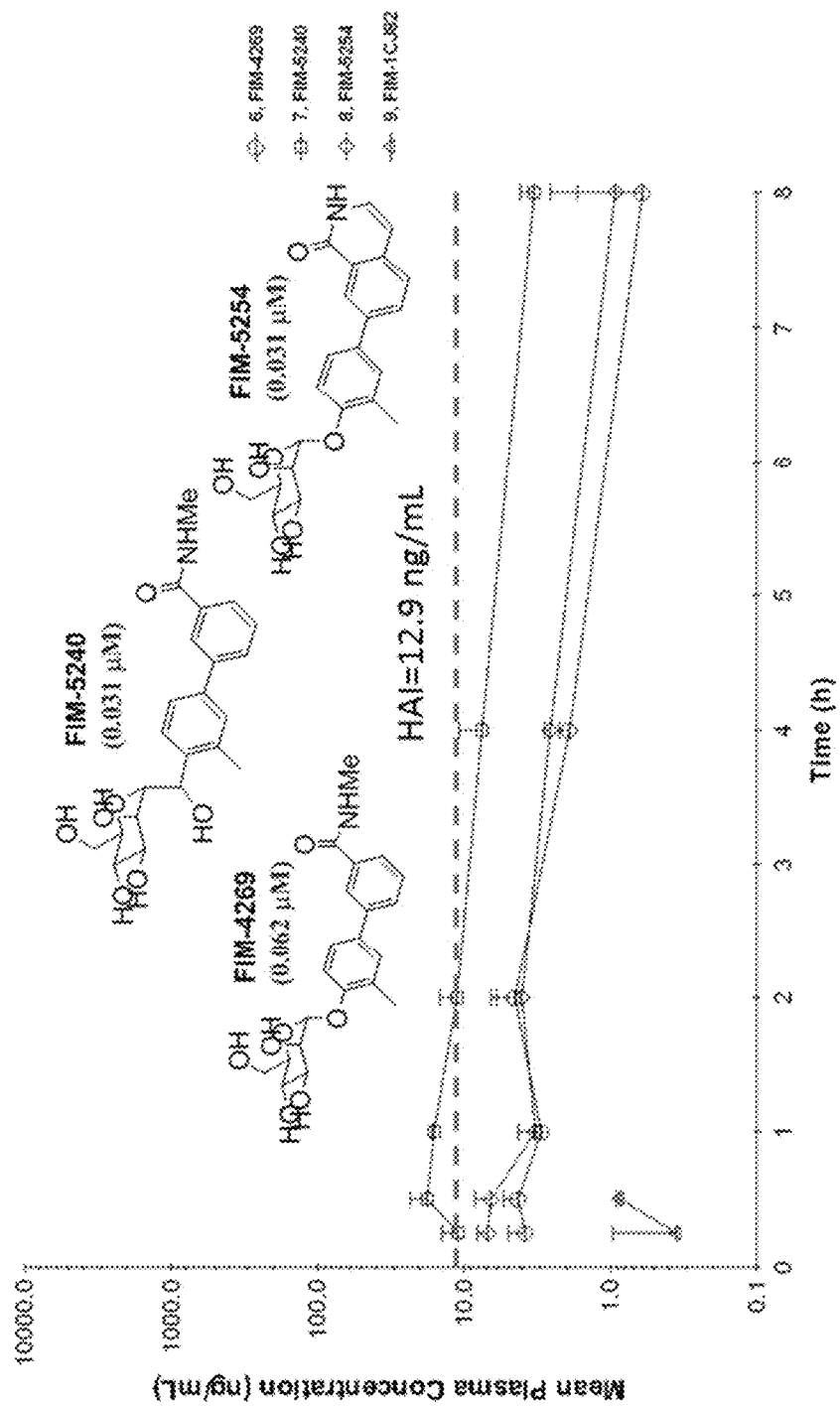
FIG. 5 depicts a graph of the pharamacokinetics of the oral (PO) dose of the mannoside compounds in rats.

Mannoside compounds FIM-4269, FIM-5240, FIM-5254, FIM-1CJ82 and FIM-1CJ66 (FIG. 3) were evaluated for pharmacokinetics in the rat. Mannosides were dose IV at 3 mg/kg and PO at 10 mg/kg. Urine and plasma were collected at 15 min, 30 min, 1 hour, 2 hours, 4 hours and 8 hours. Following IV dosing, the mean plasma concentration of FIM-5240 was the highest relative to the other 4 mannosides and remained above the limit of detection to 2.5 hours (FIG. 4). Following PO dosing, again FIM-5240 exhibited the best pharmacokinetics relative to the other mannosides and feel below the limit of dection at 2 hours post-treatment (FIG. 5).

Figure 6A:
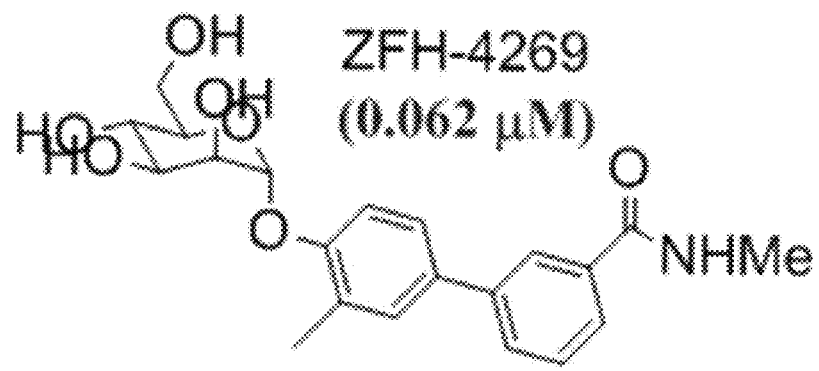
FIG. 6A, FIG. 6B, FIG. 6C and FIG. 6D depict the pharmacokinetics of mannoside compounds in the mouse urine. The structures of compounds (FIG. 6A) ZFH-4269, (FIG. 6B) ZFH-5254 (Example 7), (FIG. 6C) ZFH-5240 (Example 18A) are depicted.
Figure 6B:
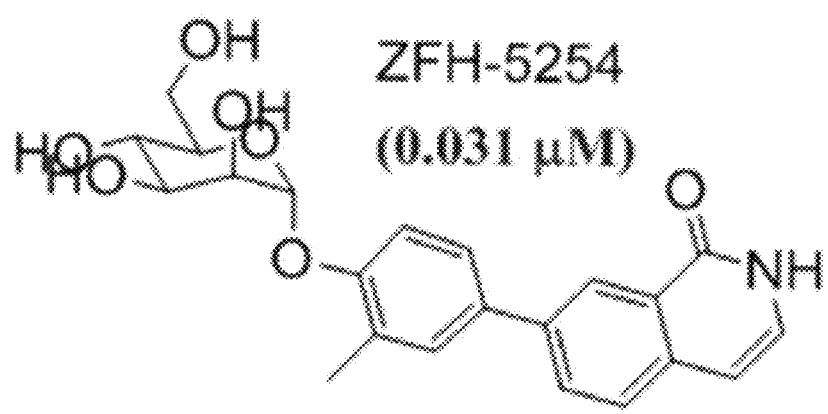
Figure 6C:
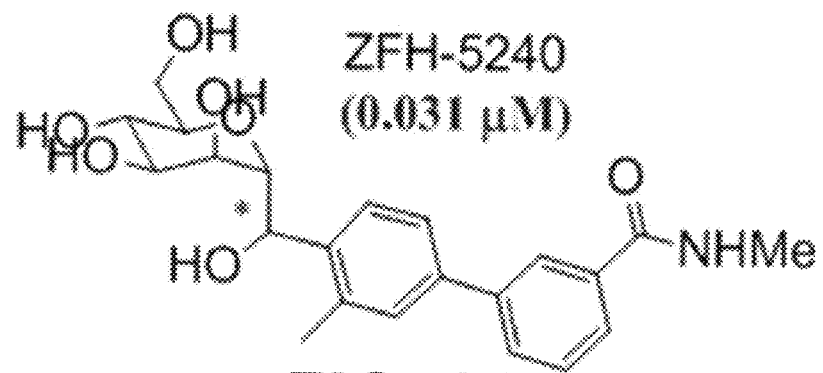
Figure 6D:
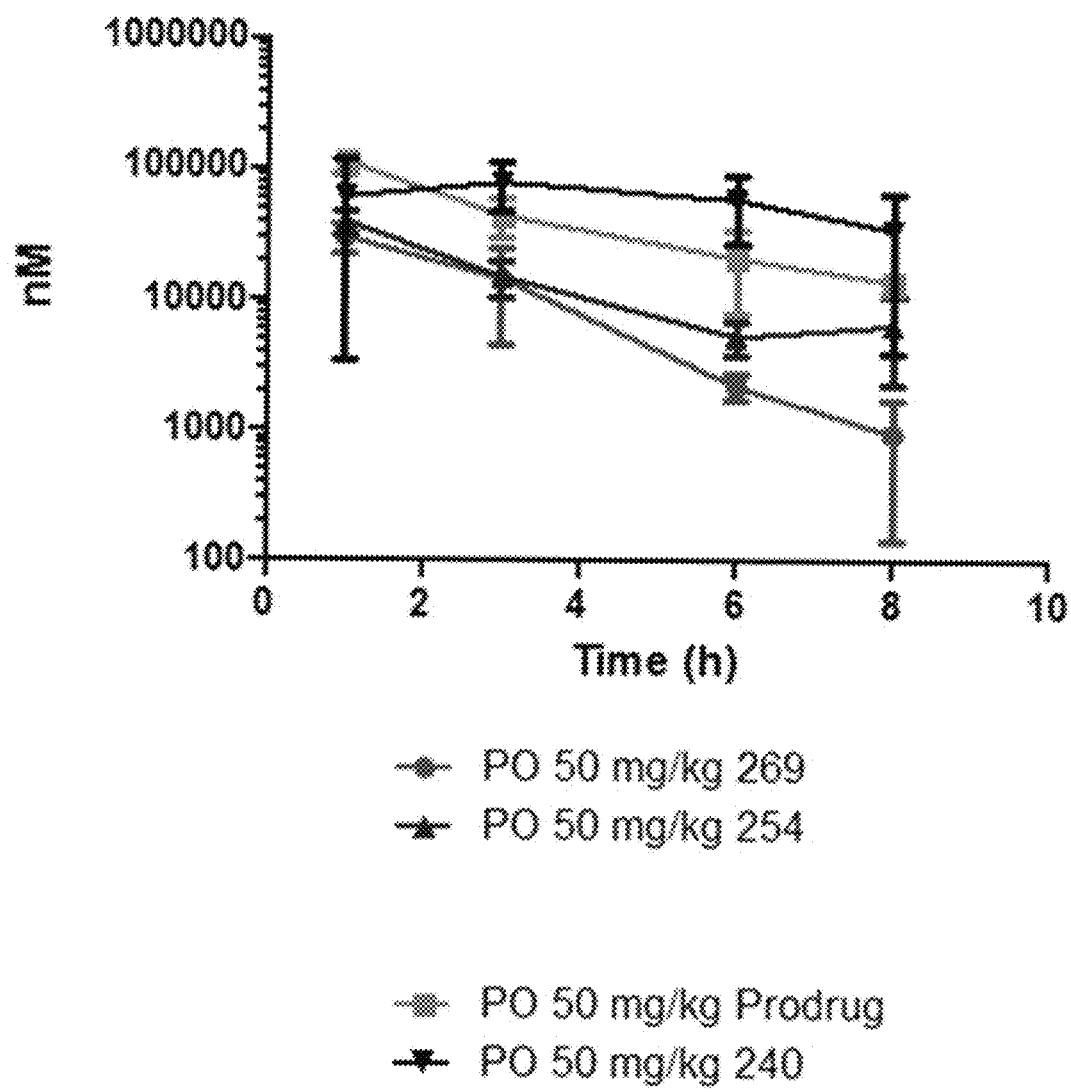

Based on these results, oral PK studies were performed in mice. Compounds ZFH-4269 (FIG. 6A), ZFH-5254 (FIG. 6B), ZFH5240 (FIG. 6C), and a Prodrug were dosed at 50 mg/kg and plasma and urine samples were taken at 1, 3, 6 and 8 hours after dosing. As demonstrated in FIG. 6D, all compounds were detectable in the urine out to 8 hours post-treatment. It was found that compounds 240 and the prodrug consistently maintained a high level of concentration in the urine, which is well above the predicted minimum effective concentration within a 6-hour period. Taken together, the high oral bioavailability and in vivo efficacy observed in animal studies support mannosides as promising therapeutic candidates for UTI treatment/prevention.

Figure 7A:
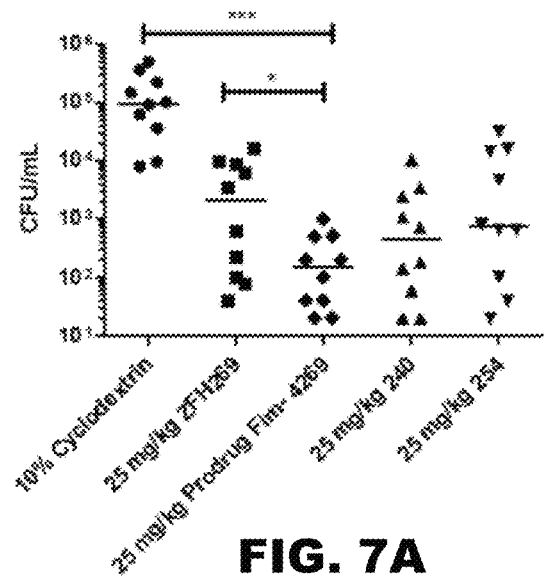
FIG. 7A and FIG. 7B depict the efficacy of various mannoside prodrugs in the mouse model of acute UTI infection.
Figure 7B:
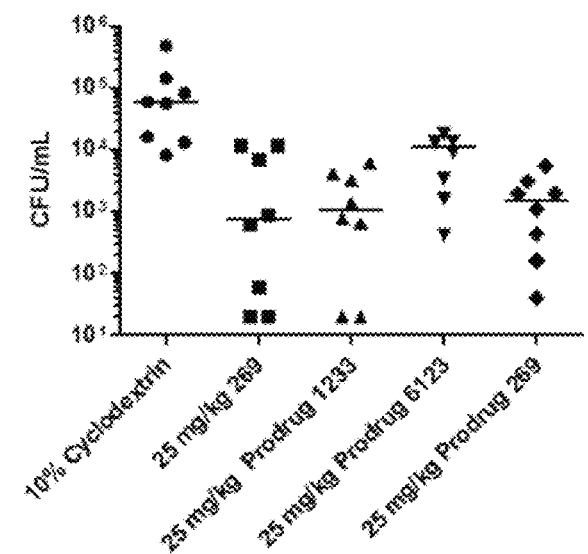
Figure 8A:
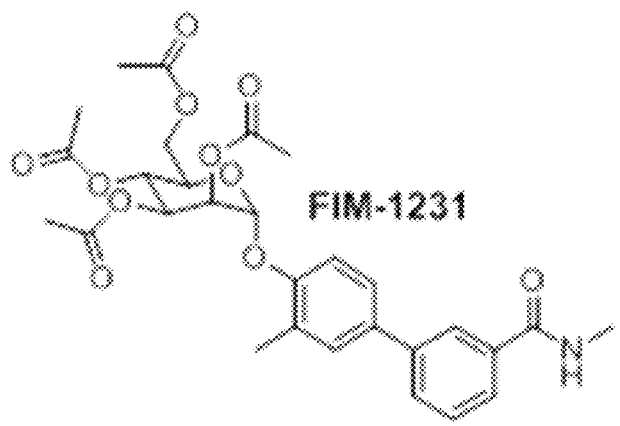
FIG. 8A, FIG. 8B and FIG. 8C depict the structure of the 3 prodrugs.
Figure 8B:
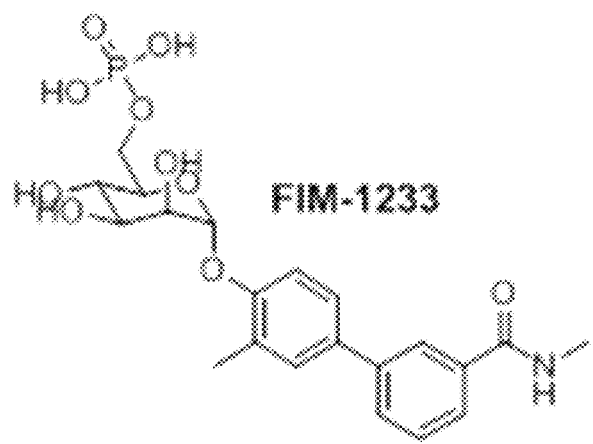
Figure 8C:
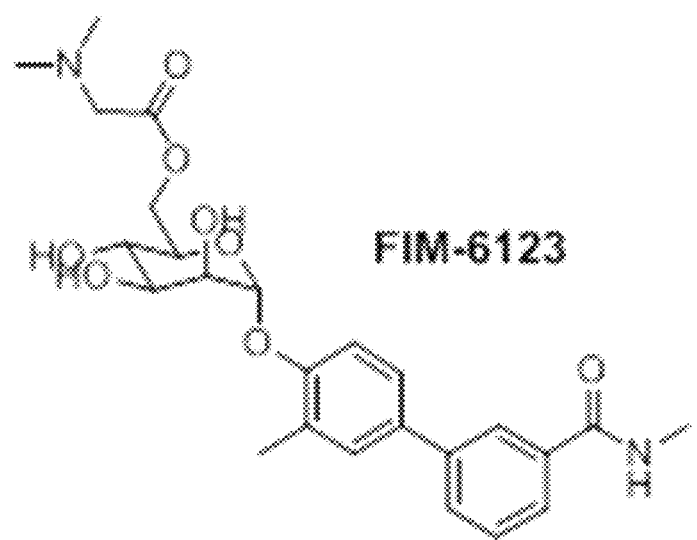
Figure 9A:
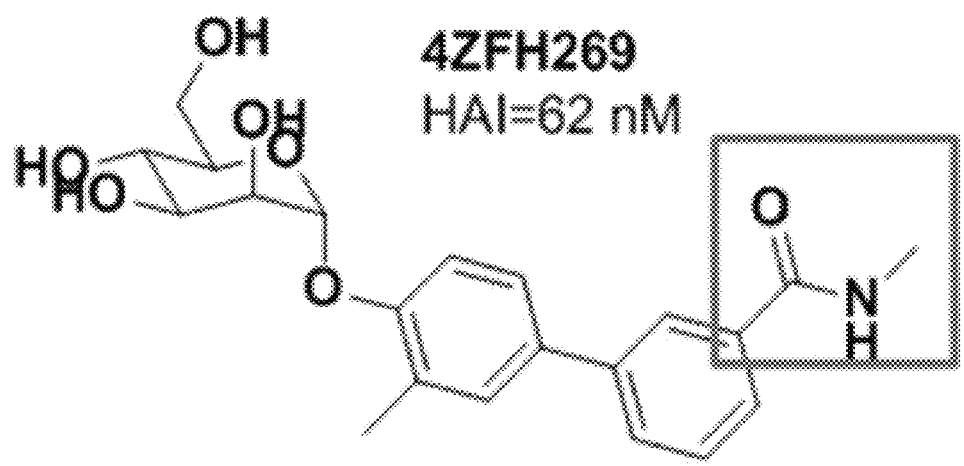
FIG. 9A, FIG. 9B, FIG. 9C, FIG. 9D and FIG. 9E depict the plasma stability and metabolism of various mannoside compounds. The structures of compounds (FIG. 9A) 4ZFH269, (FIG. 9B) 5ZFH240 (Example 18A), (FIG. 9C) 5ZFH61 and (FIG. 9D) 1CJ87 (Example 4) are depicted. Compounds 5ZFH61 and 1CJ87 had more than twice the half life ($t_{1/2}$) relative to 4ZFH269 and 5ZFH240.
Figure 9B:
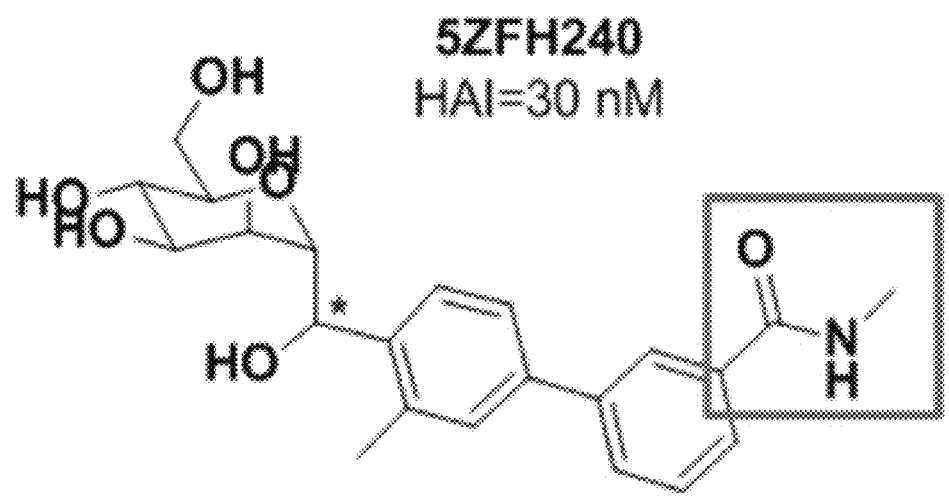
Figure 9C:
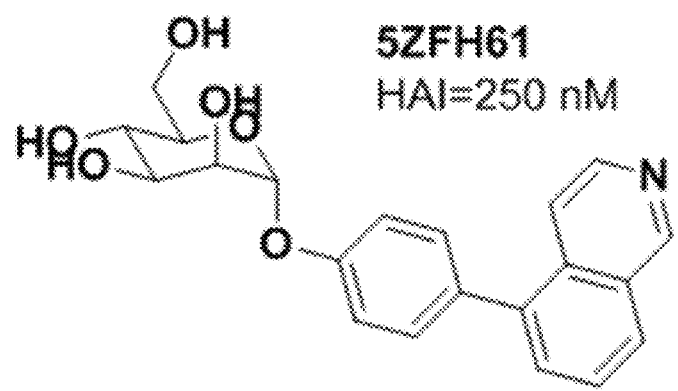
Figure 9D:
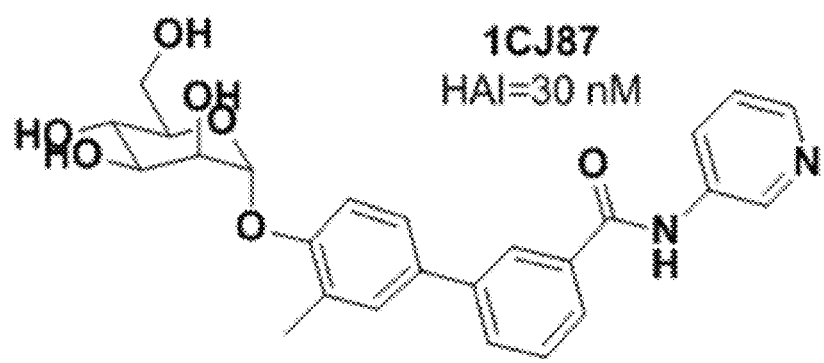
Figure 9E:
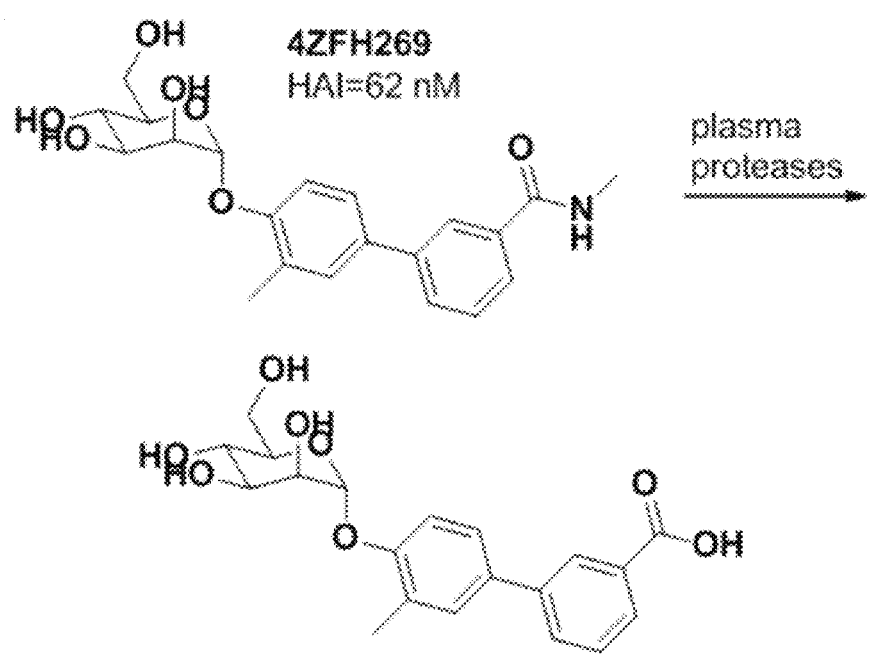

The efficacy of in vivo mannoside treatment was evaluated after orally dosing animals with 25 mg/kg of mannosides ZFH269, Prodrug FIM-4269, ZFH-5254, and ZFH-5240 in 10% cyclodextrin or 10% cyclodextrin 30 min prior to infecting with UTI89. At 6 hours post-infection (hpi) the bladders were removed and total bacterial CFUs were quantitated. In all of the mannoside-treated cohorts, there was a drop in bacterial counts demonstrating the efficacy of these mannosides in reducing overall colonization of the bladder (FIG. 7A). Importantly, the prodrug of ZFH269 exhibited significantly better activity than ZFH269. Next, several different prodrugs were evaluated in the same mouse model of urinary tract infection. Animals were orally dosed with 25 mg/kg of mannosides ZFH-4269, prodrug FIM-1233 (FIG. 8B), prodrug FIM-6123 (FIG. 8C) and prodrug 269 in 10% cyclodextrin or 10% cyclodextrin 30 min prior to infecting with UT189. In all of the mannoside-treated cohorts, there was a drop in bacterial counts demonstrating the efficacy of these mannosides in reducing overall colonization of the bladder (FIG. 7B).

Example 24. Uropathogenic E. coli (UPEC) Pathogenesis in the Urinary Tract

Clinically, it has been presumed that UPEC infection consists of a relatively simple extracellular colonization of the luminal surface after inoculation of fecal flora into the bladder via the urethra. In contrast, using a murine model of UPEC infection of the UT, the inventors have detailed an unexpectedly complex UPEC pathogenesis cycle that involves both intracellular and extracellular niches. Using genetic, biochemical and cell biological approaches together with a variety of imaging techniques including transmission, quick freeze-deep etch and scanning electron microscopy, as well as confocal and time lapse video microscopy, the inventors discovered that UPEC invade bladder facet cells via a FimH-dependent mechanism (see below). After invasion, cytoplasmic intracellular bacterial communities (IBCs) are formed. Rapid replication of the initial invading bacteria results in the formation of an early IBC of loosely-packed rod-shaped bacteria. The bacteria continue to replicate and progress to form a large densely packed mid-stage IBC of morphologically coccoid bacteria, with biofilm-like characteristics including positive periodic acid-Schiff (PAS) staining and differential gene expression throughout the community. After the IBC matures, bacteria detach from the biomass, often become filamentous, and spread to neighboring cells forming new generation IBCs. Thus, the IBC pathway facilitates massive expansion of the invading bacteria in a niche protected from host defenses. Translational studies have shown that the majority of UPEC isolates form IBCs when introduced into the murine bladder and that IBCs and filamentous bacteria occur in the urine of human UTI patients. Population dynamic studies conducted by the inventors using ex vivo gentamicin protection assays demonstrated that ~$10^4$ UPEC of an initial $10^7$ inoculum invaded the bladder tissue within 15 minutes after infection and that one percent of the invaded bacteria went on to form IBCs, resulting in an average of 100 IBCs per infected mouse bladder. If this is extrapolated to the human situation, innate defenses in the bladder most likely prevent the majority of bacterial inoculation events into the bladder from leading to disease. However, the ramifications of the IBC cascade are striking. Invasion of a single infecting bacterium can lead to rapid expansion of the infection via IBC formation, replicating within hours to $10^4$ bacteria and even higher numbers followed by dispersal of the bacteria from the biomass and spreading to neighboring cells to reinitiate the IBC cascade. This process allows the bacteria to gain a critical foothold. Bacterial descendents of the acute IBC cascade have been shown using a murine model, to be able to form a quiescent intracellular reservoir (QIR) that can persist, protected from antibiotics and seemingly undetected by the host immune system even after the acute infection is resolved and bacteria are no longer detectable in the urine. Bacteria in the QIR can later seed a recurrent infection, manifested by IBC formation, bacteruria and inflammation.

Example 25. FimH as a Therapeutic Target

There are several key implications from understanding UPEC pathogenesis. Mannosides and pilicides that block FimH function will prevent bacterial adherence and invasion and thus prevent bacterial amplification in the IBC and subsequent spreading and repeated rounds of amplification via new generation IBCs. These compounds will have potent therapeutic activity by preventing bacterial expansion which may also have the consequence of eliminating or significantly reducing the QIR thus reducing predisposition to recurrent infection.

Type 1 Pili/FimH are Critical for UPEC Pathogenesis in the UT.

Figure 11A:
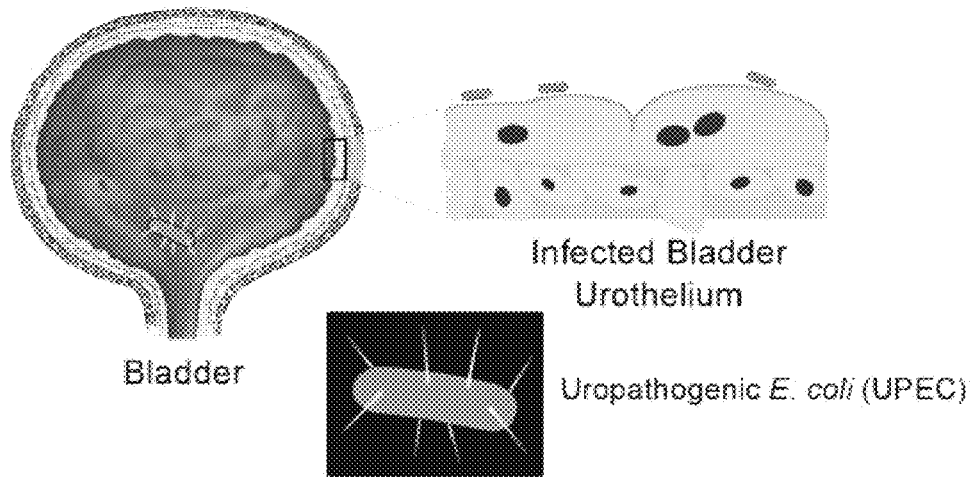
FIG. 11A, FIG. 11B and FIG. 11C depict illustrations and images of FimH-mediated adhesion to the bladder.
Figure 11B:
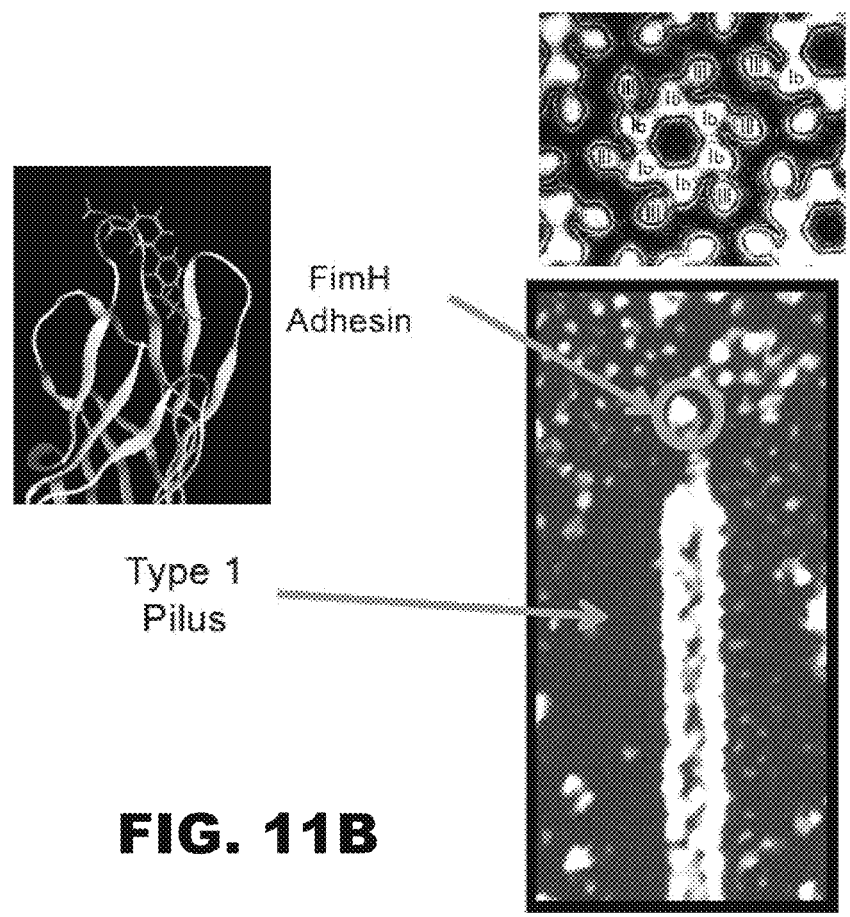
Figure 11C:
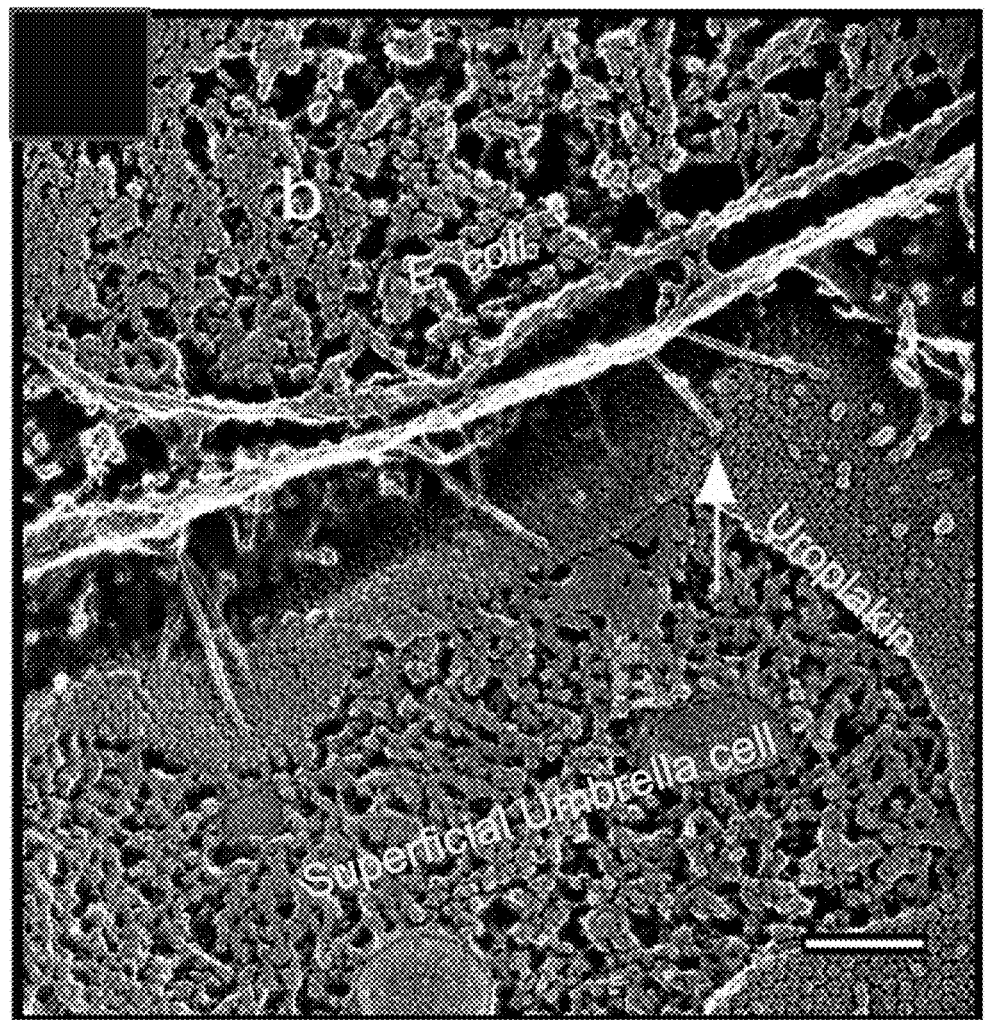

Type 1 pili are essential cystitis virulence determinants. Using scanning and high-resolution EM and the mouse cystitis model developed by the inventors, it was shown that adhesive type 1 piliated bacteria are able to bind and invade host superficial umbrella cells, while UPEC lacking type 1 pili are not. Colonization and invasion of the bladder epithelium is dependent on the FimH adhesion located at the distal end of the pilus that binds mannose residues on bladder epithelial cells. High-resolution freeze-dry/deep-etch EM revealed that FimH interacts directly with receptors on the luminal surface of the bladder (FIG. 11). Standard gentamicin protection assays of infected tissue culture cells and ex vivo gentamicin treatment of infected bladders demonstrated that fimH$^+$ type 1 piliated clinical cystitis isolates, but not fimH$^-$ mutants, could invade bladder epithelial cells. Using immunohistochemistry and Pfim-gfp transcriptional fusions it was demonstrated that type 1 pili are expressed within IBCs. Using high-resolution EM, pilus-like fibers radiating from bacteria and interacting with matrix material within the intracellular IBC were also visualized. These results combined with work showing that type 1 pili are required for biofilm formation in in vitro systems led to the hypothesis that type 1 pili promote IBC formation and/or maintenance. Therefore, an anhydrotetracycline (AHT) inducible fim strain was constructed which can be "pre-piliate" UTI89 in vitro by growth in AHT before infecting mouse bladders, allowing the initial invasion event to normally. However, once inoculated into the mouse, AHT is no longer present, fim transcription ceases and piliation is diluted upon each bacterial division. Using this system, the earliest events of colonization and invasion were identical between the wild type and conditional strain. However, the inability of the conditional strain to produce type 1 pili intracellularly abolished its ability to form IBCs, as shown by confocal microscopy, and thus dramatically attenuated virulence as determined by CFUs at later time points. These results strongly suggest that type 1 pili are required for the survival and proliferation of UPEC within superficial facet cells. Additionally, this conditional mutant is significantly impaired in its ability to form QIRs, arguing that the bacteria in QIRs are descendents and thus dependent on the acute IBC cascade.

Structural Studies of FimH and its Ligand.

Figure 12A:
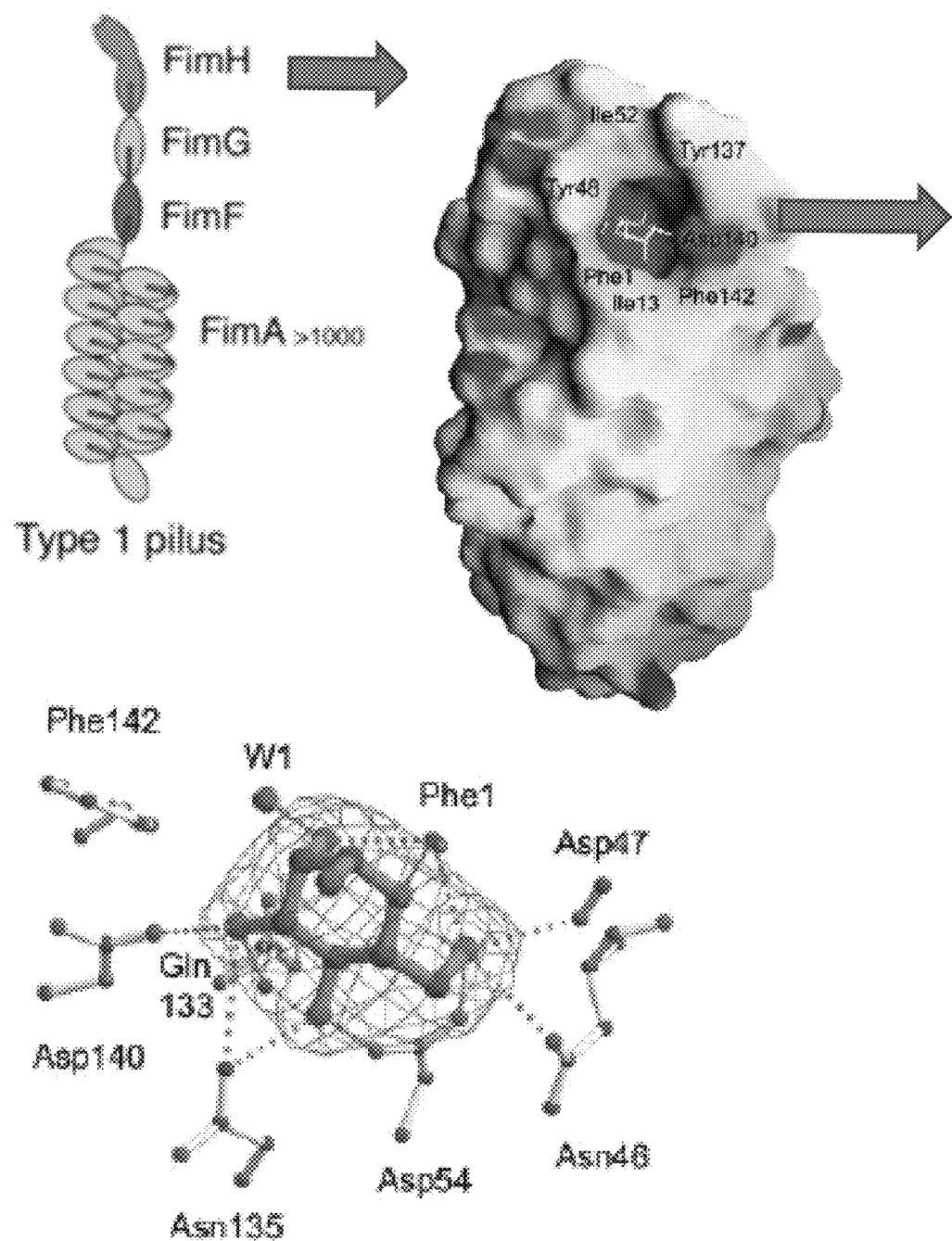
FIG. 12A and FIG. 12B depict illustrations and graphs showing the FimH lectin domain and D-mannose binding.
Figure 12B:
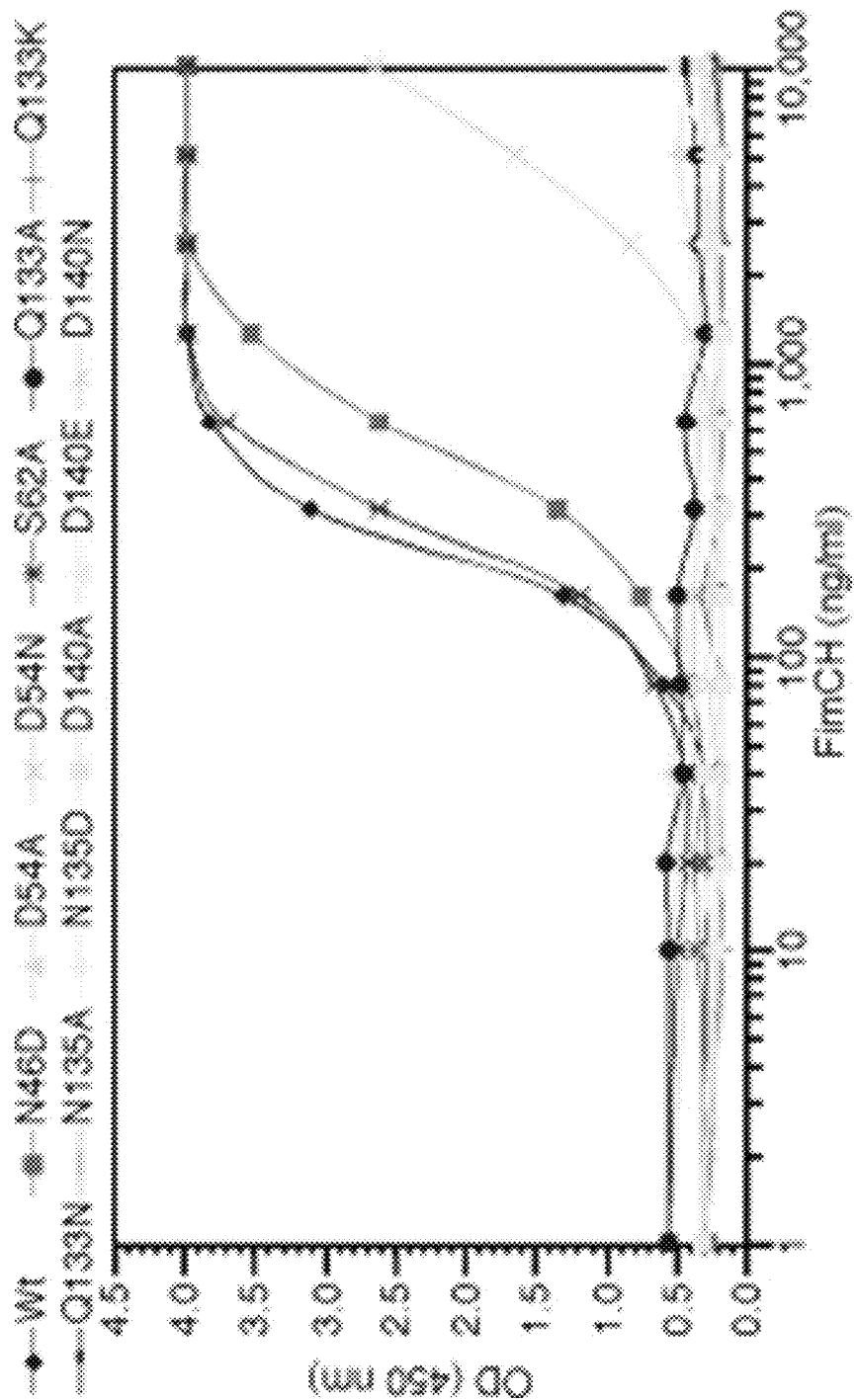
Figure 13:
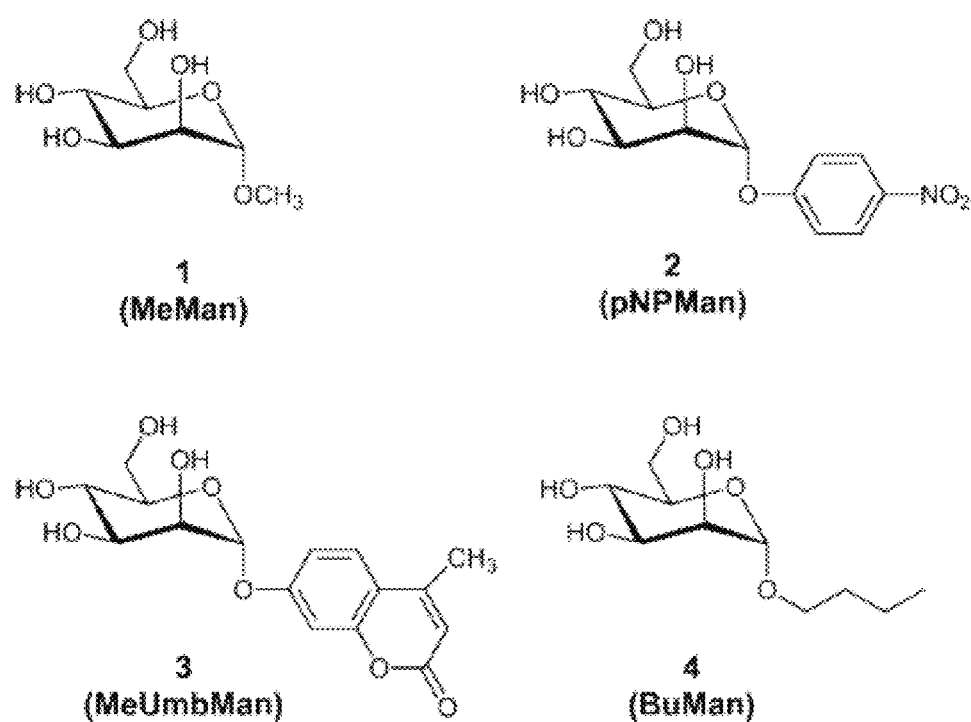
FIG. 13 depicts the history of mannosides as UTI virulence inhibitors. 1987 to present the focus was on multivalent mannosides to increase avidity, low potency of monomeric mannosides was observed and there was a lack of target and structural information. Importantly, no oral bioavailability or in vivo studies were reported.

Adhesive type 1 pili are prototypic structures of a family of adhesive fibers produced by diverse Gram-negative bacteria via the chaperone/usher assembly pathway. Using biochemistry, mutational studies, nuclear magnetic resonance, and x-ray crystallography, the molecular basis of pili assembled by the chaperone/usher pathway in gram-negative bacteria, including type 1 pili of UPEC, were delineated (FIG. 12) The three dimensional structure of FimH bound to its mannose receptor was solved in order to gain a molecular snapshot of a critical initial event in UTI pathogenesis.

Figure 14:
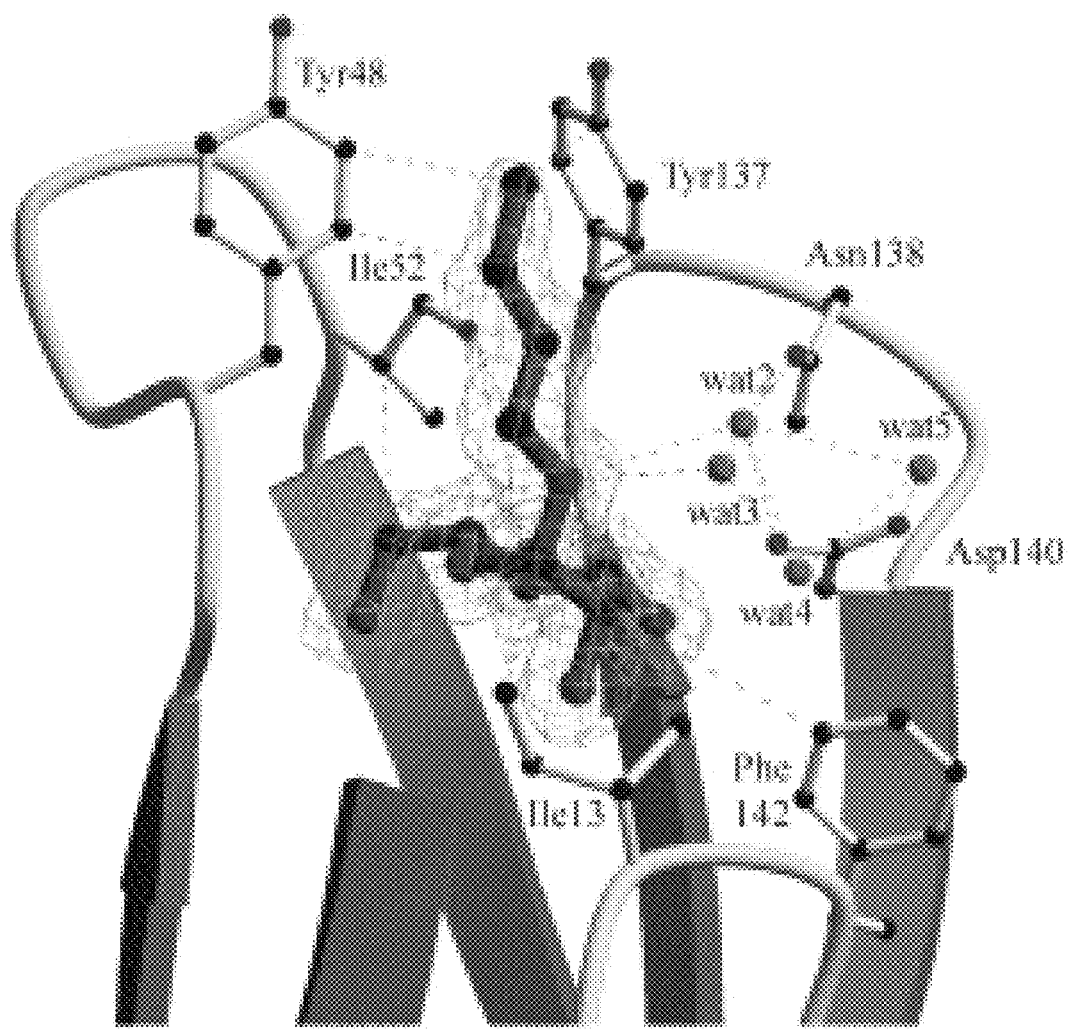
FIG. 14 depicts a ribbon diagram of butyl mannose bound to FimH. The shape of the binding pocket and orientation of the mannose ring are similar to the D-mannose-FimH structure. There are new hydrophobic interactions between the butyl group and Tyr48, Try137 and Ile52.
Figure 15:
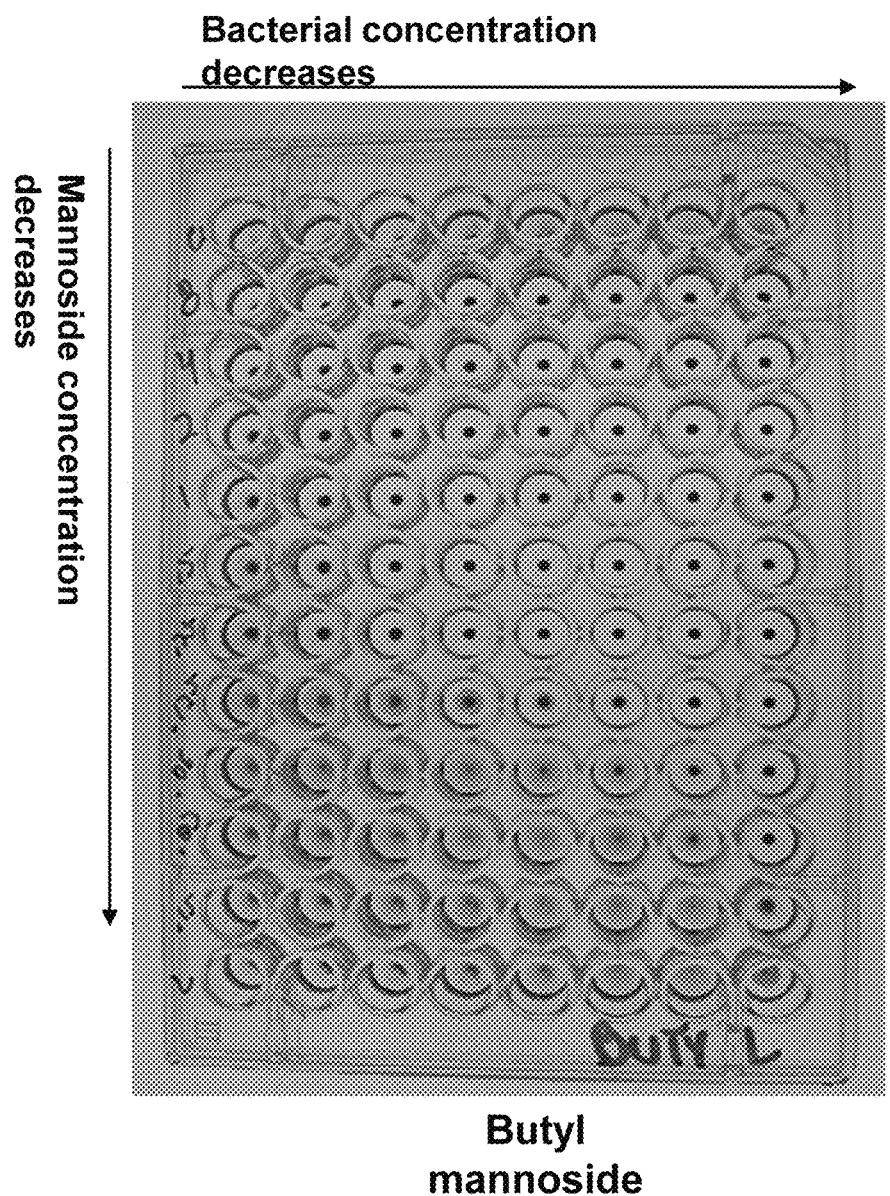
FIG. 15 depicts the hemagglutination assay (HA) used to assess the compounds' ability to block FimH mediated binding. The HAI titer quantitatively measure the effect of inhibitors on blocking the FimH-mediated hemagglutination (HA) of guinea pig red blood cell infected with *E. coli*. HAI titer is defined as the effective concentration of compound which inhibits >90% hemagglutination of the red blood cells.
Figure 16A:
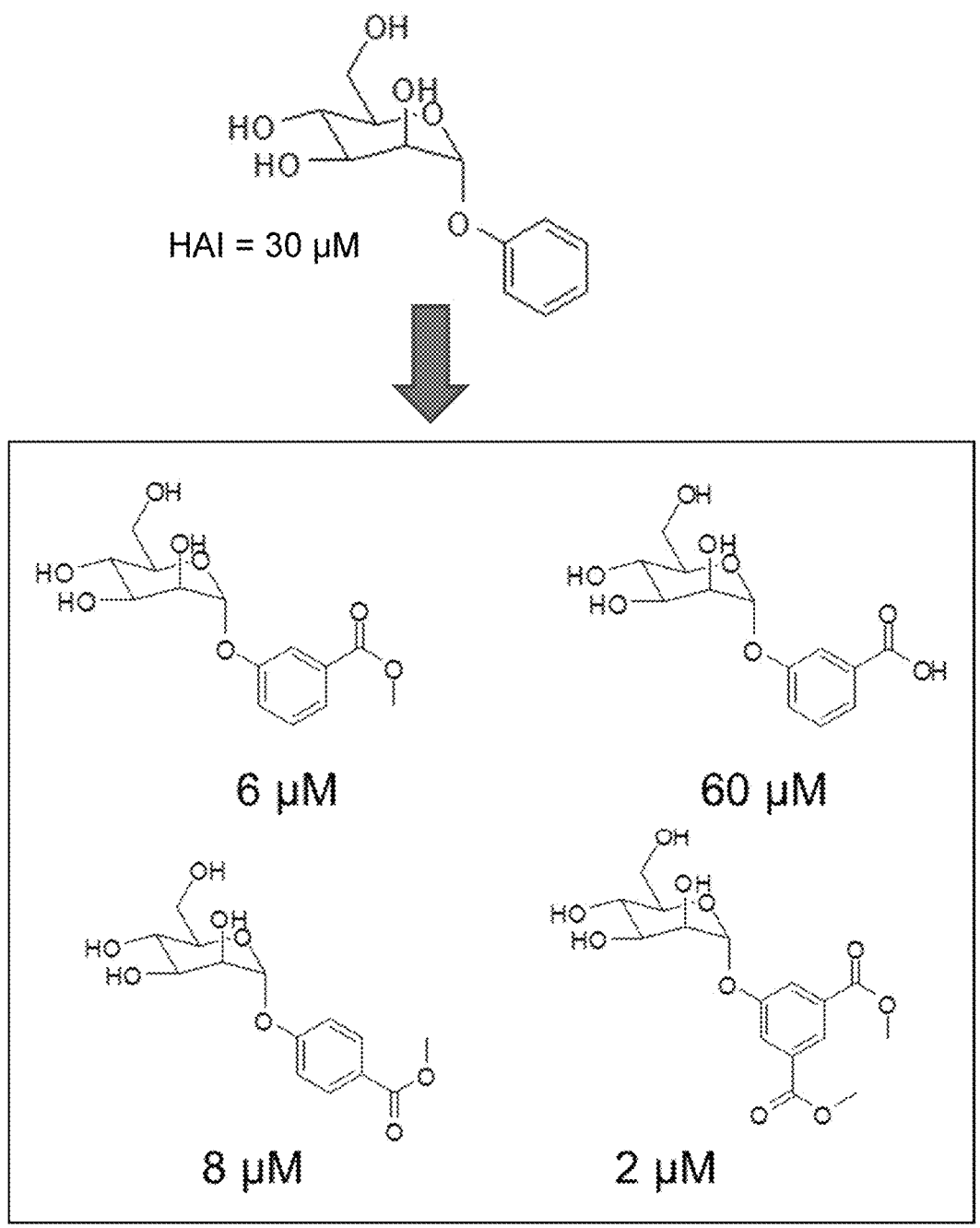
FIG. 16A, FIG. 16B and FIG. 16C depict the initial structure activity relationship (SAR) of phenyl mannosides.
Figure 16B:
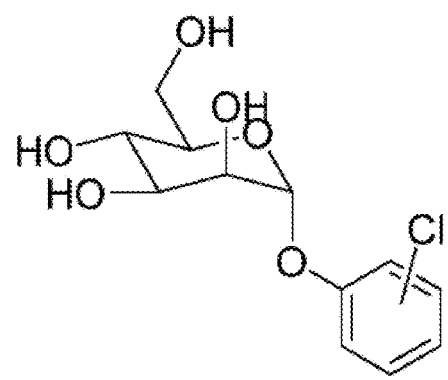
Figure 16C:
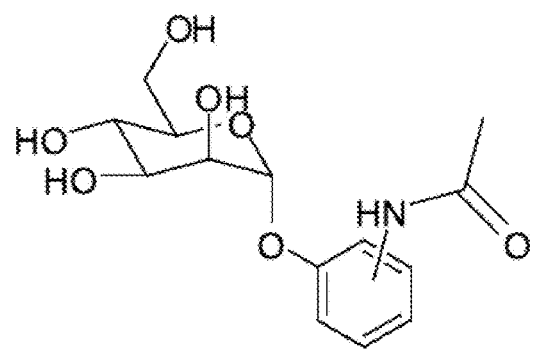
Figure 17:
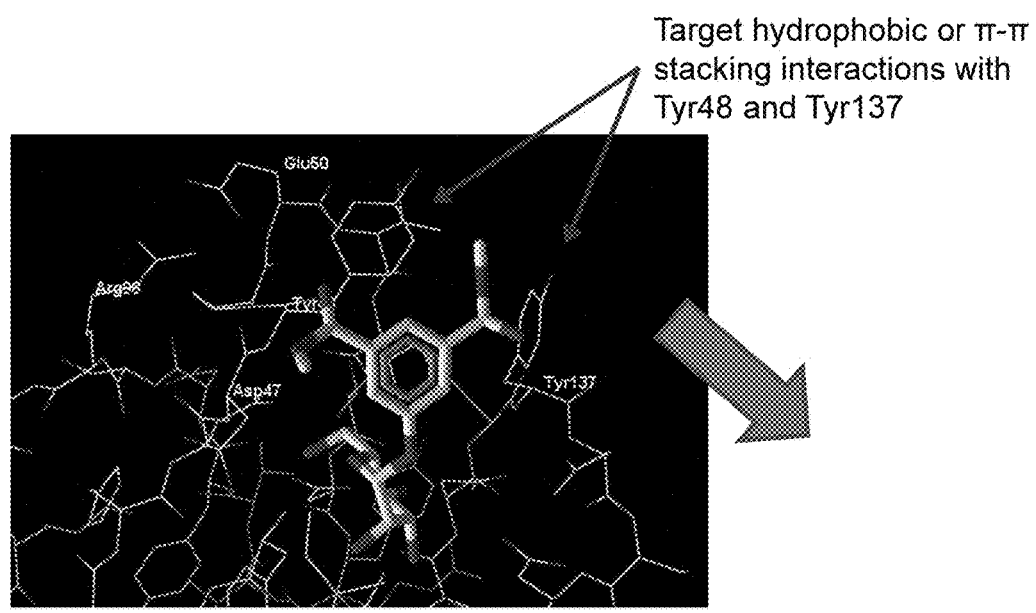
FIG. 17 depicts images showing the rational designed behind multi-ring mannosides. Multi-ring mannosides can target hydrophobic or π-π stacking interactions with Tyr48 and Try137.
Figure 17:
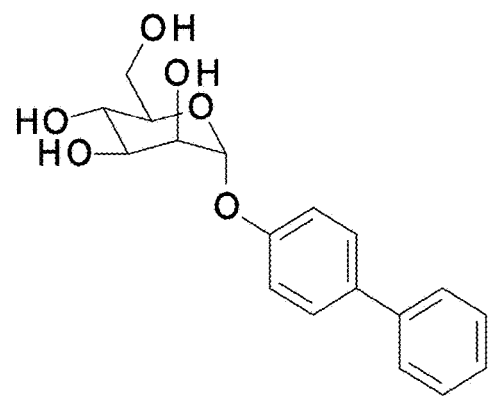
Figure 18A:
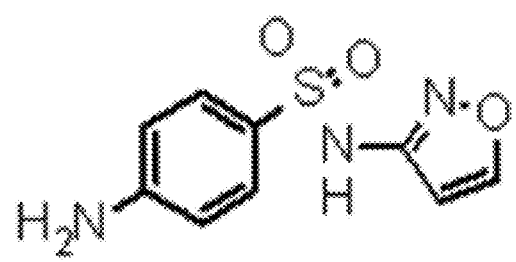
FIG. 18A, FIG. 18B, FIG. 18C, FIG. 18D and FIG. 18E depict a graph showing compound 6 potentiates TMP-SMZ treatment.
Figure 18B:
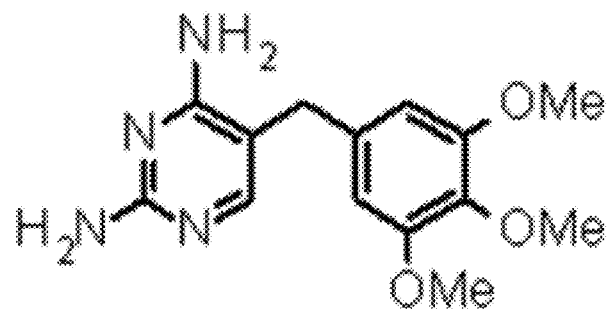
Figure 18C:
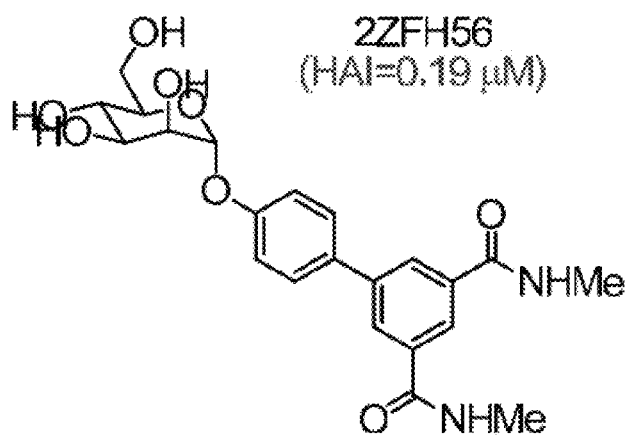
Figure 18D:
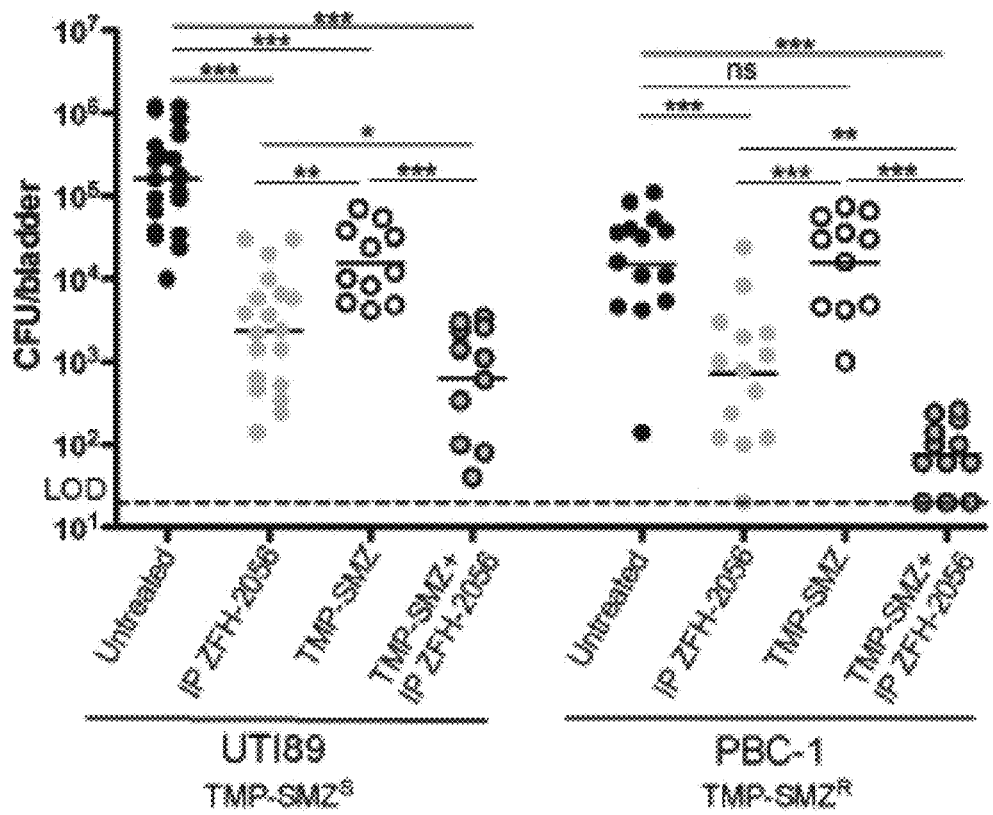
Figure 18E:
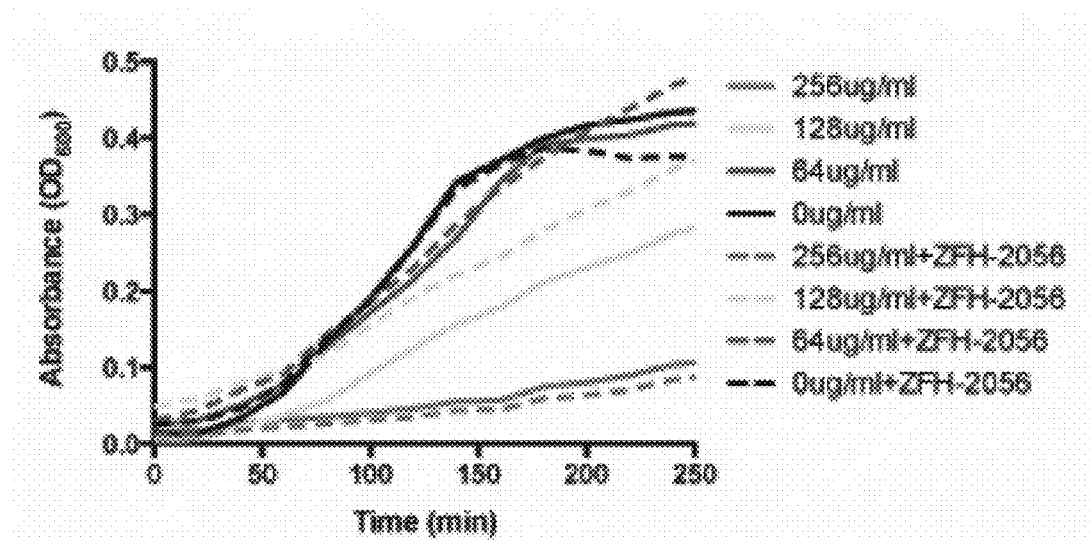
Figure 19:
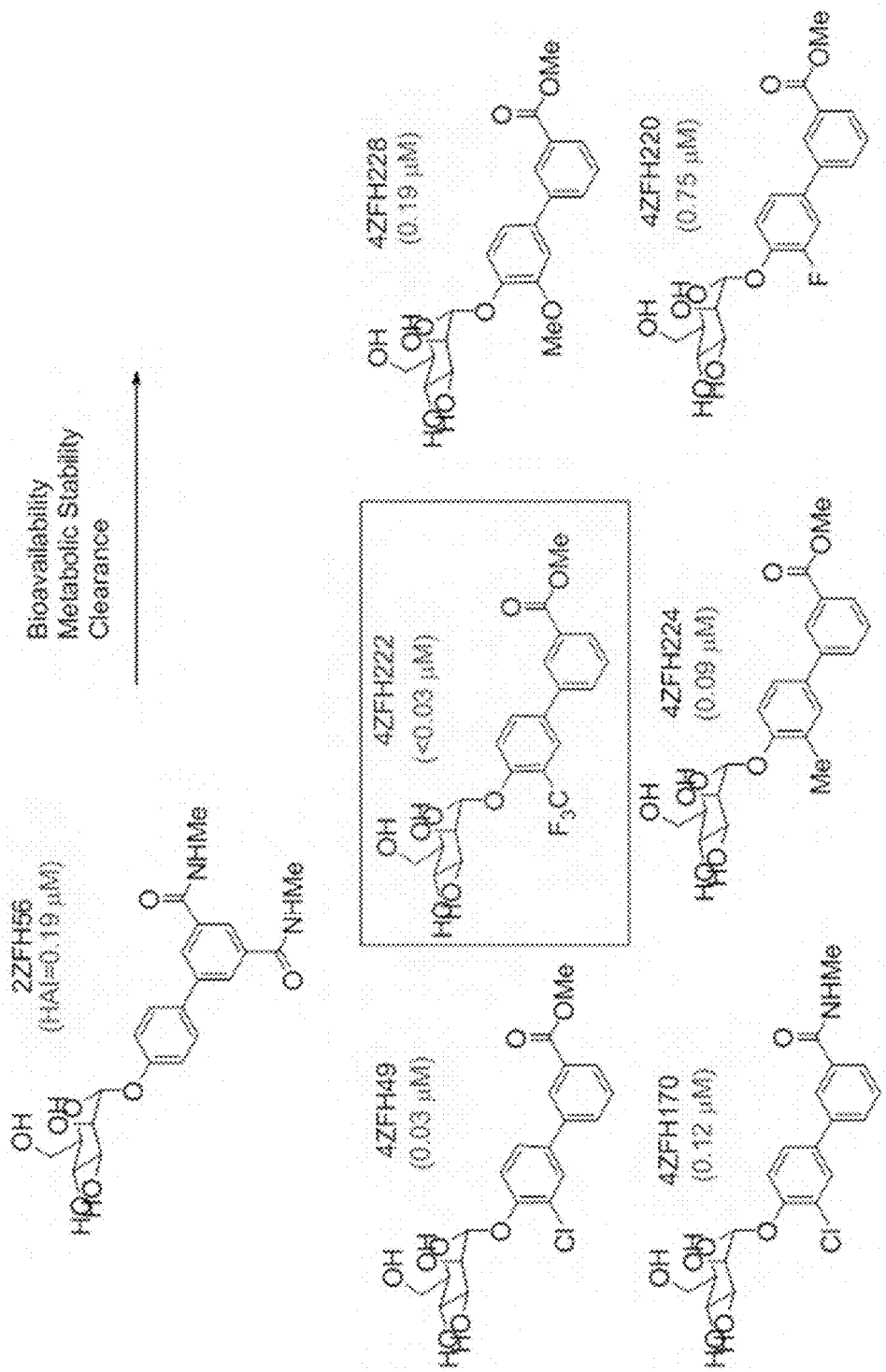
FIG. 19 depicts A-ring ortho group compounds. A-ring ortho groups significantly enhance potency.
Figure 20A:
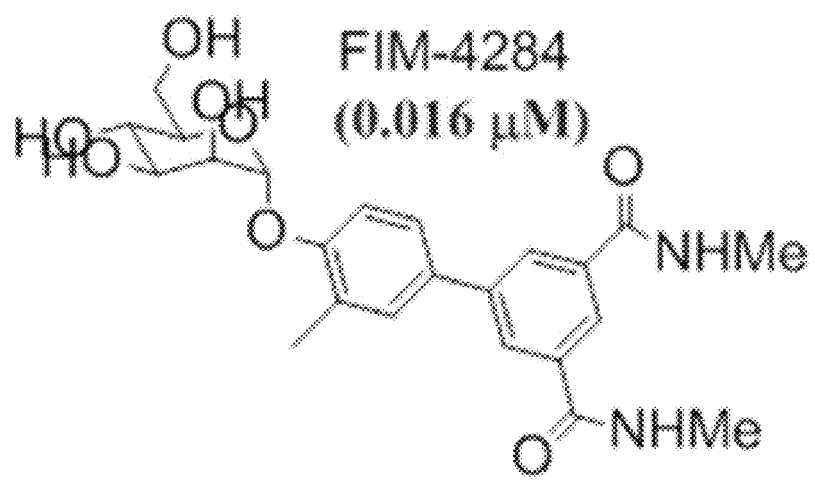
FIG. 20A, FIG. 20B and FIG. 20C depict the FimH structure in the presence of ortho-mannosides. The structure of mannoside compounds (FIG. 20A) FIM-4284 and (FIG. 20B) FIM-4269 are depicted.
Figure 20B:
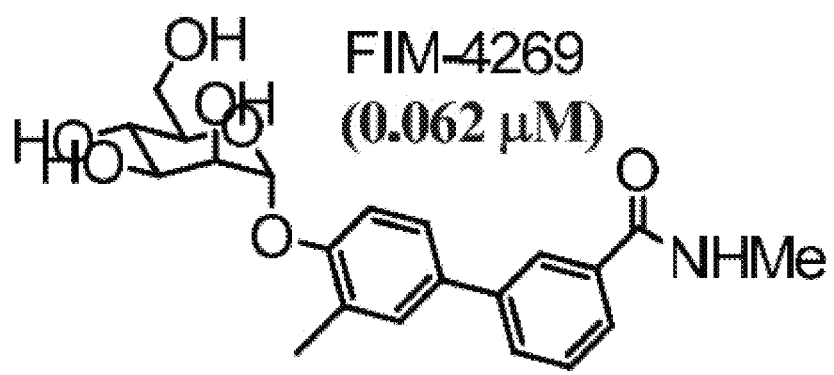
Figure 20C:
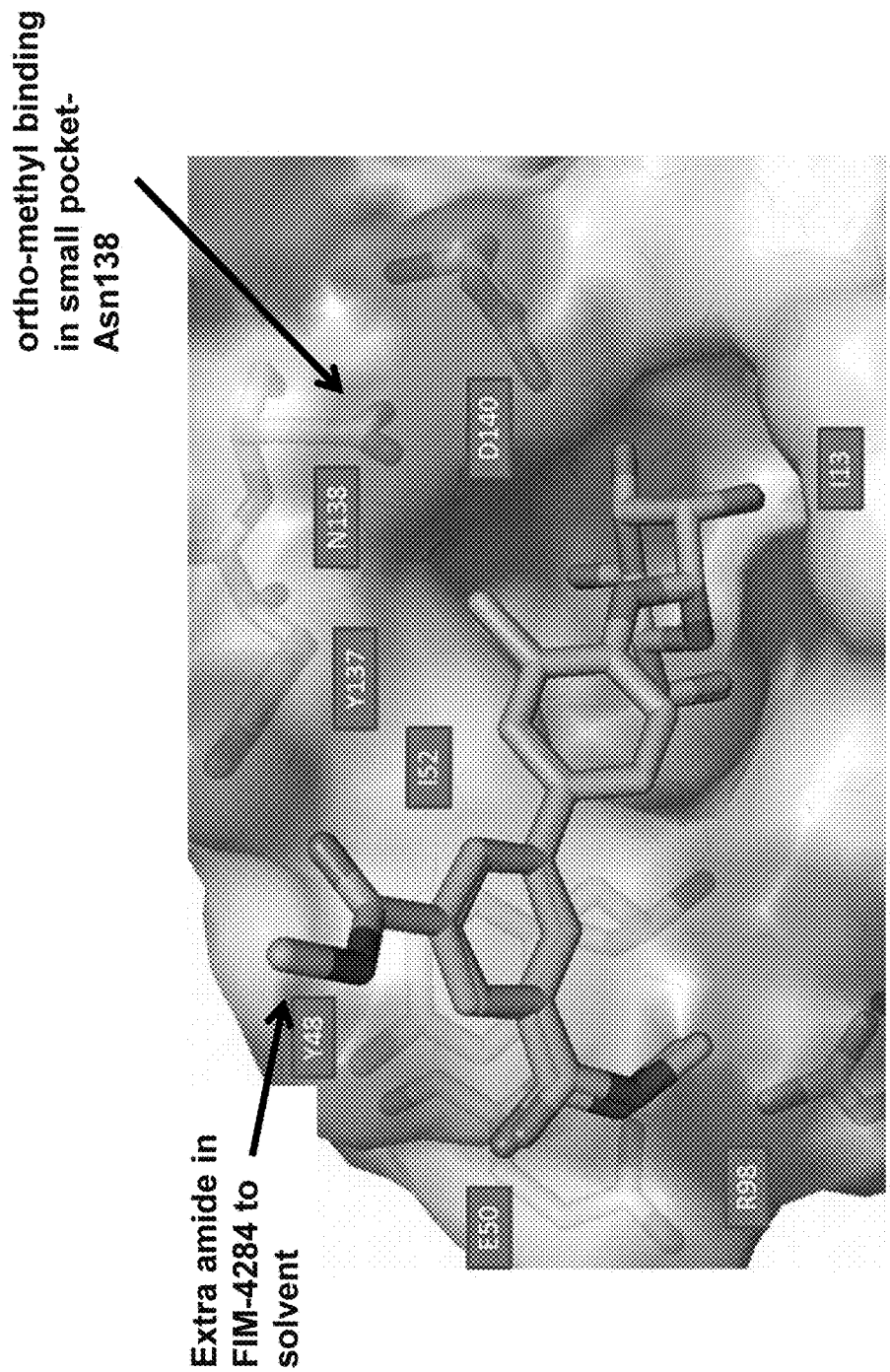
Figure 21A:
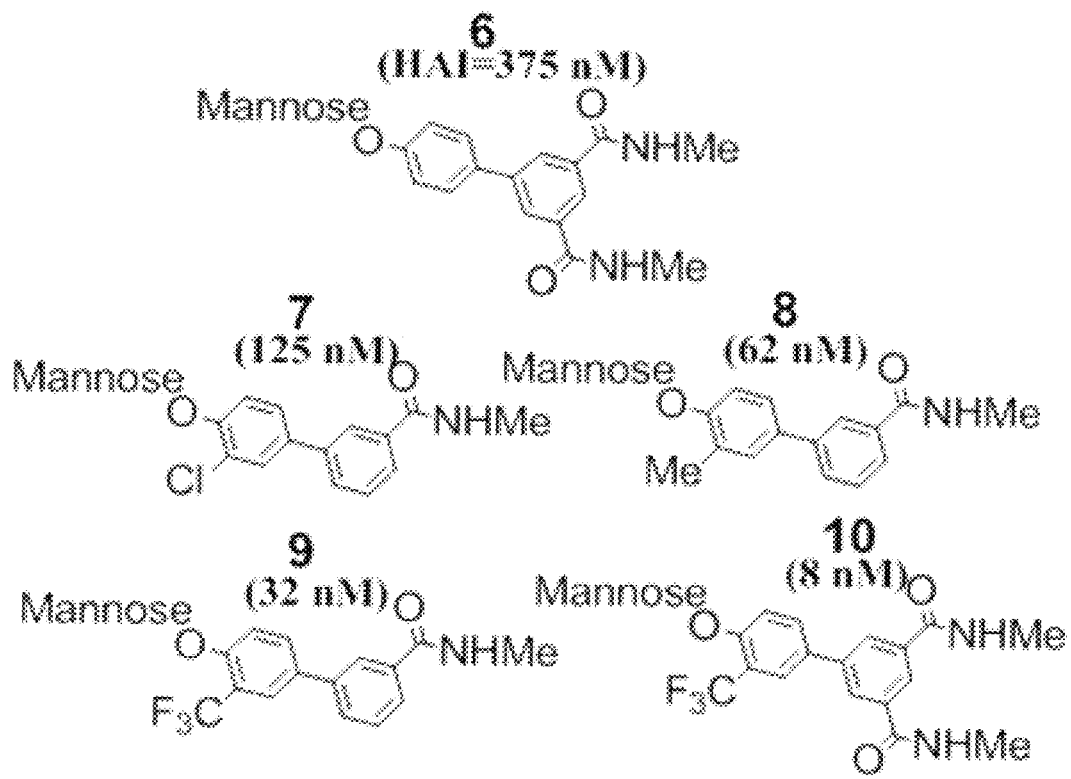
FIG. 21A and FIG. 21B depict compounds 7 to 10 show enhanced pharmacokinetics and potency at treating infection.
Figure 21B:
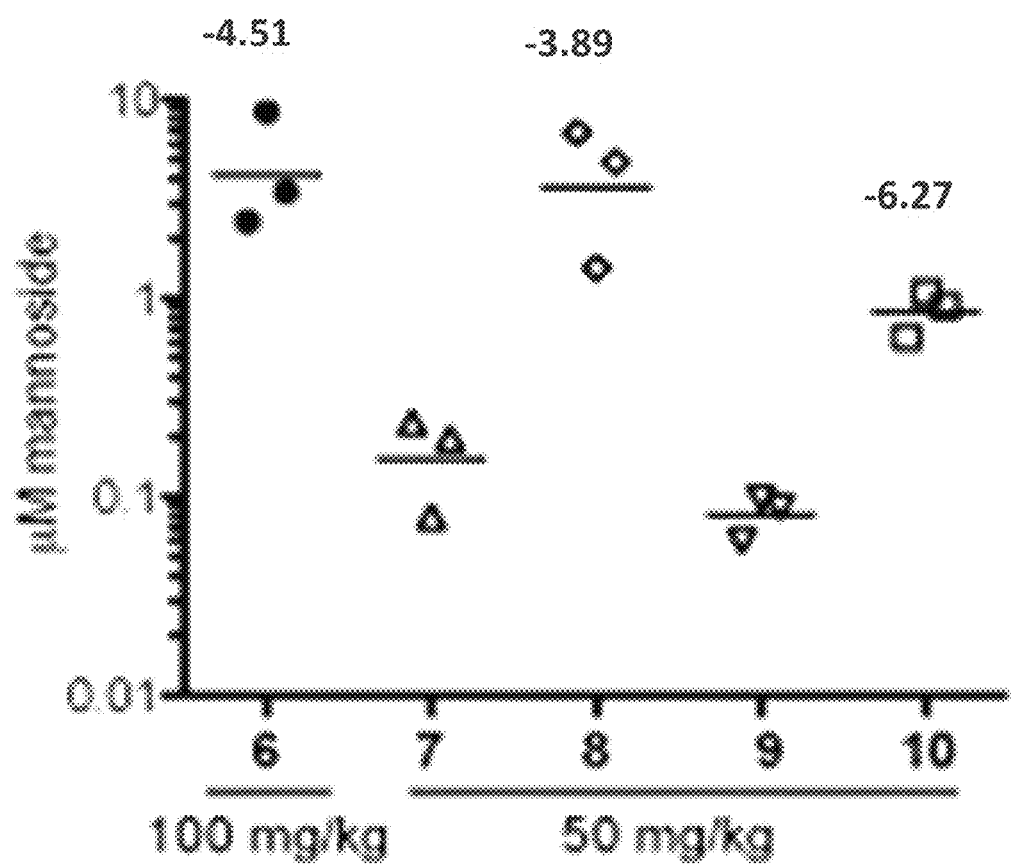
Figure 22A:
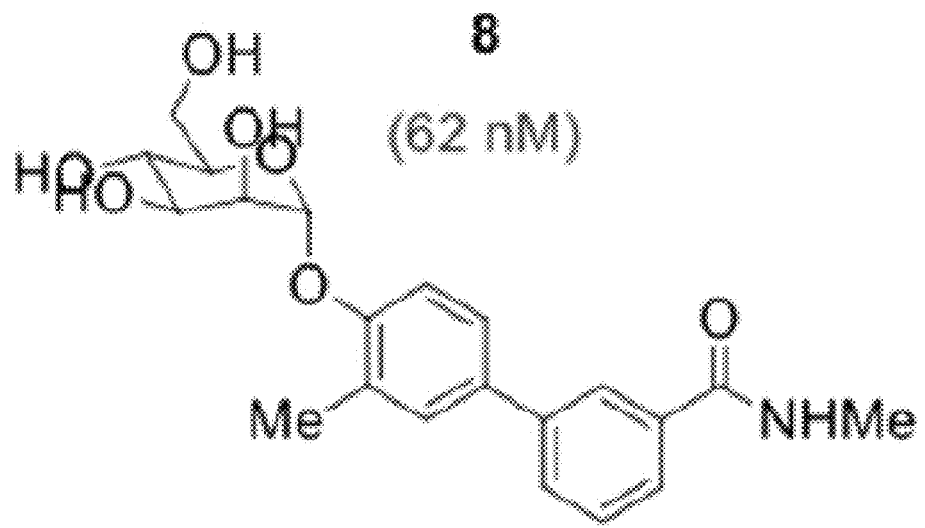
FIG. 22A, FIG. 22B, FIG. 22C and FIG. 22D depict the efficacy of biphenyl mannosides in chronic cystitis.
Figure 22B:
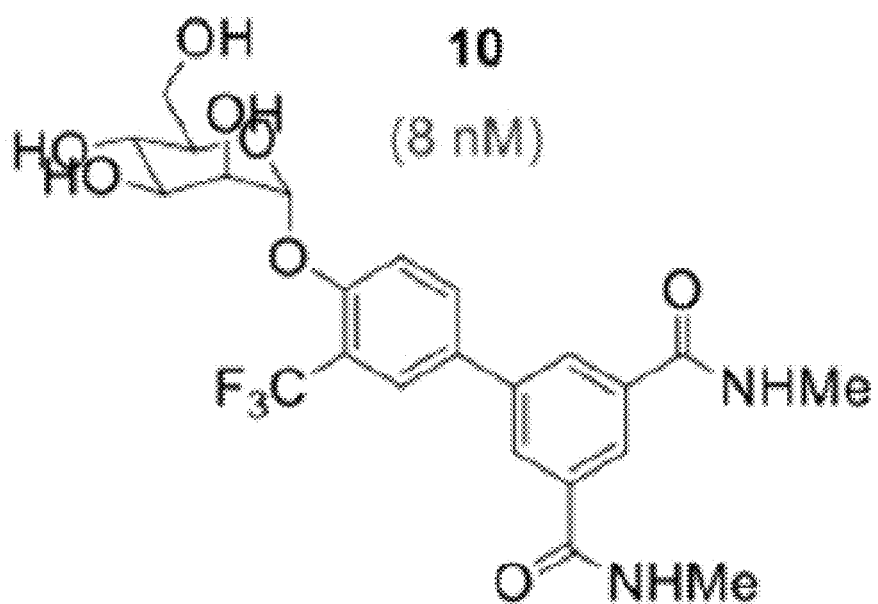
Figure 22C:
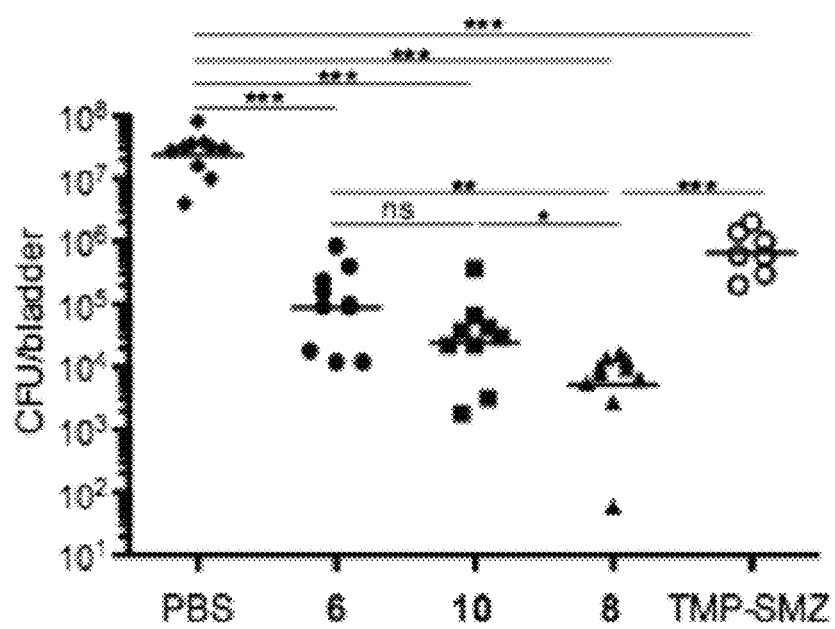
Figure 22D:
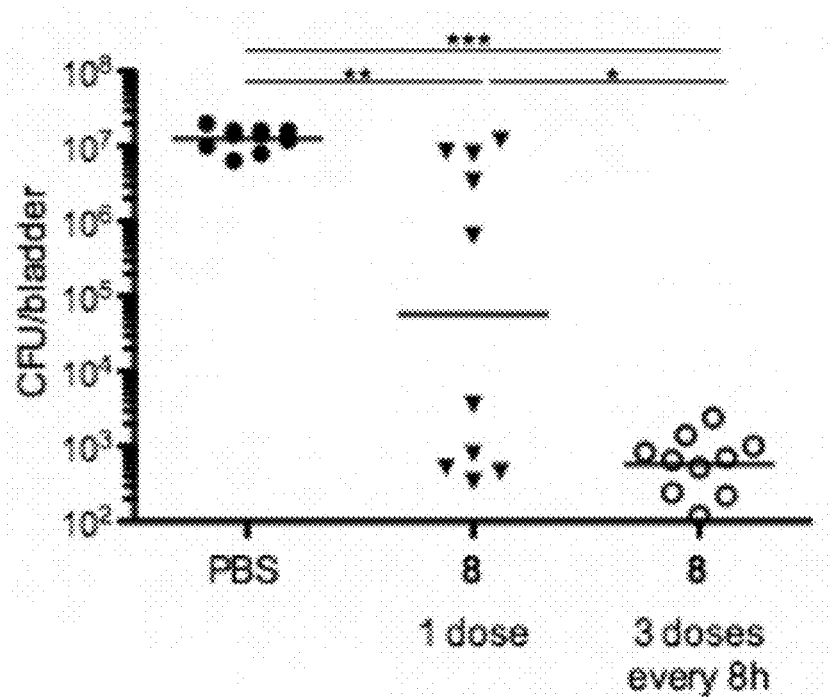
Figure 23:
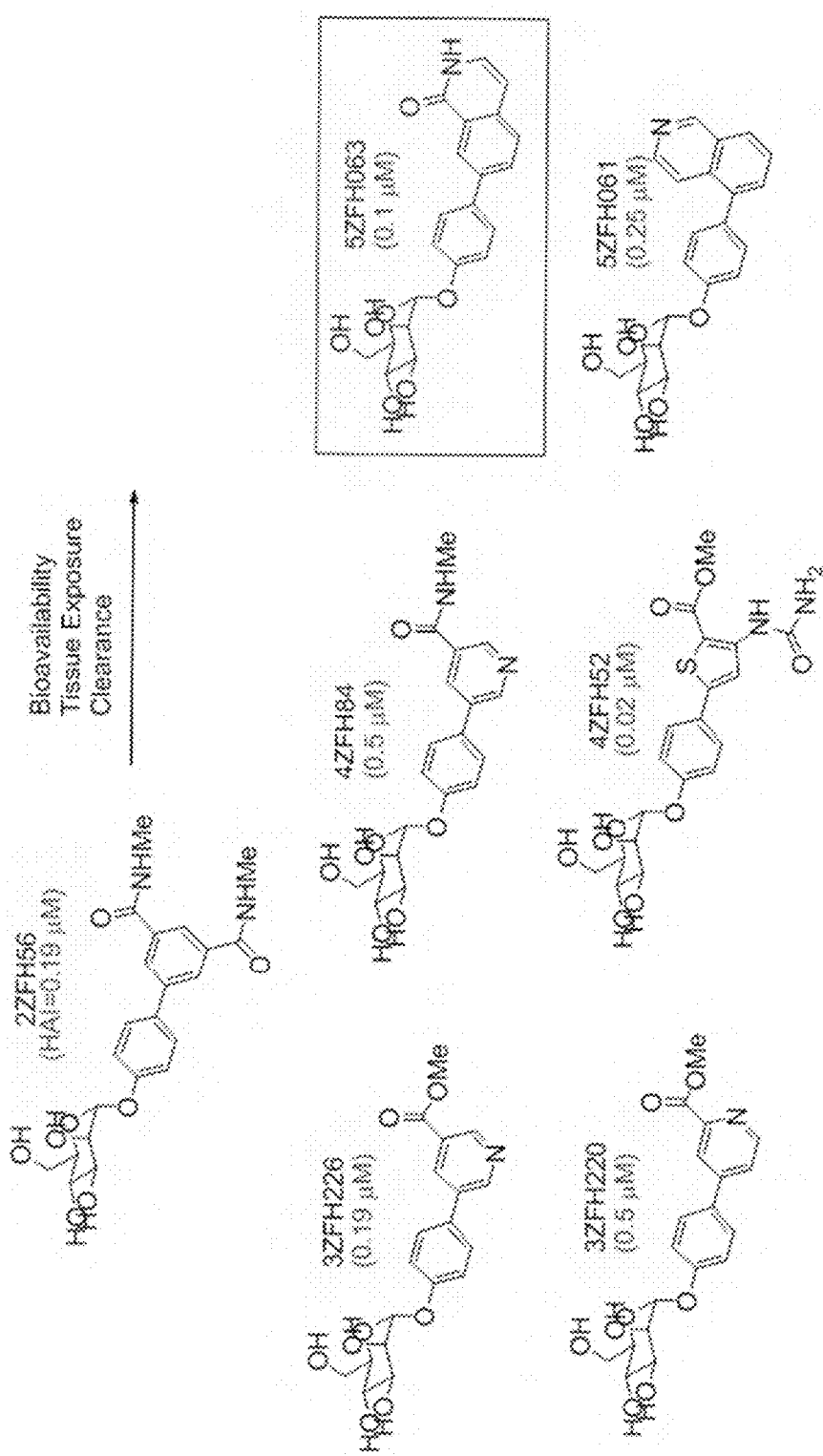
FIG. 23 depicts B ring heterocycles. The physical properties of B ring heterocycles are shown with HAI titer.
Figure 24A:
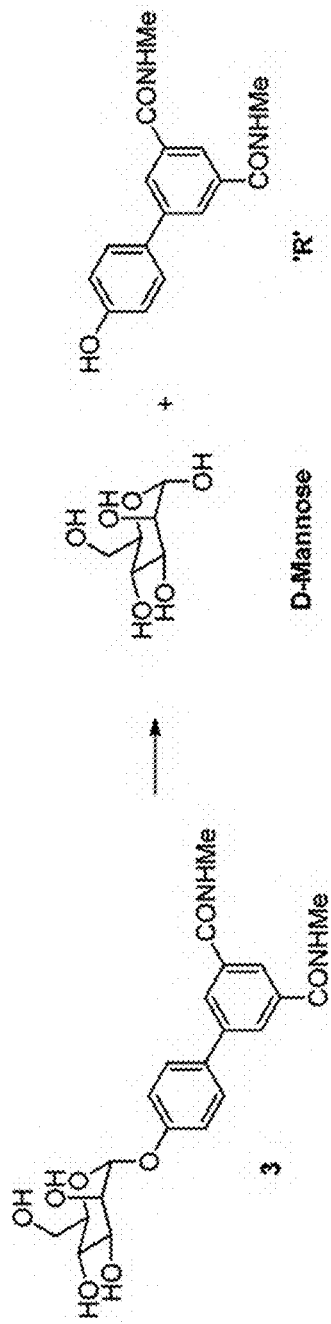
FIG. 24A and FIG. 24B depict the metabolism to D-mannose after PO dosing.
Figure 24B:
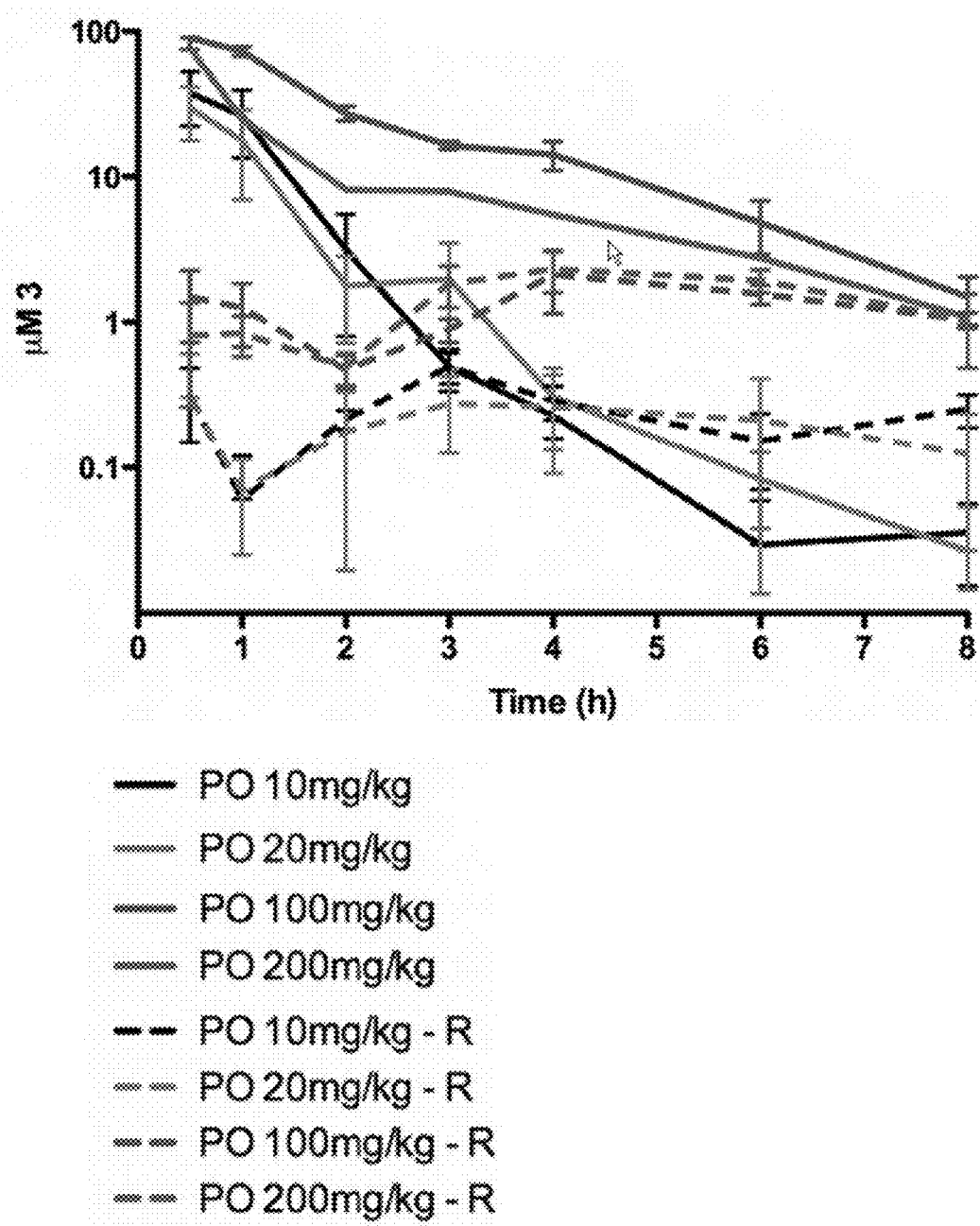
Figure 25A:
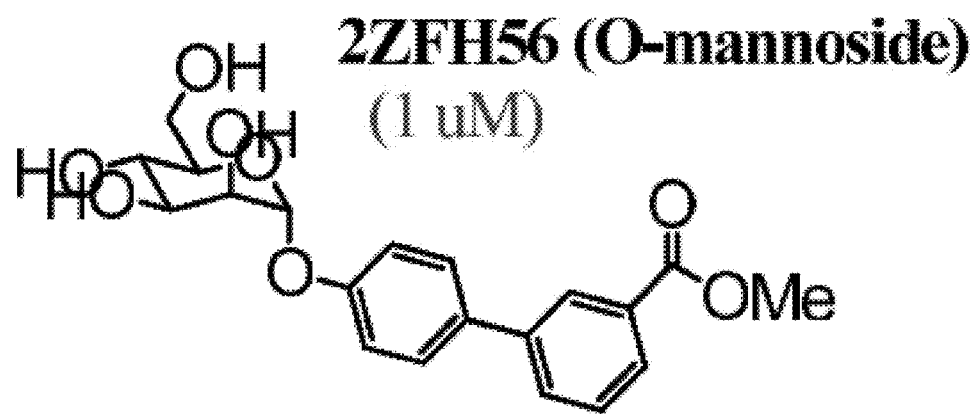
FIG. 25A, FIG. 25B, FIG. 25C, FIG. 25D, FIG. 25E, FIG. 25F, FIG. 25G, FIG. 25H, FIG. 25I and FIG. 25J depict various derviatives substituted at the glycoside bond. The substitution was evaluated to improve metabolic stability.
Figure 25B:
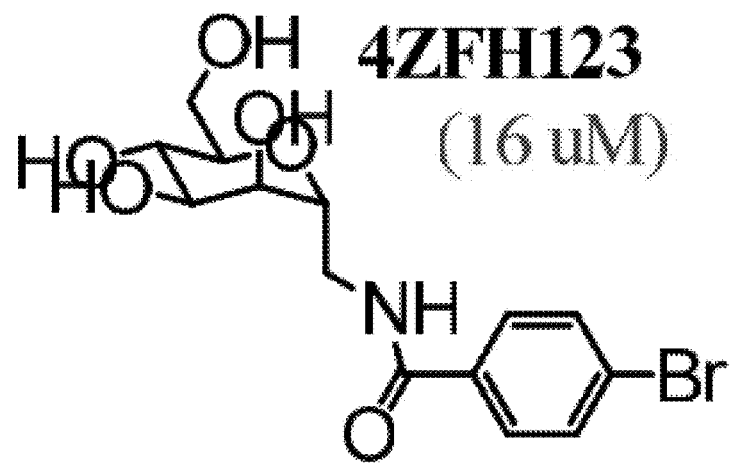
Figure 25C:
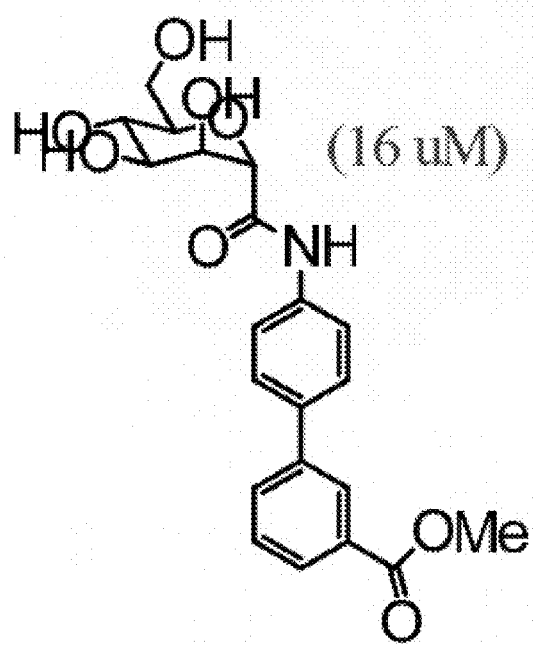
Figure 25D:
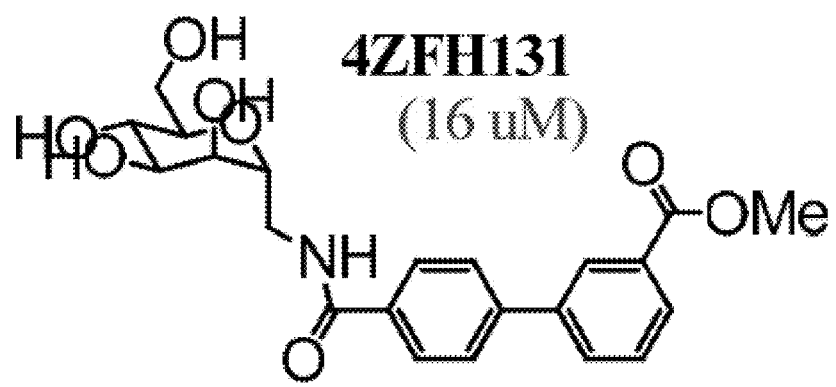
Figure 25E:
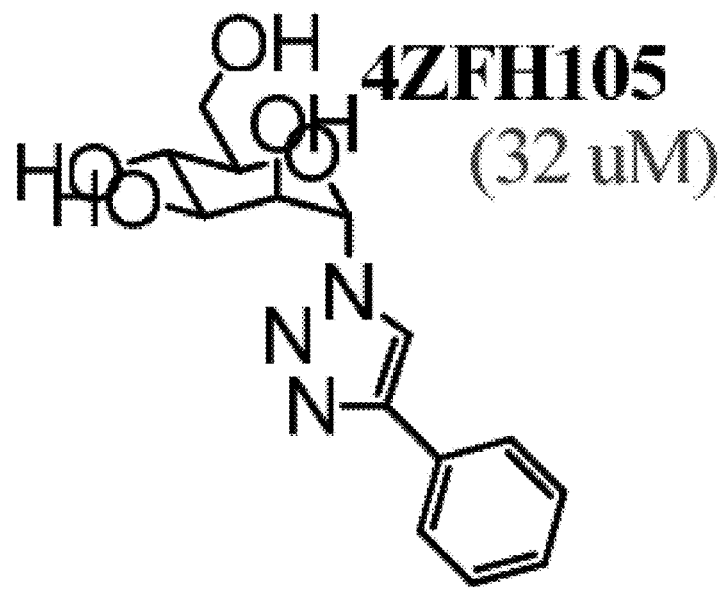
Figure 25F:
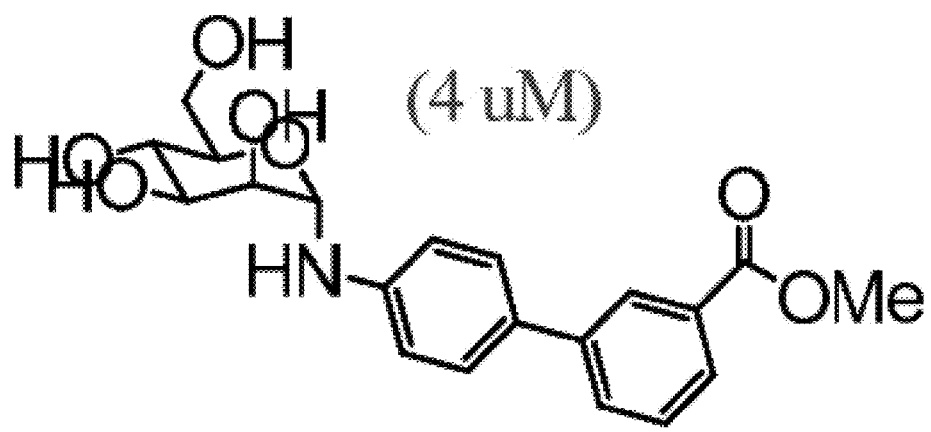
Figure 25G:
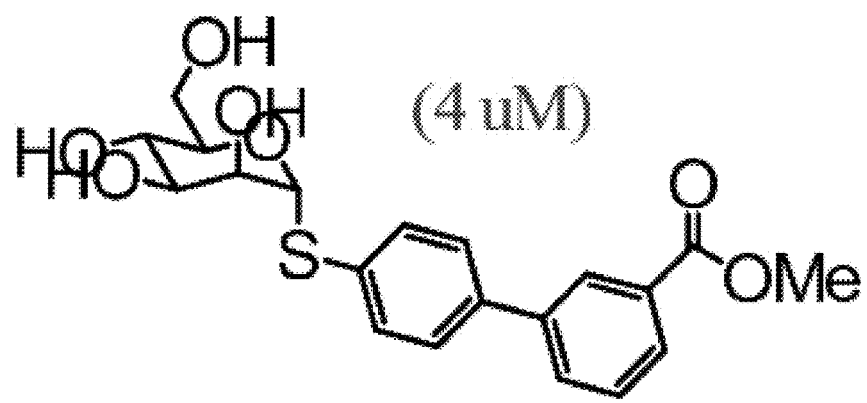
Figure 25H:
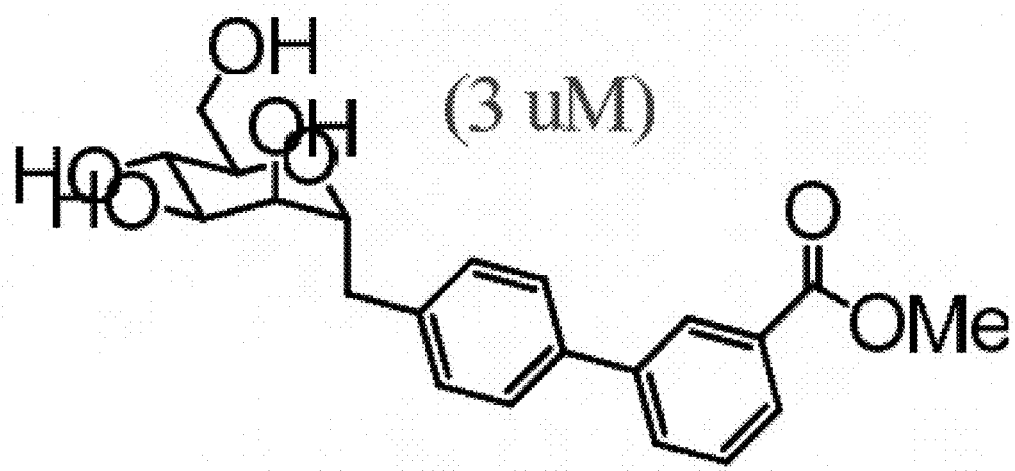
Figure 25I:
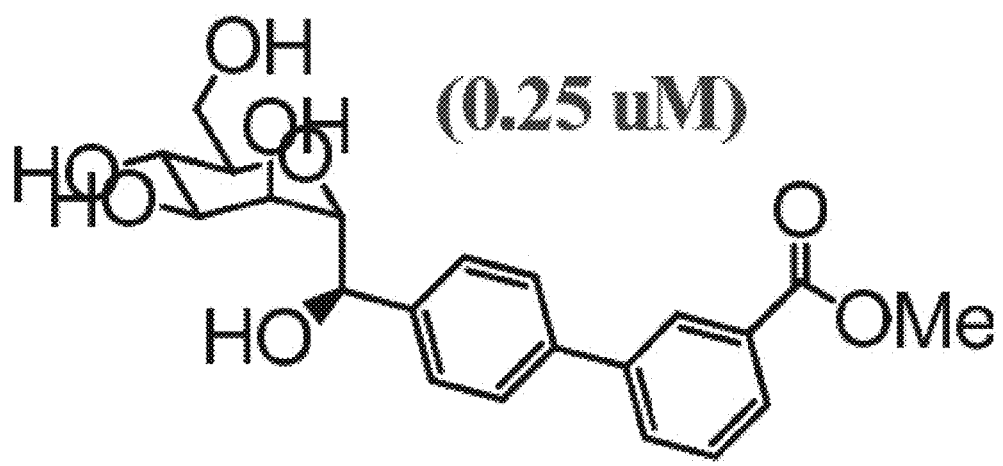
Figure 25J:
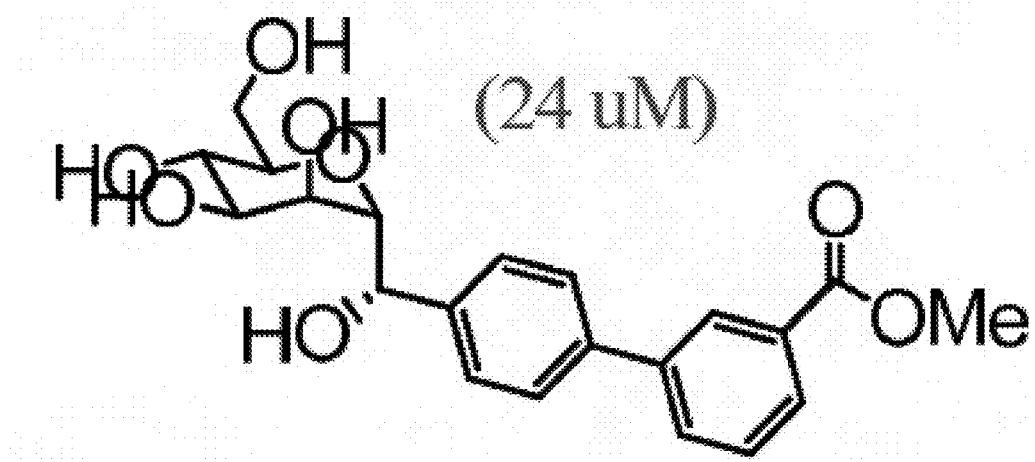
Figure 26A:
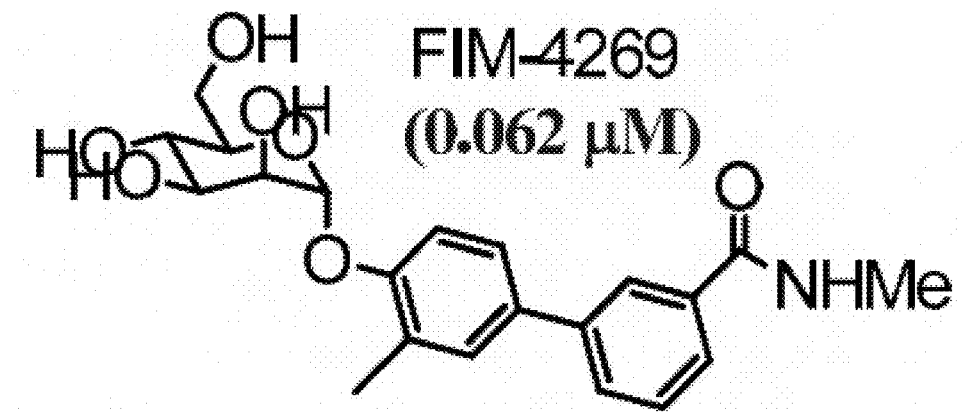
FIG. 26A, FIG. 26B, FIG. 26C and FIG. 26D depict the mouse pharmacokinetics of lead compounds (FIG. 26A) FIM-4269, (FIG. 26B) FIM-5254 (Example 7), and (FIG. 26C) FIM-5240 (Example 18A).
Figure 26B:
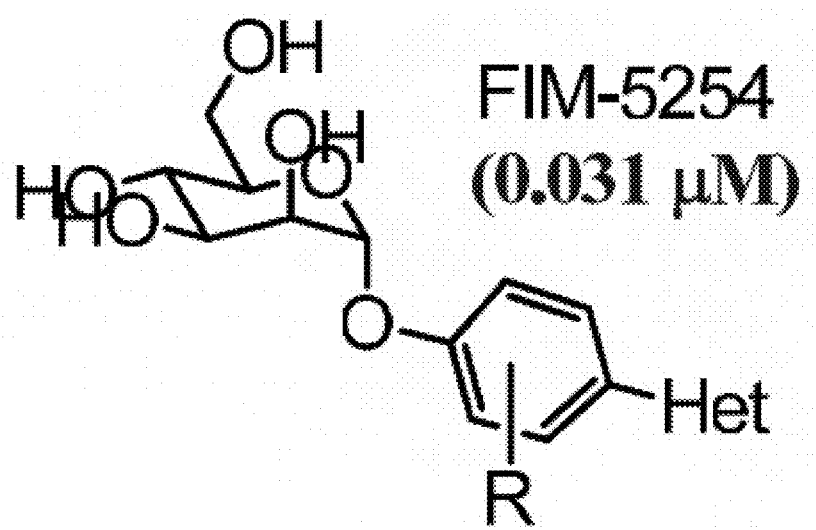
Figure 26C:
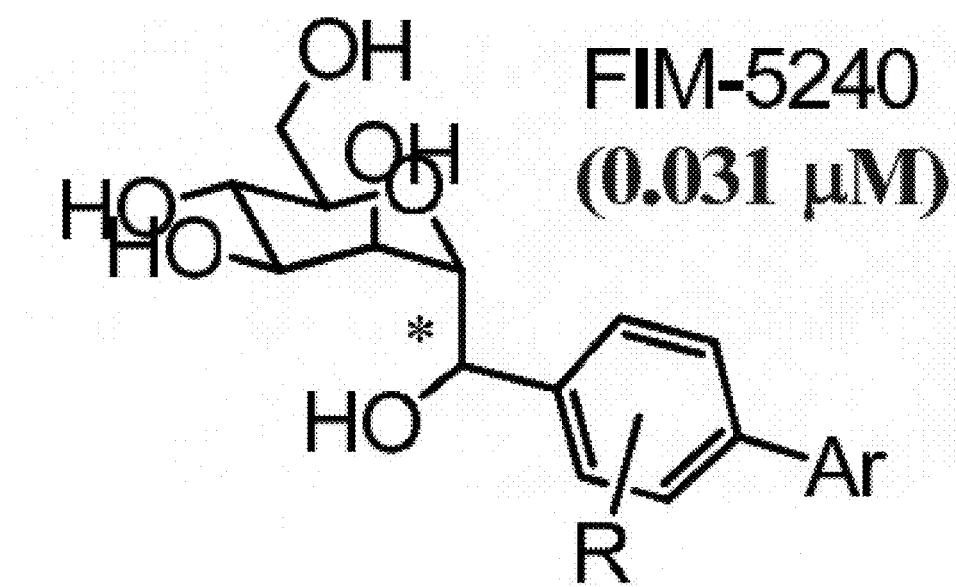
Figure 26D:
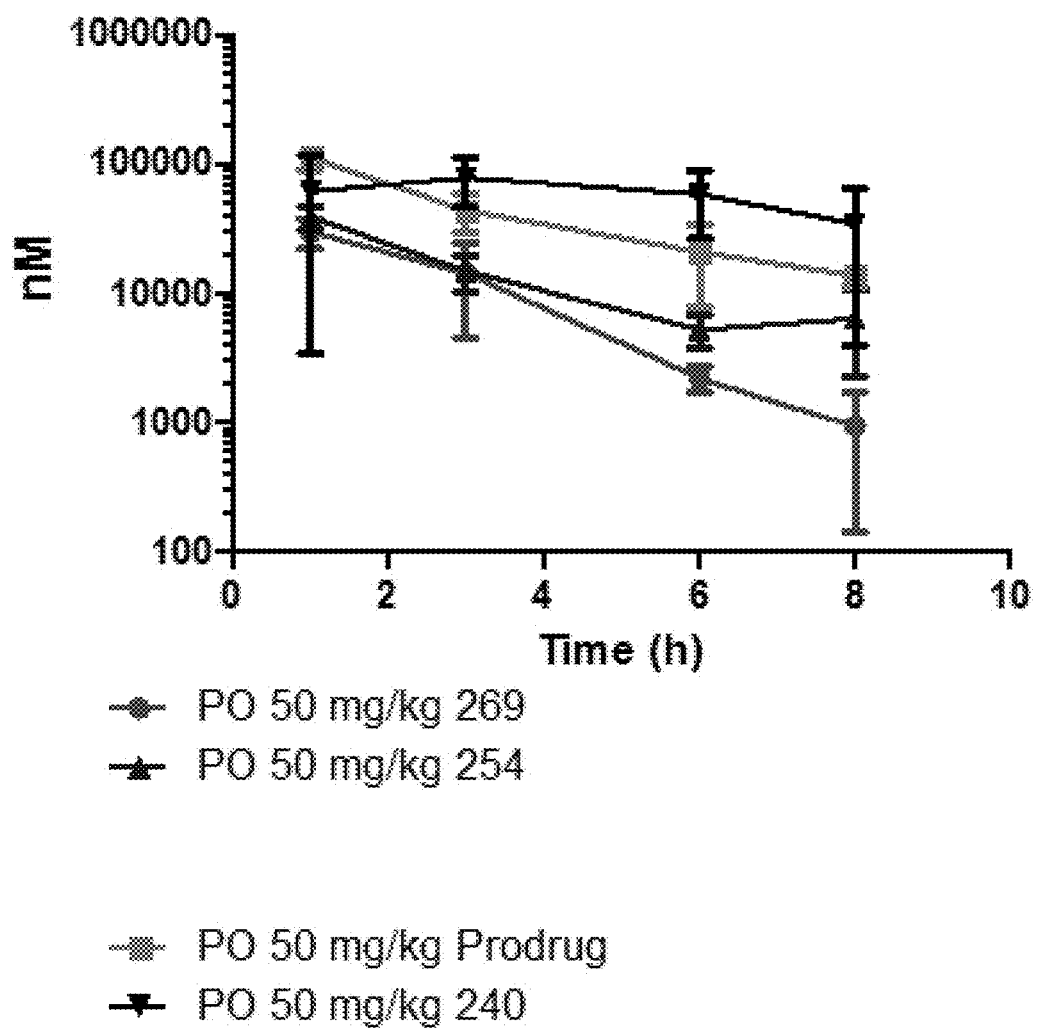
Figure 27A:
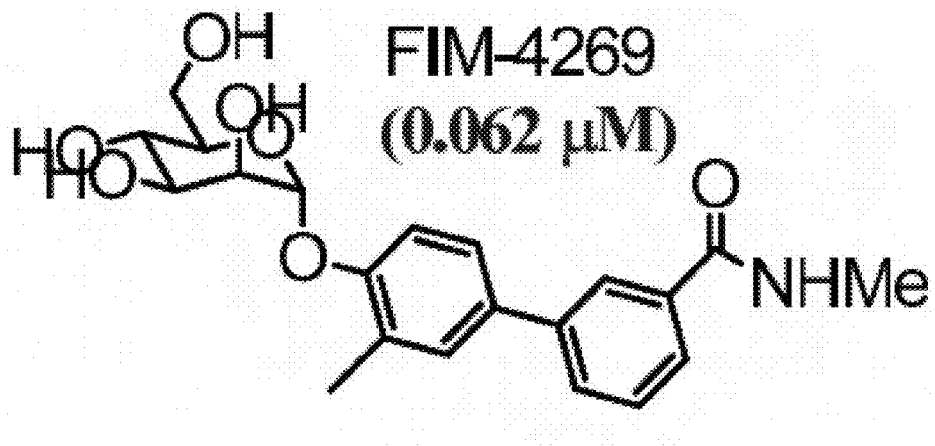
FIG. 27A, FIG. 27B, FIG. 27C, FIG. 27D and FIG. 27E depict the lead compounds in an acute UTI model. The structure of mannoside compounds (FIG. 27A) FIM-4269, (FIG. 27B) FIM-5254 (Example 7), and (FIG. 27C) FIM-5240 (Example 18A) are depicted.
Figure 27B:
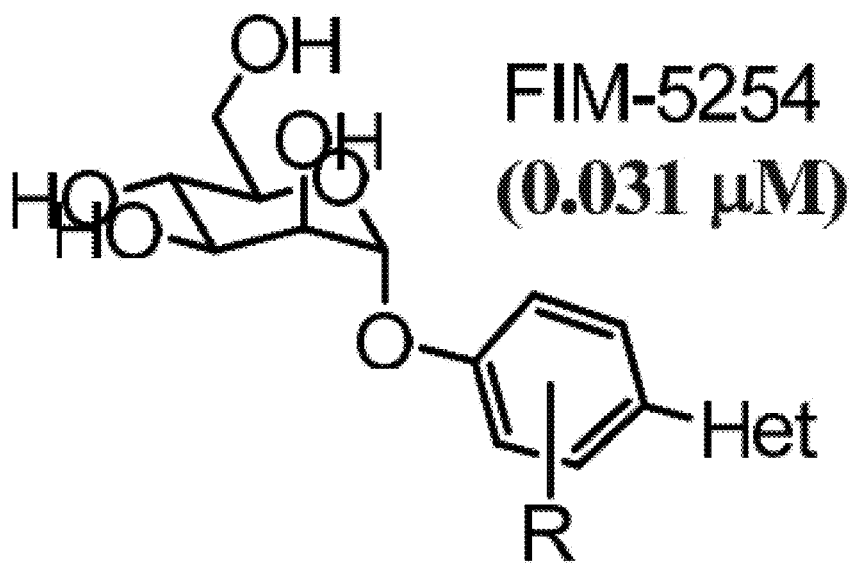
Figure 27C:
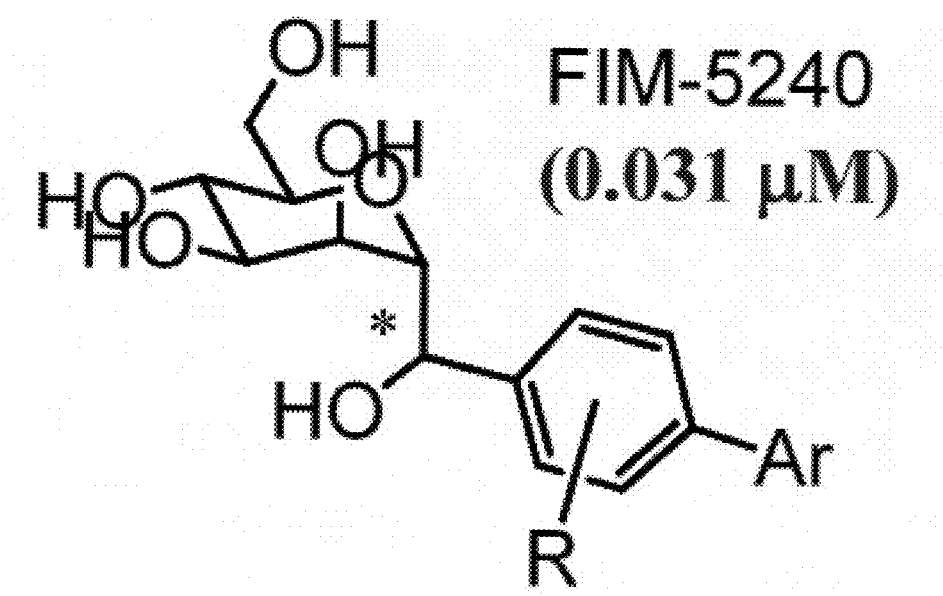
Figure 27D:
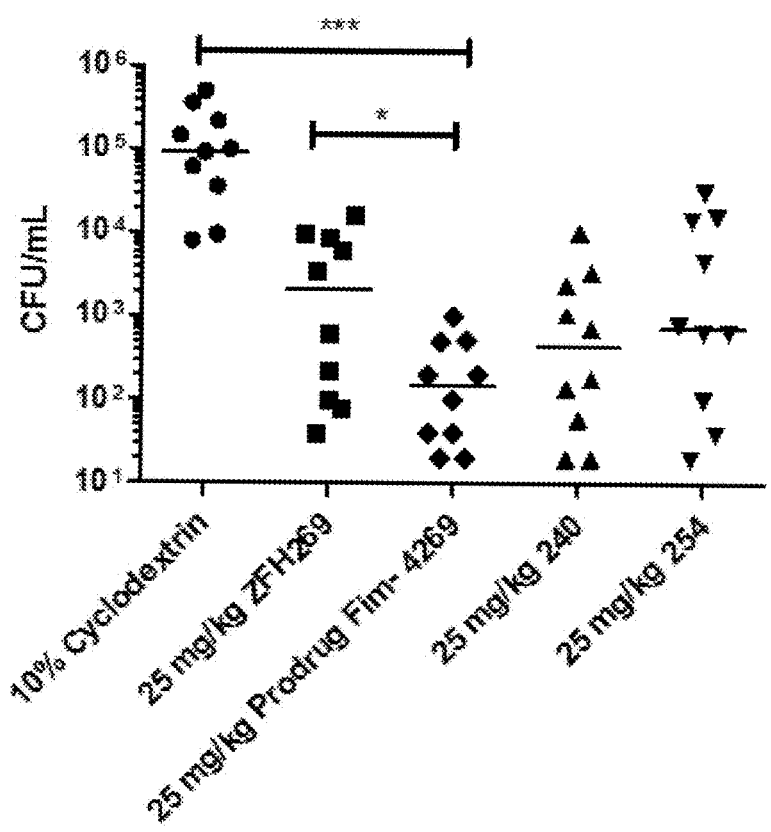
Figure 27E:
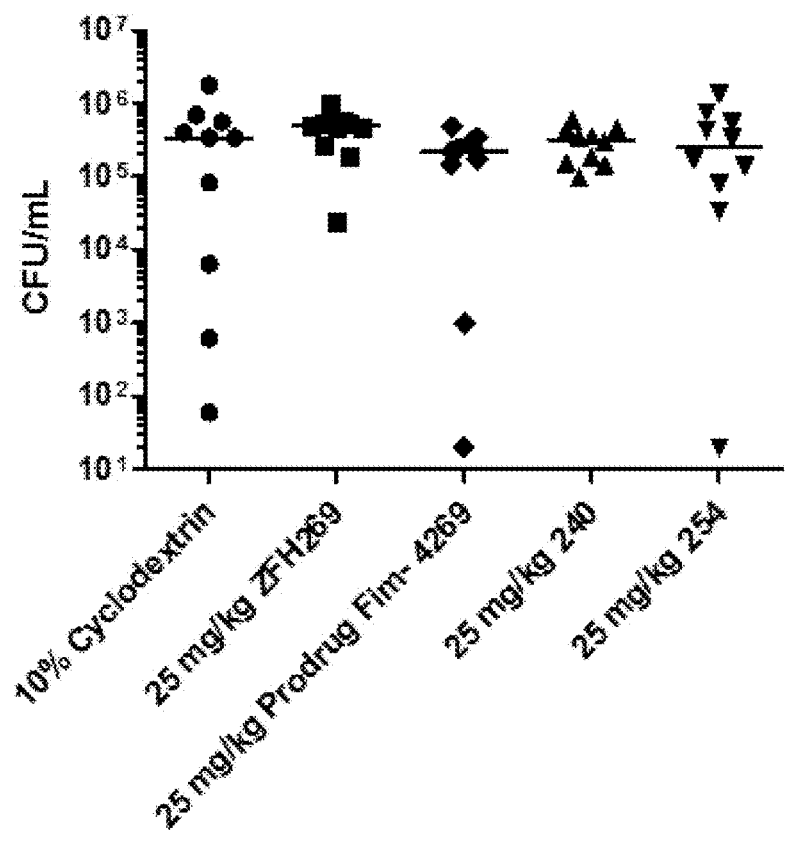
Figure 28:
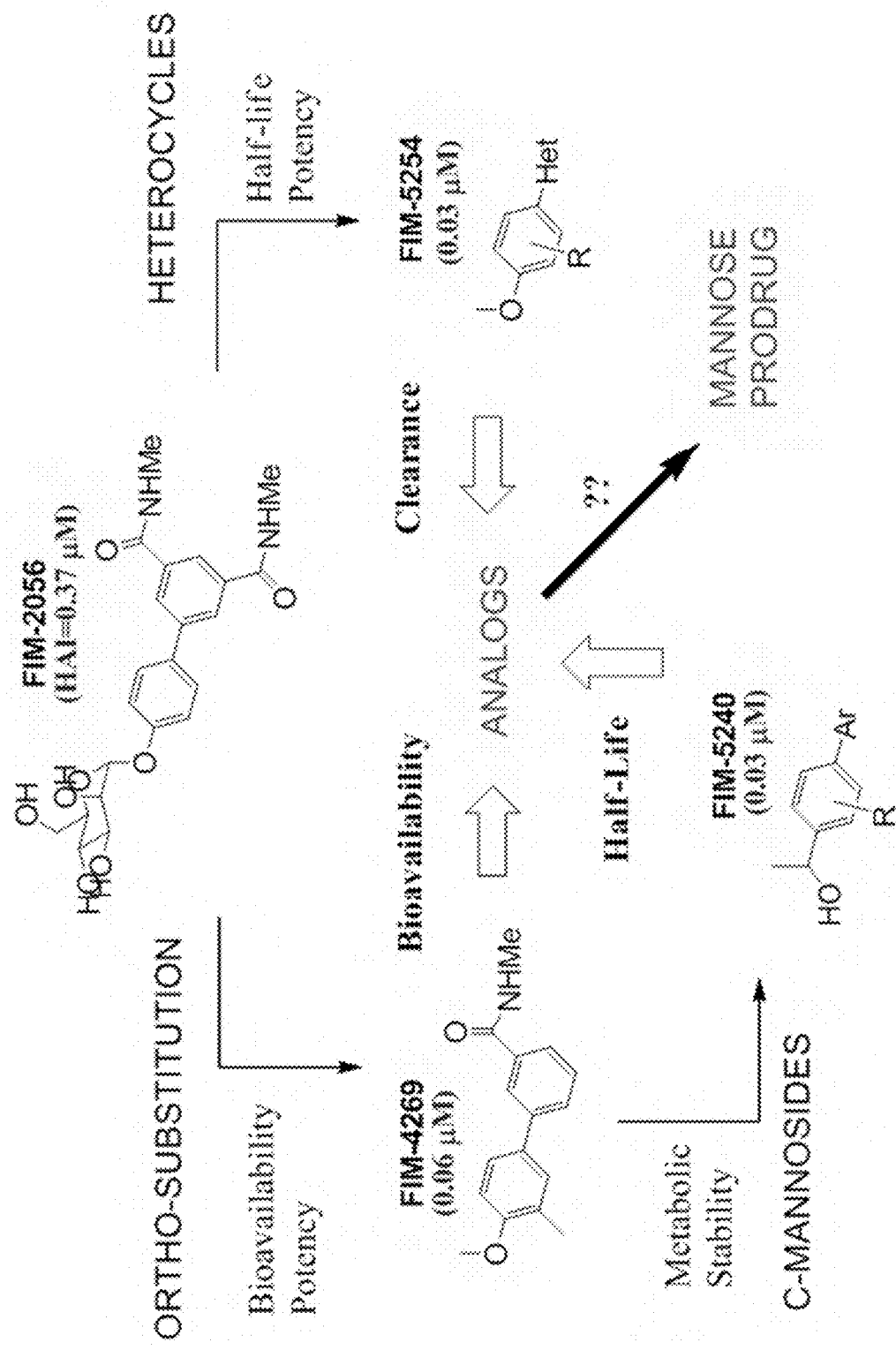
FIG. 28 depicts the lead optimization pharmacokinetics scheme.
Figure 29A:
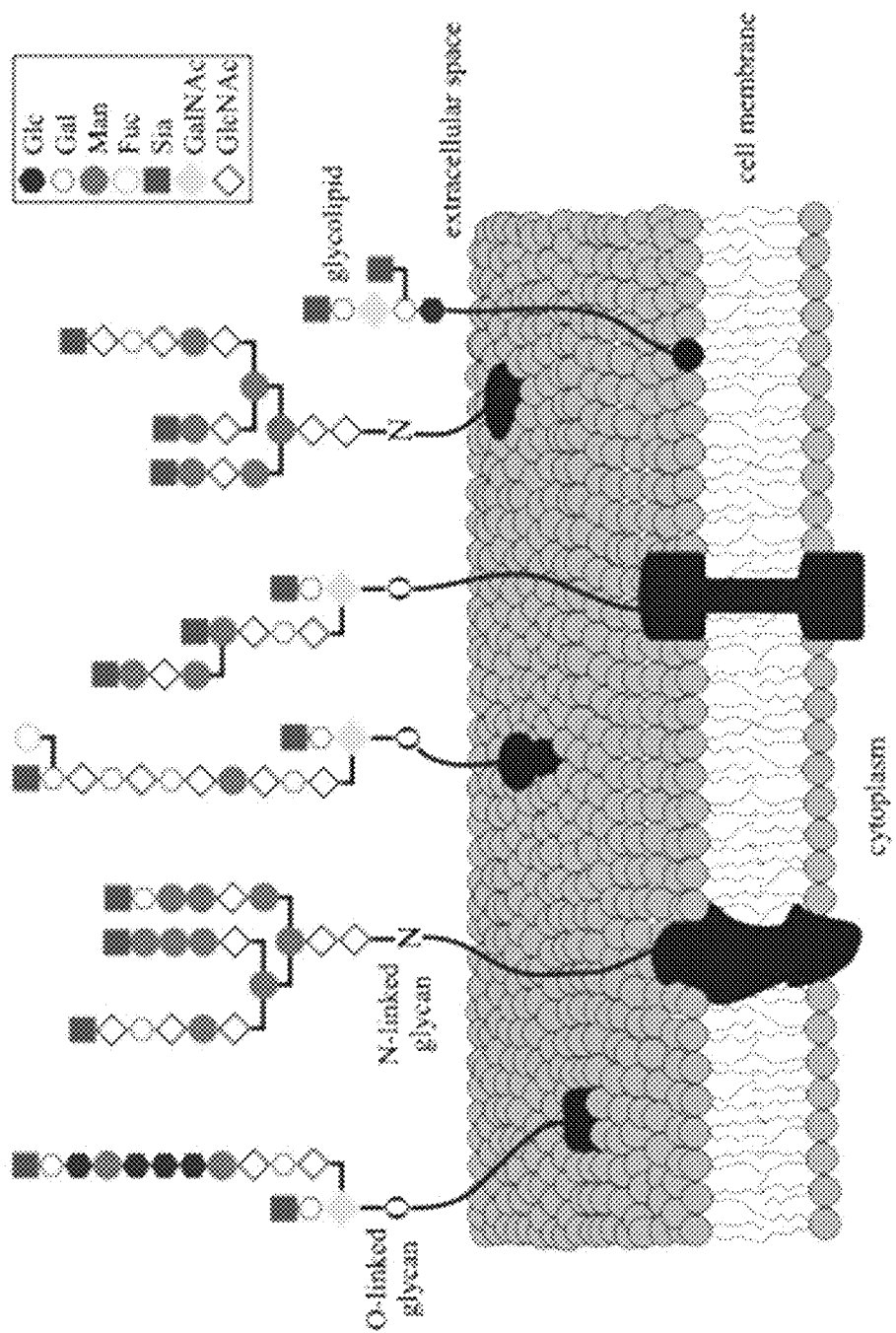
FIG. 29A and FIG. 29B depict the structure of mammalian glycoproteins.
Figure 29B:
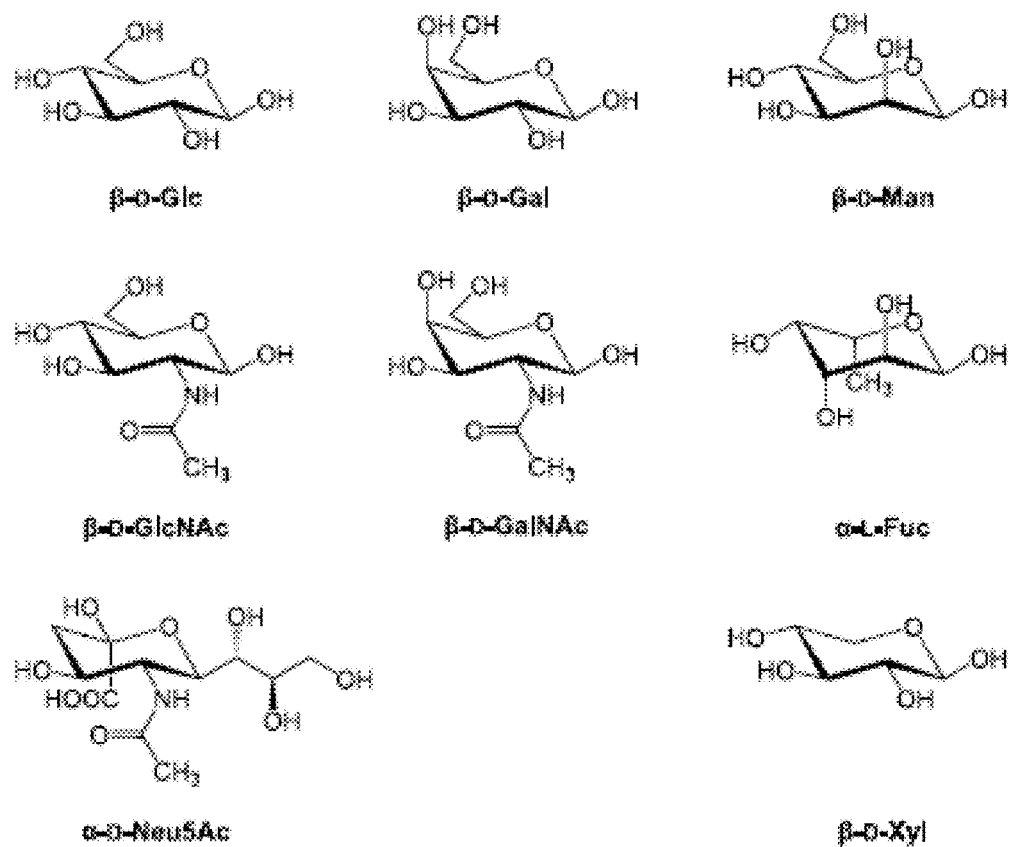
Figure 30:
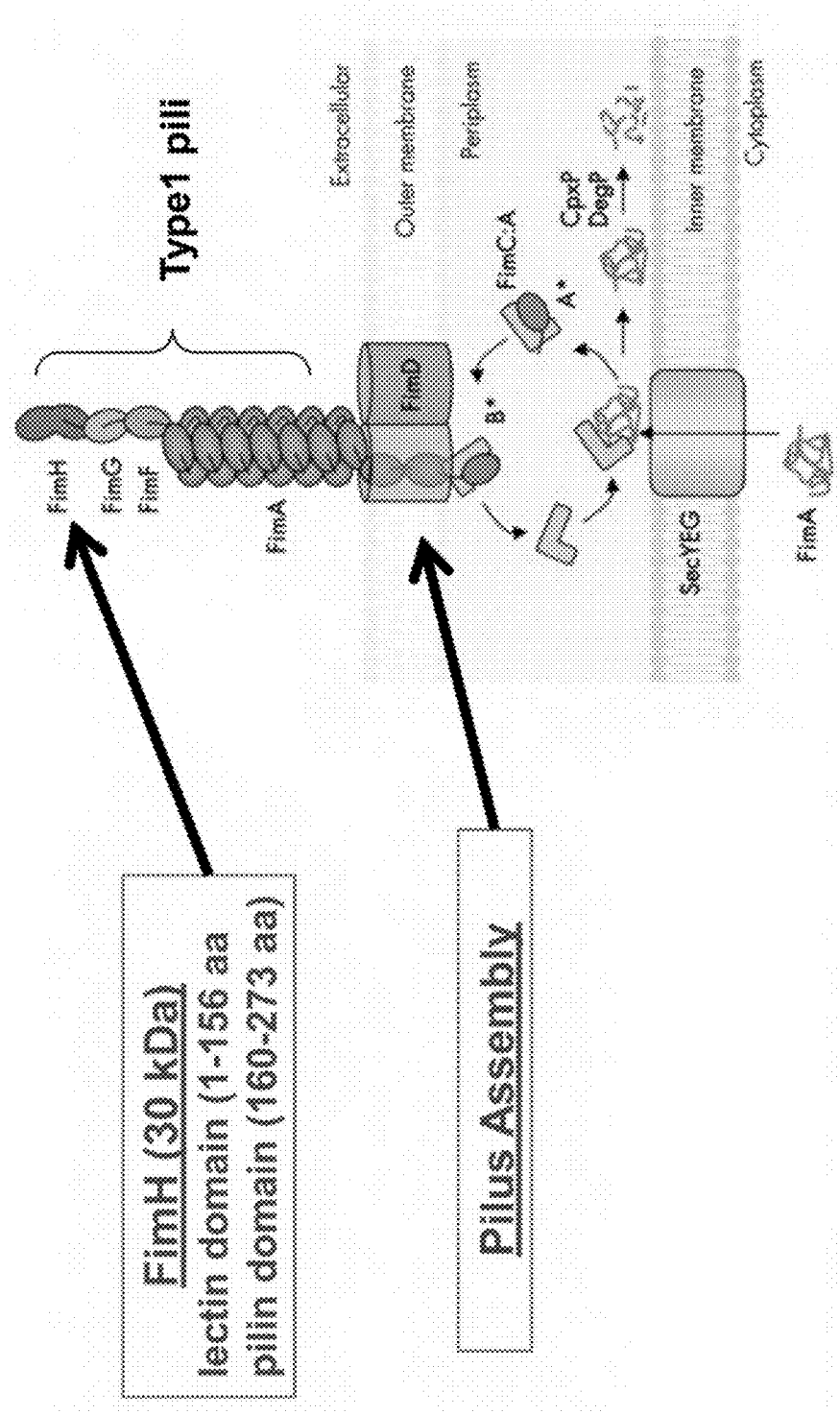
FIG. 30 depicts the structure and assembly of type 1 pili.
Figure 31:
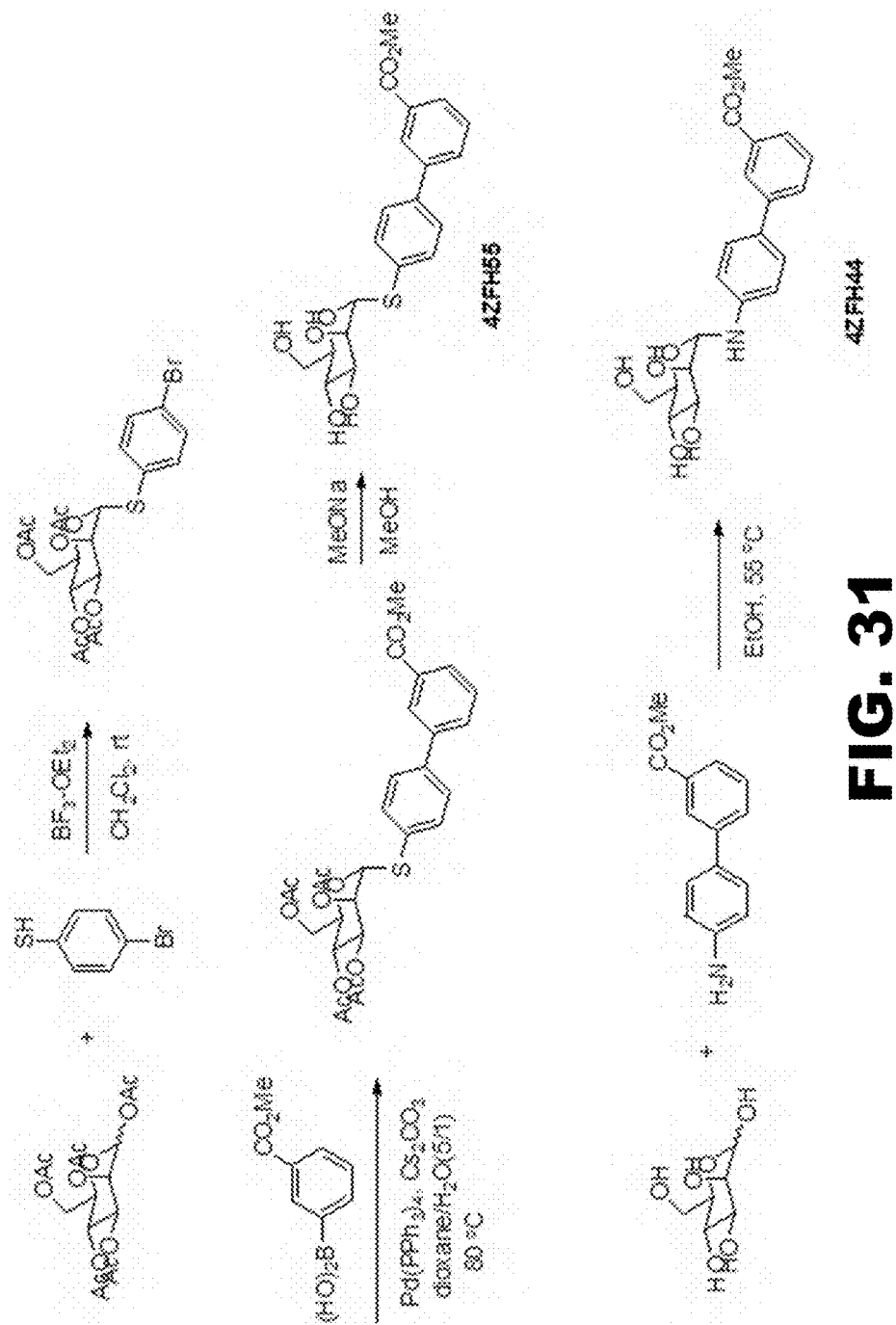
FIG. 31 depicts a schematic of the synthesis of S- and N-glycosides.
Figure 32:
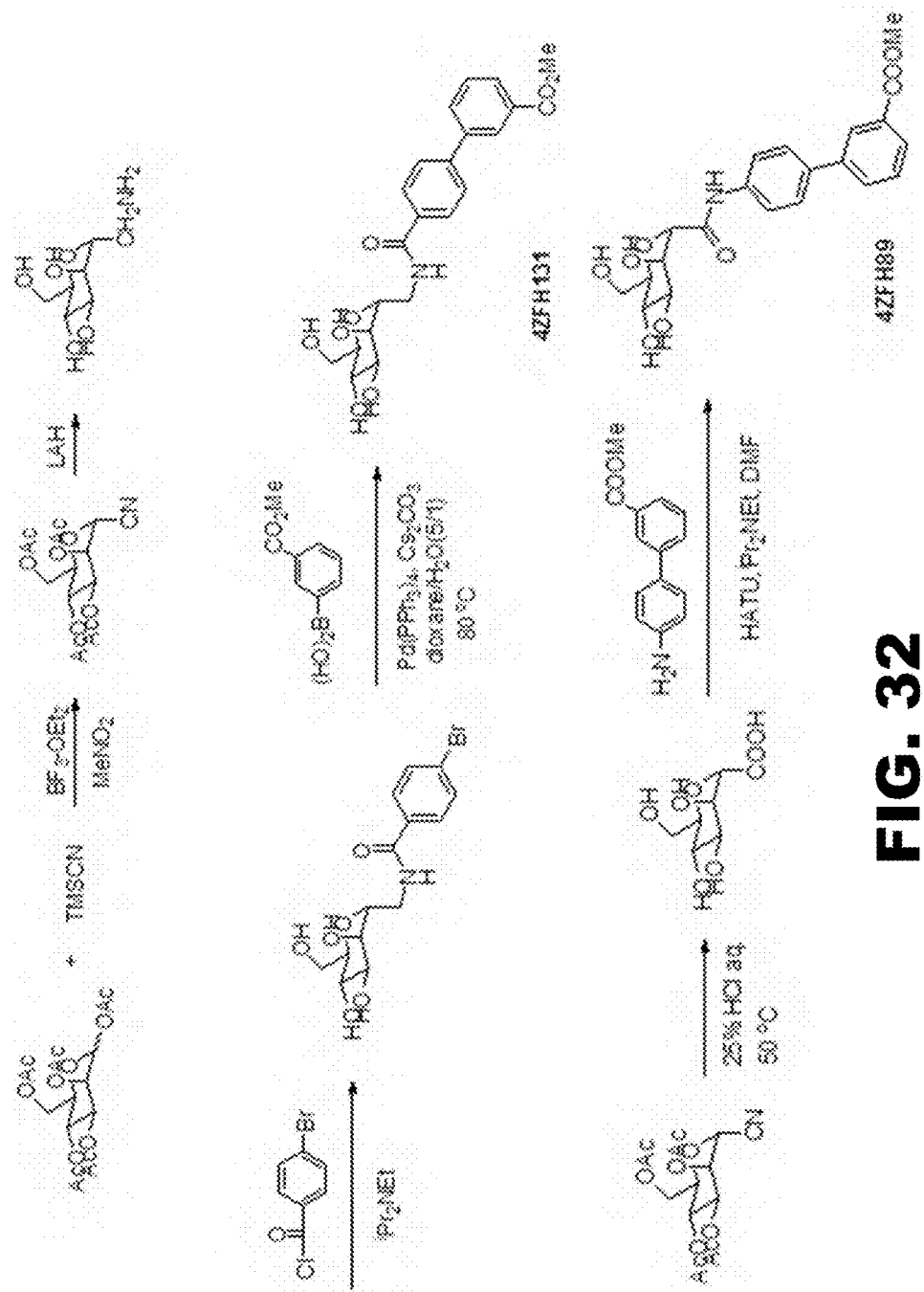
FIG. 32 depicts a schematic of the synthesis of C-linked glycosides.
Figure 33:
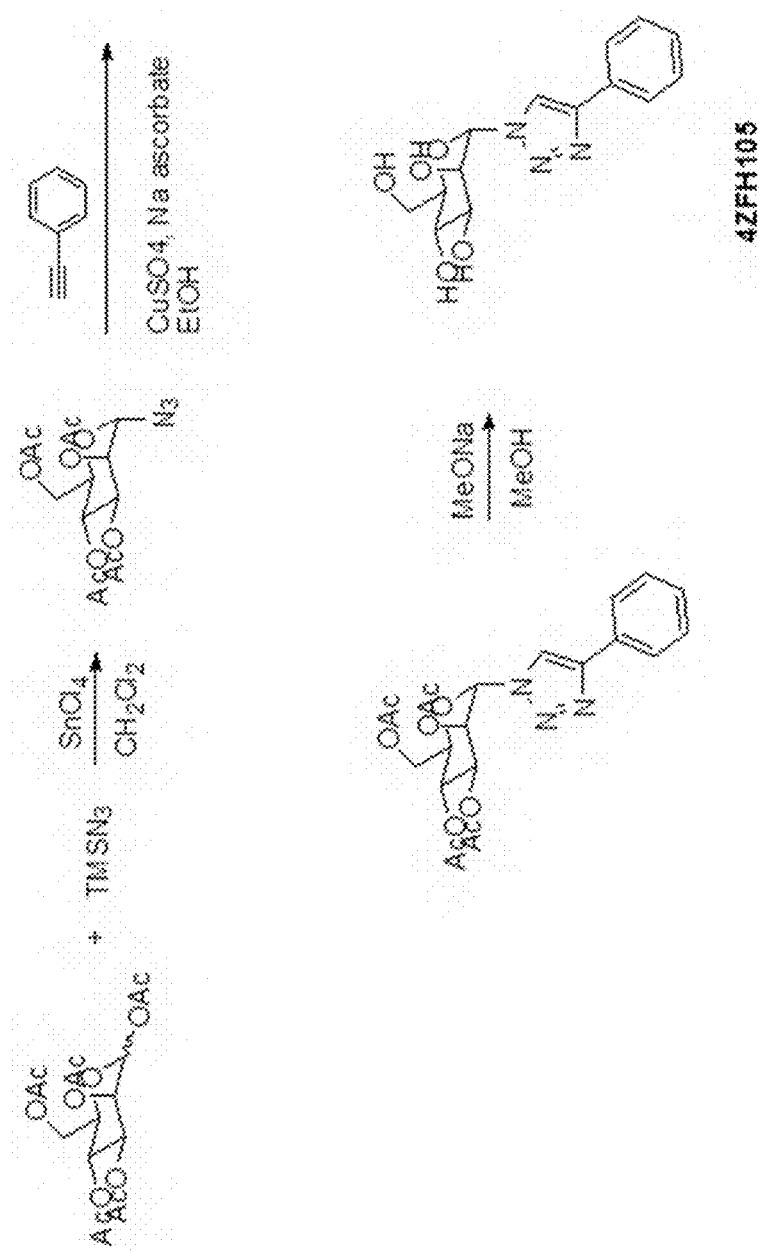
FIG. 33 depicts a schematic of the synthesis of N-linked heterocycles.
Figure 34:
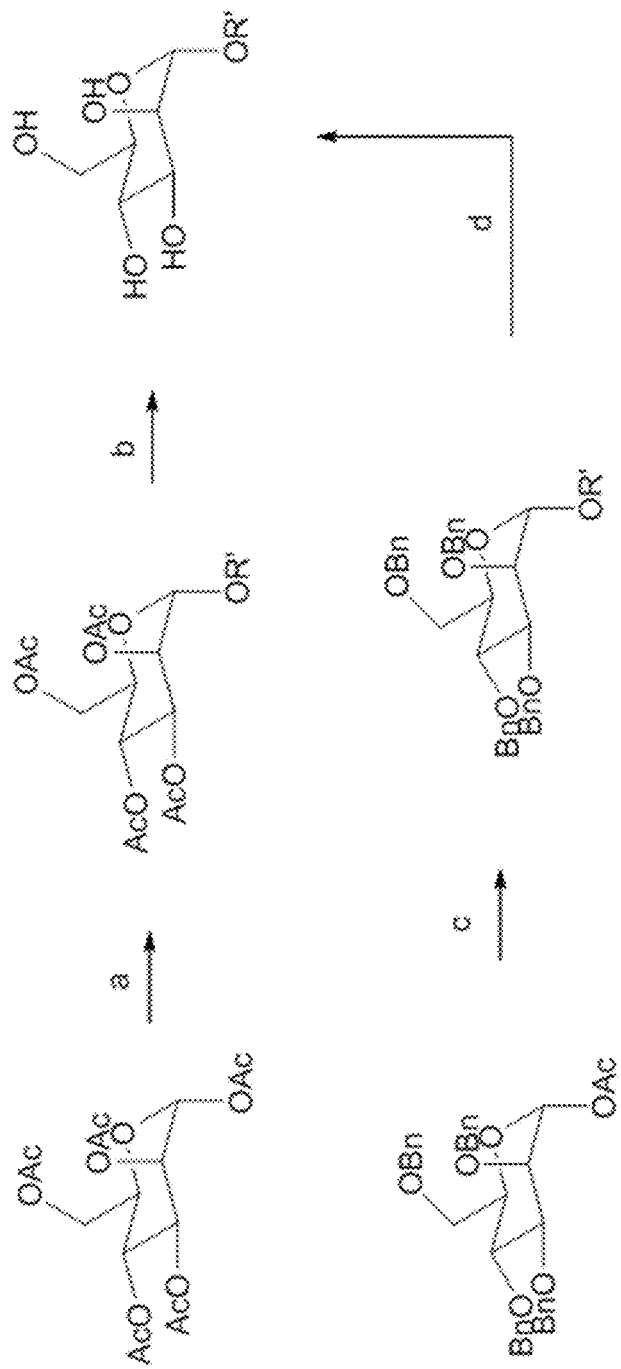
FIG. 34 depicts a schematic of the synthesis of a biaryl mannoside SAR library.
Figure 35:
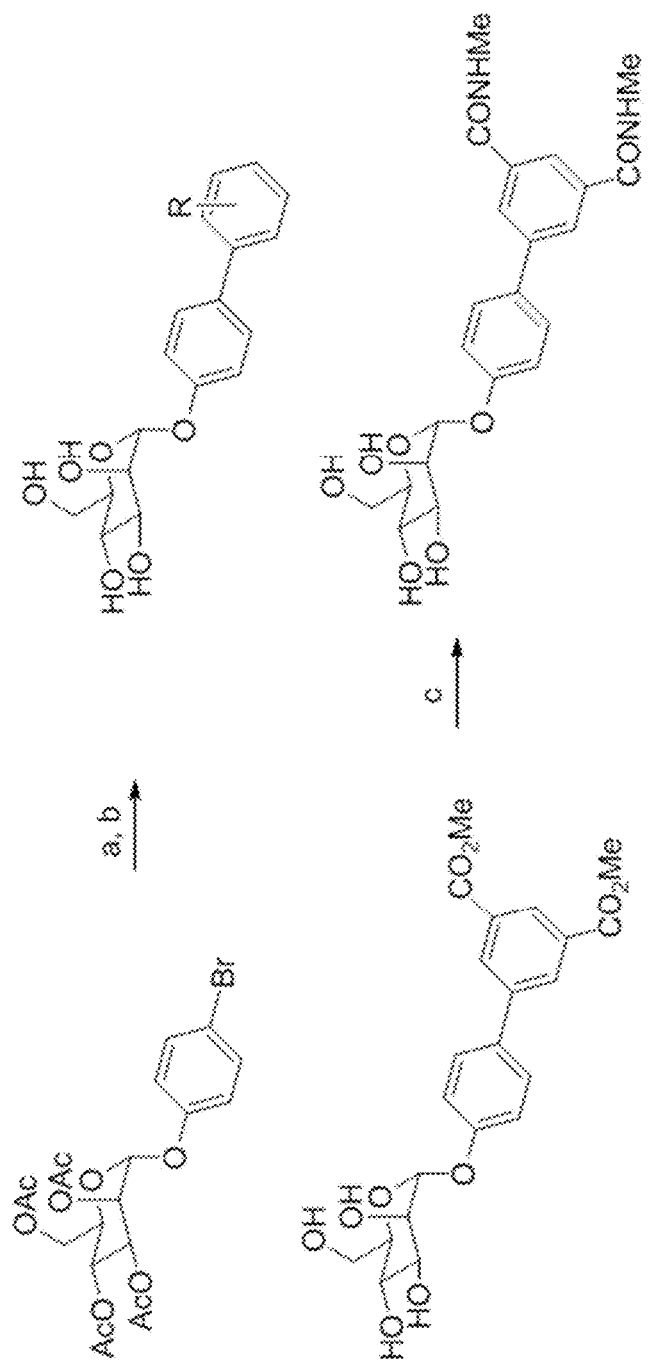
FIG. 35 depicts a schematic of the synthesis of a biphenyl mannoside Suzuki library.
Figure 36A:
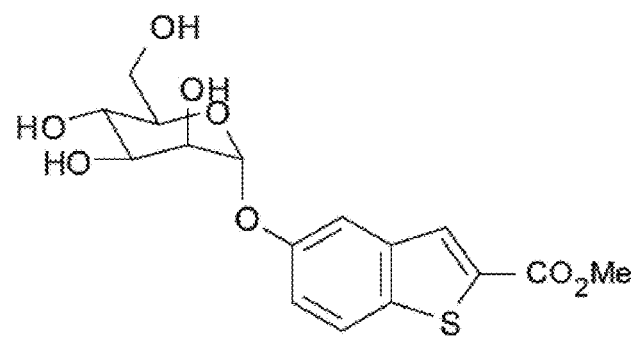
FIG. 36A, FIG. 36B and FIG. 36C depict a schematic and the physical properties of heterocycles.
Figure 36B:
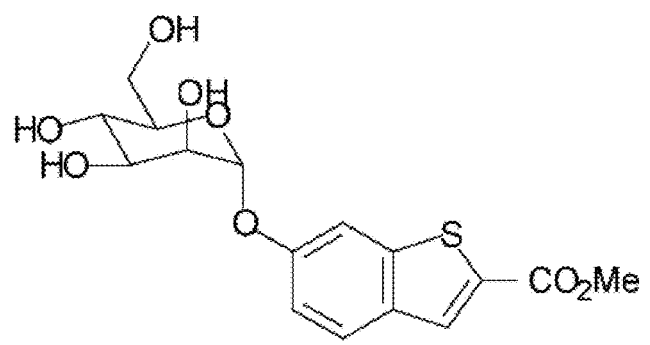
Figure 36C:
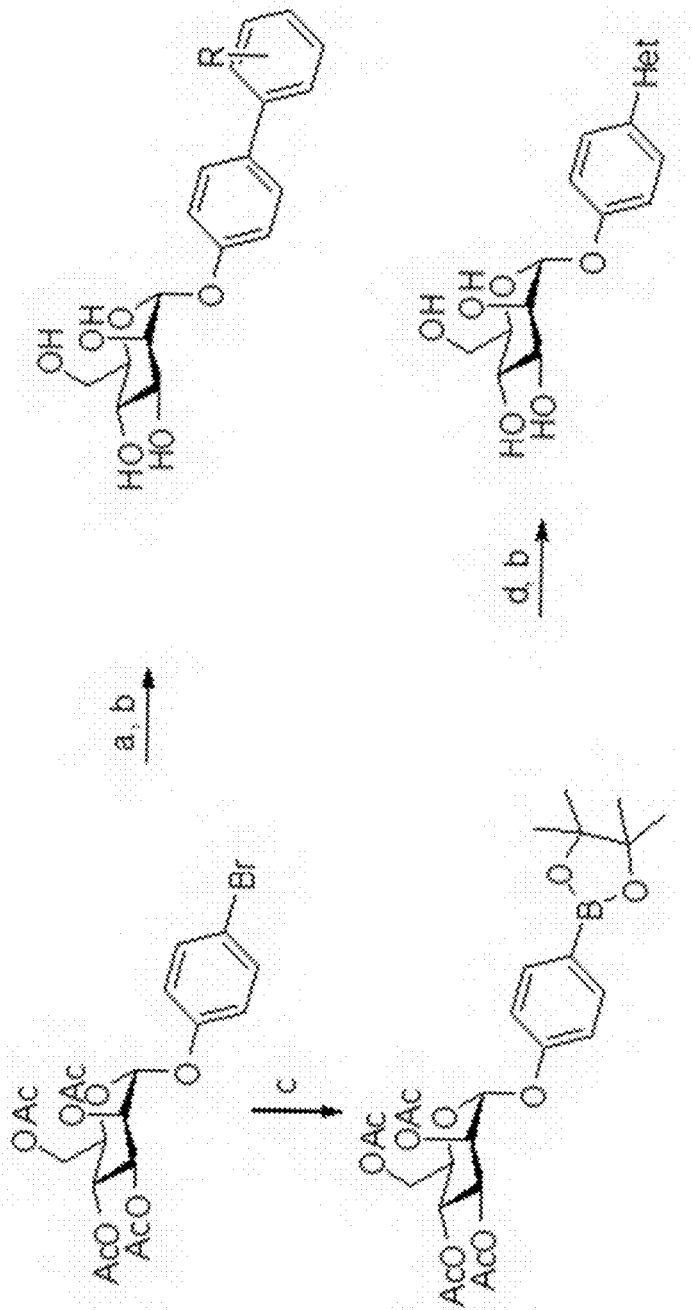

FimH is a two domain protein, with a receptor binding domain linked to a typical pilin domain that joins the adhesin to the pilus fiber. The structure of the complex of the FimC chaperone bound to FimH (which was bound to D-mannopyranoside) was determined to 2.8 Å resolution. The mannose binding site of FimH is a deep negatively charged pocket at the tip of its receptor-binding domain. The FimH pocket engages in extensive hydrogen bonding to mannose (FIG. 14), which are abundant in the oligosaccharide moieties of uroplakins that coat the lumenal surface of the bladder epithelium. A hydrophobic ridge surrounds the mannose binding pocket in a manner that may facilitate polar interactions within the FimH pocket. Mutational studies revealed that each residue is critical in mannose binding and pathogenesis, emphasizing why the pocket is invariant among UPEC isolates.

Development of Anti-Adhesives.

The FimH-mannose interaction was further investigated in an effort to develop potential ligand-based antagonists of UTIs. The chitobiose unit on oligomannose was found to bridge various mannose derivatives to the asparagine in the Asn-X-Ser/Thr motif of FimH resulting in higher affinity binding. Crystallization of FimH in complex with oligomannose-3 revealed the mechanism of this higher affinity binding. The non-reducing Man4 anchors into the mannose-binding pocket while the GlcNAc folds over Thr51 allowing specific interactions with a hydrophobic tyrosine gate. Heptyl mannoside mimics the GlcNAc tail of oligomannose-3 and extends it further to increase interactions outside the binding pocket resulting in high affinity binding (Kd=5 nM). Based on the high affinity of heptyl mannose for FimH, the ability of heptyl mannose to reduce bacterial infection in our mouse model of UTI was tested. First, biofilm formation as a surrogate for IBCs formed in the bladder was evaluated. Heptyl mannose at 1 mM inhibited UPEC biofilm formation in vitro, suggesting that the mannose binding properties of the FimH adhesin is required for biofilm formation. Thus, UPEC strain UTI89 was incubated with heptyl mannose prior to inoculation into the bladders of mice. This resulted in a significant attenuation of virulence at 6 hours post-infection at 5 mM heptyl mannose. The ability of these compounds to significantly attenuate virulence establishes mannosides as a potential treatment for UTI. Therefore, more potent mannosides that mimic the natural receptor for FimH but with increased affinity and avidity in order to ultimately block bacterial colonization, invasion, IBC formation and disease were developed as described below.

Example 26. Mannosides Inhibit the Invasion of UPEC into the Bladder Tissue and Potentiate the Efficacy of TMP-SMZ The first-line treatment of choice for UTI has traditionally been a 3-day course of TMP-SMZ. Women suffering from chronic/recurrent UTIs are often given TMP-SMZ prophylactically to prevent recurrence. However, resistance to this TMP-SMZ regimen is rapidly expanding. It was hypothesized that by preventing bacterial invasion into the bladder tissue, a FimH inhibitor may result in anti-virulence synergism with TMP-SMZ and may curtail or circumvent the problem of TMP-SMZ resistance. This theory was evaluated in a preclinical animal model where mice given TMP-SMZ for 3 days were infected with either UTI89 or the TMP-SMZ$^R$ strain, PBC-1. Mice were IP treated with 6 30 min prior to inoculation with bacteria and compared to a control group of untreated animals. After inoculation with UTI89 or PBC-1, bacterial CFUs were quantified at 6 hpi. As expected, treatment with TMP-SMZ alone resulted in a significant drop in bacterial load in the UT189-infected mice but had no effect on PBC-1, since it is resistant to TMP-SMZ. Upon treatment with 6 alone there was a significant drop in bacterial load of both strains in the bladder. In the dual treatment group there was also a significant drop in bacterial CFUs compared to mannoside alone or TMP-SMZ alone for both strains which was most pronounced for PBC-1 (FIG. 18). It was determined that the presence of mannoside had no effect on growth or killing efficiency of either strain during growth in vitro in the presence or absence of TMP-SMZ. Therefore, the observation that in combination with 6, the TMP-SMZ$^R$ strain PBC-1 succumbed to antibiotic treatment suggested that the mannoside potentiates the efficacy of TMP-SMZ by a unique mechanism. Based on growth curves in TMP-SMZ, PBC-1 was calculated to have a Minimum Inhibition Concentration (MIC) of 256 and 1280 µg/ml for TMP and SMZ, respectively and UTI89 was calculated to have an MIC of 0.05 µg/ml TMP and 0.25 µg/ml SMZ. The presence of mannoside had no effect on growth or killing efficiency of either strain. It is well established that TMP concentrates in the urine and this serendipitous feature is a major reason TMP-SMZ has been the preferred antibiotic for UTI over the last several decades. Using quantitative HPLC-MS, the concentration of TMP-SMZ was measured in the urine of mice after 3 days of treatment with 54 µg/ml and 270 µg/ml TMP and SMZ, respectively. TMP concentrations were determined to be 9.95+/−4.36 mg/ml and SMZ at 67.17+/−32.51 µg/ml. These results indicate that by preventing bacterial invasion, 6 compartmentalizes the microbes to the bladder lumen thus exposing them to TMP-SMZ concentrations above the MIC of PBC-1, resulting in augmentation of bacterial cell killing. Presumably TMP-SMZ concentrations reach tissue concentrations above the MIC needed for UTI89 killing but fail to reach tissue levels needed for killing PBC-1. These results clearly highlight the importance of the intracellular pathway in bacterial persistence. In addition to escaping the immune system in their intracellular niche, bacteria are also able to evade exposure to antibiotics as highlighted by the clinically TMP-SMZ resistant strain. In summary, mannosides could benefit those women on suppressive antibiotic therapy by inhibiting the invasion of UPEC into the bladder tissue and potentiating the efficacy of TMP-SMZ creating a cost-effective treatment, which is predicted to lower the rate of treatment failures.

Example 27. Mannoside Treatment Reduces IBC Formation in CAUTI

Having established that FimH is required for UPEC virulence in implanted bladders, we investigated this as a potential therapeutic target for CAUTI using small molecules inhibitors designed to interfere with FimH binding to mannosylated residues. This family of small molecules, called mannosides, has recently been shown to prevent acute and chronic UPEC infections and potentiated the effectiveness of antibiotics in combinatorial treatment.

To investigate the potential therapeutic effects of mannosides on CAUTI, we first assessed the inhibitory effects of methyl-a-D-mannopyranoside (methyl mannose), on UTI89 biofilm formation in urine under flow. Similar to the deletion of fimH, UTI89 biofilms grown in presence of 1% methyl mannose had significantly reduced biomass (p=0.0022) and biofilm-adherent cells (p=0.0012), compared to untreated controls. Since methyl mannose is a FimH antagonist, these data confirm the critical role of type 1 pili to biofilm formation in urine as was previously described for biofilms formed in LB media.

The effects of mannoside treatment were then assessed in vivo by using IBC formation as well as implant and urinary tract colonization as benchmarks of disease progression. Mice were treated intraperitoneally (i.p.) with saline or 5 mg/kg of mannoside 6, which is more potent than methyl mannose in vitro and in vivo, in PBS 30 min prior to urinary implantation. Catheter implantation was immediately followed by transurethral inoculation of UT189. IBC formation and bacterial colonization were assayed by LacZ staining and CFU enumeration of implants, bladders, and kidneys at 6 hpi and 24 hpi, respectively. Mannoside treatment further reduced IBC formation (p=0.0051) and bladder colonization (p=0.0114) in implanted animals at 6 hpi, suggesting that this treatment prevents intracellular infection. While eliminated from their intracellular niche, data further indicated that UPEC were able to persist in the extracellular milieu where they can colonize the surface of the implants to relatively similar levels as saline-treated animals (p=0.0547). No statistical difference was observed in kidney colonization in the presence or absence of mannosides. By 24 hpi, a time point at which the mannosides have been eliminated from the bladder, similar bacterial loads were recovered from implants, bladders, and kidneys in implanted animals in the presence or absence of mannoside treatment.

Example 28. Mannoside Treatment Increases the Efficiency of TMP-SMZ in Preventing UPEC Colonization In order to examine whether mannosides could prevent establishment of CAUTI when used in combination with antibiotics, animals were treated with 54 and 270 µg/ml of TMP-SMZ, respectively, in their drinking water for three days and then treated with saline or mannoside (5 mg/kg) i.p. 30 min prior to implantation and bacterial inoculation. At 6 hpi, UPEC colonized the implants and bladders at significantly lower levels in animals that only received antibiotics compared to those who received water or were only administered mannoside. Interestingly, mannoside treatment in addition to TMP-SMZ further decreased UPEC colonization of implants, bladders, and kidneys compared to treatment with antibiotic alone (p<0.0005 in all cases). Furthermore, treatment with mannosides alone did not reduce bacterial titers from a 24 h old UPEC infection and in combination with TMP-SMZ showed no additive effects on established UPEC CAUTI 24 hpi (data not shown). Together, these findings indicate that virulence-targeted therapies in combination with established antibiotic treatment can help prevent or delay the onset of CAUTI and that further research is warranted for enhancing mannosides potential as therapeutics against CAUTIs.

Methods for the Examples

Biofilm Assay.

UTI89 was grown in LB broth in wells of PVC microtiter plates at 23° C. in the presence of individual mannosides at varying concentrations. After 48 h of growth, wells were rinsed with water and stained with crystal violet for quantification as described. For biofilm disruption activity in PVC plates, UTI89 was grown in LB broth in wells of PVC microtiter plates at 23° C. After 24 h of growth, mannoside was added and biofilms were grown for an additional 16 h. Wells were then rinsed, stained with crystal violet and quantified. For biofilm disruption activity on PVC coverslips, UTI89 was grown in LB broth in 50 mL conicals containing PBC coverslips at 23° C. After 24 h of growth, 0.3 µM ZFH-2056 was added and biofilm was grown for an additional 16 h. Coverslips were then rinsed, fixed with 2% paraformaldehyde (v/v), stained with SYTO9 (1:1000 in PBS; Molecular Probes) and observed with a Zeiss LSM410 confocal laser scanning microscope under a 63× objective.

Animal Infections.

Bacteria were grown under type 1 pili-inducing conditions (2×24 h at 37° C. statically in LB). The bacteria were harvested and resuspended to an $OD_{600}$ of 0.5 in PBS. Eight-week-old C3H/HeN (Harlan) female mice were anesthetized by inhalation of isoflurane and infected via transurethral catheterization with 50 pl of the bacterial suspension, resulting in $1-2\times10^7$ inoculum. At 6 hpi, mice were sacrificed by cervical dislocation under anesthesia and the bladders were immediately harvested and processed as described below. All animal studies using mice were approved by the Animal Studies Committee of Washington University (Animal Protocol Number 20100002).

Pharamacokinetic Analysis.

For intraperitoneal dosing, 50 µl of a 2 mg/ml (5 mg/kg) or 4 mg/ml (10 mg/kg) solution of ZFH-2056 in PBS was injected into the peritoneal cavity of the mouse. For oral dosing, 100 µl of a 20 mg/ml (100 mg/kg) solution of ZFH-2056 in 8% DMSO was inoculated with a gavage needle into the mouse stomach. Urine was collected at 30 min, 1, 2, 3, 4, 6, and 8 h post-treatment. An equal volume of 10 µM internal standard (ZFH-2050) was added to the urine. Mannosides were extracted from the urine by loading on C18 columns (100 mg, Waters), washing with 30% methanol, and eluting with 60% methanol. Vacuum-concentrated eluates were analyzed using liquid chromatography-mass spectrometry system30 with a lower heated capillary temperature of 190° C. and a gradiert as follows: Solvent B (80% acetonitrile in 0.1% formic acid) was held constant at 5% for 5 minutes, increased to 44% B by 45 minutes, and then to a 95% B by 65 minutes. SRM mode quantification was performed with collision gas energy of 30% for the following MS/MS transitions (precursor m/z/product m/z): compound ZFH-2056, 447/285; compound ZFH-2050, 390/228. Absolute quantification was achieved by comparison to a calibration curve.

Bladder Tissue Bacterial Titer Determination.

Mannoside ZFH-2056 was administered either IP (5 mg/kg) or orally (100 mg/kg) 30 min prior to inoculation with UTI89. To enumerate the bacteria present, mice were sacrificed at 6 hpi and bladders were aseptically removed and homogenized in 1 ml PBS, serially diluted and plated onto LB agar plates. CFU was enumerated after 16 h of growth at 37° C.

Gentamicin Protection Assay.

To enumerate bacteria present in the intracellular versus extracellular compartments, bladders were aseptically harvested at 6 hpi. The bladders were then bisected twice and washed three times in 500 µl of PBS each. The wash fractions were pooled, lightly spun at 500 rpm for 5 min to pellet exfoliated bladder cells, serially diluted, and plated onto LB agar to obtain the luminal fraction. The bladders were treated with 100 µg of gentamicin/ml for 90 min at 37° C. After treatment, the bladders were washed twice with PBS to eliminate residual gentamicin, homogenized in 1 ml of PBS, serially diluted, and plated onto LB agar to enumberate the CFUs in the intracellular fraction.

Antibiotic Treatment.

Mice were given TMP-SMZ in the drinking water at a concentration of 54 µg/ml and 270 µg/ml, respectively. Water was changed daily for 3 days prior to inoculation with UTI89. Mice remained on TMP-SMZ during the infection. To determine TMP-SMZ concentration in the urine, urine was collected after 3 days of TMP-SMZ treatment and quantified by LC-MS following addition of sulfisoxazole as an internal standard.

Growth Curve.

An overnight culture of PBC-1 was diluted 1:1000 in LB in the absence or presence of TMP-SMZ and/or mannoside ZFH-2056. The highest concentration of TMP-SMZ used was 512 µg/ml and 2560 µg/ml, respectively. Two-fold dilutions of TMP-SMZ were performed. Mannoside ZFH-2056 was added at 100 µM. Growth curves were performed in a 96-well plate at 37° C. with A600 readings taken every 30 min for 8 h.

Hemagglutination Assay.

PBC-1 was grown statically in LB in the absence or presence of TMP-SMZ for 2×24 h at 37° C. The highest concentration of TMP-SMZ used was 256 µg/ml and 1280 µg/ml, respectively. Two-fold dilutions of TMP-SMZ were performed. Hemagglutination assays for mannose-sensitive agglutination of guinea pig red blood cells were performed as previously described.

Statistical analysis. Observed differences in bacterial titers and IBC numbers were analyzed for significance using the nonparametric Mann-Whitney U test (Prizm; GraphPad Software).

What is claimed is:
1. A compound, the compound comprising Formula (IV):

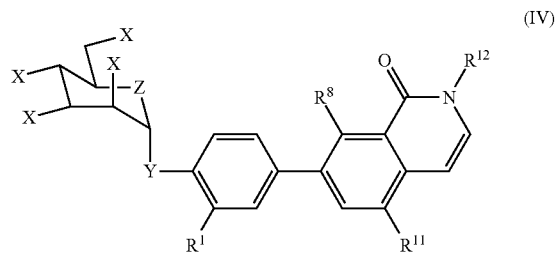

wherein:
X is selected from the group consisting of hydrogen and $OR^2$;

R² is independently selected from the group consisting of hydrogen, PO(OH)₂, acetyl, COR⁵, CO(OR⁵), CO(CH₂)ₙNR⁵R⁶, hydrocarbyl and substituted hydrocarbyl;

n is an integer from 1 to 10;

Z is O;

Y is selected from the group consisting of O, CH(OH), CH(OR⁵), CHNR⁵R⁶, CH₂, S, and NR⁵;

R¹ is selected from the group consisting of CH₃, CF₃, halogen, Cl, F, Br, I, OH, NH₂, NR⁵R⁶, OCH₃, CO₂CH₃, CONHCH₃, alkyl, cyclopropyl, OR⁵, CO₂R⁵, CONR⁵R⁶, hydrocarbyl, and substituted hydrocarbyl;

R⁵ is selected from the group consisting of H and an optionally substituted alkyl, aryl, heterocycle, and cycloalkyl;

R⁶ and R⁷ are selected from the group consisting of an optionally substituted alkyl, cycolalkyl, aryl, and heterocycle;

R⁸ and R¹¹ are independently selected from the group consisting of CONHCH₃, COOCH₃, COOH, CONH(heterocycle), heterocycle, H, alkyl, cyclopropyl, aryl, OR⁵, NR⁵R⁶, NR⁵COR⁶, NR⁵COOR⁶, NR⁵CONR⁶, NR⁵SO₂R⁶, COR⁵, SO₂R⁵, halogen, CN, NO₂, COOR⁵, CONR⁵R⁶, NCOR⁷, NCONR⁷, NCOOR⁷, SO₂NR⁵R⁶, and NHSO₂R⁷;

R¹² is selected from the group consisting of H, alkyl, CH₂R¹³, CH₂COR¹³, CH₂CONHR¹³, CH₂CONHR¹³R¹⁴, CH₂CONH(CH₂)₂R¹⁴, (CH₂)₂NR¹³, (CH₂)ₙNR¹³, CH₂COOH, CH₂CONH(CH₂)₂NH₂, and (CH₂)₂N(CH₃)₂;

R¹³ is selected from the group consisting of —OH and an optionally substituted heterocycle, hydrocarbyl, and substituted hydrocarbyl;

R¹⁴ is selected from the group consisting of alkyl and NH₂.

2. A method of treating a urinary tract infection, the method comprising administering a compound of claim 1 to a subject in need thereof.

3. The method of claim 2, wherein the subject is further administered a bactericidal composition.

4. A method of preventing a urinary tract infection, the method comprising administering a compound of claim 1 to a subject in need thereof.

5. The method of claim 4, wherein the subject is further administered a bactericidal composition.

6. A method of reducing the resistance of a bacterium to a bactericidal compound, the method comprising administering a compound of claim 1 to a subject in need thereof.

7. A method of treating inflammatory bowel disease, the method comprising administering a compound of claim 1 to a subject in need thereof.

8. The method of claim 7, wherein the inflammatory bowel disease is Crohn's disease.

9. The method of claim 7, wherein treating comprises reducing symptoms associated with inflammatory bowel disease.

10. A method of inhibiting FimH binding to mannose, the method comprising contacting a compound of claim 1 with FimH, wherein the compound binds FimH and inhibits binding to mannose.

11. The method of claim 10, wherein the mannose is exposed on a bladder cell.

12. The method of claim 10, wherein the mannose is exposed on an intestinal cell.

13. A method of treating a catheter-associated urinary tract infection, the method comprising administering a compound of claim 1 to a subject in need thereof.

14. The compound of claim 1, wherein the compound is selected from the group consisting of:

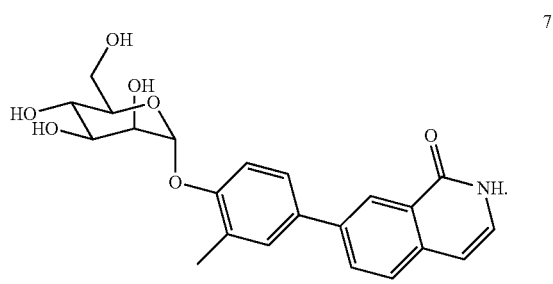

7

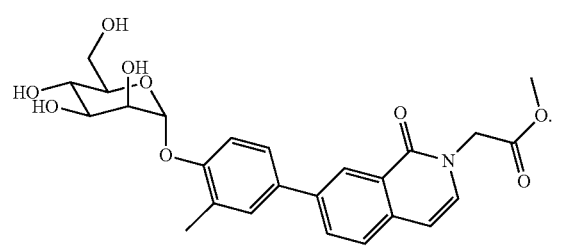

8

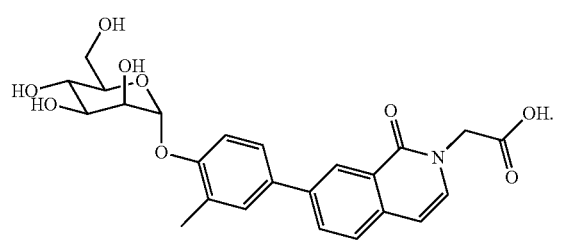

9

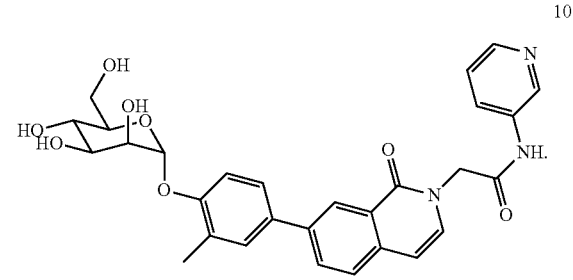

10

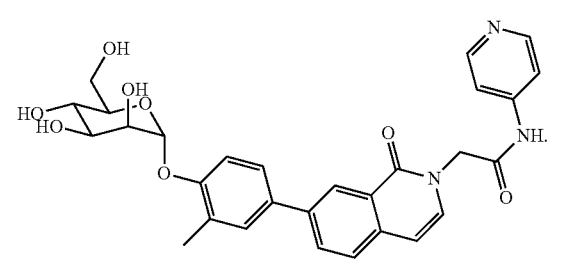

11

-continued
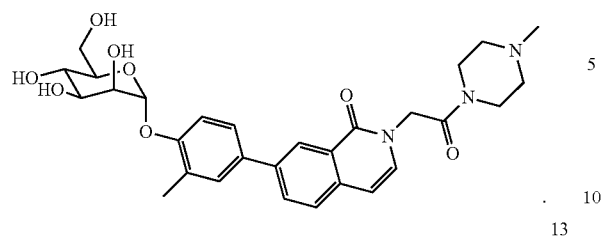
12
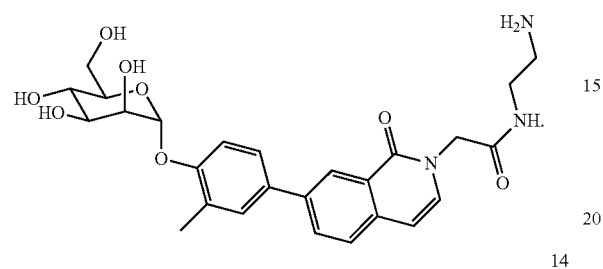
13
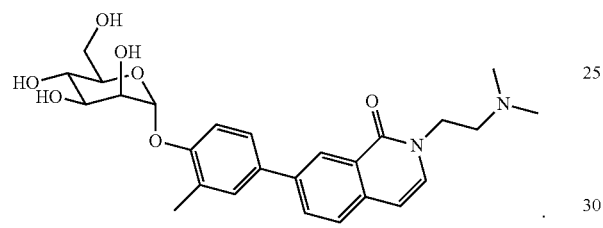
14
* * * * *

UNITED STATES PATENT AND TRADEMARK OFFICE
CERTIFICATE OF CORRECTION

PATENT NO. : 9,957,289 B2  
APPLICATION NO. : 14/894927  
DATED : May 1, 2018  
INVENTOR(S) : James W. Janetka et al.

It is certified that error appears in the above-identified patent and that said Letters Patent is hereby corrected as shown below:

In the Specification

Column 1, Lines 16-19, delete:
"This invention was made with government support under grants numbered 1RC1DK086378, RO1AI029549, P50DK064540 and RO1BK051406-12 each of which were awarded by the National Institutes of Health. The government has certain rights in the invention."

And replace with:
-- "This invention was made with government support under AI029549, DK086378, DK064540 and DK051406 awarded by the National Institutes of Health (NIH). The government has certain rights in the invention." --

Signed and Sealed this  
Ninth Day of February, 2021

Drew Hirshfeld  
*Performing the Functions and Duties of the*  
*Under Secretary of Commerce for Intellectual Property and*  
*Director of the United States Patent and Trademark Office*